US012281170B2

(12) United States Patent
Ogrunc et al.

(10) Patent No.: US 12,281,170 B2
(45) Date of Patent: Apr. 22, 2025

(54) SENESCENT CELL-ASSOCIATED ANTIGEN-BINDING DOMAINS, ANTIBODIES AND CHIMERIC ANTIGEN RECEPTORS COMPRISING THE SAME, AND USES THEREOF

(71) Applicant: StarkAge Therapeutics, Lille (FR)

(72) Inventors: Müge Ogrunc, Paris (FR); Thierry Mathieu, Brussels (BE)

(73) Assignee: StarkAge Therapeutics, Lille (FR)

( * ) Notice: Subject to any disclaimer, the term of this patent is extended or adjusted under 35 U.S.C. 154(b) by 0 days.

(21) Appl. No.: 18/340,242

(22) Filed: Jun. 23, 2023

(65) Prior Publication Data

US 2024/0009242 A1 Jan. 11, 2024

Related U.S. Application Data

(60) Division of application No. 17/032,510, filed on Sep. 25, 2020, now Pat. No. 11,723,926, which is a continuation-in-part of application No. 16/585,256, filed on Sep. 27, 2019, now abandoned.

(30) Foreign Application Priority Data

Sep. 27, 2019 (EP) .................................... 19200182

(51) Int. Cl.
*C07K 16/28* (2006.01)
*A61K 39/00* (2006.01)
*C12N 5/0783* (2010.01)

(52) U.S. Cl.
CPC ...... *C07K 16/2896* (2013.01); *A61K 39/4611* (2023.05); *A61K 39/4631* (2023.05); *A61K 39/464402* (2023.05); *C12N 5/0636* (2013.01); *C07K 2317/24* (2013.01); *C07K 2317/31* (2013.01)

(58) Field of Classification Search
CPC ... A61K 35/17; C07K 16/2896; C12N 5/0636
See application file for complete search history.

(56) References Cited

FOREIGN PATENT DOCUMENTS

| | | | |
|---|---|---|---|
| EP | 3029069 | A1 | 6/2016 |
| WO | 2001064750 | A2 | 9/2001 |
| WO | 2002092127 | A1 | 11/2002 |
| WO | 2005118643 | A2 | 12/2005 |
| WO | 2007014169 | A2 | 2/2007 |
| WO | 2018002358 | A1 | 1/2018 |
| WO | 2018027197 | A1 | 2/2018 |
| WO | 2018160768 | A1 | 9/2018 |
| WO | 2020160518 | A1 | 8/2020 |

OTHER PUBLICATIONS

Fidler IJ. "Biological heterogeneity of cancer: implication to therapy", Hum Vaccin Immunother. Aug. 2012;8(8):1141-2 (Year: 2012).*

The Merck Manuals Online Medical Library, [online]. Whitehouse Station, NJ: Merck Research Laboratories, 2006-2007. [retrieved on Oct. 19, 2020]. <URL: https://www.merckmanuals.com/professional/hematology-and-oncology/overview-of-cancer/cellular-and-molecular-basis-of-cancer> (Year: 2020).*

Althubiti et al., "Characterization of novel markers of senescence and their prognostic potential in cancer". Cell Death Dis. Nov. 20, 2014;5(11):e1528.

Baar et al., "Targeted Apoptosis of Senescent Cells Restores Tissue Homeostasis in Response to Chemotoxicity and Aging". Cell. Mar. 23, 2017;169(1):132-147.e16.

Chang et al., "Clearance of senescent cells by ABT263 rejuvenates aged hematopoietic stem cells in mice". Nat Med. Jan. 2016;22(1):78-83.

Guedan et al., "Engineering and Design of Chimeric Antigen Receptors". Mol Ther Methods Clin Dev. Dec. 31, 2018;12:145-156.

Hashimoto et al., "Elimination of p19ARF-expressing cells enhances pulmonary function in mice". JCI Insight. Aug. 4, 2016;1(12):e87732.

Kim et al., "Identification of senescent cell surface targetable protein DPP4". Genes Dev. Aug. 1, 2017;31 (15):1529-1534.

Kral et al., "Sustained PI3K Activation exacerbates BLM-induced Lung Fibrosis via activation of pro-inflammatory and pro-fibrotic pathways". Sci Rep. Mar. 14, 2016;6:23034.

Lehmann et al., "Senolytic drugs target alveolar epithelial cell function and attenuate experimental lung fibrosis ex vivo". Eur Respir J. Aug. 3, 2017;50(2).pii:1602367.

Muñoz-Espin et al., "Cellular senescence: from physiology to pathology". Nat Rev Mol Cell Biol. Jul. 2014; 15(7):482-96.

Myrianthopoulos et al., "Senescence and senotherapeutics: a new field in cancer therapy". Pharmacol Ther. Jan. 2019;193:31-49.

Nho et al., "IPF fibroblasts are desensitized to type I collagen matrix-induced cell death by suppressing low autophagy via aberrant Akt/mTOR kinases". PLoS One. Apr. 11, 2014;9(4):e94616.

Schafer et al., "Cellular senescence mediates fibrotic pulmonary disease". Nat Commun. Feb. 23, 2017;8:14532.

Senis et al., "Targeting receptor-type protein tyrosine phosphatases with biotherapeutics: is outside-in better than inside-out?". Molecules. Mar. 2, 2018;23(3):569.

Soare et al., "Dipeptidylpeptidase 4 as a marker of activated fibroblasts and a potential target for the treatment of fibrosis in systemic sclerosis". Arthritis Rheumatol. Jan. 2020;72(1):137-149.

Takahashi et al., "A monoclonal antibody against CD148, a receptor-like tyrosine phosphatase, inhibits endothelial-cell growth and angiogenesis". Blood. Aug. 15, 2006;108(4):1234-42.

Tangye et al., "CD148: a receptor-type protein tyrosine phosphatase involved in the regulation of human T cell activation". J Immunol. Oct. 1, 1998;161(7):3249-55.

(Continued)

*Primary Examiner* — Amy E Juedes
*Assistant Examiner* — Peter Johansen
(74) *Attorney, Agent, or Firm* — Panitch Schwarze Belisario & Nadel LLP; Erin M. Dunston

(57) ABSTRACT

Disclosed are senescent cell-associated antigen-binding domain and related antibodies and related chimeric antigen receptors. In addition, disclosed are DPP4-binding domains and related antibodies and related chimeric antigen receptors. Also disclosed are methods for treating, preventing or alleviating senescence-related diseases or disorders. Methods for depleting and/or killing senescent cells are also disclosed.

12 Claims, 8 Drawing Sheets

Specification includes a Sequence Listing.

(56) References Cited

OTHER PUBLICATIONS

Tsuboi et al., "The tyrosine phosphatase CD148 interacts with the p85 regulatory subunit of phosphoinositide 3-kinase". Biochem J. Jul. 1, 2008;413(1):193-200.
Yosef et al., "Directed elimination of senescent cells by inhibition of BCL-W and BCL-XL". Nat Commun. Apr. 6, 2016;7:11190.
Cartellieri et al., "Chimeric Antigen Receptor-Engineered T Cells for Immunotherapy of Cancer," Journal of Biomedicine and Biotechnology, vol. 2010, Article ID 956304, (2010).
Chicaybam et al., "Chimeric Antigen Receptors in Cancer Immuno-Gene Therapy: Current Status and Future Directions," International Reviews of Immunology, 30:5-6, 294-311 (2011).
He et al., "Senescence in Health and Disease," Cell. Jun. 1, 2017; 169(6): 1000-1011 (2017).

* cited by examiner

SENESCENT CELL-ASSOCIATED ANTIGEN-BINDING DOMAINS, ANTIBODIES AND CHIMERIC ANTIGEN RECEPTORS COMPRISING THE SAME, AND USES THEREOF

CROSS-REFERENCE TO RELATED APPLICATIONS

This application is a Divisional Application of Ser. No. 17/032,510, filed on Sep. 25, 2020, which is a Continuation-In-Part of U.S. patent application Ser. No. 16/585,256, filed on Sep. 27, 2019, now abandoned, and which claims priority to European Patent Application 19200182.4, filed on Sep. 27, 2019, all of which are incorporated herein by reference in their entireties for all purposes.

REFERENCE TO SEQUENCE LISTING SUBMITTED ELECTRONICALLY

This application contains a sequence listing, which is submitted electronically as an XML formatted sequence listing with a file name "689515-4U2 Sequence Listing", creation date of Jun. 22, 2023, and having a size of 296,686 bytes. The sequence listing submitted electronically is part of the specification and is herein incorporated by reference in its entirety.

FIELD OF INVENTION

The invention relates to DPP4-binding domains, as well as antibodies and chimeric antigen receptors (CAR) comprising the same. Also disclosed are methods for treating, preventing or alleviating senescence-related diseases or disorders, or for depleting and/or killing senescent cells.

BACKGROUND OF INVENTION

Cellular senescence is an evolutionarily conserved state of stable replicative arrest induced by several pro-ageing stressors, including telomere attrition, oxidative stress, DNA damage and oncogene activation. Cellular senescence is associated with apoptosis resistance, and results in secretion of a broad repertoire of cytokines, chemokines, growth factors, matrix remodeling proteases: the so-called senescence-associated secretory phenotype (SASP). This cellular state also promotes proliferation and tissue deterioration.

Conversely, senescence is also anti-proliferative, and may be requisite for optimal cutaneous wound healing. Therefore, cellular senescence is an example of antagonistic pleiotropy in which natural selection favors processes that are beneficial early in life, even if they cause harmful effects later in post-reproduction life.

Since its discovery, senescence, once defined as the limited replicative capacity of primary human fibroblasts, now serves as a key player driving organismal aging via exhaustion of tissue repair capacity. Several human pathologies have been associated with detrimental effects of senescence such as lung fibrosis, type 2 diabetes, obesity, osteoarthritis, ocular diseases, Alzheimer's and Parkinson's disease (Munoz-Espin and Serrano, 2014. Nat Rev Mol Cell Biol. 2014 July; 15(7):482-96). Therapeutic strategies so far to balance these pathologies related to accumulation of senescent cells are dependent on direct elimination of senescent cells based on their intrinsic properties (e.g., their apoptotic resistance or P53 dependence) (Yosef et al., 2016. *Nat Commun.* 7:11190; Chang et al., 2016. *Nat Med.* 22(1):78-83; Baar et al., 2017. *Cell.* 169(1):132-147). Although these first-generation senolytic approaches serve as a proof-of-principle for drug discovery targeting senescence, they are limited by their observed toxic side effects.

While the role of senescence and the contribution of senescent cells are increasingly recognized in the context of aging and a variety of disease states, relatively little is known regarding the influences of senescent cells in normal lung growth and aging per se, or in the induction or progression of lung diseases across the age spectrum, such as bronchopulmonary dysplasia, asthma, chronic obstructive pulmonary disease, or pulmonary fibrosis. However, crucial evidences have been recently provided by several groups that cellular senescence contributes to lung ageing (Hashimoto et al., 2016. *JCI Insight.* 1(12):e87732; Lehmann et al., 2017. *Eur Respir J.* 50(2):1602367; Schafer et al., 2017. *Nat Commun.* 8:14532).

Among lung diseases, idiopathic pulmonary fibrosis (IPF) is a typical example of an ageing disease characterized by a progressive destruction of lung parenchyma and interstitial remodeling, leading to IPF symptoms (i.e., chronic shortness of breath, cough, fatigue and weight loss) and resulting in dramatic truncation of healthspan and lifespan.

The potential to blunt lung disease by targeting senescent cells using a novel class of drugs called "senolytics" is currently discussed. Indeed, two studies by Lehmann et al. and Schafer et al. suggest that cellular senescence is a salient feature of lung fibrosis, and that targeting/elimination of these cells could be beneficial. In particular, they show that cellular senescence markers such as SAβG, P21, P16INK4a and DNA damage response are detectable within IPF patients, as well as in experimental models of lung fibrosis. They further demonstrate that senescent cell elimination rejuvenates pulmonary health in aged mice. However, it is unclear whether and how senescent cells regulate IPF in humans or if their removal may be an efficacious intervention strategy.

Although promising, it cannot be excluded that senolytic drugs could be detrimental in IPF patients. Indeed, senolytic drug treatment may result in massive epithelial cell depletion by apoptosis, which could trigger diffuse alveolar damage and acute exacerbation, since the regenerative capacity of epithelial cells in IPF patients is impaired.

There remains thus a need for alternative strategies for depleting senescent cells and improving health and lung functions of IPF patients.

The Inventors have developed such alternative strategy, by potentiating an immune response against senescent cells in a way that would lead to their clearance from lung tissue. They provide herein a new association of two cell surface markers, DPP4 and DEP1, which are targeted to detect and deplete senescent cells in the lung. Senescent cells are immunogenic in nature and are subject to immune surveillance mechanisms.

Dipeptidyl peptidase 4 (DPP4, also named CD26) is a cell surface protease with a wide range of biological functions. As a serine-type protease, DPP4 preferentially cleaves off substrates with proline and alanine at the penultimate position. Expression of DPP4 is widespread throughout the body. Interestingly, DPP4 has been identified as a senescent cell surface targetable protein, functionally required for fibroblast activation and tissue fibrosis (Kyoung et al., 2017. *Genes Dev.* 31(15):1529-1534).

Density Enhanced Protein Tyrosine Phosphatase (DEP1, also named CD148, HPTP-eta, or PTP receptor type J (PTPRJ)) is an enzyme that removes phosphate groups covalently attached to tyrosine residues in proteins. DEP1 is highly expressed on both hematopoietic and nonhematopoietic cells, including lung cells. It has been shown that DEP1 can directly interact with and dephosphorylate the regulatory subunit of PI3K (p85) (Tsuboi et al., 2008. *Biochem J.* 413(1):193-200) and that hyperactivation of PI3K/Akt plays an important role in the profibrotic phenotype of IPF-derived lung fibroblasts by promoting cell proliferation and migration and myofibroblast differentiation (Kral et al., 2016. *Sci Rep.* 6:23034; Nho et al., 2014. *PLoS One.* 9(4):e94616).

The Inventors herein provide antibodies, bispecific antibodies, chimeric antigen receptors (CARs) and bispecific CARs, including immune cell populations expressing said CARs directed specifically against senescent cells for treatment and prophylaxis of age-related diseases and disorders, and other diseases and disorders associated or exacerbated by the presence of senescent cells, such as, for example, pulmonary fibrosis. The antibodies and CARs described herein are specific for at least one senescent cell-associated antigen (e.g., DEP1 and/or DPP4), and induce the clearance (i.e., removal, elimination, destruction) of senescent cells. Said clearance may, for example, be mediated by antibody-dependent cell cytotoxicity (ADCC) or complement dependent cytotoxicity (CDC) or both.

SUMMARY

The present invention relates to a DPP4-binding domain, comprising a combination of three heavy chain variable region (HCVR)'s complementary-determining regions (CDRs) and three light chain variable region (LCVR)'s CDRs, said combination being as defined in Table 3.

In one embodiment, the DPP4-binding domain comprises:

a) a HCVR which comprises the following three CDRs:
   - $V_H$-CDR1 selected from the group consisting of SEQ ID NO: 109 and 108;
   - $V_H$-CDR2 selected from the group consisting of SEQ ID NO: 122 and 127;
   - $V_H$-CDR3 selected from the group consisting of SEQ ID NO: 139 and 138;

b) a LCVR which comprises the following three CDRs:
   - $V_L$-CDR1 selected from the group consisting of SEQ ID NO: 148 and 147;
   - $V_L$-CDR2 selected from the group consisting of SEQ ID NO: 160 and 159;
   - $V_L$-CDR3 selected from the group consisting of SEQ ID NO: 172 and 171.

In one embodiment, the DPP4-binding domain is selected from the group consisting of:

i. a DPP4-binding domain comprising a $V_H$-CDR1 with SEQ ID NO: 109, a $V_H$-CDR2 with SEQ ID NO: 122, a $V_H$-CDR3 with SEQ ID NO: 139, a $V_L$-CDR1 with SEQ ID NO: 148, a $V_L$-CDR2 with SEQ ID NO: 160 and a $V_L$-CDR3 with SEQ ID NO: 172; and ii. a DPP4-binding domain comprising a $V_H$-CDR1 with SEQ ID NO: 108, a $V_H$-CDR2 with SEQ ID NO: 127, a $V_H$-CDR3 with SEQ ID NO: 138, a $V_L$-CDR1 with SEQ ID NO: 147, a $V_L$-CDR2 with SEQ ID NO: 159 and a $V_L$-CDR3 with SEQ ID NO: 171.

In one embodiment, the DPP4-binding domain is selected from the group consisting of:

i. a DPP4-binding domain comprising a HCVR with a sequence sharing at least 80% of sequence identity with the non-CDR regions of SEQ ID NO: 185 and a LCVR with a sequence sharing at least 80% of sequence identity with the non-CDR regions of SEQ ID NO: 213; and ii. a DPP4-binding domain comprising a HCVR with a sequence sharing at least 80% of sequence identity with the non-CDR regions of SEQ ID NO: 197 and a LCVR with a sequence sharing at least 80% of sequence identity with the non-CDR regions of SEQ ID NO: 212.

The present invention also relates to a DEP1-binding domain, comprising a combination of three heavy chain variable region (HCVR)'s complementary-determining regions (CDRs) and three light chain variable region (LCVR)'s CDRs, said combination being as defined in Table 1.

In one embodiment, the DEP1-binding domain comprises:

a) a HCVR which comprises the following three CDRs:
   - $V_H$-CDR1 selected from the group consisting of SEQ ID NO: 10, 11 and 5;
   - $V_H$-CDR2 selected from the group consisting of SEQ ID NO: 21, 25 and 12;
   - $V_H$-CDR3 selected from the group consisting of SEQ ID NO: 30, 32 and 29;

b) a LCVR which comprises the following three CDRs:
   - $V_L$-CDR1 selected from the group consisting of SEQ ID NO: 37, 38 and 33;
   - $V_L$-CDR2 selected from the group consisting of SEQ ID NO: 44, 46 and 40;
   - $V_L$-CDR3 selected from the group consisting of SEQ ID NO: 53, 52 and 49.

In one embodiment, the DEP1-binding domain is selected from the group consisting of:

i. a DEP1-binding domain comprising a $V_H$-CDR1 with SEQ ID NO: 10, a $V_H$-CDR2 with SEQ ID NO: 21, a $V_H$-CDR3 with SEQ ID NO: 30, a $V_L$-CDR1 with SEQ ID NO: 37, a $V_L$-CDR2 with SEQ ID NO: 44 and a $V_L$-CDR3 with SEQ ID NO: 53;

ii. a DEP1-binding domain comprising a $V_H$-CDR1 with SEQ ID NO: 11, a $V_H$-CDR2 with SEQ ID NO: 25, a $V_H$-CDR3 with SEQ ID NO: 32, a $V_L$-CDR1 with SEQ ID NO: 38, a $V_L$-CDR2 with SEQ ID NO: 46 and a $V_L$-CDR3 with SEQ ID NO: 52; and iii. a DEP1-binding domain comprising a $V_H$-CDR1 with SEQ ID NO: 5, a $V_H$-CDR2 with SEQ ID NO: 12, a $V_H$-CDR3 with SEQ ID NO: 29, a $V_L$-CDR1 with SEQ ID NO: 33, a $V_L$-CDR2 with SEQ ID NO: 40 and a $V_L$-CDR3 with SEQ ID NO: 49.

In one embodiment, the DEP1-binding domain is selected from the group consisting of:

i. a DEP1-binding domain comprising a HCVR with a sequence sharing at least 80% of sequence identity with the non-CDR regions of SEQ ID NO: 68 and a LCVR with a sequence sharing at least 80% of sequence identity with the non-CDR regions of SEQ ID NO: 89;

ii. a DEP1-binding domain comprising a HCVR with a sequence sharing at least 80% of sequence identity with the non-CDR regions of SEQ ID NO: 72 and a LCVR with a sequence sharing at least 80% of sequence identity with the non-CDR regions of SEQ ID NO: 93; and iii. a DEP1-binding domain comprising a HCVR with a sequence sharing at least 80% of sequence identity with the non-CDR regions of SEQ ID NO: 58 and a LCVR with a sequence sharing at least 80% of sequence identity with the non-CDR regions of SEQ ID NO: 78.

The present invention also relates to an isolated antibody or antigen-binding fragment thereof comprising the DPP4-binding domain or the DEP1-binding domain of the invention.

In one embodiment, the isolated antibody or antigen-binding fragment thereof is a bispecific antibody comprising the DPP4-binding domain and the DEP1-binding domain of the invention.

The present invention also relates to a chimeric antigen receptor (CAR) comprising:

a. at least one extracellular binding domain, comprising at least one DPP4-binding domain and/or at least one DEP1-binding domain of the invention,
b. an extracellular spacer domain,
c. a transmembrane domain,
d. optionally, at least one costimulatory domain, and
e. at least one intracellular signaling domain.

The present invention also relates to an immune cell engineered to express the CAR of the invention at its surface.

The present invention also relates to a population of immune cells, comprising a plurality of immune cells of the invention.

In one embodiment, the population of immune cells of the invention comprises:

a) a plurality of immune cells of the invention, engineered to express a CAR comprising at least one DPP4-binding domain of the invention at its surface; and a plurality of immune cells of the invention, engineered to express a CAR comprising at least one DEP1-binding domain of the invention at its surface; or
b) a plurality of immune cells of the invention, engineered to express a CAR comprising at least one DPP4-binding domain of the invention and a CAR comprising at least one DEP1-binding domain of the invention, at its surface; or
c) a plurality of immune cells of the invention, engineered to express a CAR comprising at least one DPP4-binding domain of the invention and at least one DEP1-binding domain of the invention at its surface.

The present invention also relates to a composition comprising:

the isolated antibody or antigen-binding fragment thereof of the invention,
the immune cell of the invention, and/or
the population of immune cells of the invention.

In one embodiment, the composition of the invention is a pharmaceutical composition and further comprising at least one pharmaceutically acceptable excipient.

In one embodiment, the composition of the invention is for use as a drug.

In one embodiment, the composition of the invention is for use in treating, preventing or alleviating a senescence-related disease or disorder, preferably selected from the group consisting of fibrotic diseases, premalignant disorders, inflammatory diseases and cancers.

In one embodiment, the senescence-related disease or disorder is a fibrotic disease, preferably a pulmonary fibrotic disease.

In one embodiment, the composition of the invention is for use in depleting and/or killing senescent cells.

Definitions

"A", "an" and "the" are intended to include both singular and plural forms, unless the context clearly indicates otherwise.

"About", preceding a figure encompasses plus or minus 10%, or less, of the value of said figure. It is to be understood that the value to which the term "about" refers is itself also specifically, and preferably, disclosed.

"Antibody-dependent cell-mediated cytotoxicity" or "ADCC" refers to a cell-mediated cytotoxicity induced in an antibody-dependent manner when the Fc region of said antibody bound to its antigen binds to the Fc receptor on effector cells such as natural killer cells, macrophages, neutrophils, eosinophils and mononuclear cells (e.g., peripheral blood mononuclear cells), thereby leading to lysis of the target cell. ADCC can be measured using assays that are known and available in the art (e.g., Clynes et al., 1998. *Proc Natl Acad Sci USA.* 95(2):652-6).

"Antibody-dependent cell-mediated phagocytosis" or "ADCP" or "opsonisation" refers to a cell-mediated reaction in which nonspecific cytotoxic cells (e.g., phagocytes, macrophages) that express Fc receptors (FcRs) recognize antibody bound on a target cell and induce phagocytosis of the target cell. ADCP can be measured using assays that are known and available in the art (e.g., Clynes et al., 1998. *Proc Natl Acad Sci USA.* 95(2):652-6).

"Adnectins", also known as monobodies, is well known in the art and refer to proteins designed to bind with high affinity and specificity to antigens. They belong to the class of molecules collectively called "antibody mimetics".

"Allogeneic" refers to a graft derived from a different animal of the same species.

"Alphabody" that may also be referred to as Cell-Penetrating Alphabodies, refer to a type of antibody mimetics consisting of small 10 kDa proteins engineered to bind to a variety of antigens. Alphabodies are able to reach and bind to intracellular protein targets.

"Affibodies" are well-known in the art and refer to affinity proteins based on a 58 amino acid residue protein domain, derived from one of the IgG binding domain of staphylococcal protein A (Frejd & Kim, 2017. *Exp Mol Med.* 49(3):e306; U.S. Pat. No. 5,831,012).

"Affilins" are well known in the art and refer to artificial proteins designed to selectively bind antigens. They resemble antibodies in their affinity and specificity to antigens but not in structure which makes them a type of antibody mimetic "Affinity" and "avidity" are well-known in the art and are used to defined the strength of an antibody-antigen complex. Affinity measures the strength of interaction between an epitope and an antigen binding site on an antibody. It may be expressed by an affinity constant KA or by a dissociation constant KD. Avidity (or functional affinity) gives a measure of the overall strength of an antibody-antigen complex. It may depend on different parameters, including in particular the affinity of the antibody or antigen-binding fragment thereof for an epitope, (ii) the valency of both the antibody and the antigen and (iii) structural arrangement of the parts that interact. Affinities of antibodies or antigen-binding fragment thereof can be readily determined using conventional techniques, for example, those described by Scatchard, 1949. *Ann NY Acad Sci.* 51:660-672. Binding properties of an antibody or antigen-binding fragment thereof to antigens, cells or tissues may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, e.g., using BIAcore®).

"Antibody" and "immunoglobulin" may be used interchangeably and refer to a protein having a combination of two heavy and two light chains whether or not it possesses any relevant specific immunoreactivity. "Antibodies" refers to such assemblies which have significant known specific immunoreactive activity to an antigen of interest (e.g., human DEP1 and/or DPP4). The term "anti-DEP1 antibodies or anti-DPP4 antibodies" is used herein to refer to antibodies which exhibit immunological specificity for human DEP1 antigen or human DPP4 antigens, respectively. As explained elsewhere herein, "specificity" for human DEP1 does not exclude cross-reaction with species homologues of human DEP1, such as, for example, with simian DEP1, and "specificity" for human DPP4 does not exclude cross-reaction with species homologues of human DPP4 such as, for example, with simian DPP4.

Antibodies and immunoglobulins comprise light and heavy chains, with or without an interchain covalent linkage between them. Basic immunoglobulin structures in vertebrate systems are relatively well understood. The generic term "immunoglobulin" comprises five distinct classes of antibody that can be distinguished biochemically. Although the following discussion will generally be directed to the IgG class of immunoglobulin molecules, all five classes of antibodies are within the scope of the present invention. With regard to IgG, immunoglobulins comprise two identical light polypeptide chains of molecular weight of about 23 kDa, and two identical heavy chains of molecular weight of about 53-70 kDa. The four chains are joined by disulfide bonds in a "Y" configuration wherein the light chains bracket the heavy chains starting at the mouth of the "Y" and continuing through the variable region. The light chains of an antibody are classified as either kappa (κ) or lambda (λ). Each heavy chain class may be bonded with either a κ or λ light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ) or epsilon (ε) with some subclasses among them (e.g., γ1-γ4). It is the nature of this chain that determines the "class" of the antibody as IgG, IgM, IgA IgD or IgE, respectively. The immunoglobulin subclasses or "isotypes" (e.g., IgG1, IgG2, IgG3, IgG4, IgA1, etc.) are well characterized and are known to confer functional specialization. Modified versions of each of these classes and isotypes are readily discernable to the skilled artisan in view of the instant disclosure and, accordingly, are within the scope of the present invention. As indicated above, the variable region of an antibody allows the antibody to selectively recognize and specifically bind epitopes on antigens. That is, the light chain variable domain (VL domain) and heavy chain variable domain (VH domain) of an antibody combine to form the variable region that defines a three-dimensional antigen binding site. This quaternary antibody structure forms the antigen binding site presents at the end of each arm of the "Y". More specifically, the antigen binding site is defined by three complementarity determining regions (CDRs) on each of the VH and VL chains.

"Anticalins" are well known in the art and refer to an antibody mimetic technology, wherein the binding specificity is derived from lipocalins. Anticalins may also be formatted as dual targeting protein, called Duocalins.

"Antigen" refers any substance that is capable of stimulating an immune response, specifically activating immunes cells. In general, two main divisions of antigens are recognized: foreign antigens (or heteroantigens) and autoantigens (or self-antigens). Antigen molecules possess by definition, at least one epitope (or antigenic sites) which produce corresponding antibodies.

"Antigen-binding fragment", as used herein, refers to a part or region of an antibody or chimeric antigen receptor (CAR), which comprises fewer amino acid residues than the whole antibody or CAR. An "antigen-binding fragment" binds to an antigen and/or competes with the whole antibody and/or CAR from which it was derived for antigen binding (e.g., specific binding to human senescent associated-cell antigen). Antigen-binding fragments encompasses, without any limitation, single chain antibodies, Fv, Fab, Fab', Fab'-SH, F(ab)'2, Fd, defucosylated antibodies, diabodies, triabodies and tetrabodies.

"Armadillo repeat protein-based scaffold", as used herein, refers to a type of antibody mimetics corresponding to artificial peptide binding scaffolds based on armadillo repeat proteins. Armadillo repeat proteins are characterized by an armadillo domain, composed of tandem armadillo repeats of approximately 42 amino acids, which mediates interactions with peptides or proteins.

"Atrimers" are well known in the art and refers to binding molecules for target protein that trimerize as a perquisite for their biological activity. They are relatively large compared to other antibody mimetic scaffolds.

"Autologous" is meant to refer to any material derived from the same individual to which it is later to be re-introduced into the individual.

"Avimers" are well known in the art and refer to an antibody mimetic technology.

"Complement-dependent cytotoxicity" or "CDC" refers to the induction of the lysis of antigen-expressing cells recognized by an antibody or antigen-binding fragment thereof of the invention in the presence of complement. The complement activation pathway is initiated by the binding of the first component of the complement system (C1q) to a molecule (e.g., an antibody) complexed with a cognate antigen. CDC can be measured using assays that are known and available in the art (e.g., Clynes et al., 1998. *Proc Natl Acad Sci USA.* 95(2):652-6; Gazzano-Santaro et al., 1997. *J Immunol Methods.* 202(2):163-71).

"CDR" or "complementarity determining region" means the non-contiguous antigen combining sites found within the variable region of both heavy and light chain polypeptides. The precise amino acid sequence boundaries of a given CDR can be determined using any of a number of well-known schemes, including those described by Kabat et al. (1991), "Sequences of Proteins of Immunological Interest" 5th Ed. Public Health Service, National Institutes of Health, Bethesda, MD ("Kabat" numbering scheme), Al-Lazikani et al., 1997. *J Mol Biol.* 273(4):927-48 ("Chothia" numbering scheme), or a combination thereof. More recently, a universal numbering system has been developed and widely adopted, ImMunoGeneTics (IMGT) Information System® (Lefranc et al., 1999. *Nucleic Acids Res.* 27(1):209-12). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues may be readily identified. This information can be used in grafting and replacement of CDR residues from immunoglobulins of one species into an acceptor framework from, typically, a human antibody. Correspondence between the Kabat numbering and the IMGT unique numbering system is also well known to one skilled in the art (e.g., Lefranc et al., supra). Thus, in one embodiment, by CDR regions or CDR, it is intended to indicate the hypervariable regions of the heavy and light chains of the immunoglobulins as defined by IMGT® numbering system (e.g. Lefranc et al., supra).

"Chimeric antigen receptor" or "CAR refers to engineered receptors, which graft an antigen specificity onto cells with intracellular signal generation (such as, for example, T cells or phagocytic cells). CARs are also known as artificial T cell receptors, chimeric T cell receptors or chimeric immunoreceptors.

"Co-stimulatory domain" or "CSD", when used in a relationship with a chimeric antigen receptor (CAR), refers to the portion of the CAR which enhances the proliferation,

| | Heavy chain variable region (HCVR or $V_H$) | | |
|---|---|---|---|
| | $V_H$-CDR1 | $V_H$-CDR2 | $V_H$-CDR3 |
| Start | Approx, at residue 26 (always 4 after a Cys) according to Chothia/AbM's definition Kabat's definition starts 5 residues later | Always 15 residues after the end of $V_H$-CDR1 according to Kabat/ AbM's definition | Always 33 residues after end of $V_H$-CDR2 Always 2 residues after a Cys |
| Residue before | Always Cys-Xaa-Xaa-Xaa, with Xaa being any amino acid according to Chothia/AbM's definition | Typically, Leu-Glu-Trp-Ile-Gly, but a number of variations | Always Cys-Xaa-Xaa, with Xaa being any amino acid Typically, Cys-Ala-Arg |
| Residue after | Always Trp Typically, Trp-Val, but also, Trp-Ile or Trp-Ala | Lys/Arg-Leu/Ile/Val/Phe/Thr/Ala-Thr/Ser/Ile/Ala | Always Trp-Gly-Xaa-Gly, with Xaa being any amino acid |
| Length | 10 to 12 residues according to AbM's definition Chothia's definition excludes the last 4 residues 5 to 7 residues according to Kabat's definition | 16 to 19 residues according to Kabat's definition AbM's definition ends 7 residues earlier | 3 to 25 residues |

| | Light chain variable region (LCVR or $V_L$) | | |
|---|---|---|---|
| | $V_L$-CDR1 | $V_L$-CDR2 | $V_L$-CDR3 |
| Start | Approx, at residue 24 | Always 16 residues after the end of $V_L$-CDR1 | Always 33 residues after end of $V_L$-CDR2 (except NEW (PDB ID: 7FAB) which has the deletion at the end of CDR-L2*) |
| Residue before | Always Cys | Generally, Ile-Tyr, but also, Val-Tyr, Ile-Lys or Ile-Phe | Always Cys |
| Residue after | Always Trp Typically, Trp-Tyr-Gln, but also, Trp-Leu-Gln, Trp-Phe-Gln or Trp-Tyr-Leu | | Always Phe-Gly-Xaa-Gly, with Xaa being any amino acid |
| Length | 10 to 17 residues | Always 7 residues (except NEW (PDB ID: 7FAB) which has a deletion in this region*) | 7 to 11 residues |

*Saul & Poljak, 1992. Proteins. 14(3):363-71

"Cell", "cell line" and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid survival and/or development of memory cells. The CARs of the invention may comprise one or more co-stimulatory domains. Co-stimulatory domains are apparent to those of skill in the art and may be used in connection with alternate embodiments of the invention.

"DARPins" or "Designed Ankyrin Repeat Proteins" are well known in the art and refer to an antibody mimetic DRP (designed repeat protein) technology developed to exploit the binding abilities of non-antibody polypeptides.

"DEP1", also known as PTPRJ, SCC1, CD148, HPTPeta or R-PTP-ETA, refers to a protein encoded by a gene which is a member of the protein tyrosine phosphatase (PTP) family. PTPs are known to be signaling molecules that regulate a variety of cellular processes, including cell growth, differentiation, mitotic cycle, and oncogenic transformation. This PTP possesses an extracellular region containing five fibronectin type III repeats, a single transmembrane region, and a single intracytoplasmic catalytic domain, and thus represents a receptor-type PTP. This protein is present in all hematopoietic lineages, and was shown to negatively regulate T cell receptor signaling possibly through interfering with the phosphorylation of Phospholipase C Gamma 1 and Linker for Activation of T Cells. This protein can also dephosphorylate the PDGF beta receptor, and may be involved in UV-induced signal transduction. In human, multiple transcript variants encoding different isoforms have been found for this gene.

In the sense of the present invention, human DEP1 (or hDEP1) is a protein with an amino acid sequence SEQ ID NO: 1 (Uniprot accession number Q12913-1; Last modified: Feb. 5, 2008 (version 3)).

SEQ ID NO: 1

```
MKPAAREARLPPRSPGLRWALPLLLLLLRLGQILCAGGTPSPIPDPSVAT

VATGENGITQISSTAESFHKQNGTGTPQVETNTSEDGESSGANDSLRTPE

QGSNGTDGASQKTPSSTGPSPVFDIKAVSISPTNVILTWKSNDTAASEYK

YVVKHKMENEKTITVVHQPWCNITGLRPATSYVFSITPGIGNETWGDPRV

IKVITEPIPVSDLRVALTGVRKAALSWSNGNGTASCRVLLESIGSHEELT

QDSRLQVNISGLKPGVQYNINPYLLQSNKTKGDPLGTEGGLDASNTERSR

AGSPTAPVHDESLVGPVDPSSGQQSRDTEVLLVGLEPGTRYNATVYSQAA

NGTEGQPQAIEFRTNAIQVFDVTAVNISATSLTLIWKVSDNESSSNYTYK

IHVAGETDSSNLNVSEPRAVIPGLRSSTFYNITVCPVLGDIEGTPGFLQV

HTPPVPVSDFRVTVVSTTEIGLAWSSHDAESFQMHITQEGAGNSRVEITT

NQSIIIGGLFPGTKYCFEIVPKGPNGTEGASRTVCNRTVPSAVFDIHVVY

VTTTEMWLDWKSPDGASEYVYHLVIESKHGSNHTSTYDKAITLQGLIPGT

LYNITISPEVDHVWGDPNSTAQYTRPSNVSNIDVSTNTTAATLSWQNFDD

ASPTYSYCLLIEKAGNSSNATQVVTDIGITDATVTELIPGSSYTVEIFAQ

VGDGIKSLEPGRKSFCTDPASMASFDCEVVPKEPALVLKWTCPPGANAGF

ELEVSSGAWNNATHLESCSSENGTEYRTEVTYLNFSTSYNISITTVSCGK

MAAPTRNTCTTGITDPPPPDGSPNITSVSHNSVKVKFSGFEASHGPIKAY

AVILTTGEAGHPSADVLKYTYEDFKKGASDTYVTYLIRTEEKGRSQSLSE

VLKYEIDVGNESTTLGYYNGKLEPLGSYRACVAGFTNITFHPQNKGLIDG

AESYVSFSRYSDAVSLPQDPGVICGAVFGCIFGALVIVTVGGFIFWRKKR

KDAKNNEVSFSQIKPKKSKLIRVENFEAYFKKQQADSNCGFAEEYEDLKL

VGISQPKYAAELAENRGKNRYNNVLPYDISRVKLSVQTHSTDDYINANYM

PGYHSKKDFIATQGPLPNTLKDFWRMVWEKNVYAIIMLTKCVEQGRTKCE

EYWPSKQAQDYGDITVAMTSEIVLPEWTIRDFTVKNIQTSESHPLRQFHF

TSWPDHGVPDTTDLLINFRYLVRDYMKQSPPESPILVHCSAGVGRTGTFI

AIDRLIYQIENENTVDVYGIVYDLRMHRPLMVQTEDQYVFLNQCVLDIVR

SQKDSKVDLIYQNTTAMTIYENLAPVTTFGKTNGYIA
```

hDEP1 is composed of several domains, as follows:

- a signal peptide, comprising or consisting of amino acid residues 1-35 of SEQ ID NO: 1;
- an extracellular domain, comprising or consisting of amino acid residues 36-975 of SEQ ID NO: 1, itself comprising:
  - a fibronectin type-III domain 1, comprising or consisting of amino acid residues 121-209 of SEQ ID NO: 1;
  - a fibronectin type-III domain 2, comprising or consisting of amino acid residues 207-291 of SEQ ID NO: 1;
  - a fibronectin type-III domain 3, comprising or consisting of amino acid residues 271-364 of SEQ ID NO: 1;
  - a fibronectin type-III domain 4, comprising or consisting of amino acid residues 368-456 of SEQ ID NO: 1;
  - a fibronectin type-III domain 5, comprising or consisting of amino acid residues 457-541 of SEQ ID NO: 1;
  - a fibronectin type-III domain 6, comprising or consisting of amino acid residues 542-623 of SEQ ID NO: 1;
  - a fibronectin type-III domain 7, comprising or consisting of amino acid residues 625-720 of SEQ ID NO: 1;
  - a fibronectin type-III domain 8, comprising or consisting of amino acid residues 721-817 of SEQ ID NO: 1; and
  - a fibronectin type-III domain 9, comprising or consisting of amino acid residues 816-902 of SEQ ID NO: 1;
- a transmembrane domain, comprising or consisting of amino acid residues 976-996 of SEQ ID NO: 1; and
- a cytoplasmic domain, comprising or consisting of amino acid residues 997-1337 of SEQ ID NO: 1.

"Diabodies", as used herein, refers to small antibody fragments prepared by constructing scFv fragments with short linkers (about 5-10 residues) between the HCVR and LCVR such that inter-chain but not intra-chain pairing of the variable domains is achieved, resulting in a bivalent fragment, i.e., fragment having two antigen-binding sites. Bispecific diabodies are heterodimers of two "crossover" scFv fragments in which the HCVR and LCVR of the two antibodies are present on different polypeptide chains. Diabodies are described more fully in European patent EP0404097, International patent application WO1993011161; and in Holliger et al., 1993. *Proc Natl Acad Sci USA*. 90(14):6444-8.

"Domain antibodies" are well-known in the art and refer to the smallest functional binding units of antibodies, corresponding to the variable regions of either the heavy or light chains of antibodies.

"Domain kunitz peptide" refer to a type of antibody mimetics, and is based on the active domains of proteins inhibiting the function of proteases.

"DPP4" (also known as ADABP, adenosine deaminase complexing protein 2, ADCP-2, dipeptidyl peptidase IV, DPP IV, CD26, or TP103) refers to an intrinsic membrane glycoprotein and a serine exopeptidase that cleaves X-proline dipeptides from the N-terminus of polypeptides.

In the sense of the present invention, human DPP4 (or hDPP4) is a protein with an amino acid sequence SEQ ID NO: 101 (Uniprot accession number P27487-1; Last modified: Feb. 1, 1996 (version 2)).

SEQ ID NO: 101

```
MKTPWKVLLGLLGAAALVTIITVPVVLLNKGTDDATADSRKTYTLTDYLK

NTYRLKLYSLRWISDHEYLYKQENNILVFNAEYGNSSVFLENSTFDEFGH

SINDYSISPDGQFILLEYNYVKQWRHSYTASYDIYDLNKRQLITEERIPN

NTQWVTWSPVGHKLAYVWNNDIYVKIEPNLPSYRITWTGKEDIIYNGITD
```

-continued

```
WVYEEEVFSAYSALWWSPNGTFLAYAQFNDTEVPLIEYSFYSDESLQYPK

TVRVPYPKAGAVNPTVKFFVVNTDSLSSVTNATSIQITAPASMLIGDHYL

CDVTWATQERISLQWLRRIQNYSVMDICDYDESSGRWNCLVARQHIEMST

TGWVGRFRPSEPHFTLDGNSFYKIISNEEGYRHICYFQIDKKDCTFITKG

TWEVIGIEALTSDYLYYISNEYKGMPGGRNLYKIQLSDYTKVTCLSCELN

PERCQYYSVSFSKEAKYYQLRCSGPGLPLYTLHSSVNDKGLRVLEDNSAL

DKMLQNVQMPSKKLDFIILNETKFWYQMILPPHFDKSKKYPLLLDVYAGP

CSQKADTVFRLNWATYLASTENIIVASFDGRGSGYQGDKIMHAINRRLGT

FEVEDQIEAARQFSKMGFVDNKRIAIWGWSYGGYVTSMVLGSGSGVFKCG

IAVAPVSRWEYYDSVYTERYMGLPTPEDNLDHYRNSTVMSRAENFKQVEY

LLIHGTADDNVHFQQSAQISKALVDVGVDFQAMWYTDEDHGIASSTAHQH

IYTHMSHFIKQCFSLP
```

hDPP4 is composed of several domains, as follows:

- a cytoplasmic domain, comprising or consisting of amino acid residues 1-6 of SEQ ID NO: 101;
- a transmembrane domain, comprising or consisting of amino acid residues 7-28 of SEQ ID NO: 101; and
- an extracellular domain, comprising or consisting of amino acid residues 29-766 of SEQ ID NO: 101.

"Epitope", also known as "antigenic determinant", refers to a specific arrangement of amino acids located on a protein or proteins (or antigen(s)) to which an antibody or antigen-binding fragment thereof or chimeric antigen receptor (CAR) binds. Epitopes often consist of a chemically active surface grouping of molecules such as amino acids or sugar side chains, and have specific three-dimensional structural characteristics as well as specific charge characteristics. Epitopes can be linear (or sequential) or conformational, i.e., involving two or more sequences of amino acids in various regions of the antigen that may not necessarily be contiguous.

"Evasins" are well known in the art and refer to a class of chemokine-binding proteins.

"Extracellular spacer domain" or "ESD" or "hinge domain", when used in a relationship with a chimeric antigen receptor (CAR), refers to the hydrophilic region which is between the antigen-specific targeting region and the transmembrane domain. The extracellular spacer domains are apparent to those of skill in the art and may be used in connection with alternate embodiments of the invention.

"Framework region" or "FR region" includes the amino acid residues that are part of the variable region, but are not part of the CDRs (e.g., using the IMGT® numbering definition of CDRs). The framework regions for the light chain are similarly separated by each of the LCVR's CDRs. In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainders of the heavy and light variable domains show less inter-molecular variability in amino acid sequence and are termed the framework regions. The framework regions largely adopt a R-sheet conformation and the CDRs form loops which connect, and in some cases form part of, the R-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Fc domain" "Fc portion" and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and μ for human antibodies), or a naturally occurring allotype thereof.

"Fynomers" are well known in the art and refer to proteins that belong to the class of antibody mimetic. They are attractive binding molecules due to their high thermal stability and reduced immunogenicity.

"Fv", as used herein, refers to the minimum antibody fragment that contains a complete antigen-recognition and -binding site. This fragment consists of a dimer of one HCVR and one LCVR in tight, non-covalent association. From the folding of these two domains emanate six hypervariable loops (three loops each from the heavy and light chain) that contribute to antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain region" includes amino acid sequences derived from the constant domains of an immunoglobulin heavy chain. A protein comprising a heavy chain region comprises at least one of a CHI domain, a hinge (e.g., upper, middle, and/or lower hinge region) domain, a $C_H2$ domain, a $C_H3$ domain, or a variant or fragment thereof. In an embodiment, the antibody or antigen-binding fragment thereof according to the present invention may comprise the Fc region of an immunoglobulin heavy chain (e.g., a hinge portion, a $C_H2$ domain, and a $C_H3$ domain). In another embodiment, the antibody or antigen-binding fragment thereof according to the present invention lacks at least a region of a constant domain (e.g., all or part of a $C_H2$ domain). In certain embodiments, at least one, and preferably all, of the constant domains are derived from a human immunoglobulin heavy chain. For example, in one preferred embodiment, the heavy chain region comprises a fully human hinge region. In other preferred embodiments, the heavy chain region comprising a fully human Fc region (e.g., hinge, $C_H2$ and $C_H3$ domain sequences from a human immunoglobulin). In certain embodiments, the constituent constant domains of the heavy chain region are from different immunoglobulin molecules. For example, a heavy chain region of a protein may comprise a $C_H2$ domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the antibody or antigen-binding fragment thereof according to the present invention may comprise alterations or modifications to one or more of the heavy chain constant domains ($C_H1$, hinge, $C_H2$ or $C_H3$) and/or to the light chain constant domain ($C_L$). Exemplary modifications include additions, deletions or substitutions of one or more amino acids in one or more domains.

"Hinge region", when used in a relationship with an antibody, includes the region of a heavy chain molecule that joins the $C_H1$ domain to the $C_H2$ domain in an antibody. This hinge region comprises approximately 25 residues and is flexible, thus allowing the two N-terminal antigen binding regions to move independently. Hinge regions can be subdivided into three distinct domains: upper, middle, and lower domains (Roux et al., 1998. *J Immunol.* 161(8):4083-90).

"Hypervariable loop" is not strictly synonymous to complementarity determining region (CDR), since the hypervariable loops (HVs) are defined on the basis of structure, whereas CDRs are defined based on sequence variability (Kabat et al., 1991. *Sequences of proteins of immunological interest* ($5^{th}$ ed.). Bethesda, MD: U.S. Dep. of Health and Human Services) and the limits of the HVs and the CDRs may be different in some $V_H$ and $V_L$ domains. The CDRs of the $V_L$ and $V_H$ domains can typically be defined by the Kabat/Chothia definition as already explained hereinabove.

"Identity" or "identical", when used in a relationship between the sequences of two or more amino acid sequences, or of two or more nucleic acid sequences, refers to the degree of sequence relatedness between amino acid sequences or nucleic acid sequences, as determined by the number of matches between strings of two or more amino acid residues or nucleic acid residues. "Identity" measures the percent of identical matches between the smaller of two or more sequences with gap alignments (if any) addressed by a particular mathematical model or computer program (i.e., "algorithms"). Identity of related amino acid sequences or nucleic acid sequences can be readily calculated by known methods. Such methods include, but are not limited to, those described in Lesk A. M. (1988). *Computational molecular biology: Sources and methods for sequence analysis*. New York, NY: Oxford University Press; Smith D. W. (1993). *Biocomputing: Informatics and genome projects*. San Diego, CA: Academic Press; Griffin A. M. & Griffin H. G. (1994). *Computer analysis of sequence data, Part* 1. Totowa, NJ: Humana Press; von Heijne G. (1987). *Sequence analysis in molecular biology: treasure trove or trivial pursuit*. San Diego, CA: Academic press; Gribskov M. R. & Devereux J. (1991). *Sequence analysis primer*. New York, NY: Stockton Press; Carillo et al., 1988. *SIAM J Appl Math.* 48(5):1073-82. Preferred methods for determining identity are designed to give the largest match between the sequences tested. Methods of determining identity are described in publicly available computer programs. Preferred computer program methods for determining identity between two sequences include the GCG program package, including GAP (Genetics Computer Group, University of Wisconsin, Madison, WI; Devereux et al., 1984. *Nucleic Acids Res.* 12(1 Pt 1):387-95), BLASTP, BLASTN, and FASTA (Altschul et al., 1990. *J Mol Biol.* 215(3):403-10). The BLASTX program is publicly available from the National Center for Biotechnology Information (NCBI) and other sources (BLAST Manual, Altschul et al. NCB/NLM/NIH Bethesda, Md. 20894). The well-known Smith Waterman algorithm may also be used to determine identity.

"Intracellular signaling domain" or "ISD" or "cytoplasmic domain", when used in a relationship with a chimeric antigen receptor (CAR), refers to the portion of the CAR which transduces the effector function signal and directs the cell to perform its specialized function. Intracellular signaling domains are be apparent to those of skill in the art and may be used in connection with alternate embodiments of the invention.

"Isolated" means altered or removed from the natural state. For example, a nucleic acid or a peptide naturally present in a living animal is not "isolated" but the same nucleic acid or peptide partially or completely separated from the coexisting materials of its natural state is "isolated". An isolated nucleic acid or protein can exist in substantially purified form, or can exist in a non-native environment such as, for example, a host cell.

"Knottin" or "inhibitor cystine knot" refer to an antibody mimetic comprising a protein structural motif containing three disulfide bridges.

"Monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies or antigen-binding fragment thereof according to the present invention may be prepared by the hybridoma methodology first described by Kohler et al., 1975. *Nature.* 256(5517):495-7, or may be made using recombinant DNA methods in bacterial, eukaryotic animal or plant cells (U.S. Pat. No. 4,816,567). The "monoclonal antibodies" may also be isolated from phage antibody libraries using the techniques described in Clackson et al., 1991. *Nature.* 352(6336):624-8 and Marks et al., 1991. *J Mol Biol.* 222(3):581-97, for example.

"Linker", when used in a relationship with a chimeric antigen receptor (CAR), refers to an oligo- or polypeptide region from about 1 to 100 amino acids in length, which links together any of the domains/regions of the CAR of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Linkers are apparent to those of skill in the art and may be used in connection with alternate embodiments of the invention.

"Nanobodies" are well-known in the art and refer to antibody-derived therapeutic proteins that contain the unique structural and functional properties of naturally-occurring heavy chain antibodies (Muyldermans, 2013. *Annu Rev Biochem.* 82:775-97). These heavy chain antibodies may contain a single variable domain (VHH) and two constant domains ($C_H2$ and $C_H3$).

"Prevent", "preventing" and "prevention" refer to prophylactic and preventative measures, wherein the object is to reduce the chances that a subject will develop the pathologic condition or disorder over a given period of time. Such a reduction may be reflected, e.g., in a delayed onset of at least one symptom of the pathologic condition or disorder in the subject.

"Proliferating cell" refers to a cell that is undergoing cell division.

"Promoter" is used to define a control sequence, that is a region of a vector at which initiation and rate of transcription are controlled. It may contain genetic elements to which regulatory proteins and molecules may bind, such as RNA polymerase and other transcription factors, to initiate the specific transcription a nucleic acid sequence. The phrases "operatively positioned" "operatively linked" "under control" and "under transcriptional control" mean that a promoter is in a correct functional location and/or orientation in relation to a nucleic acid to control transcriptional initiation and/or expression of that nucleic acid.

A promoter typically comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer", which refers to a cis-acting regulatory sequence involved in the transcriptional activation of a nucleic acid sequence. A promoter may be one naturally associated with a nucleic acid, as may be obtained by isolating the 5' non-coding sequences located upstream of the coding segment and/or exon. Such a promoter can be referred to as "endogenous". Similarly, an enhancer may be one naturally associated with a nucleic acid, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring", i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906). Furthermore, it is contemplated the control sequences that direct transcription and/or expression of sequences within non-nuclear organelles such as mitochondria, chloroplasts, and the like, can be employed as well. Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989). The promoters employed may be constitutive, tissue-specific, inducible, and/or useful under the appropriate conditions to direct high-level expression of the introduced DNA segment, such as is advantageous in the large-scale production of recombinant proteins and/or peptides. The promoter may be heterologous or endogenous.

Additionally, any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize a specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

"Recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g., a mouse) which is transgenic due to human immunoglobulin genes; or antibodies which are produced, expressed, generated or isolated in any other way in which particular immunoglobulin gene sequences (such as human immunoglobulin gene sequences) are assembled with other DNA sequences. Recombinant antibodies include, for example, chimeric and humanized antibodies.

"Senescent cells" refers to cells that are in cell cycle arrest, generally during the G1 transition of the cell cycle or in few cases in G2, elicited by replicative exhaustion due to telomere attrition or in response to stresses such as DNA damage, chemotherapeutic drugs, or aberrant expression of oncogenes. According to one embodiment, the senescent cells are generally characterized by at least one or more of the following characteristics: activation of the p53/p21CIP1 and/or pRb/pl6INK4A tumor suppressor pathways, cells whose proliferation is irreversibly arrested, shortening of telomere size, expression of senescent-associated beta-galactosidase activity, specific chromatin modification, specific secretome, increase in reactive oxygen species and altered overall mitochondrial activity. Senescent cells and senescent cell-associated antigens can be detected by techniques and procedures described in the art.

"Single chain antibody", as used herein, refers to any antibody or fragment thereof that is a protein having a primary structure comprising or consisting of one uninterrupted sequence of contiguous amino acid residues, including without limitation (1) single-chain Fv molecules (scFv);

(2) single chain proteins containing only one light chain variable domain, or a fragment thereof that contains the three CDRs of the light chain variable domain, without an associated heavy chain moiety; and (3) single chain proteins containing only one heavy chain variable region, or a fragment thereof containing the three CDRs of the heavy chain variable region, without an associated light chain moiety.

"Single-chain Fv", also abbreviated as "sFv" or "scFv", refers to antibody fragments that comprise the $V_H$ and $V_L$ antibody domains connected into a single amino acid chain. Preferably, the scFv amino acid sequence further comprises a flexible peptidic linker between the $V_H$ and $V_L$ domains that enables the scFv to form the desired structure for antigen binding (Pluckthun, 1994. "Antibodies from *Escherichia coli*". In Rosenberg & Moore (Eds.), *The pharmacology of monoclonal antibodies*. Handbook of Experimental Pharmacology, 113:269-315. Springer: Berlin, Heidelberg). Flexible peptidic linkers are generally composed of small, non-polar (e.g., glycine, Gly, G) or polar (e.g., serine, Ser, S; or threonine, Thr, T) amino acids, as suggested by Argos (1990. *J Mol Biol.* 211(4):943-958). The small size of these amino acids provides flexibility, and allows for mobility of the connecting functional domains, such as the $V_H$ and $V_L$ domains. In one embodiment, the flexible peptidic linker may be a short oligo- or polypeptide, preferably having a length ranging from 2 to 30 amino acids. In one embodiment, the flexible peptidic linker comprises glycine-serine repeats. In one embodiment, the flexible peptidic linker comprises one, or several repeats of, such as 2, 3, 4, 5 or more repeats of, GS linker(s) (i.e., a sequence of one Gly and one Ser), G2S linker(s) (i.e., a sequence of two Gly and one Ser), G3S linker(s) (i.e., a sequence of three Gly and one Ser), G4S linker(s) (i.e., a sequence of four Gly and one Ser), or G5S linker(s) (i.e., a sequence of five Gly and one Ser).

"Subject" refers to a mammal, preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of a disease. The term "mammal" refers here to any mammal, including humans, domestic and farm animals, and zoo, sports, or pet animals, such as dogs, cats, cattle, horses, sheep, pigs, goats, rabbits, etc. Preferably, the mammal is a primate, more preferably a human.

"Therapeutically effective amount" refers to the level or amount of an antibody as described herein that is aimed at, without causing significant negative or adverse side effects to the target, (1) delaying or preventing the onset of a disease, disorder, or condition; (2) slowing down or stopping the progression, aggravation, or deterioration of one or more symptoms of the disease, disorder, or condition; (3) bringing about ameliorations of the symptoms of the disease, disorder, or condition; (4) reducing the severity or incidence of the disease, disorder, or condition; or (5) curing the disease, disorder, or condition. A therapeutically effective amount may be administered prior to the onset of the disease, disorder, or condition, for a prophylactic or preventive action. Alternatively or additionally, the therapeutically effective amount may be administered after initiation of the disease, disorder, or condition, for a therapeutic action.

"Transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid.

"Transmembrane domain" or "TMD", when used in a relationship with a chimeric antigen receptor (CAR), refers to the region of the CAR which crosses the plasma membrane. The transmembrane domain of the CAR of the invention is the transmembrane region of a transmembrane protein (for example Type I transmembrane proteins), an artificial hydrophobic sequence or a combination thereof. Other transmembrane domains are apparent to those of skill in the art and may be used in connection with alternate embodiments of the invention.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a cancer or an infection if, after receiving a therapeutic amount of an antibody according to the methods of the present invention, the patient shows observable and/or measurable reduction in or absence of one or more of the following: reduction in the number of cancer cells (or tumor size), or pathogenic cells; reduction in the percent of total cells that are cancerous or pathogenic; and/or relief to some extent, one or more of the symptoms associated with the specific disease or condition; reduced morbidity and mortality, and improvement in quality of life issues. The above parameters for assessing successful treatment and improvement in the disease are readily measurable by routine procedures familiar to a physician.

"Unibodies" are well known in the art and refer to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

"Variable" refers to the fact that certain regions of the variable domains $V_H$ and $V_L$ differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the $V_L$ domain and the $V_H$ domain which form part of the antigen binding site. The first, second and third hypervariable loops of the Vλ light chain domain are referred to herein as L1 (λ), L2 (λ) and L3 (λ) and may be defined as comprising residues 24-33 (L1(λ), consisting of 9, 10 or 11 amino acid residues), 49-53 L2 (λ), consisting of 3 residues) and 90-96 (L3(λ), consisting of 6 residues) in the $V_L$ domain (Morea et al., 2000. *Methods.* 20(3):267-79). The first, second and third hypervariable loops of the Vκ light chain domain are referred to herein as L1(κ), L2(κ) and L3(κ) and may be defined as comprising residues 25-33 (L1(κ), consisting of 6, 7, 8, 11, 12 or 13 residues), 49-53 (L2(λ), consisting of 3 residues) and 90-97 (L3(κ), consisting of 6 residues) in the $V_L$ domain (Morea et al., 2000. *Methods.* 20(3):267-79). The first, second and third hypervariable loops of the $V_H$ domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the $V_H$ domain (Morea et al., 2000. *Methods.* 20(3):267-79). Unless otherwise indicated, the terms L1, L2 and L3 respectively refer to the first, second and third hypervariable loops of a $V_L$ domain, and encompass hypervariable loops obtained from both Vκ and Vλ isotypes. The terms H1, H2 and H3 respectively refer to the first, second and third hypervariable loops of the $V_H$ domain, and encompass hypervariable loops obtained from any of the known heavy chain isotypes, including gamma (γ), mu (μ), alpha (α), delta (δ) or epsilon (ε). The hypervariable loops L1, L2, L3, H1, H2 and H3 may each comprise part of a "complementarity determining region" or "CDR", as defined hereinabove.

"Vector" is used to refer to a carrier nucleic acid molecule into which a nucleic acid sequence can be inserted, for introduction into a cell where it can be replicated. A nucleic acid sequence can be "exogenous", which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One skilled in the art would be well equipped to construct a vector through standard recombinant techniques (see, e.g., Maniatis et al., 1988 and Ausubel et al., 1994).

In one embodiment, the vector can be an "expression vector". This term refers to any type of genetic construct comprising a nucleic acid coding for an RNA capable of being transcribed. In some cases, RNA molecules are then translated into a protein, polypeptide, or peptide. In other cases, these sequences are not translated, e.g., in the production of antisense molecules or ribozymes. Expression vectors can contain a variety of control sequences, which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described herein. In particular, expression vectors can contain one or several promoter(s), enhancer(s), internal ribosome entry site(s) (IRES), multiple cloning site(s) (MCS), splicing site(s), termination signal(s), origin(s) of replication, and/or selectable marker(s).

The vector may be a "plasmid vector". In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 hours, the cells are collected by centrifugation and washed to remove residual media.

The vector may be a "viral vector". The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells).

In one embodiment, the viral vector may be an adenoviral vector. Although adenoviral vectors are known to have a low capacity for integration into genomic DNA, this feature is counterbalanced by the high efficiency of gene transfer afforded by these vectors.

In one embodiment, the viral vector may be an adeno-associated viral (AAV) vector. Increased transfection efficiencies have been reported in cell systems using adenovirus coupled systems (Kelleher & Vos, 1994. *Biotechniques*. 17(6):1110-7; Cotten et al., 1992. *Proc Natl Acad Sci USA*. 89(13):6094-8; Curiel, 1994. *Nat Immun*. 13(2-3):141-64). AAV is an attractive vector system as it has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368.

In one embodiment, the viral vector may be a retroviral vector. Retroviruses are useful as delivery vectors because of their ability to integrate their genes into the host genome, transferring a large amount of foreign genetic material, infecting a broad spectrum of species and cell types and of being packaged in special cell lines. In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed. When a recombinant plasmid containing a cDNA, together with the retroviral LTR and packaging sequences is introduced into a special cell line (e.g., by calcium phosphate precipitation), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells. Lentiviruses are complex retroviruses, which, in addition to the common retroviral genes gag, pol, and env, contain other genes with regulatory or structural function. Lentiviral vectors are well known in the art (see, e.g., U.S. Pat. Nos. 6,013,516 and 5,994,136).

Some examples of lentivirus include the human immunodeficiency viruses HIV-1 and HIV-2, and the simian immunodeficiency virus SIV. Lentiviral vectors have been generated by attenuating the HIV virulence genes, for example, the genes env, vif, vpr, vpu and nef are deleted making the vector biologically safe. Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other viral vectors may also be employed in the present invention. Vectors derived from viruses such as vaccinia virus, sindbis virus, cytomegalovirus and herpes simplex virus may be employed. They offer several attractive features for various mammalian cells.

"Versabodies" are well known in the art and refer to another antibody mimetic technology. They are small proteins of 3-5 kDa with >15% cysteines, which form a high disulfide density scaffold, replacing the hydrophobic core the typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T cell epitopes, because the residues that contribute most to MHC presentation are hydrophobic. All four of these properties are well-known to affect immunogenicity, and together they are expected to cause a large decrease in immunogenicity.

"Xenogeneic" refers to a graft derived from an animal of a different species.

DETAILED DESCRIPTION

A first object of the present invention is an antigen-binding domain directed to a senescent cell-associated antigen.

In one embodiment, the antigen-binding domain of the invention recognizes and is capable of binding to a senescent cell-associated antigen.

The presence of senescent cells can be determined by detection of senescent cell-associated molecules include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP, i.e., which includes secreted factors which may make up the pro-inflammatory phenotype of a senescent cell), senescent-messaging secretome, and DNA damage secretory program (DDSP). For example, the presence of senescent cells in tissues can be analyzed by histochemistry or immunohistochemistry techniques that detect the senescence marker, SA-beta gal (SA-Bgal) (see, for example, Dimri et al., 1995. *Proc Natl Acad Sci USA*. 92(20):9363-7).

Senescent cell-associated antigens include molecules that are overexpressed in senescent cells compared to their quiescent or non-senescent counterparts. Certain senescent cell-associated antigens are tissue specific while others are ubiquitously overexpressed in senescent cells. In particular embodiments of the immunogenic compositions described herein, a senescent cell-associated antigen is an antigen present on the cell surface of a senescent cell (e.g., receptor proteins, channel forming proteins, proteins that facilitate diffusion or active transport of molecules and ion across the membrane, cell recognition proteins, and enzymes). These antigens may be present on the cell surface of a cell exclusively or at a greater level on senescent cells compared with non-senescent cells and are therefore useful as immunogens for evoking a specific immune response. Examples of senescent cell-associated antigens include polypeptides and proteins (including glycoproteins), lipids, glycolipids, and carbohydrate molecules that contribute to or are markers of a senescence cell.

In one embodiment, the senescent cell according to the present invention expresses a senescent cell-associated antigen or a combination of senescent cell-associated antigens that are characteristic of senescence. Such senescent cell-associated antigens include, but are not limited to, actin cytoplasmic 1 (ACTB), A disintegrin and metalloproteinase with thrombospondin motifs 7 (ADAMTS7), amyloid-like protein 2 (APLP2), armadillo repeat-containing X-linked protein 3 (ARMCX-3), ATP synthase subunit alpha mitochondrial (ATP5F1A), V-type proton ATPase subunit d 2 (ATP6V0D2), beta-2-microglobulin (B2MG), cholinesterase (BCHE), uncharacterized protein C11orf87 (C11orf87), membrane cofactor protein (CD46), CD57, cyclin-dependent kinase inhibitor 2A "p16INK4a" (CDKN2A), cathepsin B (CTSB), neuferricin (CYB5D2), dipeptidyl peptidase 4 "DPP4" (DPP4), electron transfer flavoprotein beta subunit lysine methyltransferase (ETFB), F-box/LRR-repeat protein 7 (FBXL7), integral membrane protein GPR137B (GPR137B), interferon alpha-inducible protein 27-like protein 1 (IFI27L1), interleukin-15 receptor subunit alpha (IL15RA), killer cell lectin-like receptor subfamily G member 1 (KLRG1), lysosome-associated membrane glycoprotein 2 (LAMP2), glutathione S-transferase LANCL1 (LANCL1), major vault protein (MVP), unconventional myosin-X (MYO10), sialidase-1 (NEU), NHS-like protein 2 (NHSL2), neurogenic locus notch homolog protein 3 (NOTCH3), neuronal PAS domain-containing protein 2 (NPAS2), olfactory receptor 1F1 (ORIF1), prolyl 4-hydroxylase beta subunit precursor (P4HB), protein disulfide isomerase (PD1), astrocytic phosphoprotein PEA-15 (PEA15), phospholipase D3 (PLD3), receptor-type tyrosine-protein phosphatase C isoform RA "CD45RA" (PTPRC), receptor-type tyrosine-protein phosphatase eta "DEP1" (PTPRJ), Ras-related protein Rab-23 (RAB23), retinoic acid receptor beta (RARB), RNA-binding region-containing protein 3 (RNPC3), protein adenylyltransferase SelO mitochondrial (SELO), thioredoxin reductase-like selenoprotein T (SELT), semaphorin-5B (SEMA5B), stress-associated endoplasmic reticulum protein 1 (SERP1), plasminogen activator inhibitor 1 (SERPINE1), sodium/hydrogen exchanger 7 (SLC9A7), sorting nexin-3 (SNX3), syntaxin-4 (STX4), TBC1 domain family member 1 (TBC1D1), transforming growth factor beta regulator 1 (TBRG1), transcription elongation factor A N-terminal and central domain-containing protein (TCEANC), tissue factor pathway inhibitor (TFPI), BTB/POZ domain-containing adapter for CUL3-mediated RhoA degradation protein 2 (TNFAIP1), tumor necrosis factor receptor superfamily member TOD "DCR2" (TNFRSF10D), tubulin gamma-2 chain (TUBG2), Ubl carboxyl-terminal hydrolase 18 (USP18), vesicle-associated membrane protein 3 (VAMP3), vacuolar protein sorting-associated protein 26A (VPS26A), and zinc finger protein 419 (ZNF419).

In one embodiment, the senescent cell-associated antigen is selected from the group comprising or consisting of DEP1 and DPP4.

In one embodiment, the senescent cell according to the present invention expresses the DEP1 and/or DPP4 antigen.

The presence of the senescent cell-associated antigens, in particular of DEP1 and/or DPP4, can be determined by any one of numerous immunochemistry methods practiced in the art, such as immunoblotting analysis.

In one embodiment, the senescent cell-associated antigen is DEP1, such as, e.g., human DEP1, or orthologs thereof, including murine and rat DEP1. In one embodiment, the senescent cell-associated antigen is human DEP1 (hDEP1) with SEQ ID NO: 1.

In one embodiment, the antigen-binding domain of the invention recognizes and is capable of binding to DEP1, such as, e.g., to human DEP1, or orthologs thereof, including murine and rat DEP1. Hence, the antigen-binding domain of the invention is a "DEP1-binding domain".

In one embodiment, the DEP1-binding domain of the invention recognizes and is capable of binding to human DEP1 (hDEP1) with SEQ ID NO: 1.

In one embodiment, the DEP1-binding domain of the invention recognizes and is capable of binding to the extracellular domain of human DEP1 (hDEP1) comprising or consisting of amino acid residues 36-975 of SEQ ID NO: 1.

The binding between the DEP1-binding domain of the invention and DEP1 implies that said DEP1-binding domain exhibits appreciable affinity for DEP1. In other words, the DEP1-binding domain of the invention is specific for, or is immunospecific for, or specifically bind to, DEPT.

The affinity between the DEP1-binding domain of the invention and DEP1 can be determined by various methods well known from the one skilled in the art. These methods include, but are not limited to, biosensor analysis (including, e.g., Biacore analysis), Blitz analysis and Scatchard plot.

Alternatively or additionally, whether the DEP1-binding domain of the invention binds to DEP1 can be tested readily by, inter alia, comparing the reaction of said DEP1-binding domain with DEP1 or a fragment thereof (in particular, a fragment comprising or consisting of an epitope of DEP1) with the reaction of said DEP1-binding domain with proteins or antigens other than DEP1 or a fragment thereof.

In one embodiment, the DEP1-binding domain of the invention recognizes and is capable of binding to DEP1 with a $K_D$-affinity constant less than or equal to $10^{-6}$ M, preferably less than or equal to $10^{-7}$ M, $5.10^{-8}$ M, $10^{-8}$ M, $5.10^{-9}$ M, $10^{-9}$ M or less; as may be determined, e.g., by biosensor analysis, particularly by Biacore Analysis.

In one embodiment, the DEP1-binding domain of the invention comprises a heavy chain variable region (abbreviated herein as HCVR or $V_H$) which comprises at least one, preferably at least two, more preferably the following three complementary-determining regions (CDRs):

$V_H$-CDR1: any one of SEQ ID NO: 5 to 11;
$V_H$-CDR2: any one of SEQ ID NO: 12 to 25;
$V_H$-CDR3: any one of SEQ ID NO: 26 to 32.

| SEQ ID NO | SEQUENCE |
|---|---|
| 5 | SYYIS |
| 6 | NIAMY |
| 7 | NYTIS |
| 8 | SDSIS |
| 9 | NYSIS |
| 10 | DYNMA |
| 11 | NYYMA |
| 12 | YINTGSGGTNYNEKFKG |
| 13 | HIRTKPHNFATYYANSVKG |
| 14 | YIYAGTGDTNYNEKFKG |
| 15 | HIRTKPHNYATYYADSVKG |
| 16 | YIHPGSGVTNYNEKFKG |
| 17 | YIHPGSGVTNYNEKFRG |
| 18 | YIYPGSGDTNYNEKFKG |
| 19 | TISYDDSRTYYRDSVKG |
| 20 | YITNSFGSAYYRDSVKG |
| 21 | TISYDDYRTYYRDSVKG |
| 22 | YITNSLGSAYYRDSVKG |
| 23 | YITNSFGSTYYRDSVKG |
| 24 | YITNGYGSTYYRDSVKG |
| 25 | YITNGFGSTYYRDSVKG |
| 26 | YFDY |
| 27 | GFGDY |
| 28 | YFDH |
| 29 | DKWVD |
| 30 | QGGIIRGVWFPY |
| 31 | VPLGAFVY |
| 32 | VPLGAFVS |

In one embodiment, the DEP1-binding domain of the invention comprises a HCVR which comprises at least one, preferably at least two, more preferably the following three complementary-determining regions (CDRs):

$V_H$-CDR1: SEQ ID NO: 5;
$V_H$-CDR2: SEQ ID NO: 12;
$V_H$-CDR3: SEQ ID NO: 26.

In one embodiment, the DEP1-binding domain of the invention comprises a HCVR which comprises at least one, preferably at least two, more preferably the following three complementary-determining regions (CDRs):

$V_H$-CDR1: SEQ ID NO: 6;
$V_H$-CDR2: SEQ ID NO: 13;
$V_H$-CDR3: SEQ ID NO: 27.

In one embodiment, the DEP1-binding domain of the invention comprises a HCVR which comprises at least one, preferably at least two, more preferably the following three complementary-determining regions (CDRs):

$V_H$-CDR1: SEQ ID NO: 7;
$V_H$-CDR2: SEQ ID NO: 14;
$V_H$-CDR3: SEQ ID NO: 28.

In one embodiment, the DEP1-binding domain of the invention comprises a HCVR which comprises at least one, preferably at least two, more preferably the following three complementary-determining regions (CDRs):

$V_H$-CDR1: SEQ ID NO: 5;
$V_H$-CDR2: SEQ ID NO: 12;
$V_H$-CDR3: SEQ ID NO: 29.

In one embodiment, the DEP1-binding domain of the invention comprises a HCVR which comprises at least one, preferably at least two, more preferably the following three complementary-determining regions (CDRs):

$V_H$-CDR1: SEQ ID NO: 6;
$V_H$-CDR2: SEQ ID NO: 15;
$V_H$-CDR3: SEQ ID NO: 27.

In one embodiment, the DEP1-binding domain of the invention comprises a HCVR which comprises at least one, preferably at least two, more preferably the following three complementary-determining regions (CDRs):

$V_H$-CDR1: SEQ ID NO: 5;
$V_H$-CDR2: SEQ ID NO: 16;
$V_H$-CDR3: SEQ ID NO: 26.

In one embodiment, the DEP1-binding domain of the invention comprises a HCVR which comprises at least one, preferably at least two, more preferably the following three complementary-determining regions (CDRs):

$V_H$-CDR1: SEQ ID NO: 8;
$V_H$-CDR2: SEQ ID NO: 16;
$V_H$-CDR3: SEQ ID NO: 26.

In one embodiment, the DEP1-binding domain of the invention comprises a HCVR which comprises at least one, preferably at least two, more preferably the following three complementary-determining regions (CDRs):

$V_H$-CDR1: SEQ ID NO: 5;
$V_H$-CDR2: SEQ ID NO: 16;
$V_H$-CDR3: SEQ ID NO: 26.

In one embodiment, the DEP1-binding domain of the invention comprises a HCVR which comprises at least one, preferably at least two, more preferably the following three complementary-determining regions (CDRs):

$V_H$-CDR1: SEQ ID NO: 8;
$V_H$-CDR2: SEQ ID NO: 17;
$V_H$-CDR3: SEQ ID NO: 26.

In one embodiment, the DEP1-binding domain of the invention comprises a HCVR which comprises at least one, preferably at least two, more preferably the following three complementary-determining regions (CDRs):

$V_H$-CDR1: SEQ ID NO: 9;
$V_H$-CDR2: SEQ ID NO: 18;
$V_H$-CDR3: SEQ ID NO: 28.

In one embodiment, the DEP1-binding domain of the invention comprises a HCVR which comprises at least one, preferably at least two, more preferably the following three complementary-determining regions (CDRs):

$V_H$-CDR1: SEQ ID NO: 10;
$V_H$-CDR2: SEQ ID NO: 19;
$V_H$-CDR3: SEQ ID NO: 30.

In one embodiment, the DEP1-binding domain of the invention comprises a HCVR which comprises at least one, preferably at least two, more preferably the following three complementary-determining regions (CDRs):

$V_H$-CDR1: SEQ ID NO: 11;
$V_H$-CDR2: SEQ ID NO: 20;
$V_H$-CDR3: SEQ ID NO: 31.

In one embodiment, the DEP1-binding domain of the invention comprises a HCVR which comprises at least one, preferably at least two, more preferably the following three complementary-determining regions (CDRs):

$V_H$-CDR1: SEQ ID NO: 10;
$V_H$-CDR2: SEQ ID NO: 21;
$V_H$-CDR3: SEQ ID NO: 30.

In one embodiment, the DEP1-binding domain of the invention comprises a HCVR which comprises at least one, preferably at least two, more preferably the following three complementary-determining regions (CDRs):

$V_H$-CDR1: SEQ ID NO: 11;
$V_H$-CDR2: SEQ ID NO: 22;
$V_H$-CDR3: SEQ ID NO: 31.

In one embodiment, the DEP1-binding domain of the invention comprises a HCVR which comprises at least one, preferably at least two, more preferably the following three complementary-determining regions (CDRs):

$V_H$-CDR1: SEQ ID NO: 11;
$V_H$-CDR2: SEQ ID NO: 23;
$V_H$-CDR3: SEQ ID NO: 31.

In one embodiment, the DEP1-binding domain of the invention comprises a HCVR which comprises at least one, preferably at least two, more preferably the following three complementary-determining regions (CDRs):

$V_H$-CDR1: SEQ ID NO: 11;
$V_H$-CDR2: SEQ ID NO: 24;
$V_H$-CDR3: SEQ ID NO: 31.

In one embodiment, the DEP1-binding domain of the invention comprises a HCVR which comprises at least one, preferably at least two, more preferably the following three complementary-determining regions (CDRs):

$V_H$-CDR1: SEQ ID NO: 11;
$V_H$-CDR2: SEQ ID NO: 25;
$V_H$-CDR3: SEQ ID NO: 32.

In one embodiment, the DEP1-binding domain of the invention comprises a light chain variable region (abbreviated herein as LCVR or $V_L$) which comprises at least one, preferably at least two, more preferably the following three complementary-determining regions (CDRs):

$V_L$-CDR1: any one of SEQ ID NO: 33 to 39;
$V_L$-CDR2: any one of SEQ ID NO: 40 to 46;
$V_L$-CDR3: any one of SEQ ID NO: 47 to 54.

| SEQ ID NO | SEQUENCE |
|---|---|
| 33 | RASQDVGIYVN |
| 34 | KSSQSLKHSDGKTYLN |
| 35 | QASQDIGNNLI |
| 36 | RSSQSLKHSDGKTYLN |
| 37 | QASQDIGNWLA |
| 38 | LASEGISNYLA |
| 39 | LASEDIYSYLA |
| 40 | RATNLAD |
| 41 | QVSKLDS |
| 42 | YATNLAN |
| 43 | RATTLAD |
| 44 | GATTLAD |

-continued

| SEQ ID NO | SEQUENCE |
|---|---|
| 45 | HANPLHD |
| 46 | YANPLHD |
| 47 | LQYDEFPPT |
| 48 | CQGSYSPYT |
| 49 | LQYDEWPYT |
| 50 | LQYDEYPPT |
| 51 | QQTSSTPWT |
| 52 | QQGYKFPYT |
| 53 | QQASSAPWT |
| 54 | QQGYKFPYS |

In one embodiment, the DEP1-binding domain of the invention comprises a LCVR which comprises at least one, preferably at least two, more preferably the following three complementary-determining regions (CDRs):

$V_L$-CDR1: SEQ ID NO: 33;
$V_L$-CDR2: SEQ ID NO: 40;
$V_L$-CDR3: SEQ ID NO: 47.

In one embodiment, the DEP1-binding domain of the invention comprises a LCVR which comprises at least one, preferably at least two, more preferably the following three complementary-determining regions (CDRs):

$V_L$-CDR1: SEQ ID NO: 34;
$V_L$-CDR2: SEQ ID NO: 41;
$V_L$-CDR3: SEQ ID NO: 48.

In one embodiment, the DEP1-binding domain of the invention comprises a LCVR which comprises at least one, preferably at least two, more preferably the following three complementary-determining regions (CDRs):

$V_L$-CDR1: SEQ ID NO: 35;
$V_L$-CDR2: SEQ ID NO: 42;
$V_L$-CDR3: SEQ ID NO: 47.

In one embodiment, the DEP1-binding domain of the invention comprises a LCVR which comprises at least one, preferably at least two, more preferably the following three complementary-determining regions (CDRs):

$V_L$-CDR1: SEQ ID NO: 33;
$V_L$-CDR2: SEQ ID NO: 40;
$V_L$-CDR3: SEQ ID NO: 49.

In one embodiment, the DEP1-binding domain of the invention comprises a LCVR which comprises at least one, preferably at least two, more preferably the following three complementary-determining regions (CDRs):

$V_L$-CDR1: SEQ ID NO: 36;
$V_L$-CDR2: SEQ ID NO: 41;
$V_L$-CDR3: SEQ ID NO: 48.

In one embodiment, the DEP1-binding domain of the invention comprises a LCVR which comprises at least one, preferably at least two, more preferably the following three complementary-determining regions (CDRs):

$V_L$-CDR1: SEQ ID NO: 33;
$V_L$-CDR2: SEQ ID NO: 40;
$V_L$-CDR3: SEQ ID NO: 50.

In one embodiment, the DEP1-binding domain of the invention comprises a LCVR which comprises at least one, preferably at least two, more preferably the following three complementary-determining regions (CDRs):

$V_L$-CDR1: SEQ ID NO: 33;
$V_L$-CDR2: SEQ ID NO: 43;
$V_L$-CDR3: SEQ ID NO: 50.

In one embodiment, the DEP1-binding domain of the invention comprises a LCVR which comprises at least one, preferably at least two, more preferably the following three complementary-determining regions (CDRs):

$V_L$-CDR1: SEQ ID NO: 37;
$V_L$-CDR2: SEQ ID NO: 44;
$V_L$-CDR3: SEQ ID NO: 51.

In one embodiment, the DEP1-binding domain of the invention comprises a LCVR which comprises at least one, preferably at least two, more preferably the following three complementary-determining regions (CDRs):

$V_L$-CDR1: SEQ ID NO: 38;
$V_L$-CDR2: SEQ ID NO: 45;
$V_L$-CDR3: SEQ ID NO: 52.

In one embodiment, the DEP1-binding domain of the invention comprises a LCVR which comprises at least one, preferably at least two, more preferably the following three complementary-determining regions (CDRs):

$V_L$-CDR1: SEQ ID NO: 37;
$V_L$-CDR2: SEQ ID NO: 44;
$V_L$-CDR3: SEQ ID NO: 53.

In one embodiment, the DEP1-binding domain of the invention comprises a LCVR which comprises at least one, preferably at least two, more preferably the following three complementary-determining regions (CDRs):

$V_L$-CDR1: SEQ ID NO: 38;
$V_L$-CDR2: SEQ ID NO: 45;
$V_L$-CDR3: SEQ ID NO: 54.

In one embodiment, the DEP1-binding domain of the invention comprises a LCVR which comprises at least one, preferably at least two, more preferably the following three complementary-determining regions (CDRs):

$V_L$-CDR1: SEQ ID NO: 39;
$V_L$-CDR2: SEQ ID NO: 45;
$V_L$-CDR3: SEQ ID NO: 52.

In one embodiment, the DEP1-binding domain of the invention comprises a LCVR which comprises at least one, preferably at least two, more preferably the following three complementary-determining regions (CDRs):

$V_L$-CDR1: SEQ ID NO: 38;
$V_L$-CDR2: SEQ ID NO: 46;
$V_L$-CDR3: SEQ ID NO: 52.

In one embodiment, the DEP1-binding domain of the invention comprises a combination of (i) at least one, preferably at least two, more preferably three HCVR's CDRs and (ii) at least one, preferably at least two, more preferably three LCVR's CDRs, said combination being as defined in Table 1.

In one embodiment, the DEP1-binding domain of the invention comprises a combination of (i) three HCVR's CDRs and (ii) three LCVR's CDRs, said combination being as defined in Table 1.

TABLE 1

Preferred combinations of HCVR's and LCVR's CDRs.
The CDRs are defined by their SEQ ID NOs.
First column indicates the clone's name.

| Clone's name | $V_H$-CDR1 | $V_H$-CDR2 | $V_H$-CDR3 | $V_L$-CDR1 | $V_L$-CDR2 | $V_L$-CDR3 |
|---|---|---|---|---|---|---|
| 5738-10-R3A-B2 | 5 | 12 | 26 | 33 | 40 | 47 |
| 5738-10-R3A-C6 | 6 | 13 | 27 | 34 | 41 | 48 |
| 5738-10-R3A-D1 | 7 | 14 | 28 | 35 | 42 | 47 |
| 5738-10-R3A-D5 | 5 | 12 | 29 | 33 | 40 | 49 |
| 5738-10-R3A-D8 | 6 | 15 | 27 | 36 | 41 | 48 |
| 5738-10-R3A-D11 | 5 | 16 | 26 | 33 | 40 | 47 |
| 5738-10-R4A-E7 | 8 | 16 | 26 | 33 | 40 | 47 |
| 5738-10-R4A-E9 | 5 | 16 | 26 | 33 | 40 | 50 |
| 5738-10-R4A-F12 | 8 | 16 | 26 | 33 | 40 | 50 |
| 5738-10-R4A-G4 | 8 | 17 | 26 | 33 | 40 | 47 |
| 5738-10-R4A-G11 | 9 | 18 | 28 | 33 | 43 | 50 |
| 5738-10-R4A-G12 | 8 | 16 | 26 | 33 | 40 | 50 |
| 5738-13-R2A-C1 | 10 | 19 | 30 | 37 | 44 | 51 |
| 5738-13-R2A-D3 | 11 | 20 | 31 | 38 | 45 | 52 |
| 5738-13-R4A-D11 | 10 | 21 | 30 | 37 | 44 | 53 |
| 5738-13-R3A-F5 | 11 | 22 | 31 | 38 | 45 | 54 |
| 5738-13-R4A-F11 | 11 | 23 | 31 | 39 | 45 | 52 |
| 5738-13-R2A-H3 | 11 | 24 | 31 | 38 | 45 | 52 |
| 5738-13-R2A-H4 | 11 | 25 | 32 | 38 | 46 | 52 |
| 5738-13-R4A-H9 | 11 | 25 | 32 | 38 | 45 | 52 |
| 5738-13-R4A-H11 | 11 | 25 | 32 | 38 | 45 | 52 |

In one embodiment, the DEP1-binding domain of the invention comprises a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the DEP1-binding domain of the invention comprises a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4.

In one embodiment, the DEP1-binding domain of the invention comprises a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4.

In one embodiment, the DEP1-binding domain of the invention comprises a combination of (i) three HCVR's CDRs and (ii) three LCVR's CDRs, said combination being that of any one of the following clones as defined in Table 1: 5738-13-R4A-D11, and 5738-13-R2A-H4.

In one embodiment, the DEP1-binding domain of the invention comprises a combination of (i) three HCVR's CDRs and (ii) three LCVR's CDRs, said combination being that of clone 5738-13-R2A-C1 as defined in Table 1. In one embodiment, the DEP1-binding domain of the invention comprises a combination of (i) three HCVR's CDRs and (ii) three LCVR's CDRs, said combination being that of clone 5738-13-R2A-D3 as defined in Table 1. In one embodiment, the DEP1-binding domain of the invention comprises a combination of (i) three HCVR's CDRs and (ii) three LCVR's CDRs, said combination being that of clone 5738-13-R4A-D11 as defined in Table 1. In one embodiment, the DEP1-binding domain of the invention comprises a combination of (i) three HCVR's CDRs and (ii) three LCVR's CDRs, said combination being that of clone 5738-13-R3A-F5 as defined in Table 1. In one embodiment, the DEP1-binding domain of the invention comprises a combination of (i) three HCVR's CDRs and (ii) three LCVR's CDRs, said combination being that of clone 5738-13-R4A-F11 as defined in Table 1. In one embodiment, the DEP1-binding domain of the invention comprises a combination of (i) three HCVR's CDRs and (ii) three LCVR's CDRs, said combination being that of clone 5738-13-R2A-H3 as defined in Table 1. In one embodiment, the DEP1-binding domain of the invention comprises a combination of (i) three HCVR's CDRs and (ii) three LCVR's CDRs, said combination being that of clone 5738-13-R2A-H4 as defined in Table 1. 5738-13-R4A-H9 as defined in Table 1. In one embodiment, the DEP1-binding domain of the invention comprises a combination of (i) three HCVR's CDRs and (ii) three LCVR's CDRs, said combination being that of clone 5738-13-R4A-H1 1 as defined in Table 1.

In one embodiment, the DEP1-binding domain of the invention comprises a HCVR comprising or consisting of the sequence SEQ ID NO: 55; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 55.

SEQ ID NO: 55

```
QVQLKQSGAELAKPGSSVKISCKASGYTFTSYYISWIKQTTGQGLEYIGY

INTGSGGTNYNEKFKGKATLTVDKSSSTAFMQLSSLTPDDSAVYYCARYF

DYWGQGVMVTVSS
```

In one embodiment, the DEP1-binding domain of the invention comprises a HCVR comprising or consisting of the sequence SEQ ID NO: 56; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 56.

SEQ ID NO: 56

EVKLVESGGGLVQPKESLKISCAASGFTFSNIAMYWVRQAPGKGLEWVAH

IRTKPHNFATYYANSVKGRFTISRDDSKNMVYLQMDNLKPEDTAMYYCSV

GFGDYWGQGVMVTVSS

In one embodiment, the DEP1-binding domain of the invention comprises a HCVR comprising or consisting of the sequence SEQ ID NO: 57; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 57.

SEQ ID NO: 57

EVQLQQSGAELAKPGSSVKISCKASGYTFTNYTISWIKQTTGQGLEYIGY

IYAGTGDTNYNEKFKGKATLTVDKSSNTAFMQLSSLTPDDSAVYYCARYF

DHWGQGVMVTVSS

In one embodiment, the DEP1-binding domain of the invention comprises a HCVR comprising or consisting of the sequence SEQ ID NO: 58; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 58.

SEQ ID NO: 58

EVQLQQSGAELAKPGSSVKISCKASGYTFTSYYISWIKQTTGQGLEYIGY

INTGSGGTNYNEKFKGKATLTVDKSSSTAFMQLSSLTPDDSAVYYCARDK

WVDWGQGVMVTVSS

In one embodiment, the DEP1-binding domain of the invention comprises a HCVR comprising or consisting of the sequence SEQ ID NO: 59; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 59.

SEQ ID NO: 59

EVQLEESGGGLVQPKESLKISCAVSGFTFSNIAMYWVRQAPGKGLEWVGH

IRTKPHNYATYYADSVKGRFTISRDDSNNMVYLEMDNLKPEDTAMYYCSV

GFGDYWGQGVMVTVSS

In one embodiment, the DEP1-binding domain of the invention comprises a HCVR comprising or consisting of the sequence SEQ ID NO: 60; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 60.

SEQ ID NO: 60

QVQLKQSGAELAKPGSSVKISCKASGYTFTSYYISWIKQTTGQGLEYIGY

IHPGSGVTNYNEKFKGKATLTVDKSSSTAFMQLSSLTPDDSAIYYCARYF

DYWGQGVMVTVSS

In one embodiment, the DEP1-binding domain of the invention comprises a HCVR comprising or consisting of the sequence SEQ ID NO: 61; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 61.

SEQ ID NO: 61

QVQLKQSGVELAKPGSSVKISCKASGYTFTSDSISWIKQTTGQGLEYIGYI

HPGSGVTNYNEKFKGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 62; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 62.

SEQ ID NO: 62

EVQLQQSGVELAKPGSSVKISCKASGYTFTSDSISWIKQTTGQGLEYIGYI

HPGSGVTNYNEKFKGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 63; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 63.

SEQ ID NO: 63

EVQLQQSGVELAKPGSSVKISCKASGYTFTSDSISWIKQTTGQGLEYIGYI

HPGSGVTNYNEKFRGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 64; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 64.

SEQ ID NO: 64

QVQLQQPRAELAKPGSSVKISCKASGYTFTNYSISWIKQTTGQGLEYIGYI

YPGSGDTNYNEKFKGKATLTVDKSSSTAFMQLSSLTPDDSAVYYCARYFDH

WGQGTLVTVSS

In one embodiment, the DEP1-binding domain of the invention comprises a HCVR comprising or consisting of the sequence SEQ ID NO: 65; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 65.

SEQ ID NO: 65
QVQLKESGAELAKPGSSVKISCKASGYTFTSDSISWIKQTTGQGLEYIGYI

HPGSGVTNYNEKFKGKATLTVDKSSSTAFMQLSSLTPDDSAIYYCARYFDY

WGQGVMVTVSS

In one embodiment, the DEP1-binding domain of the invention comprises a HCVR comprising or consisting of the sequence SEQ ID NO: 66; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 66.

SEQ ID NO: 66
QVQLKESGGGLVQPGRSLKLSCAASGFTFSDYNMAWVRQAPKKGLEWVATI

SYDDSRTYYRDSVKGRFAISRDDAKGTLNLQMDSLRSEDTATYYCARQGGI

IRGVWFPYWGQGTLVTVSS

In one embodiment, the DEP1-binding domain of the invention comprises a HCVR comprising or consisting of the sequence SEQ ID NO: 67; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 67.

SEQ ID NO: 67
EVKLVESGGGLVQPGGSLKLSCAASGFTFSNYYMAWVRQAPTKGLEWVAYI

TNSFGSAYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 68; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 68.

SEQ ID NO: 68
QVQLKESGGGLVQPGRSLKLSCAASGFSFGDYNMAWVRQAPKKGLEWVATI

SYDDYRTYYRDSVKGRFTISRDDAKATLYLQMDSLRSEDTATYYCARQGGI

IRGVWFPYWGQGTLVTVSS

In one embodiment, the DEP1-binding domain of the invention comprises a HCVR comprising or consisting of the sequence SEQ ID NO: 69; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 69.

SEQ ID NO: 69
EVKLVESGGGLVQPGGSLKLSCAASGFTFSNYYMAWVRQAPTKGLEWVAYI

TNSLGSAYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 70; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 70.

SEQ ID NO: 70
EVKLVESGGGLVQPGGSLKLSCAASGFTFSNYYMAWVRQAPTKGLEWVAYI

TNSFGSTYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 71; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 71.

SEQ ID NO: 71
EVKLVESGGGLVQPGRSLKLSCAASGFTFSNYYMAWVRQAPTKGLEWVAYI

TNGYGSTYYRDSVKGRFTISRDNAKSTLYLQMDSLRSEDTATYYCSTVPLG

AFVYWGQGTLVTVSS

In one embodiment, the DEP1-binding domain of the invention comprises a HCVR comprising or consisting of the sequence SEQ ID NO: 72; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 72.

SEQ ID NO: 72
EVKLVESGGGLVQPGRSLKLSCAASGFTFSNYYMAWVRQAPTKGLEWVAYI

TNGFGSTYYRDSVKGRFTISRDNAKSTLYLQMDSLRSEDTATYYCSTVPLG

AFVSWGQGTLVTVSS

In one embodiment, the DEP1-binding domain of the invention comprises a HCVR comprising or consisting of the sequence SEQ ID NO: 73; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 73.

SEQ ID NO: 73
EVKLVESGGGLVQPGRSLKLSCAASGFTFSNYYMAWVRQAPTKGLEWVAYI

TNGFGSTYYRDSVKGRFTISRDNAKSTLYLQMDSLRSEDAATYYCSTVPLG

AFVSWGQGTLVTVSS

In one embodiment, the DEP1-binding domain of the invention comprises a HCVR comprising or consisting of the sequence SEQ ID NO: 74; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 74.

SEQ ID NO: 74
EVKLVESGGGLVQPGGSLKLSCAASGFTFSNYYMAWVRQAPTKGLEWVAYI

TNGFGSTYYRDSVKGRFTISRDNAKSTLYLQMDSLRSEDTATYYCSTVPLG

AFVSWGQGTLVTVSS

In one embodiment, the DEP1-binding domain of the invention comprises a LCVR comprising or consisting of the sequence SEQ ID NO: 75; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 75.

SEQ ID NO: 75
DIVMTQSPSSMSVSLGDTVTITCRASQDVGIYVNWFQQKPGKPPRRMIYRA

TNLADGVPSRFSGTRSGSDYSLTISSLESEDVADYHCLQYDEFPPTFGSGT

KLDIK

In one embodiment, the DEP1-binding domain of the invention comprises a LCVR comprising or consisting of the sequence SEQ ID NO: 76; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 76.

SEQ ID NO: 76
DIVMTQAPLSLSVAIGQSASISCKSSQSLKHSDGKTYLNWIFQSPGQSPKR

LIYQVSKLDSGVPDRFSGTGSETDFTLKISRVEAEDLGVYYCCQGSYSPYT

FGAGTKLELK

In one embodiment, the DEP1-binding domain of the invention comprises a LCVR comprising or consisting of the sequence SEQ ID NO: 77; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 77.

SEQ ID NO: 77
DILMTQSPSSMSASLGDRVTITCQASQDIGNNLIWFQQKPGKSPRRMIYYA

TNLANGVPSRFSGSRSGSDYSLSISSLESEDVADYHCLQYDEFPPTFGSGT

KLEIK

In one embodiment, the DEP1-binding domain of the invention comprises a LCVR comprising or consisting of the sequence SEQ ID NO: 78; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 78.

SEQ ID NO: 78
DILMTQSPSSMSVSLGDTVTITCRASQDVGIYVNWFQQKPGKPPRRMIYRA

TNLADGVPSRFSGSRSGSNYSLTIRSLESEDVADYHCLQYDEWPYTFGAGT

KLELK

In one embodiment, the DEP1-binding domain of the invention comprises a LCVR comprising or consisting of the sequence SEQ ID NO: 79; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 79.

SEQ ID NO: 79
DIVMTQAPLSLSVDIGQSASISCRSSQSLKHSDGKTYLNWVFQSPGQSPKR

LIYQVSKLDSGVPDRFSGSGSEADFTLKISRVEAEDLGVYYCCQGSYSPYT

FGAGTKLELK

In one embodiment, the DEP1-binding domain of the invention comprises a LCVR comprising or consisting of the sequence SEQ ID NO: 80; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 80.

SEQ ID NO: 80
DIQLTQSPSSMSVSQGDTVTITCRASQDVGIYVNWFQQKPGKSPRRMIYRA

TNLADGVPSRFSGSRSGSDYSLTIASLESEDVADYHCLQYDEFPPTFGSGT

NLEIK

In one embodiment, the DEP1-binding domain of the invention comprises a LCVR comprising or consisting of the sequence SEQ ID NO: 81; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 81.

SEQ ID NO: 81
DILMTQSPSSMSVSLGDTVTITCRASQDVGIYVNWFQQIPGKSPRRLIYRA

TNLADGVPSRFSGSRSGSDYSLTIASLESEDVADYHCLQYDEFPPTFGSGT

KLEIK

In one embodiment, the DEP1-binding domain of the invention comprises a LCVR comprising or consisting of the sequence SEQ ID NO: 82; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 82.

SEQ ID NO: 82
DILMTQSPSSMSVSQGDTVTITCRASQDVGIYVNWFQQKPGKSPRRMIHRA

TNLADGVPSRFSGSRSGSDYSLTITSLESEDVADYHCLQYDEYPPTFGSGT

NLEIK

In one embodiment, the DEP1-binding domain of the invention comprises a LCVR comprising or consisting of the sequence SEQ ID NO: 83; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 83.

SEQ ID NO: 83
DILMTQSPSSMSVSLGDTVTITCRASQDVGIYVNWFQQKPGKSPRRMIHRA

TNLADGVPSRFSGSRSGSDYSLTISSLESEDVADYHCLQYDEYPPTFGSGT

KLEIK

In one embodiment, the DEP1-binding domain of the invention comprises a LCVR comprising or consisting of the sequence SEQ ID NO: 84; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 84.

SEQ ID NO: 84
DIVMTQSPSSMSVSLGDTVTITCRASQDVGIYVNWFQQKPGKSPRRMIYRA

TNLADGVPSRFSGSRSGSDYSLTIASLESEDVADYHCLQYDEFPPTFGSGT

KLEIK

In one embodiment, the DEP1-binding domain of the invention comprises a LCVR comprising or consisting of the sequence SEQ ID NO: 85; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 85.

SEQ ID NO: 85
DILMTQSPSSMSVSLGDTVTITCRASQDVGIYVNWFQQKPGKSPRRMIYRA

TTLADGVPSRFSGSRSGSDYSLTISSLESEDVADYHCLQYDEYPPTFGSGT

KLEIK

In one embodiment, the DEP1-binding domain of the invention comprises a LCVR comprising or consisting of the sequence SEQ ID NO: 86; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 86.

SEQ ID NO: 86
DILMTQSPSSMSVSLGDTVTITCRASQDVGIYVNWFQQKPGKSPRRMIYRA

TNLADGVPSRFSGSRSGSDYSLTISSLESEDVADYHCLQYDEYPPTFGGGT

KLELK

In one embodiment, the DEP1-binding domain of the invention comprises a LCVR comprising or consisting of the sequence SEQ ID NO: 87; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 87.

SEQ ID NO: 87
DIQLTQSPASLSASLEEIVTITCQASQDIGNWLAWYQQKPGKSPHLLIYGA

TTLADGVPSRSGSRSGTQYSLKISRLQVEDVGMYYCQQTSSTPWTFGGGTK

LELK

In one embodiment, the DEP1-binding domain of the invention comprises a LCVR comprising or consisting of the sequence SEQ ID NO: 88; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 88.

SEQ ID NO: 88
DIQMTQTPHSLSASLGETVSIECLASEGISNYLAWYQQKPGKSPQLLISHA

NPLHDGVPSRFSGDGSGTQYSLKIRNMQPEDEGVYYCQQGYKFPYTFGAGT

KLELK

In one embodiment, the DEP1-binding domain of the invention comprises a LCVR comprising or consisting of the sequence SEQ ID NO: 89; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 89.

SEQ ID NO: 89
DIQMTQTPASLSASLEEIVTITCQASQDIGNWLAWYQQKPGKSPHLLIYGA

TTLADGVPSRFSGSRSGTQYSLKISRLQAEDIGIYYCQQASSAPWTFGGGT

KLELK

In one embodiment, the DEP1-binding domain of the invention comprises a LCVR comprising or consisting of the sequence SEQ ID NO: 90; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 90.

SEQ ID NO: 90
DIQMTQTPHSLSASLGETVSIECLASEGISNYLAWYQQKPGKSPQLLISHA

NPLHDGVPSRFSGSGSGTQYSLKIRNMQPEDEGVYYCQQGYKFPYSFGAGT

KLELK

In one embodiment, the DEP1-binding domain of the invention comprises a LCVR comprising or consisting of the sequence SEQ ID NO: 91; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 91.

SEQ ID NO: 91
DIQLTQSPASLSASLGETVSIECLASEDIYSYLAWYQQKPGKSPQLLISHA

NPLHDGVPSRFSGSGSGTQYSLKIRNMQPEDEGVYYCQQGYKFPYTFGAGT

KLELK

In one embodiment, the DEP1-binding domain of the invention comprises a LCVR comprising or consisting of the sequence SEQ ID NO: 92; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 92.

SEQ ID NO: 92

```
DIQMTQTPHSLSASLGETVSIECLASEGISNYLAWYQQKPGKSPQLLISHA

NPLHDGVPSRFSGSGSGTQYSLKIRNMQPEDEGVYYCQQGYKFPYTFGAGT

KLELK
```

In one embodiment, the DEP1-binding domain of the invention comprises a LCVR comprising or consisting of the sequence SEQ ID NO: 93; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 93.

SEQ ID NO: 93

```
DIQMTQTPHSLSASLGETVSIECLASEGISNYLAWYQQKPGKSPQLLISYA

NPLHDGVPSRFSGSGSGTQFSLKIRNMQPEDEGVYYCQQGYKFPYTFGAGT

KLELT
```

In one embodiment, the DEP1-binding domain of the invention comprises a LCVR comprising or consisting of the sequence SEQ ID NO: 94; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 94.

SEQ ID NO: 94

```
DIQMTQTPHSLSASLGETVSIECLASEGISNYLAWYQQKPGKSPQLLISHA

NPLHDGVPSRFSGSGSGTQFSLKIRNMQPEDEGVYYCQQGYKFPYTFGAGT

KLELK
```

In one embodiment, the DEP1-binding domain of the invention comprises a combination of (i) a HCVR and (ii) a LCVR, said combination being as defined in Table 2.

TABLE 2

Preferred combinations of HCVR and LCVR. The HCVR and LCVR are defined by their SEQ ID NOs. First column indicates the clone's name.

| Clone's name | HCVR | LCVR |
|---|---|---|
| 5738-10-R3A-B2 | 55 | 75 |
| 5738-10-R3A-C6 | 56 | 76 |
| 5738-10-R3A-D1 | 57 | 77 |
| 5738-10-R3A-D5 | 58 | 78 |
| 5738-10-R3A-D8 | 59 | 79 |
| 5738-10-R3A-D11 | 60 | 80 |
| 5738-10-R4A-E7 | 61 | 81 |
| 5738-10-R4A-E9 | 60 | 82 |
| 5738-10-R4A-F12 | 62 | 83 |
| 5738-10-R4A-G4 | 63 | 84 |
| 5738-10-R4A-G11 | 64 | 85 |
| 5738-10-R4A-G12 | 65 | 86 |
| 5738-13-R2A-C1 | 66 | 87 |
| 5738-13-R2A-D3 | 67 | 88 |
| 5738-13-R4A-D11 | 68 | 89 |
| 5738-13-R3A-F5 | 69 | 90 |
| 5738-13-R4A-F11 | 70 | 91 |
| 5738-13-R2A-H3 | 71 | 92 |
| 5738-13-R2A-H4 | 72 | 93 |
| 5738-13-R4A-H9 | 73 | 94 |
| 5738-13-R4A-H11 | 74 | 94 |

In one embodiment, the DEP1-binding domain of the invention comprises a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the DEP1-binding domain of the invention comprises a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4.

In one embodiment, the DEP1-binding domain of the invention comprises a combination of (i) a HCVR and (ii) a LCVR, combination being that of any one of the following clones as defined in Table 2: 5738-10-R4A-G12, 5738-13-R4A-D11, and 5738-13-R2A-H4.

In one embodiment, the DEP1-binding domain of the invention comprises a combination of (i) a HCVR and (ii) a LCVR, combination being that of any one of the following clones as defined in Table 2: 5738-13-R4A-D11, and 5738-13-R2A-H4.

In one embodiment, the DEP1-binding domain of the invention comprises a combination of (i) a HCVR and (ii) a LCVR, combination being that of clone 5738-13-R2A-C1 as defined in Table 2. In one embodiment, the DEP1-binding domain of the invention comprises a combination of (i) a HCVR and (ii) a LCVR, combination being that of clone 5738-13-R2A-D3 as defined in Table 2. In one embodiment, the DEP1-binding domain of the invention comprises a combination of (i) a HCVR and (ii) a LCVR, combination being that of clone 5738-13-R4A-D11 as defined in Table 2. In one embodiment, the DEP1-binding domain of the invention comprises a combination of (i) a HCVR and (ii) a LCVR, combination being that of clone 5738-13-R3A-F5 as defined in Table 2. In one embodiment, the DEP1-binding domain of the invention comprises a combination of (i) a HCVR and (ii) a LCVR, combination being that of clone 5738-13-R4A-F11 as defined in Table 2. In one embodiment, the DEP1-binding domain of the invention comprises a combination of (i) a HCVR and (ii) a LCVR, combination being that of clone 5738-13-R2A-H3 as defined in Table 2. In one embodiment, the DEP1-binding domain of the invention comprises a combination of (i) a HCVR and (ii) a LCVR, combination being that of clone 5738-13-R2A-H4 as defined in Table 2. In one embodiment, the DEP1-binding domain of the invention comprises a combination of (i) a HCVR and (ii) a LCVR, combination being that of clone 5738-13-R4A-H9 as defined in Table 2. 5738-13-R4A-H11 as defined in Table 2.

In one embodiment, the senescent cell-associated antigen is DPP4, such as, e.g., human DPP4 or orthologs thereof, including murine and rat DPP4. In one embodiment, the senescent cell-associated antigen is human DPP4 (hDPP4) with SEQ ID NO: 101.

In one embodiment, the antigen-binding domain of the invention recognizes and is capable of binding to DPP4, such as, e.g., to human DPP4, or orthologs thereof, including murine and rat DPP4. Hence, the antigen-binding domain of the invention is a "DPP4-binding domain".

In one embodiment, the DPP4-binding domain of the invention recognizes and is capable of binding to human DPP4 (hDPP4) with SEQ ID NO: 101.

In one embodiment, the DPP4-binding domain of the invention recognizes and is capable of binding to the extracellular domain of human DPP4 (hDPP4) comprising or consisting of amino acid residues 29-766 of SEQ ID NO: 101.

The binding between the DPP4-binding domain of the invention and DPP4 implies that said DPP4-binding domain exhibits appreciable affinity for DPP4. In other words, the DPP4-binding domain of the invention is specific for, or is immunospecific for, or specifically bind to, DPP4.

The affinity between the DPP4-binding domain of the invention and DPP4 can be determined by various methods well known from the one skilled in the art. These methods include, but are not limited to, biosensor analysis (including, e.g., Biacore analysis), Blitz analysis and Scatchard plot.

Alternatively or additionally, whether the DPP4-binding domain of the invention binds to DPP4 can be tested readily by, inter alia, comparing the reaction of said DPP4-binding domain with DPP4 or a fragment thereof (in particular, a fragment comprising or consisting of an epitope of DPP4) with the reaction of said DPP4-binding domain with proteins or antigens other than DPP4 or a fragment thereof.

In one embodiment, the DPP4-binding domain of the invention recognizes and is capable of binding to DPP4 with a $K_D$-affinity constant less than or equal to $10^{-6}$ M, preferably less than or equal to $10^{-7}$ M, $5.10^{-8}$ M, $10^{-9}$ M, $5.10^{-9}$ M, $10^{-9}$ M or less; as may be determined, e.g., by biosensor analysis, particularly by Biacore Analysis.

In one embodiment, the DPP4-binding domain of the invention comprises a heavy chain variable region (abbreviated herein as HCVR or $V_H$) which comprises at least one, preferably at least two, more preferably the following three complementary-determining regions (CDRs):

$V_H$-CDR1: any one of SEQ ID NO: 104 to 112;

$V_H$-CDR2: any one of SEQ ID NO: 113 to 129;

$V_H$-CDR3: any one of SE ID NO: 130 to 142.

| SEQ ID NO | SEQUENCE | SEQ ID NO | SEQUENCE |
|---|---|---|---|
| 104 | NYGMA | 124 | YINPGGGGIGYNEKFKG |
| 105 | TSDRCVS | 125 | QISHSGSTSYNPSLKS |
| 106 | NFGMA | 126 | SINPGSGGIGYNEKFKG |
| 107 | DNYWG | 127 | SINPGGGGTGYNEKFKG |
| 108 | TYDIG | 128 | QISHSGSTSYNPSLIS |
| 109 | GNYLA | 129 | QISHTGSSTYNPSLKS |
| 110 | SNYWG | 130 | HRLIYTTDYYYEVMDV |
| 111 | TYDRG | 131 | HRLIYTTDYYYEVMDA |
| 112 | GNYWG | 132 | NSGDGRFAY |
| 113 | TISYDGNDTYYRDSVKG | 133 | HKLIYTTDYYYEVMDA |
| 114 | TTSYDGNDTYYRDSVKG | 134 | HRLMYTTDYYYEVMDD |
| 115 | TICWDDSKGYNPSLKN | 135 | HRLIYTTDYYYEVLDA |
| 116 | TINYDGRNTYYRDSVKG | 136 | HKLIYTTDYYYEVMDV |
| 117 | TINYDGSNTYYRDSVKG | 137 | YGAGASFDY |
| 118 | TINYDGRDTYYRDSVKG | 138 | PLRRVLDY |
| 119 | HISHSGSSTYNPSLKS | 139 | HGHYVMDV |
| 120 | YINPGSGGIGYNEKFKG | 140 | YGAGSSFDY |

-continued

| SEQ ID NO | SEQUENCE | SEQ ID NO | SEQUENCE |
|---|---|---|---|
| 121 | SINPGSGGIAYSEKFKG | 141 | PLRRVLDN |
| 122 | HIKSSGTTTYNPSLKS | 142 | PLRVLDY |
| 123 | SINPGSGGIGYNERFKG | | |

In one embodiment, the DPP4-binding domain of the invention comprises a HCVR which comprises at least one, preferably at least two, more preferably the following three complementary-determining regions (CDRs):

$V_H$-CDR1: SEQ ID NO: 104;
$V_H$-CDR2: SEQ ID NO: 113;
$V_H$-CDR3: SEQ ID NO: 130.

In one embodiment, the DPP4-binding domain of the invention comprises a HCVR which comprises at least one, preferably at least two, more preferably the following three complementary-determining regions (CDRs):

$V_H$-CDR1: SEQ ID NO: 104;
$V_H$-CDR2: SEQ ID NO: 114;
$V_H$-CDR3: SEQ ID NO: 131.

In one embodiment, the DPP4-binding domain of the invention comprises a HCVR which comprises at least one, preferably at least two, more preferably the following three complementary-determining regions (CDRs):

$V_H$-CDR1: SEQ ID NO: 105;
$V_H$-CDR2: SEQ ID NO: 115;
$V_H$-CDR3: SEQ ID NO: 132.

In one embodiment, the DPP4-binding domain of the invention comprises a HCVR which comprises at least one, preferably at least two, more preferably the following three complementary-determining regions (CDRs):

$V_H$-CDR1: SEQ ID NO: 104;
$V_H$-CDR2: SEQ ID NO: 116;
$V_H$-CDR3: SEQ ID NO: 133.

In one embodiment, the DPP4-binding domain of the invention comprises a HCVR which comprises at least one, preferably at least two, more preferably the following three complementary-determining regions (CDRs):

$V_H$-CDR1: SEQ ID NO: 104;
$V_H$-CDR2: SEQ ID NO: 117;
$V_H$-CDR3: SEQ ID NO: 134.

In one embodiment, the DPP4-binding domain of the invention comprises a HCVR which comprises at least one, preferably at least two, more preferably the following three complementary-determining regions (CDRs):

$V_H$-CDR1: SEQ ID NO: 104;
$V_H$-CDR2: SEQ ID NO: 113;
$V_H$-CDR3: SEQ ID NO: 135.

In one embodiment, the DPP4-binding domain of the invention comprises a HCVR which comprises at least one, preferably at least two, more preferably the following three complementary-determining regions (CDRs):

$V_H$-CDR1: SEQ ID NO: 104;
$V_H$-CDR2: SEQ ID NO: 116;
$V_H$-CDR3: SEQ ID NO: 136.

In one embodiment, the DPP4-binding domain of the invention comprises a HCVR which comprises at least one, preferably at least two, more preferably the following three complementary-determining regions (CDRs):

$V_H$-CDR1: SEQ ID NO: 106;
$V_H$-CDR2: SEQ ID NO: 118;
$V_H$-CDR3: SEQ ID NO: 131.

In one embodiment, the DPP4-binding domain of the invention comprises a HCVR which comprises at least one, preferably at least two, more preferably the following three complementary-determining regions (CDRs):

$V_H$-CDR1: SEQ ID NO: 107;

$V_H$-CDR2: SEQ ID NO: 119;

$V_H$-CDR3: SEQ ID NO: 137.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 120;

$V_H$-CDR3: SEQ ID NO: 138.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 121;

$V_H$-CDR3: SEQ ID NO: 138.

In one embodiment, the DPP4-binding domain of the invention comprises a HCVR which comprises at least one, preferably at least two, more preferably the following three complementary-determining regions (CDRs):

$V_H$-CDR1: SEQ ID NO: 109;

$V_H$-CDR2: SEQ ID NO: 122;

$V_H$-CDR3: SEQ ID NO: 139.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 123;

$V_H$-CDR3: SEQ ID NO: 138.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 124;

$V_H$-CDR3: SEQ ID NO: 138.

In one embodiment, the DPP4-binding domain of the invention comprises a HCVR which comprises at least one, preferably at least two, more preferably the following three complementary-determining regions (CDRs):

$V_H$-CDR1: SEQ ID NO: 110;

$V_H$-CDR2: SEQ ID NO: 125;

$V_H$-CDR3: SEQ ID NO: 140.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 126;

$V_H$-CDR3: SEQ ID NO: 141.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 126;

$V_H$-CDR3: SEQ ID NO: 138.

In one embodiment, the DPP4-binding domain of the invention comprises a HCVR which comprises at least one, preferably at least two, more preferably the following three complementary-determining regions (CDRs):

$V_H$-CDR1: SEQ ID NO: 111;

$V_H$-CDR2: SEQ ID NO: 127;

$V_H$-CDR3: SEQ ID NO: 138.

In one embodiment, the DPP4-binding domain of the invention comprises a HCVR which comprises at least one, preferably at least two, more preferably the following three complementary-determining regions (CDRs):

$V_H$-CDR1: SEQ ID NO: 110;

$V_H$-CDR2: SEQ ID NO: 128;

$V_H$-CDR3: SEQ ID NO: 140.

In one embodiment, the DPP4-binding domain of the invention comprises a HCVR which comprises at least one, preferably at least two, more preferably the following three complementary-determining regions (CDRs):

$V_H$-CDR1: SEQ ID NO: 112;

$V_H$-CDR2: SEQ ID NO: 125;

$V_H$-CDR3: SEQ ID NO: 140.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 127;

$V_H$-CDR3: SEQ ID NO: 138.

In one embodiment, the DPP4-binding domain of the invention comprises a HCVR which comprises at least one, preferably at least two, more preferably the following three complementary-determining regions (CDRs):

$V_H$-CDR1: SEQ ID NO: 108;

$V_H$-CDR2: SEQ ID NO: 127;

$V_H$-CDR3: SEQ ID NO: 142.

In one embodiment, the DPP4-binding domain of the invention comprises a light chain variable region (abbreviated herein as LCVR or $V_L$) which comprises at least one, preferably at least two, more preferably the following three complementary-determining regions (CDRs):

$V_L$-CDR1: any one of SEQ ID NO: 143 to 151;

$V_L$-CDR2: any one of SEQ ID NO: 152 to 163;

$V_L$-CDR3: any one of SEQ ID NO: 164 to 173.

| SEQ ID NO | SEQUENCE | SEQ ID NO | SEQUENCE |
|---|---|---|---|
| 143 | KSSQSLLYNENKKNYLA | 159 | YTSNLQS |
| 144 | KSSQSLLHSNGNTYLN | 160 | DASHLAS |
| 145 | RSSQSLLHSNGNTYLN | 161 | YTSSFQD |
| 146 | LASEGISNYLA | 162 | YTISLQD |
| 147 | RASQGISNKLN | 163 | YASSLQD |
| 148 | RASQSVSTSTYNFMH | 164 | QEYYKFPWT |
| 149 | RASQGIGNKLN | 165 | QDYYHFPWT |
| 150 | RASQGISKKLN | 166 | MQATHAPFT |
| 151 | GASQGIGNKVN | 167 | QQYYKFPWP |
| 152 | WASTRES | 168 | QQYYKFPWT |
| 153 | SVSKLES | 169 | QQYYKFPYT |
| 154 | WASTREA | 170 | QQGYKYPWT |

-continued

| SEQ ID NO | SEQUENCE | SEQ ID NO | SEQUENCE |
|---|---|---|---|
| 155 | WASTRKS | 171 | QQDASFPPT |
| 156 | SVSNLES | 172 | QQSRELPLT |
| 157 | YTSSLQD | 173 | QQDTSFPPT |
| 158 | YTSRLQS | | |

In one embodiment, the DPP4-binding domain of the invention comprises a LCVR which comprises at least one, preferably at least two, more preferably the following three complementary-determining regions (CDRs):

$V_L$-CDR1: SEQ ID NO: 143;
$V_L$-CDR2: SEQ ID NO: 152,
$V_L$-CDR3: SEQ ID NO: 164.

In one embodiment, the DPP4-binding domain of the invention comprises a LCVR which comprises at least one, preferably at least two, more preferably the following three complementary-determining regions (CDRs):

$V_L$-CDR1: SEQ ID NO: 143;
$V_L$-CDR2: SEQ ID NO: 152;
$V_L$-CDR3: SEQ ID NO: 165.

In one embodiment, the DPP4-binding domain of the invention comprises a LCVR which comprises at least one, preferably at least two, more preferably the following three complementary-determining regions (CDRs):

$V_L$-CDR1: SEQ ID NO: 144;
$V_L$-CDR2: SEQ ID NO: 153;
$V_L$-CDR3: SEQ ID NO: 166.

In one embodiment, the DPP4-binding domain of the invention comprises a LCVR which comprises at least one, preferably at least two, more preferably the following three complementary-determining regions (CDRs):

$V_L$-CDR1: SEQ ID NO: 143;
$V_L$-CDR2: SEQ ID NO: 154;
$V_L$-CDR3: SEQ ID NO: 167.

In one embodiment, the DPP4-binding domain of the invention comprises a LCVR which comprises at least one, preferably at least two, more preferably the following three complementary-determining regions (CDRs):

$V_L$-CDR1: SEQ ID NO: 143;
$V_L$-CDR2: SEQ ID NO: 155;
$V_L$-CDR3: SEQ ID NO: 168.

In one embodiment, the DPP4-binding domain of the invention comprises a LCVR which comprises at least one, preferably at least two, more preferably the following three complementary-determining regions (CDRs):

$V_L$-CDR1: SEQ ID NO: 145;
$V_L$-CDR2: SEQ ID NO: 156;
$V_L$-CDR3: SEQ ID NO: 166.

In one embodiment, the DPP4-binding domain of the invention comprises a LCVR which comprises at least one, preferably at least two, more preferably the following three complementary-determining regions (CDRs):

$V_L$-CDR1: SEQ ID NO: 143;
$V_L$-CDR2: SEQ ID NO: 154;
$V_L$-CDR3: SEQ ID NO: 169.

In one embodiment, the DPP4-binding domain of the invention comprises a LCVR which comprises at least one, preferably at least two, more preferably the following three complementary-determining regions (CDRs):

$V_L$-CDR1: SEQ ID NO: 146;
$V_L$-CDR2: SEQ ID NO: 157;
$V_L$-CDR3: SEQ ID NO: 170.

In one embodiment, the DPP4-binding domain of the invention comprises a LCVR which comprises at least one, preferably at least two, more preferably the following three complementary-determining regions (CDRs):

$V_L$-CDR1: SEQ ID NO: 147;
$V_L$-CDR2: SEQ ID NO: 158;
$V_L$-CDR3: SEQ ID NO: 171.

In one embodiment, the DPP4-binding domain of the invention comprises a LCVR which comprises at least one, preferably at least two, more preferably the following three complementary-determining regions (CDRs):

$V_L$-CDR1: SEQ ID NO: 147;
$V_L$-CDR2: SEQ ID NO: 159;
$V_L$-CDR3: SEQ ID NO: 171.

In one embodiment, the DPP4-binding domain of the invention comprises a LCVR which comprises at least one, preferably at least two, more preferably the following three complementary-determining regions (CDRs):

$V_L$-CDR1: SEQ ID NO: 148;
$V_L$-CDR2: SEQ ID NO: 160;
$V_L$-CDR3: SEQ ID NO: 172.

In one embodiment, the DPP4-binding domain of the invention comprises a LCVR which comprises at least one, preferably at least two, more preferably the following three complementary-determining regions (CDRs):

$V_L$-CDR1: SEQ ID NO: 149;
$V_L$-CDR2: SEQ ID NO: 159;
$V_L$-CDR3: SEQ ID NO: 171.

In one embodiment, the DPP4-binding domain of the invention comprises a LCVR which comprises at least one, preferably at least two, more preferably the following three complementary-determining regions (CDRs):

$V_L$-CDR1: SEQ ID NO: 146;
$V_L$-CDR2: SEQ ID NO: 161;
$V_L$-CDR3: SEQ ID NO: 170.

In one embodiment, the DPP4-binding domain of the invention comprises a LCVR which comprises at least one, preferably at least two, more preferably the following three complementary-determining regions (CDRs):

$V_L$-CDR1: SEQ ID NO: 150;
$V_L$-CDR2: SEQ ID NO: 159;
$V_L$-CDR3: SEQ ID NO: 171.

In one embodiment, the DPP4-binding domain of the invention comprises a LCVR which comprises at least one, preferably at least two, more preferably the following three complementary-determining regions (CDRs):

$V_L$-CDR1: SEQ ID NO: 151;
$V_L$-CDR2: SEQ ID NO: 159;
$V_L$-CDR3: SEQ ID NO: 171.

In one embodiment, the DPP4-binding domain of the invention comprises a LCVR which comprises at least one, preferably at least two, more preferably the following three complementary-determining regions (CDRs):

$V_L$-CDR1: SEQ ID NO: 146;
$V_L$-CDR2: SEQ ID NO: 162;
$V_L$-CDR3: SEQ ID NO: 170.

In one embodiment, the DPP4-binding domain of the invention comprises a LCVR which comprises at least one, preferably at least two, more preferably the following three complementary-determining regions (CDRs):

$V_L$-CDR1: SEQ ID NO: 149;
$V_L$-CDR2: SEQ ID NO: 159;
$V_L$-CDR3: SEQ ID NO: 173.

In one embodiment, the DPP4-binding domain of the invention comprises a LCVR which comprises at least one, preferably at least two, more preferably the following three complementary-determining regions (CDRs):

$V_L$-CDR1: SEQ ID NO: 146;

$V_L$-CDR2: SEQ ID NO: 163;

$V_L$-CDR3: SEQ ID NO: 170.

In one embodiment, the DPP4-binding domain of the invention comprises a combination of (i) at least one, preferably at least two, more preferably three HCVR's CDRs and (ii) at least one, preferably at least two, more preferably three LCVR's CDRs, said combination being as defined in Table 3.

In one embodiment, the DPP4-binding domain of the invention comprises a combination of (i) three HCVR's CDRs and (ii) three LCVR's CDRs, said combination being as defined in Table 3.

3: 5826-8-R6A-E10, 5826-8-R5A-G8, 5826-8-R6A-H11, 5826-13-R3A-D5, 5826-13-R4A-H5, and 5826-13-R4A-H12.

In one embodiment, the DPP4-binding domain of the invention comprises a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12.

In one embodiment, the DPP4-binding domain of the invention comprises a combination of (i) three HCVR's CDRs and (ii) three LCVR's CDRs, said combination being that of clone 5826-13-R3A-A10 as defined in Table 3. In one embodiment, the DPP4-binding domain of the invention comprises a combination of (i) three HCVR's CDRs and (ii)

TABLE 3

Preferred combinations of HCVR's and LCVR's CDRs. The CDRs are defined by their SEQ ID NOs. First column indicates the clones name.

| Clone's name | $V_H$-CDR1 | $V_H$-CDR2 | $V_H$-CDR3 | $V_L$-CDR1 | $V_L$-CDR2 | $V_L$-CDR3 |
|---|---|---|---|---|---|---|
| 5826-8-R6A-A10 | 104 | 113 | 130 | 143 | 152 | 164 |
| 5826-8-R6A-B11 | 104 | 114 | 131 | 143 | 152 | 165 |
| 5826-8-R6A-D12 | 105 | 115 | 132 | 144 | 153 | 166 |
| 5826-8-R6A-E10 | 104 | 116 | 133 | 143 | 154 | 167 |
| 5826-8-R5A-G6 | 104 | 117 | 134 | 143 | 152 | 165 |
| 5826-8-R5A-G8 | 104 | 113 | 135 | 143 | 155 | 168 |
| 5826-8-R6A-H9 | 104 | 116 | 136 | 143 | 154 | 167 |
| 5826-8-R6A-H11 | 105 | 115 | 132 | 145 | 156 | 166 |
| 5826-8-R6A-H12 | 106 | 118 | 131 | 143 | 154 | 169 |
| 5826-13-R3A-A10 | 107 | 119 | 137 | 146 | 157 | 170 |
| 5826-13-R3A-B1 | 108 | 120 | 138 | 147 | 158 | 171 |
| 5826-13-R3A-B3 | 108 | 121 | 138 | 147 | 159 | 171 |
| 5826-13-R3A-D5 | 109 | 122 | 139 | 148 | 160 | 172 |
| 5826-13-R3A-D6 | 108 | 123 | 138 | 149 | 159 | 171 |
| 5826-13-R4A-E2 | 108 | 124 | 138 | 147 | 159 | 171 |
| 5826-13-R4A-E6 | 110 | 125 | 140 | 146 | 161 | 170 |
| 5826-13-R4A-E9 | 108 | 126 | 141 | 149 | 159 | 171 |
| 5826-13-R4A-F10 | 108 | 126 | 138 | 150 | 159 | 171 |
| 5826-13-R4A-G11 | 108 | 126 | 138 | 150 | 159 | 171 |
| 5826-13-R4A-G12 | 111 | 127 | 138 | 151 | 159 | 171 |
| 5826-13-R4A-H1 | 110 | 128 | 140 | 146 | 162 | 170 |
| 5826-13-R4A-H2 | 108 | 126 | 141 | 149 | 159 | 171 |
| 5826-13-R4A-H3 | 108 | 126 | 138 | 149 | 159 | 173 |
| 5826-13-R4A-H4 | 112 | 125 | 140 | 146 | 162 | 170 |
| 5826-13-R4A-H5 | 108 | 127 | 138 | 147 | 159 | 171 |
| 5826-13-R4A-H6 | 108 | 127 | 142 | 147 | 159 | 171 |
| 5826-13-R4A-H9 | 108 | 123 | 138 | 149 | 159 | 171 |
| 5826-13-R4A-H10 | 110 | 125 | 140 | 146 | 162 | 170 |
| 5826-13-R4A-H11 | 110 | 128 | 140 | 146 | 162 | 170 |
| 5826-13-R4A-H12 | 110 | 125 | 140 | 146 | 163 | 170 |

In one embodiment, the DPP4-binding domain of the invention comprises a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the DPP4-binding domain of the invention comprises a combination of (i) three HCVR's CDRs and (ii) three LCVR's CDRs, said combination being that of any one of the following clones as defined in Table three LCVR's CDRs, said combination being that of clone 5826-13-R3A-B1 as defined in Table 3. In one embodiment, the DPP4-binding domain of the invention comprises a combination of (i) three HCVR's CDRs and (ii) three LCVR's CDRs, said combination being that of clone 5826-13-R3A-B3 as defined in Table 3. In one embodiment, the DPP4-binding domain of the invention comprises a combination of (i) three HCVR's CDRs and (ii) three LCVR's CDRs, said combination being that of clone 5826-13-R3A-D5 as defined in Table 3. In one embodiment, the DPP4-binding domain of the invention comprises a combination of (i) three HCVR's CDRs and (ii) three LCVR's CDRs, said combination being that of clone 5826-13-R3A-D6 as defined in Table 3. In one embodiment, the DPP4-binding domain of the invention comprises a combination of (i) three HCVR's CDRs and (ii) three LCVR's CDRs, said combination being that of clone 5826-13-R4A-E2 as defined in Table 3. In one embodiment, the DPP4-binding domain of the invention comprises a combination of (i) three HCVR's CDRs and (ii) three LCVR's CDRs, said combination being that of clone 5826-13-R4A-E6 as defined in Table 3. In one embodiment, the DPP4-binding domain of the invention comprises a combination of (i) three HCVR's CDRs and (ii) three LCVR's CDRs, said combination being that of clone 5826-13-R4A-E9 as defined in Table 3. In one embodiment, the DPP4-binding domain of the invention comprises a combination of (i) three HCVR's CDRs and (ii) three LCVR's CDRs, said combination being that of clone 5826-13-R4A-F10 as defined in Table 3. In one embodiment, the DPP4-binding domain of the invention comprises a combination of (i) three HCVR's CDRs and (ii) three LCVR's CDRs, said combination being that of clone 5826-13-R4A-G11 as defined in Table 3. In one embodiment, the DPP4-binding domain of the invention comprises a combination of (i) three HCVR's CDRs and (ii) three LCVR's CDRs, said combination being that of clone 5826-13-R4A-G12 as defined in Table 3. In one embodiment, the DPP4-binding domain of the invention comprises a combination of (i) three HCVR's CDRs and (ii) three LCVR's CDRs, said combination being that of clone 5826-13-R4A-H1 as defined in Table 3. In one embodiment, the DPP4-binding domain of the invention comprises a combination of (i) three HCVR's CDRs and (ii) three LCVR's CDRs, said combination being that of clone 5826-13-R4A-H2 as defined in Table 3. In one embodiment, the DPP4-binding domain of the invention comprises a combination of (i) three HCVR's CDRs and (ii) three LCVR's CDRs, said combination being that of clone 5826-13-R4A-H3 as defined in Table 3. In one embodiment, the DPP4-binding domain of the invention comprises a combination of (i) three HCVR's CDRs and (ii) three LCVR's CDRs, said combination being that of clone 5826-13-R4A-H4 as defined in Table 3. In one embodiment, the DPP4-binding domain of the invention comprises a combination of (i) three HCVR's CDRs and (ii) three LCVR's CDRs, said combination being that of clone 5826-13-R4A-H5 as defined in Table 3. In one embodiment, the DPP4-binding domain of the invention comprises a combination of (i) three HCVR's CDRs and (ii) three LCVR's CDRs, said combination being that of clone 5826-13-R4A-H6 as defined in Table 3. In one embodiment, the DPP4-binding domain of the invention comprises a combination of (i) three HCVR's CDRs and (ii) three LCVR's CDRs, said combination being that of clone 5826-13-R4A-H9 as defined in Table 3. In one embodiment, the DPP4-binding domain of the invention comprises a combination of (i) three HCVR's CDRs and (ii) three LCVR's CDRs, said combination being that of clone 5826-13-R4A-H10 as defined in Table 3. In one embodiment, the DPP4-binding domain of the invention comprises a combination of (i) three HCVR's CDRs and (ii) three LCVR's CDRs, said combination being that of clone 5826-13-R4A-H11 as defined in Table 3. In one embodiment, the DPP4-binding domain of the invention comprises a combination of (i) three HCVR's CDRs and (ii) three LCVR's CDRs, said combination being that of clone 5826-13-R4A-H12 as defined in Table 3.

In one embodiment, the DPP4-binding domain of the invention comprises a HCVR comprising or consisting of the sequence SEQ ID NO: 174; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 174.

SEQ ID NO: 174

```
EVQLEESGGGLVQPGRSLKLSCAASGFTFNNYGMAWVRQAPTKGLEWVATI

SYDGNDTYYRDSVKGRFTVSRDNAKSTLYLQMDSLRSEDTATYYCVRHRLI

YTTDYYYEVMDVWGQGASVTVSS
```

In one embodiment, the DPP4-binding domain of the invention comprises a HCVR comprising or consisting of the sequence SEQ ID NO: 175; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 175.

SEQ ID NO: 175

```
QVQLKESGGGLVQPGRSLKLSCAASGFTFSNYGMAWVRQAPTKGLEWVATT

SYDGNDTYYRDSVKGRFTVSRDNAKNTLYLQMDSLRSEDTATYYCVRHRLI

YTTDYYYEVMDAWGQGASVTVSS
```

In one embodiment, the DPP4-binding domain of the invention comprises a HCVR comprising or consisting of the sequence SEQ ID NO: 176; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 176.

SEQ ID NO: 176

```
QVTLKESGPGILQPSQTLSLTCSFSGFSLSTSDRCVSWIRQPSGKGLEWLA

TICWDDSKGYNPSLKNRLTISKDTSNNQAFLKITSVGTADIAKYYCARNSG

DGRFAYWGQGTLVTVSS
```

In one embodiment, the DPP4-binding domain of the invention comprises a HCVR comprising or consisting of the sequence SEQ ID NO: 177; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 177.

SEQ ID NO: 177

```
EVQLEESGGGLVQPGRSLKLSCAASGFTFSNYGMAWVRQAPTKGLEWVATI

NYDGRNTYYRDSVKGRFTISRDNAKSTLYLQVDSLQSEDTATYYCTRHKLI

YTTDYYYEVMDAWGQGASVTVSS
```

In one embodiment, the DPP4-binding domain of the invention comprises a HCVR comprising or consisting of the sequence SEQ ID NO: 178; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 178.

SEQ ID NO: 178

```
EVKLVESGGGLVQPGRSLKLSCAASGFSFTNYGMAWVRQAPTKGLEWVATI

NYDGSNTYYRDSVKGRFTISRDNAKRTLDLQMDSLRSEDTATYYCARHRLM

YTTDYYYEVMDDWGQGASVTVSS
```

In one embodiment, the DPP4-binding domain of the invention comprises a HCVR comprising or consisting of the sequence SEQ ID NO: 179; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 179.

SEQ ID NO: 179
EVKLVESGGGLVQPGRSLKLSCAASGFSFRNYGMAWVRQAPTKGQEWVATI
SYDGNDTYYRDSVKGRFTVSRDNAKSTLYLQMDSLRSEDTATYYCTRHRLI
YTTDYYYEVLDAWGQGASVTVSS

In one embodiment, the DPP4-binding domain of the invention comprises a HCVR comprising or consisting of the sequence SEQ ID NO: 180; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 180.

SEQ ID NO: 180
EVKLVESGGGLVQPGRSLKLSCTASGFTFSNYGMAWVRQAPTKGLEWVATI
NYDGRNTYYRDSVKGRFTISRDNAKSTLYLQVDSLQSEDTATYYCTRHKLI
YTTDYYYEVMDVWGQGASVAVSS

In one embodiment, the DPP4-binding domain of the invention comprises a HCVR comprising or consisting of the sequence SEQ ID NO: 181; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 181.

SEQ ID NO: 181
EVKLVESGGALVQPGRSLKLSCAASGFTFSNFGMAWVRQAPTKGLEWVATI
NYDGRDTYYRDSVKGRFTVSRDNAKSTLYLQMDSLRSEDTATYYCTRHRLI
YTTDYYYEVMDAWGRGASVTVSS

In one embodiment, the DPP4-binding domain of the invention comprises a HCVR comprising or consisting of the sequence SEQ ID NO: 182; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 182.

SEQ ID NO: 182
EVKLVESGPGLVKPSQSLSLACSITDYSITDNYWGWIRKFPGNKMEWIGHI
SHSGSSTYNPSLKSRISFTRDTSKNQFFLQLNSVTPEDTATYFCARYGAGA
SFDYWGQGVMVTVSS

In one embodiment, the DPP4-binding domain of the invention comprises a HCVR comprising or consisting of the sequence SEQ ID NO: 183; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 183.

SEQ ID NO: 183
EVQLQQSGAELTKPGSSVKISCKASGFTFTTYDIGWLKQRPGQALEWIGYI
NPGSGGIGYNEKFKGKATLTVDKSSSTAFMQLSSLTPEDTAVYYCARPLRR
VLDYWGQGVMVTVSS

In one embodiment, the DPP4-binding domain of the invention comprises a HCVR comprising or consisting of the sequence SEQ ID NO: 184; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 184.

SEQ ID NO: 184
EVQLQQSGAGLTKPGASVKISCKASGYTFTTYDIGWIKQRPGQALEWIGSI
NPGSGGIAYSEKFKGKATLTVDKSSSTAFMQLSSLTPEDTAVYYCARPLRR
VLDYWGQGVLVTVSS

In one embodiment, the DPP4-binding domain of the invention comprises a HCVR comprising or consisting of the sequence SEQ ID NO: 185; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 185.

SEQ ID NO: 185
EVKLVESGPGLVKPSQSLSLTCSVTGYFITGNYLAWIRKFPGNKMEWIGHI
KSSGTTTYNPSLKSRVSITRDTSKNQFFLQLNSVTSEDTATYYCARHGHYV
MDVWGQGASVTVSS

In one embodiment, the DPP4-binding domain of the invention comprises a HCVR comprising or consisting of the sequence SEQ ID NO: 186; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 186.

SEQ ID NO: 186
EVQLQQSGAELTKPGSSVKISCKASGYTFTTYDIGWIKQRPGQALEWIGSI
NPGSGGIGYNERFKGKATLTVDKSSSTAFMQLSSLTPEDTAVYYCARPLRR
VLDYWGQGVMVTVSS

In one embodiment, the DPP4-binding domain of the invention comprises a HCVR comprising or consisting of the sequence SEQ ID NO: 187; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 187.

SEQ ID NO: 187
QVQLKQSGAELTKPGSSVKISCKASGYTFTTYDIGWLKQRPGQALEWIGYI
NPGGGGIGYNEKFKGKATLTVDKSSSTAFMQLSSLTPEDTAVYYCARPLRR
VLDYWGQGVMVTVSS

In one embodiment, the DPP4-binding domain of the invention comprises a HCVR comprising or consisting of the sequence SEQ ID NO: 188; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 188.

SEQ ID NO: 188

DVKLQESGPGLVKPSQSLSLTCSVTGHSITSNYWGWIRKFPGNKMEWIGQI

SHSGSTSYNPSLKSRISITRDTSKNQFFLQLNSVTTEDTATYYCGRYGAGS

SFDYWGQGVMVTVSS

In one embodiment, the DPP4-binding domain of the invention comprises a HCVR comprising or consisting of the sequence SEQ ID NO: 189; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 189.

SEQ ID NO: 189

EVQLQQSGAELTKPGSSVKISCKASGYTFTTYDIGWIKQRPGQALEWIGSI

NPGSGGIGYNEKFKGKATLTVDKSSSTVFMQLSSLTPEDTAVYYCARPLRR

VLDNWGQGVLVTVSS

In one embodiment, the DPP4-binding domain of the invention comprises a HCVR comprising or consisting of the sequence SEQ ID NO: 190; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 190.

SEQ ID NO: 190

EVQLQQSGAELAKPGSSVKISCKASGYTFTTYDIGWIKQRPGQALEWIGSI

NPGSGGIGYNEKFKGKATLTVDKSSRTVFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 191; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 191.

SEQ ID NO: 191

EVQLQQSGPELAKPGSSVKISCKASGYTFTTYDIGWIKQRPGQALEWIGSI

NPGSGGIGYNEKFKGKATLTVDKSSSTAFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 192; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 192.

SEQ ID NO: 192

EVQLQQSGAGLTKPGASVKISCTASGYTFTTYDRGWLRQRPGQALEWIGSI

NPGGGGTGYNEKFKGNATLTVDKSSSTAFMQLSSLTPEDTADYYCARPLRR

VLDYWGQGVLVTVSS

In one embodiment, the DPP4-binding domain of the invention comprises a HCVR comprising or consisting of the sequence SEQ ID NO: 193; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 193.

SEQ ID NO: 193

DVKLQESGPGLVKPSQSLSLTCSVTGHSITSNYWGWIRKLPGNKMEWIGQI

SHSGSTSYNPSLISRISITRDTSNQFFLQLNSVTTEDTATYYCGRYGAGSS

FDYWGQGVMVTVSS

In one embodiment, the DPP4-binding domain of the invention comprises a HCVR comprising or consisting of the sequence SEQ ID NO: 194; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 194.

SEQ ID NO: 194

EVQLQQSGAELTKPGSSVKISCKASGYTFTTYDIGWIKQRPGQALEWIGSI

NPGSGGIGYNEKFKGKATLTVDRSSSTAFMQLSSLTPEDTAVYYCARPLRR

VLDNWGQGVLVTVSS

In one embodiment, the DPP4-binding domain of the invention comprises a HCVR comprising or consisting of the sequence SEQ ID NO: 195; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 195.

SEQ ID NO: 195

EVQLQQSGGELTKPGSSVKISCKASGYTFSTYDIGWIKQRPGQALEWIGSI

NPGSGGIGYNEKFKGKATLTVDKSSSTAFMQLSSLTPEDTAVYYCARPLRR

VLDYWGQGVMVTVSS

In one embodiment, the DPP4-binding domain of the invention comprises a HCVR comprising or consisting of the sequence SEQ ID NO: 196; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 196.

SEQ ID NO: 196

DVKLQESGPGLVKPSQSLSLTCSVTGHSITGNYWGWIRKFPGNKMEWIGQI

SHSGSTSYNPSLKSRISITRDTSKNQFFLQLNSVTTEDTATYYCGRYGAGS

SFDYWGQGVMVTVSS

In one embodiment, the DPP4-binding domain of the invention comprises a HCVR comprising or consisting of the sequence SEQ ID NO: 197; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 197.

SEQ ID NO: 197
EVQLQQSGAGLTKPGGSVKISCKVSGYTFTTYDIGWLKQRPGQALEWIGSI

NPGGGGTGYNEKFKGKATLTVDKSSSTAFMQLSSLTPEDTAVYYCARPLRR

VLDYWGQGVLVTVSS

In one embodiment, the DPP4-binding domain of the invention comprises a HCVR comprising or consisting of the sequence SEQ ID NO: 198; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 198.

SEQ ID NO: 198
EVQLQQSGAGLTKPGASVKISCKASGYTFTTYDIGWLKQRPGQALEWIGSI

NPGGGGTGYNEKFKGKATLTVDKSSSTAFMQLSSLTPEDTAVYYCARPLRV

LDYWGQGVLVTVSS

In one embodiment, the DPP4-binding domain of the invention comprises a HCVR comprising or consisting of the sequence SEQ ID NO: 199; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 199.

SEQ ID NO: 199
EVQLQQSGAELTKPGSSVKISCKASGYTFTTYDIGWIKQRPGQALEWIGSI

NPGSGGIGYNERFKGKATLTVDKSSSTAFMQLSSLTPEDTAVYYCARPLRR

VLDYWGRGVMVTVSS

In one embodiment, the DPP4-binding domain of the invention comprises a HCVR comprising or consisting of the sequence SEQ ID NO: 200; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 200.

SEQ ID NO: 200
EVQLEESGPGLVKPSQSLSLTCSVTGHSITSNYWGWIRKFPGNKMEWIGQI

SHSGSTSYNPSLKSRISITRDTSKNQFFLQLNSVTTEDTATYYCGRYGAGS

SFDYWGQGVMVTVSS

In one embodiment, the DPP4-binding domain of the invention comprises a HCVR comprising or consisting of the sequence SEQ ID NO: 201; or a HCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 201.

SEQ ID NO: 201
QVQLKESGPGLVKPSHSLSLTCSVTGHSITSNYWGWIRKFPGNKMEWIGQI

SHTGSSTYNPSLKSRISFTRDTSKNQFFLQLNSVTTEDSATYYCGRYGAGS

SFDYWGQGVMVTVSS

In one embodiment, the DPP4-binding domain of the invention comprises a LCVR comprising or consisting of the sequence SEQ ID NO: 202; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 202.

SEQ ID NO: 202
DVLMTQTPSSQAASAGEKVTMSCKSSQSLLYNENKKNYLAWFQQKPGQSPK

LLIYWASTRESGVPDRFIGGGSGTDFTLTISSVQAEDLAVYYCQEYYKFPW

TFGGGTKLELK

In one embodiment, the DPP4-binding domain of the invention comprises a LCVR comprising or consisting of the sequence SEQ ID NO: 203; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 203.

SEQ ID NO: 203
DIVMTQSPSSQAVSAGEKVTMSCKSSQSLLYNENKKNYLAWFQQKPGQSPK

LLIYWASTRESGVPDRFIGSGSGTDFTLTISSVQAEDLAVYYCQDYYHFPW

TFGGGTKLELK

In one embodiment, the DPP4-binding domain of the invention comprises a LCVR comprising or consisting of the sequence SEQ ID NO: 204; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 204.

SEQ ID NO: 204
DVLMTQTPPTLSATIGQSVSISCKSSQSLLHSNGNTYLNWLLQRPGQSPQL

LIYSVSKLESGVPNRFSGSGSQTDFTLKISEVEAEDMGVYYCMQATHAPFT

FGSWTKLEIK

In one embodiment, the DPP4-binding domain of the invention comprises a LCVR comprising or consisting of the sequence SEQ ID NO: 205; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 205.

SEQ ID NO: 205
DIVMTQAPSSQAVSPGEKVTMSCKSSQSLLYNENKKNYLAWYQQKPGQSPK

LLIYWASTREAGVPDRFIGSGSGTDFTLTISSVQAEDLAVYYCQQYYKFPW

PFGGGTKLELK

In one embodiment, the DPP4-binding domain of the invention comprises a LCVR comprising or consisting of the sequence SEQ ID NO: 206; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 206.

SEQ ID NO: 206
DIVMTQAPSSQAVSAGEKVTMSCKSSQSLLYNENKKNYLAWFQQKPGQSPK

LLIYWASTRKSGVPDRFIGSGSGTDFTLTISSVQAEDLAVYYCQQYYKFPW

TFGGGTKLELR

In one embodiment, the DPP4-binding domain of the invention comprises a LCVR comprising or consisting of the sequence SEQ ID NO: 207; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 207.

SEQ ID NO: 207
DIVMTQSPSSQAVSPGEKVTMNCKSSQSLLYNENKKNYLAWYQQKPGQSPK

LLIYWASTREAGVPDRFIGSGSGTDFTLTISSVQAEDLAVYYCQQYYKFPW

PFGGGTKLELK

In one embodiment, the DPP4-binding domain of the invention comprises a LCVR comprising or consisting of the sequence SEQ ID NO: 208; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 208.

SEQ ID NO: 208
DVLMTQTPPTLSATIGQSVSISCRSSQSLLHSNGNTYLNWLLQRPGQSPQL

LIYSVSNLESGVPNRFSGSGSETDFTLKISGVEAEDLGVYYCMQATHAPFT

FGSGTKLEIK

In one embodiment, the DPP4-binding domain of the invention comprises a LCVR comprising or consisting of the sequence SEQ ID NO: 209; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 209.

SEQ ID NO: 209
DIVMTQSPSSQAVSPGEKVTMNCKSSQSLLYNENKKNYLAWYQQKPGQSPK

LLIYWASTREAGVPDRFIGSGSGTDFTLTISSVQAEDLAVYYCQQYYKFPY

TFGAGTKLELK

In one embodiment, the DPP4-binding domain of the invention comprises a LCVR comprising or consisting of the sequence SEQ ID NO: 210; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 210.

SEQ ID NO: 210
DIQLTQSPHSLSASLGETVSIECLASEGISNYLAWYQQKPGKSPQLLIYYT

SSLQDGVPSRFSGSGSGTQYSLKISNMQPEDEGVYYCQQGYKYPWTFGGGT

KLELK

In one embodiment, the DPP4-binding domain of the invention comprises a LCVR comprising or consisting of the sequence SEQ ID NO: 211; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 211.

SEQ ID NO: 211
DIVMTQSPSSLPASLGERVTISCRASQGISNKLNWYQQKPDGTIKPLIYYT

SRLQSGVPSRFSGSGSGTDYSLTISSLEPEDFAMYYCQQDASFPPTFGAGT

KVELK

In one embodiment, the DPP4-binding domain of the invention comprises a LCVR comprising or consisting of the sequence SEQ ID NO: 212; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 212.

SEQ ID NO: 212
DIQLTQSPSSLPASLGERVTISCRASQGISNKLNWYQQKPDGTIKPLIYYT

SNLQSGVPSRFSGSGSGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 213; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 213.

SEQ ID NO: 213
DIVLTQSPVLAVSLGQRATISCRASQSVSTSTYNFMHWYQQKPGQQPRLLI

YDASHLASSVPARFSGSGSGTDFTLTINPVQADDIATYYCQQSRELPLTFG

SGTKLEIK

In one embodiment, the DPP4-binding domain of the invention comprises a LCVR comprising or consisting of the sequence SEQ ID NO: 214; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 214.

SEQ ID NO: 214
DILMTQSPSSLSASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK

In one embodiment, the DPP4-binding domain of the invention comprises a LCVR comprising or consisting of the sequence SEQ ID NO: 215; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 215.

```
SEQ ID NO: 215
DIQLTQSPSSLPASLGERVTISCRASQGISNKLNWYQQKPDGTIKPLIYYT

SNLQSGVPSRFSGSGSGTDYSLTISSLEPEDFAMYFCQQDASFPPTFGGGT

KLELK
```

In one embodiment, the DPP4-binding domain of the invention comprises a LCVR comprising or consisting of the sequence SEQ ID NO: 216; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 216.

```
SEQ ID NO: 216
DIQMTQTPHSLSASLGETVSIECLASEGISNYLAWYQQKPGKSPQLLIYYT

SSFQDGVPSRFSGSGSGTQYSLKISNMQPEDEGVYYCQQGYKYPWTFGGGT

KLELK
```

In one embodiment, the DPP4-binding domain of the invention comprises a LCVR comprising or consisting of the sequence SEQ ID NO: 217; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 217.

```
SEQ ID NO: 217
DILMTQSPSSRPASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK
```

In one embodiment, the DPP4-binding domain of the invention comprises a LCVR comprising or consisting of the sequence SEQ ID NO: 218; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 218.

```
SEQ ID NO: 218
DIQMTQTPSSLPASLGERVTISCRASQGISKKLNWYQQKPDGTIKPLIYYT

SNLQSGVPSRFSGSGSGTDYSLTISSLEPEDFAIYYCQQDASFPPTFGGGT

KLELK
```

In one embodiment, the DPP4-binding domain of the invention comprises a LCVR comprising or consisting of the sequence SEQ ID NO: 219; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 219.

```
SEQ ID NO: 219
DIQLTQSPSSLPASLGERVTISCRASQGISKKLNWYQQKPDGTIKPLIYYT

SNLQSGVPSRFSGSSGTDYSLTISSLEPEDFAMYYCQQDASFPPTFGGGTK

LELK
```

In one embodiment, the DPP4-binding domain of the invention comprises a LCVR comprising or consisting of the sequence SEQ ID NO: 220; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 220.

```
SEQ ID NO: 220
DILMTQSPSSLPASLGERVTISCGASQGIGNKVNWYQQKPDGTIKPLIYYT

SNLQSGVPSRFSGSGTGTDYSLTISSLEPEDFAMYYCQQDASFPPTFGGGT

KLELK
```

In one embodiment, the DPP4-binding domain of the invention comprises a LCVR comprising or consisting of the sequence SEQ ID NO: 221; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 221.

```
SEQ ID NO: 221
DIQMTQTPHSLSASLGETVSIECLASEGISNYLAWYQRKPGKSPQLLIYYT

ISLQDGVPSRFSGSGSGTQYSLKISNMQPEDEGVFYCQQGYKYPWTFGGGT

KLELK
```

In one embodiment, the DPP4-binding domain of the invention comprises a LCVR comprising or consisting of the sequence SEQ ID NO: 222; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 222.

```
SEQ ID NO: 222
DIQLTQSPSSLPASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK
```

In one embodiment, the DPP4-binding domain of the invention comprises a LCVR comprising or consisting of the sequence SEQ ID NO: 223; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 223.

```
SEQ ID NO: 223
DILMTQSPSSLSASLGERVTISCRASQGIGNKLNWYQQKPDGTIKPLIYYT

SNLQSGVPSRFSGSGSGTDYSLTISSLEPEDFAMYYCQQDTSFPPTFGAGT

KLELK
```

In one embodiment, the DPP4-binding domain of the invention comprises a LCVR comprising or consisting of the sequence SEQ ID NO: 224; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 224.

```
SEQ ID NO: 224
DIQMTQTPHSLSASLGETVSIECLASEGISNYLAWYQQKPGKSPQLLIYYT

ISLQDGVPSRFSGSGSGTQYSLKISNMQPEDEGVFYCQQGYKYPWTFGGGT

KLELK
```

In one embodiment, the DPP4-binding domain of the invention comprises a LCVR comprising or consisting of the sequence SEQ ID NO: 225; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 225.

```
SEQ ID NO: 225
DIQMTQTPSSLPASLERVTISCRASQGISNKLNWYQKKPDGTIKPLIYYTS

NLQSGVPSRFSGSGSGTDYSLTISSLEPEDFAMYFCQQDASFPPTFGGGTQ

LELK
```

In one embodiment, the DPP4-binding domain of the invention comprises a LCVR comprising or consisting of the sequence SEQ ID NO: 226; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 226.

```
SEQ ID NO: 226
DIQLTQSPSSRPASLGERVTISCRASQGIGNKLNWYQQKPDGTIKPLIYYT

SNLQSGVPSRFSGSGSGTDYSLTISSLEPEDFAMYYCQQDASFPPTFGGGT

KLELK
```

In one embodiment, the DPP4-binding domain of the invention comprises a LCVR comprising or consisting of the sequence SEQ ID NO: 227; or a LCVR comprising or consisting of a sequence sharing at least 70%, 75%, 80%, 85%, 90%, 95%, 96%, 97%, 98%, 99% or more sequence identity with the non-CDR regions (i.e., the framework regions) of SEQ ID NO: 227.

```
SEQ ID NO: 227
DIQMTQTPHSLSASLGETVSIECLASEGISNYLAWYQQKPGKSPQLLIYYA

SSLQDGVPSRFSGSGSGTQYSLKISNMQPEDEGVYYCQQGYKYPWTFGGGT

KLELK
```

In one embodiment, the DPP4-binding domain of the invention comprises a combination of (i) a HCVR and (ii) a LCVR, said combination being as defined in Table 4.

TABLE 4

Preferred combinations of HCVR and LCVR. The HCVR and LCVR are defined by their SEQ ID NOs. First column indicates the clone's name.

| Clone's name | HCVR | LCVR |
|---|---|---|
| 5826-8-R6A-A10 | 174 | 202 |
| 5826-8-R6A-B11 | 175 | 203 |
| 5826-8-R6A-D12 | 176 | 204 |
| 5826-8-R6A-E10 | 177 | 205 |
| 5826-8-R5A-G6 | 178 | 203 |
| 5826-8-R5A-G8 | 179 | 206 |
| 5826-8-R6A-H9 | 180 | 207 |
| 5826-8-R6A-H11 | 176 | 208 |
| 5826-8-R6A-H12 | 181 | 209 |
| 5826-13-R3A-A10 | 182 | 210 |
| 5826-13-R3A-B1 | 183 | 211 |
| 5826-13-R3A-B3 | 184 | 212 |
| 5826-13-R3A-D5 | 185 | 213 |
| 5826-13-R3A-D6 | 186 | 214 |
| 5826-13-R4A-E2 | 187 | 215 |
| 5826-13-R4A-E6 | 188 | 216 |
| 5826-13-R4A-E9 | 189 | 217 |
| 5826-13-R4A-F10 | 190 | 218 |
| 5826-13-R4A-G11 | 191 | 219 |
| 5826-13-R4A-G12 | 192 | 220 |
| 5826-13-R4A-H1 | 193 | 221 |
| 5826-13-R4A-H2 | 194 | 222 |
| 5826-13-R4A-H3 | 195 | 223 |
| 5826-13-R4A-H4 | 196 | 224 |
| 5826-13-R4A-H5 | 197 | 212 |
| 5826-13-R4A-H6 | 198 | 225 |
| 5826-13-R4A-H9 | 199 | 226 |
| 5826-13-R4A-H10 | 200 | 224 |
| 5826-13-R4A-H11 | 201 | 224 |
| 5826-13-R4A-H12 | 200 | 227 |

In one embodiment, the DPP4-binding domain of the invention comprises a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the DPP4-binding domain of the invention comprises a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12.

In one embodiment, the DPP4-binding domain of the invention comprises a combination of (i) a HCVR and (ii) a LCVR, combination being that of any one of the following clones as defined in Table 4: 5826-13-R3A-D5, 5826-13-R4A-H5, and 5826-13-R4A-H12.

In one embodiment, the DPP4-binding domain of the invention comprises a combination of (i) a HCVR and (ii) a LCVR, combination being that of clone 5826-13-R3A-A10 as defined in Table 4. In one embodiment, the DPP4-binding domain of the invention comprises a combination of (i) a HCVR and (ii) a LCVR, combination being that of clone 5826-13-R3A-B1 as defined in Table 4. In one embodiment, the DPP4-binding domain of the invention comprises a combination of (i) a HCVR and (ii) a LCVR, combination being that of clone 5826-13-R3A-B3 as defined in Table 4. In one embodiment, the DPP4-binding domain of the invention comprises a combination of (i) a HCVR and (ii) a LCVR, combination being that of clone 5826-13-R3A-D5 as defined in Table 4. In one embodiment, the DPP4-binding domain of the invention comprises a combination of (i) a HCVR and (ii) a LCVR, combination being that of clone 5826-13-R3A-D6 as defined in Table 4. In one embodiment, the DPP4-binding domain of the invention comprises a combination of (i) a HCVR and (ii) a LCVR, combination being that of clone 5826-13-R4A-E2 as defined in Table 4. In one embodiment, the DPP4-binding domain of the invention comprises a combination of (i) a HCVR and (ii) a LCVR, combination being that of clone 5826-13-R4A-E6 as defined in Table 4. In one embodiment, the DPP4-binding domain of the invention comprises a combination of (i) a HCVR and (ii) a LCVR, combination being that of clone 5826-13-R4A-E9 as defined in Table 4. In one embodiment, the DPP4-binding domain of the invention comprises a combination of (i) a HCVR and (ii) a LCVR, combination being that of clone 5826-13-R4A-F10 as defined in Table 4. In one embodiment, the DPP4-binding domain of the invention comprises a combination of (i) a HCVR and (ii) a LCVR, combination being that of clone 5826-13-R4A-G11 as defined in Table 4. In one embodiment, the DPP4-binding domain of the invention comprises a combination of (i) a HCVR and (ii) a LCVR, combination being that of clone 5826-13-R4A-G12 as defined in Table 4. In one embodiment, the DPP4-binding domain of the invention comprises a combination of (i) a HCVR and (ii) a LCVR, combination being that of clone 5826-13-R4A-H1 as defined in Table 4. In one embodiment, the DPP4-binding domain of the invention comprises a combination of (i) a HCVR and (ii) a LCVR, combination being that of clone 5826-13-R4A-H2 as defined in Table 4. In one embodiment, the DPP4-binding domain of the invention comprises a combination of (i) a HCVR and (ii) a LCVR, combination being that of clone 5826-13-R4A-H3 as defined in Table 4. In one embodiment, the DPP4-binding domain of the invention comprises a combination of (i) a HCVR and (ii) a LCVR, combination being that of clone 5826-13-R4A-H4 as defined in Table 4. In one embodiment, the DPP4-binding domain of the invention comprises a combination of (i) a HCVR and (ii) a LCVR, combination being that of clone 5826-13-R4A-H5 as defined in Table 4. In one embodiment, the DPP4-binding domain of the invention comprises a combination of (i) a HCVR and (ii) a LCVR, combination being that of clone 5826-13-R4A-H6 as defined in Table 4. In one embodiment, the DPP4-binding domain of the invention comprises a combination of (i) a HCVR and (ii) a LCVR, combination being that of clone 5826-13-R4A-H9 as defined in Table 4. In one embodiment, the DPP4-binding domain of the invention comprises a combination of (i) a HCVR and (ii) a LCVR, combination being that of clone 5826-13-R4A-H10 as defined in Table 4. In one embodiment, the DPP4-binding domain of the invention comprises a combination of (i) a HCVR and (ii) a LCVR, combination being that of clone 5826-13-R4A-H11 as defined in Table 4. In one embodiment, the DPP4-binding domain of the invention comprises a combination of (i) a HCVR and (ii) a LCVR, combination being that of clone 5826-13-R4A-H12 as defined in Table 4.

Another object of the present invention is an isolated antibody or antigen-binding fragment thereof, wherein said antibody or antigen-binding fragment thereof recognizes and is capable of binding to a senescent cell-associated antigen, as defined hereinabove.

In one embodiment, the senescent cell-associated antigen is selected from the group comprising or consisting of DEP1 and DPP4.

In one embodiment, the isolated antibody or antigen-binding fragment thereof of the invention recognizes and is capable of binding to DEP1, such as, e.g., human DEP1, or orthologs thereof, including murine and rat DEP1. In one embodiment, the isolated antibody or antigen-binding fragment thereof of the invention recognizes and is capable of binding to human DEP1 (hDEP1) with SEQ ID NO: 1. In one embodiment, the isolated antibody or antigen-binding fragment thereof of the invention recognizes and is capable of binding to the extracellular domain of human DEP1 (hDEP1) comprising or consisting of amino acid residues 36-975 of SEQ ID NO: 1. Hence, the isolated antibody or antigen-binding fragment thereof of the invention is an isolated "anti-DEP1 antibody or antigen-binding fragment thereof".

In one embodiment, the isolated antibody or antigen-binding fragment thereof of the invention recognizes and is capable of binding to DPP4, such as, e.g., human DPP4 or orthologs thereof, including murine and rat DPP4. In one embodiment, the isolated antibody or antigen-binding fragment thereof of the invention recognizes and is capable of binding to human DPP4 (hDPP4) with SEQ ID NO: 101. In one embodiment, the isolated antibody or antigen-binding fragment thereof of the invention recognizes and is capable of binding to the extracellular domain of human DPP4 (hDPP4) comprising or consisting of amino acid residues 29-766 of SEQ ID NO: 101. Hence, the antigen-binding fragment of the invention is an isolated "anti-DPP4 antibody or antigen-binding fragment thereof".

In one embodiment, the isolated antibody or antigen-binding fragment thereof of the invention recognizes and is capable of binding to DEP1 and DPP4.

The binding between the anti-DEP1 antibody or antigen-binding fragment thereof of the invention and DEP1, or between the anti-DPP4 antibody or antigen-binding fragment thereof of the invention and DPP4, implies that said antibody or antigen-binding fragment thereof exhibits appreciable affinity for DEP1 or DPP4, respectively. In other words, the anti-DEP1 antibody or antigen-binding fragment thereof of the invention or the anti-DPP4 antibody or antigen-binding fragment thereof of the invention, is specific for, or is immunospecific for, or specifically binds to, DEP1 or DPP4, respectively.

An antibody or antigen-binding fragment thereof is said to be "specific for", "immunospecific for" or to "specifically bind to" an antigen if it reacts with said antigen (e.g., DEP1 and/or DPP4). An antibody or antigen-binding fragment thereof is said to be "specific for", "immunospecific for" or to "specifically bind to" an antigen if it recognizes and is capable of binding to antigen with a $K_D$-affinity constant less than or equal to $10^{-6}$ M, preferably less than or equal to $10^{-7}$ M, $5.10^{-8}$ M, $10^{-8}$ M, $5.10^{-9}$ M, $10^{-9}$ M or less; as may be determined, e.g., by biosensor analysis, particularly by Biacore Analysis.

In one embodiment, the isolated antibody or antigen-binding fragment thereof of the invention comprises an antigen-binding domain, as described hereinabove.

In one embodiment, the anti-DEP1 antibody or antigen-binding fragment thereof of the invention comprises a DEP1-binding domain, as described hereinabove.

In one embodiment, the anti-DEP1 antibody or antigen-binding fragment thereof of the invention comprises a DEP1-binding domain comprising a combination of (i) at least one, preferably at least two, more preferably three HCVR's CDRs and (ii) at least one, preferably at least two, more preferably three LCVR's CDRs, said combination being as defined in Table 1.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being as defined in Table 1.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of any one of the following clones as defined in Table 1: 5738-13-R4A-D11, and 5738-13-R2A-H4.

In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-C1 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-D3 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-D11 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R3A-F5 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-F1 1 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-H3 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R2A-H4 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-H9 as defined in Table 1. In one embodiment, the anti-DEP1 antibody or antigen-binding fragment thereof of the invention comprises a DEP1-binding domain comprising a combination of (i) three HCVR's CDRs and (ii) three LCVR's CDRs, said combination being that of clone 5738-13-R4A-H11 as defined in Table 1.

In one embodiment, the anti-DEP1 antibody or antigen-binding fragment thereof of the invention comprises a DEP1-binding domain comprising a combination of (i) a HCVR and (ii) a LCVR, said combination being as defined in Table 2.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-10-R4A-G12, 5738-13-R4A-D11, and 5738-13-R2A-H4.

In one embodiment, the anti-DEP1 antibody or antigen-binding fragment thereof of the invention comprises a DEP1-binding domain comprising a combination of (i) a HCVR and (ii) a LCVR, combination being that of any one of the following clones as defined in Table 2: 5738-13-R4A-D11, and 5738-13-R2A-H4.

In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-C1 as defined in Table 2.

In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-D3 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-D11 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R3A-F5 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-F11 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-H3 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R2A-H4 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-H9 as defined in Table 2. In one embodiment, the anti-DEP1 antibody or antigen-binding fragment thereof of the invention comprises a DEP1-binding domain comprising a combination of (i) a HCVR and (ii) a LCVR, combination being that of clone 5738-13-R4A-H11 as defined in Table 2.

In one embodiment, the anti-DPP4 antibody or antigen-binding fragment thereof of the invention comprises a DPP4-binding domain, as described hereinabove.

In one embodiment, the anti-DPP4 antibody or antigen-binding fragment thereof of the invention comprises a DPP4-binding domain comprising a combination of (i) at least one, preferably at least two, more preferably three HCVR's CDRs and (ii) at least one, preferably at least two, more preferably three LCVR's CDRs, said combination being as defined in Table 3.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being as defined in Table 3.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of any one of the following clones as defined in Table 3: 5826-8-R6A-E10, 5826-8-R5A-G8, 5826-8-R6A-H11, 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-A10 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-B1 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-B3 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-D5 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R3A-D6 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-E2 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-E6 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-E9 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-F10 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-G11 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-G12 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H1 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H2 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H3 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H4 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H5 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H6 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H9 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H10 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H11 as defined in Table 3. In one embodiment, the anti-DPP4 antibody or antigen-binding fragment thereof of the invention comprises a DPP4-binding domain comprising a combination of (i) three HCVR's CDRs and (ii) three LCVR's CDRs, said combination being that of clone 5826-13-R4A-H12 as defined in Table 3.

In one embodiment, the anti-DPP4 antibody or antigen-binding fragment thereof of the invention comprises a DPP4-binding domain comprising a combination of (i) a HCVR and (ii) a LCVR, said combination being as defined in Table 4.

In one embodiment, the anti-DPP4 antibody or antigen-binding fragment thereof of the invention comprises a DPP4-binding domain comprising a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the anti-DPP4 antibody or antigen-binding fragment thereof of the invention comprises a DPP4-binding domain comprising a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12.

In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-A10 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-B1 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-B3 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-D5 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R3A-D6 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-E2 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-E6 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-E9 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-F10 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-G11 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-G12 as defined in Table 4. 5826-13-R4A-H1 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H2 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H3 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H4 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H5 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H6 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H9 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H10 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H11 as defined in Table 4. In one embodiment, the anti-DPP4 antibody or antigen-binding fragment thereof of the invention comprises a DPP4-binding domain comprising a combination of (i) a HCVR and (ii) a LCVR, combination being that of clone 5826-13-R4A-H12 as defined in Table 4.

In one embodiment, the isolated antibody or antigen-binding fragment thereof of the invention is a molecule selected from the group comprising or consisting of a whole antibody, a single-chain variable fragment (scFv), a dimeric single-chain variable fragment (di-scFv, such as a tandem scFv or a diabody), a trimeric single-chain variable fragment (tri-scFv, such as a triabody), a tetrameric single-chain variable fragment (tetra-scFv, such as a tetrabody), a Fv, a Fab, a Fab', a Fab'-SH, a $F(ab')_2$, a Fabc, and a Fd.

In one embodiment, the isolated antibody or antigen-binding fragment thereof of the invention is a mimetic selected from the group comprising or consisting of an affibody, an alphabody, an armadillo repeat protein based scaffold, a knottin, a kunitz domain peptide, an affilin, an affitin, an adnectin, an atrimer, an evasin, a DARPin, an anticalin, an avimer, a fynomer, a versabody or a duocalin.

Antigen-binding fragment of antibodies comprising specific antigen-binding domains may be generated by known methods. Methods for producing such antigen-binding fragments of antibodies are known in the art, for example as described in Lo (Ed.), 2004. *Antibody Engineering: Methods and Protocols* (1$^{st}$ ed., Vol. 248). Totowa, NJ: Humana Press, and McCafferty. Hoogenboom & Chiswell (Eds.) 1996. *Antibody Engineering: a Practical Approach* (1$^{st}$ ed., Vol. 169). Oxford: IRL Press at Oxford University Press. For example, $F(ab')_2$ fragments can be produced by pepsin digestion of the whole antibody molecule, and Fab fragments can be generated by reducing the disulfide bridges of the $F(ab')_2$ fragments. Alternatively, Fab expression libraries may be constructed to allow rapid and easy identification of monoclonal Fab fragments with the desired specificity, as described for example in Huse et al., 1989. *Science.* 246 (4935):1275-81.

Antibodies may be generated using known methods. For the production of antibodies, various hosts including goats, rabbits, rats, mice, humans, and others, may be immunized by injection with an appropriate antigen. Depending on the host species, various adjuvants may be used to increase an immunological response. Such adjuvants include Freund's adjuvant, mineral gels such as aluminium hydroxide, and surface-active substances such as lysolecithin, pluronic polyols, polyanions, peptides, oil emulsions, keyhole limpet hemocyanin, and dinitrophenol. Adjuvants are commercially available.

In one embodiment, the isolated antibody or antigen-binding fragment thereof of the invention is polyclonal. In another embodiment, the isolated antibody or antigen-binding fragment thereof of the invention is monoclonal.

Methods of producing polyclonal and monoclonal antibodies as well as fragments thereof are well known in the art (see, for example, Harlow and Lane, Antibodies: A Laboratory Manual, Cold Spring Harbor Laboratory, New York, 1988).

In one embodiment, the isolated antibody or antigen-binding fragment thereof of the invention is a purified antibody or a purified antigen-binding fragment thereof. In one embodiment, the isolated antibody or antigen-binding fragment thereof of the invention is purified to:

(1) greater than 80%, 85%, 90%, 91%, 92%, 93%, 94%, 95% or more by weight of antibody or antigen-binding fragment thereof, as may be determined, e.g., by the Lowry method; and most preferably more than 96%, 97%, 98% or 99% by weight of antibody or antigen-binding fragment thereof;

(2) a degree sufficient to obtain at least 15 amino acid residues of the N-terminal, or of an internal, amino acid sequence, e.g., by use of a spinning cup sequenator; and/or (3) homogeneity as shown, e.g., by SDS-PAGE under reducing or non-reducing conditions and using, e.g., Coomassie blue staining or more preferably silver staining.

In one embodiment, the isolated antibody or antigen-binding fragment thereof of the invention has an isotype selected from the group comprising or consisting of IgG (including IgG1, IgG2, IgG3 and IgG4), IgM, IgA (including IgA1 and IgA2), IgD and IgE. The immunoglobulin subclasses or "isotypes" (e.g., IgA1, etc.).

The constant region of an antibody is important in the ability of an antibody to fix complement and mediate cell-dependent cytotoxicity and phagocytosis. Thus, as discussed herein, the isotype of an antibody may be selected on the basis of whether it is desirable for the antibody to mediate cytotoxicity/phagocytosis. Determination or selection of the isotype of an antibody may be by known methods in the art.

In one embodiment, the isolated antibody or antigen-binding fragment thereof of the invention is a murine, a chimeric or a humanized antibody or antigen-binding fragment thereof.

In one embodiment, the isolated antibody or antigen-binding fragment thereof of the invention is a murine antibody or antigen-binding fragment thereof.

A "murine antibody or antigen-binding fragment thereof" refers to those antibodies or antigen-binding fragments thereof in which the variable region (including the CDRs and FRs) and the constant region are derived from a mouse.

In one embodiment, the isolated antibody or antigen-binding fragment thereof of the invention is a chimeric antibody or antigen-binding fragment thereof.

A "chimeric antibody or antigen-binding fragment thereof" broadly refers to an antibody or antigen-binding fragment thereof comprising a first amino acid sequence linked to a second amino acid sequence with which it is not naturally linked in nature. The amino acid sequences may normally exist in separate proteins that are brought together in the fusion protein or they may normally exist in the same protein but are placed in a new arrangement in the fusion protein. A chimeric protein may be created, for example, by chemical synthesis, or by creating and translating a polynucleotide in which the peptide regions are encoded in the desired relationship. The term "chimeric antibody or antigen-binding fragment thereof" encompasses herein antibodies and antigen-binding fragments thereof in which:

(a) the constant region (Fc), or a portion thereof, is altered, replaced or exchanged so that the variable region is linked to a constant region of a different or altered class, effector function and/or species, or an entirely different molecule which confers new properties to the chimeric antibody, e.g., an enzyme, toxin, hormone, growth factor, drug, etc.; or (b) the variable region (Fv), or a portion thereof, is altered, replaced or exchanged with a variable region, or portion thereof, having a different or altered antigen specificity; or with corresponding sequences from another species or from another antibody class or subclass.

Method to produce chimeric antibodies are well known in the art. For example, chimeric antibodies may be produced as described in Morrison et al., 1984. *Proc Natl Acad Sci USA*. 81(21):6851-5; Neuberger et al., 1984. *Nature*. 312 (5995):604-608; and Takeda et al., 1985. *Nature*. 314(6010): 452-454.

In one embodiment, the isolated antibody or antigen-binding fragment thereof of the invention is a humanized antibody or antigen-binding fragment thereof.

A "humanized antibody or antigen-binding fragment thereof" refers to a chimeric antibody or antigen-binding fragment thereof which contains only minimal sequence derived from a non-human immunoglobulin. It includes antibodies made by a non-human cell having variable and constant regions which have been altered to more closely resemble antibodies that would be made by a human cell, e.g., by altering the non-human antibody amino acid sequence to incorporate amino acids found in human germline immunoglobulin sequences. Humanized antibodies or antigen-binding fragment thereof of the invention may include amino acid residues not encoded by human germline immunoglobulin sequences (e.g., mutations introduced by random or site-specific mutagenesis in vitro or by somatic mutation in vivo), for example in the CDRs. The term "humanized antibody or antigen-binding fragment thereof" also includes antibodies and antigen-binding fragment thereof in which CDR sequences derived from the germline of another mammalian species, such as a mouse, have been grafted onto human framework sequences. In other words, the term "humanized antibody or antigen-binding fragment thereof" refers to an antibody or antigen-binding fragment thereof in which the CDRs of a recipient human antibody are replaced by CDRs from a donor non-human antibody. Humanized antibodies or antigen-binding fragments thereof may also comprise residues of donor origin in the framework sequences. The humanized antibody or antigen-binding fragment thereof can also comprise at least a portion of a human immunoglobulin constant region. Humanized antibodies and or antigen-binding fragments thereof may also comprise residues which are found neither in the recipient antibody nor in the imported CDR or framework sequences. Humanization can be performed using methods known in the art (e.g., Jones et al., 1986. *Nature*. 321(6069):522-5; Riechmann et al., 1988. *Nature*. 332(6162):323-7; Verhoeyen et al., 1988. *Science*. 239(4847):1534-6; Presta, 1992. *Curr Opin Biotechnol*. 3(4):394-8; U.S. Pat. No. 4,816,567), including techniques such as "superhumanizing" antibodies (e.g., Tan et al., 2002. *J Immunol*. 169(2):1119-25) and "resurfacing" (e.g., Staelens et al., 2006. *Mol Immunol*. 43(8):1243-57; Roguska et al., 1994. *Proc Natl Acad Sci USA*. 91(3):969-73). A "humanized antibody or antigen-binding fragment thereof" retains a similar antigenic specificity as the original antibody. However, using certain methods of humanization, the affinity and/or specificity of binding of the antibody may be increased.

Methods for humanizing the isolated antibody or antigen-binding fragment thereof of the invention are well-known in the art. The choice of human variable domains, both light and heavy, to be used in making the humanized antibody or antigen-binding fragment thereof is very important to reduce antigenicity. According to the so-called "best-fit" method, the sequence of the variable domain of an isolated antibody or antigen-binding fragment thereof of the invention is screened against the entire library of known human variable-domain sequences. The human sequence that is closest to the mouse sequence is then accepted as the human framework (FR) for the humanized antibody (Sims et al., 1993. *J Immunol*. 151(4):2296-308; Chothia & Lesk, 1987. *J Mol Biol*. 196(4):901-17). Another method for humanizing the isolated antibody or antigen-binding fragment thereof of the invention uses a particular framework from the consensus sequence of all human antibodies of a particular subgroup of light or heavy chains. The same framework can be used for several different humanized antibodies (Carter et al., 1992. *Proc Natl Acad Sci USA*. 89(10):4285-9; Presta et al., 1993. J Immunol. 151(5):2623-32). It is further important that antibodies be humanized with retention of high affinity for DEP1 or DPP4 and other favorable biological properties. To achieve this goal, according to a preferred method, humanized antibodies and antigen-binding fragments thereof are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its epitope. In this way, CDR residues can be selected and combined from the consensus and import sequences so that the desired antibody characteristic, such as an increased affinity for DEP1 or DPP4, is achieved. In general, the CDR residues are directly and most substantially involved in influencing antigen binding.

Another method for humanizing the isolated antibody or antigen-binding fragment thereof of the invention is to use a transgenic or transchromosomic animal carrying parts of the human immune system for immunization. As a host, these animals have had their immunoglobulin genes replaced by functional human immunoglobulin genes. Thus, antibodies produced by these animals or in hybridomas made from the B cells of these animals are already humanized. Examples of such transgenic or transchromosomic animal include, without limitation:

the XenoMouse (Abgenix, Fremont, CA), described in U.S. Pat. Nos. 5,939,598, 6,075,181, 6,114,598, 6,150,584 and 6,162,963;

the HuMAb Mouse® (Medarex, Inc.), described in Lonberg et al., 1994. Nature. 368(6474):856-859; Lonberg & Huszar, 1995. *Int Rev Immunol*. 13(1):65-93; Harding & Lonberg, 1995. *Ann N Y Acad Sci*. 764:536-46; Taylor et al., 1992. *Nucleic Acids Res*. 20(23):6287-95; Chen et al., 1993. *Int Immunol*. 5(6):647-56; Tuaillon et al., 1993. *Proc Natl Acad Sci USA*. 90(8):3720-4; Choi et al., 1993. *Nat Genet.* 4(2):117-23; Chen et al., 1993. *EMBO J.* 12(3):821-30; Tuaillon et al., 1994. *J Immunol.* 152(6):2912-20; Taylor et al., 1994. *Int Immunol.* 6(4):579-91; Fishwild et al., 1996. *Nat Biotechnol.* 14(7):845-51;

the KM Mouse®, described in Patent application WO2002043478;

the TC mice, described in Tomizuka et al., 2000. *Proc Natl Acad Sci USA.* 97(2):722-7; and the OmniRat™ (OMT, Inc.), described in Patent application WO2008151081; Geurts et al., 2009. *Science.* 325(5939):433; Menoret et al., 2010. *Eur J Immunol.* 40(10):2932-41.

Humanized antibodies and antigen-binding fragments thereof may also be produced according to various other techniques, such as by using, for immunization, other transgenic animals that have been engineered to express a human antibody repertoire (Jakobovitz et al., 1993. *Nature.* 362 (6417):255-8), or by selection of antibody repertoires using phage display methods. Such techniques are known to the skilled person and can be implemented starting from monoclonal antibodies or antigen-binding fragments thereof as disclosed in the present application.

Whether chimeric or humanized, the isolated antibody or antigen-binding fragment thereof of the invention may comprise a constant region (Fc) of human origin.

In one embodiment, especially when the isolated antibody or antigen-binding fragment thereof of the invention is intended for human therapeutic uses, it is typical for the entire constant region (Fc), or at least a part thereof, to have a fully or substantially human amino acid sequence. Therefore, one or more of, or any combination of, the $C_H1$ domain, hinge region, $C_H2$ domain, $C_H3$ domain and $C_L$ domain and $C_H4$ domain (when present) may be fully or substantially human with respect to its amino acid sequence. Advantageously, the CHI domain, hinge region, $C_H2$ domain, $C_H3$ domain and $C_L$ domain and $C_H4$ domain (when present) may all have a fully or substantially human amino acid sequence.

The term "substantially human", in the context of the constant region (Fc) of a chimeric or humanized antibody or antigen-binding fragment thereof, refers to an amino acid sequence identity of at least 70%, preferably at least 75%, 80%, 85%, 90%, 95%, 96%, 97%, 98%, 99% or more with a human constant region (Fc).

The term "human amino acid sequence", in this context, refers to an amino acid sequence which is encoded by a human immunoglobulin gene, which includes germline, rearranged and somatically mutated genes. The present invention also contemplates proteins comprising constant domains of "human" sequence which have been altered, by one or more amino acid additions, deletions or substitutions with respect to the human sequence, excepting those embodiments where the presence of a "fully human hinge region" is expressly required.

The presence of a "fully human hinge region" in the isolated antibody or antigen-binding fragment thereof of the invention may be beneficial both to minimize immunogenicity and to optimize stability of the antibody. It is considered that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g., by addition or deletion of N- or O-linked glycosylation sites). Depending on the intended use of the antibody or antigen-binding fragment thereof, it may be desirable to modify the isolated antibody or antigen-binding fragment thereof of the invention with respect to its binding properties to Fc receptors, for example to modulate effector function. For example, cysteine residue(s) may be introduced in the Fc region, thereby allowing interchain disulfide bond formation in this region. The homodimeric antibody thus generated may have improved effector function (Caron et al., 1992. *J Exp Med.* 176(4):1191-5; Shopes, 1992. *J Immunol.* 148(9): 2918-22).

In one embodiment, the isolated antibody or antigen-binding fragment thereof of the invention may be a bispecific antibody (BsAb) with antigen binding to at least two senescent cell-associated antigens. In one embodiment, the isolated antibody or antigen-binding fragment thereof of the invention may be a bispecific antibody (BsAb) which binds to both DEP1 and DPP4.

In one embodiment, the isolated antibody or antigen-binding fragment thereof of the invention may be a bispecific antibody (BsAb) with antigen binding to at one senescent cell-associated antigen and one non-senescent cell-associated antigen. In one embodiment, the isolated antibody or antigen-binding fragment thereof of the invention may be a bispecific antibody (BsAb) which binds to either of DEP1 or DPP4 on the one hand, and to one non-senescent cell-associated antigen on the other hand.

In one embodiment, the non-senescent cell-associated antigen is a T cell receptor or part thereof, such as, e.g., any one of the CD3δ, CD3γ, CD3ε or CD3ζ subunit.

Examples of bispecific antibodies (BsAb) include, but are not limited to, quadromas, knobs-in-holes, CrossMab Fab, CrossMab VH-VL, CrossMab $C_H1$-$C_L$, TriMab, one-arm single-chain Fab-immunoglobulin gamma (OAscFab-IgG), disulfide stabilized Fv-IgG (dsFv-IgG), DuetMab, controlled Fab-arm exchanged-IgG1 (cFAE-IgG1), charged pair scFv-Fc, strand-exchange engineered domain body (SEED-body), two-arm leucine zipper heterodimeric monoclonal antibodies (two-arm LUZ-Y), kappa lambda body (κλ-body), bi-specific T cell engagers (BiTEs), diabodies, .tandab, dual-affinity retargeting molecules (DARTs), bispecific killer cell engagers (BiKEs), trispecific killer cell engagers (TriKEs), monomeric Fc-VH (mFc-VH) and Fc antigen binding (Fcab), all reviewed and described in Liu et al., 2017 (*Front Immunol.* 8:38).

Methods for producing bispecific antibodies (BsAb) are well known in the art.

In one embodiment, the isolated antibody or antigen-binding fragment thereof of the invention is a recombinant isolated antibody or antigen-binding fragment thereof.

Thus accordingly, the isolated antibody or antigen-binding fragment thereof of the invention may be produced recombinantly by methods known in the art, such as, e.g., by expression in *Escherichia coli* expression systems (see, e.g., U.S. Pat. No. 4,816,567). Antigen binding fragment may also be produced by phage display technologies, which are known in the art.

It will also be appreciated that the isolated antibody or antigen-binding fragment thereof of the invention can be modified using methods well known in the art, e.g., to improve the properties of the isolated antibody or antigen-binding fragment thereof. For example, to slow clearance in vivo and obtain a more desirable pharmacokinetic profile, the isolated antibody or antigen-binding fragment thereof may be modified with polyethylene glycol (PEG). Methods for coupling and site-specifically conjugating PEG to an antibody or antigen-binding fragment thereof are described in, e.g., Leong et al., 2001. *Cytokine.* 16(3):106-19; Delgado et al., 1996. *Br J Cancer.* 73(2):175-82. Another non-limiting example of modification consist in the modification of the human Fc region of the antibody in order to enhance their affinity for an Fcγ receptor. Methods of enhancing Fc receptor binding include Fc amino acid modification and modification of Fc carbohydrate structures. For immunoglobulins, it has been demonstrated that the attachment of an N-linked oligosaccharide to Asn-297 of the $C_H2$ domain is critical for ADCC activity.

Removal of the N-linked oligosaccharide through mutation of the N-linked consensus site or by enzymatic means results in little or no ADCC activity. Removal of the core α-1,6-fucose moiety from IgG1 Fc oligosaccharides has been demonstrated to improve FcγRIII binding and ADCC activity (see, e.g., Carter, 2001. *Nat Rev Cancer.* 1(2):118-29; Kanda et al., 2007. *Glycobiology.* 17(1):104-18; Shields et al., 2002. *J Biol Chem.* 277(30):26733-40; Shinkawa et al., 2003. *J Biol Chem.* 278(5):3466-73; Niwa et al., 2004. *Cancer Res.* 64(6):2127-33). The level of another glycoform, bisected N-linked carbohydrate, has also been suggested to increase ADCC (see, e.g., Umaña et al., 1999. *Nat Biotechnol.* 17(2):176-80; Hodoniczky et al., 2005. *Biotechnol Prog.* 21(6):1644-52). A variety of Fc sequence variants with optimized binding affinity for FcγRs and/or enhanced ADCC have been described and are known in the art.

In one embodiment, the isolated antibody or antigen-binding fragment thereof of the invention targets, blocks, depletes and/or kills senescent cells to which it is bound.

In one embodiment, the isolated antibody or antigen-binding fragment thereof of the invention targets, blocks, depletes and/or kills senescent cells expressing at least one senescent cell-associated antigen, as defined hereinabove.

In one embodiment, the isolated antibody or antigen-binding fragment thereof of the invention may comprise human HCCRs (heavy chain constant regions) and allows to target, block, deplete and/or kill DEP1-expressing cells to which it is bound.

In one embodiment, the isolated antibody or antigen-binding fragment thereof of the invention may comprise human HCCRs (heavy chain constant regions) and allow to target, block, deplete and/or kill DPP4-expressing cells to which it is bound.

In one embodiment where the isolated antibody or antigen-binding fragment thereof is a bispecific antibody as described above, said bispecific antibody may comprise human HCCRs (heavy chain constant regions) and allow to target, block, and/or deplete DEP1- and/or DPP4-expressing cells to which it is bound.

In one embodiment, the isolated antibody or antigen-binding fragment thereof of the invention depletes and/or kills DEP1-expressing cells to which it is bound.

In one embodiment, the isolated antibody or antigen-binding fragment thereof of the invention depletes and/or kills DPP4-expressing cells to which it is bound.

In one embodiment where the isolated antibody or antigen-binding fragment thereof is a bispecific antibody as described above, said bispecific antibody depletes and/or kills DEP1- and/or DPP4-expressing cells to which it is bound.

By "deplete" or "depleting", it is referred to the killing, elimination, lysis, or induction of such killing, elimination or lysis, so as to negatively affect the number of cells to which the isolated antibody or antigen-binding fragment thereof is bound (such as, e.g., DEP1- and/or DPP4-expressing cells) present in a sample or in a subject. In one embodiment, such depletion occurs via ADCC. In one embodiment, such depletion occurs via ADCP. In one embodiment, such depletion occurs via CDC.

Thus, in one embodiment, the isolated antibody or antigen-binding fragment thereof of the invention leads, directly or indirectly, to the depletion of senescent cells, in particular of DEP1- and/or DPP4-expressing cells.

In one embodiment, the isolated antibody or antigen-binding fragment thereof of the invention leads, directly or indirectly, to the depletion of 10%, 20%, 30%, 40%, 50%, 60%, 70%, 80%, 90% or more of senescent cells, in particular of DEP1- and/or DPP4-expressing cells.

In one embodiment, the isolated antibody or antigen-binding fragment thereof of the invention leads, directly or indirectly, to a decrease by 10%, 20%, 30%, 40%, 50%, 60%, 70%, 80%, 90% or more elimination of the number of senescent cells, in particular of DEP1- and/or DPP4-expressing cells.

In one embodiment, the isolated antibody or antigen-binding fragment thereof of the invention induces any one or several, such as two or three, of:

antibody dependent cellular cytotoxicity (ADCC);
antibody-dependent cell-mediated phagocytosis (ADCP);
complement-dependent cytotoxicity (CDC).

In one embodiment, the isolated antibody or antigen-binding fragment thereof of the invention is from the IgG1 subclass and has any one or several, such as two or three, of:

antibody dependent cellular cytotoxicity (ADCC);
antibody-dependent cell-mediated phagocytosis (ADCP);
complement-dependent cytotoxicity (CDC).

In one embodiment, the isolated antibody or antigen-binding fragment thereof of the invention is linked/fused/conjugated to a payload, e.g., a therapeutic moiety. Such conjugates are referred to herein as an "antibody drug conjugates" or "ADCs".

In one embodiment, the payload is selected from chemotherapeutic agents, targeted therapy agents, cytotoxic agents, antibiotics, antivirals, cell cycle-synchronizing agents, ligands for cellular receptor(s), immunomodulatory agents, pro-apoptotic agents, anti-angiogenic agents, cytokines, growth factors, hormones, coding or non-coding oligonucleotides, photodetectable labels, contrast agents, radiolabels, and the like. Another object of the present invention is a nucleic acid encoding the antigen-binding domain, the antibody or the antigen-binding fragment thereof of the invention.

Another object of the present invention is a vector comprising the nucleic acid encoding the antigen-binding domain, the antibody or the antigen-binding fragment thereof of the invention.

In one embodiment, the vector is an expression vector and further comprises regulatory elements allowing for expression of the antigen-binding domain, the antibody or the antigen-binding fragment thereof, in a cell.

In one embodiment, the expression vector may be monocistronic. By "monocistronic", it is meant that a single nucleic acid encoding a single protein is expressed in a single expression vector.

In one embodiment, the expression vector comprises a sequence encoding the HCVR of the antigen-binding domain, the antibody or the antigen-binding fragment thereof of the invention, preferably operably linked to regulatory elements.

In one embodiment, the expression vector comprises a sequence encoding the HCVR of the DEP1-binding domain, the anti-DEP1 antibody or the antigen-binding fragment thereof of the invention, preferably operably linked to regulatory elements.

In one embodiment, the expression vector comprises a sequence encoding the HCVR of the DEP1-binding domain, the anti-DEP1 antibody or the antigen-binding fragment of the invention, preferably operably linked to regulatory elements, said sequence being selected from the group comprising or consisting of SEQ ID NOs: 55 to 74.

In one embodiment, the expression vector comprises a sequence encoding the HCVR of the DPP4-binding domain, the anti-DPP4 antibody or the antigen-binding fragment of the invention, preferably operably linked to regulatory elements.

In one embodiment, the expression vector comprises a sequence encoding the HCVR of the DPP4-binding domain, the anti-DPP4 antibody or the antigen-binding fragment of the invention, preferably operably linked to regulatory elements, said sequence being selected from the group comprising or consisting of SEQ ID NOs: 174 to 201.

In one embodiment, the expression vector comprises a sequence encoding the LCVR of the antigen-binding domain, the antibody or the antigen-binding fragment thereof of the invention, preferably operably linked to regulatory elements.

In one embodiment, the expression vector comprises a sequence encoding the LCVR of the DEP1-binding domain, the anti-DEP1 antibody or the antigen-binding fragment of the invention, preferably operably linked to regulatory elements.

In one embodiment, the expression vector comprises a sequence encoding the LCVR of the DEP1-binding domain, the anti-DEP1 antibody or the antigen-binding fragment of the invention, preferably operably linked to regulatory elements, said sequence being selected from the group comprising or consisting of SEQ ID NOs: 75 to 94.

In one embodiment, the expression vector comprises a sequence encoding the LCVR of the DPP4-binding domain, the anti-DPP4 antibody or the antigen-binding fragment of the invention, preferably operably linked to regulatory elements.

In one embodiment, the expression vector comprises a sequence encoding the LCVR of the DPP4-binding domain, the anti-DPP4 antibody or the antigen-binding fragment of the invention, preferably operably linked to regulatory elements, said sequence being selected from the group comprising or consisting of SEQ ID NOs: 202 to 227.

In one embodiment, the expression vector may be polycistronic. By "polycistronic", it is meant that at least two or more nucleic acids, each encoding a single protein, are expressed in a single expression vector.

In one embodiment, the expression vector comprises:

- a sequence encoding the HCVR of the antigen-binding domain, the antibody or the antigen-binding fragment thereof of the invention, preferably operably linked to regulatory elements, and
- a sequence encoding the LCVR of the antigen-binding domain, the antibody or the antigen-binding fragment thereof of the invention, preferably operably linked to regulatory elements.

In one embodiment, the expression vector comprises:

- a sequence encoding the HCVR of the DEP1-binding domain, the anti-DEP1 antibody or the antigen-binding fragment of the invention, preferably operably linked to regulatory elements, and
- a sequence encoding the LCVR of the DEP1-binding domain, the anti-DEP1 antibody or the antigen-binding fragment of the invention, preferably operably linked to regulatory elements.

In one embodiment, the expression vector comprises:

- a sequence encoding the HCVR of the DEP1-binding domain, the anti-DEP1 antibody or the antigen-binding fragment of the invention, preferably operably linked to regulatory elements, said sequence being selected from the group comprising or consisting of SEQ ID NOs: 55 to 74, and
- a sequence encoding the LCVR of the DEP1-binding domain, the anti-DEP1 antibody or the antigen-binding fragment of the invention, preferably operably linked to regulatory elements, said sequence being selected from the group comprising or consisting of SEQ ID NOs: 75 to 94.

In one embodiment, the expression vector comprises:

- a sequence encoding the HCVR of the DEP1-binding domain, the anti-DEP1 antibody or the antigen-binding fragment of the invention, preferably operably linked to regulatory elements, and
- a sequence encoding the LCVR of the DEP1-binding domain, the anti-DEP1 antibody or the antigen-binding fragment of the invention, preferably operably linked to regulatory elements, wherein said sequence encoding the HCVR and said sequence encoding the LCVR are selected from the group comprising or consisting of the combinations of HCVR and LCVR as defined in Table 2.

In one embodiment, the expression vector comprises:

- a sequence encoding the HCVR of the DPP4-binding domain, the anti-DPP4 antibody or the antigen-binding fragment of the invention, preferably operably linked to regulatory elements, and
- a sequence encoding the LCVR of the DPP4-binding domain, the anti-DPP4 antibody or the antigen-binding fragment of the invention, preferably operably linked to regulatory elements.

In one embodiment, the expression vector comprises:

- a sequence encoding the HCVR of the DPP4-binding domain, the anti-DPP4 antibody or the antigen-binding fragment of the invention, preferably operably linked to regulatory elements, said sequence being selected from the group comprising or consisting of SEQ ID NOs: 174 to 201, and
- a sequence encoding the LCVR of the DPP4-binding domain, the anti-DPP4 antibody or the antigen-binding fragment of the invention, preferably operably linked to regulatory elements, said sequence being selected from the group comprising or consisting of SEQ ID NOs: 202 to 227.

In one embodiment, the expression vector comprises:

- a sequence encoding the HCVR of the DPP4-binding domain, the anti-DPP4 antibody or the antigen-binding fragment of the invention, preferably operably linked to regulatory elements, and
- a sequence encoding the LCVR of the DPP4-binding domain, the anti-DPP4 antibody or the antigen-binding fragment of the invention, preferably operably linked to regulatory elements, wherein said sequence encoding the HCVR and said sequence encoding the LCVR are selected from the group comprising or consisting of the combinations of HCVR and LCVR as defined in Table 4.

Another object of the invention is a method of producing and purifying the isolated antibody or antigen-binding fragment thereof of the invention.

In one embodiment, the method comprises:

culturing host cells comprising the nucleic acid or expression vector of the present invention, under conditions suitable for expression of the antibody or antigen-binding fragment thereof, and recovering the expressed antibody or antigen-binding fragment thereof.

This recombinant process can be used for large scale production of antibodies or antigen-binding fragments thereof, including monoclonal antibodies intended for in vitro, ex vivo and/or in vivo therapeutic and/or diagnostic uses.

The nucleic acid or expression vector encoding the antibody or antigen-binding fragment, as described herein, may be propagated and expressed according to any of a variety of routinely practiced procedures for nucleic acid excision, ligation, transformation, and transfection. In certain embodiments, expression of the antibody or antigen-binding fragment thereof may be carried out in a prokaryotic host cell (i.e., the host cell comprising the nucleic acid or expression vector of the present invention is a prokaryotic host cell), such as *Escherichia coli* (see, e.g., Pluckthun et al., 1989. Methods Enzymol. 178:497-515). In certain other embodiments, the antibody or antigen-binding fragment thereof may be expressed in a eukaryotic host cell (i.e., the host cell comprising the nucleic acid or expression vector of the present invention is an eukaryotic host cell), including animal cells (such as mammalian cells), yeast (e.g., *Saccharomyces cerevisiae, Schizosaccharomyces pombe*, or *Pichia pastoris*); and plant cells. Examples of suitable animal cells include, but are not limited to, myeloma, HEK293, COS, or CHO cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the cellular polypeptide may be inserted. The regulatory elements will vary as appropriate for the particular host.

All these processes are well known in the art (Subramanian (Ed.), 2004. *Antibodies* (1st ed., Vol. 1: Production and Purification). New York, NY: Springer US).

In an embodiment, the expressed antibody or antigen-binding fragment thereof is further purified.

Methods to purify the antibody or antigen-binding fragment thereof of the invention are well known in the art (Subramanian (Ed.), 2004. *Antibodies* (1st ed., Vol. 1: Production and Purification). New York, NY: Springer US), and include, without limitation, chromatography, preferably by affinity chromatography, more preferably by affinity chromatography on protein L agarose.

Another object of the present invention is a chimeric antigen receptor (CAR) comprising:

(i) at least one extracellular binding domain, comprising or consisting of at least one antigen-binding domain directed to a senescent cell-associated antigen, (ii) an extracellular spacer domain, (iii) a transmembrane domain, (iv) optionally, at least one costimulatory domain, and (v) at least one intracellular signaling domain.

In one embodiment, the CAR of the invention comprises at least one extracellular binding domain (also called ectodomain), wherein said at least one extracellular binding domain recognizes and is capable of binding to a senescent cell-associated antigen, as defined hereinabove. In one embodiment, the extracellular binding domain comprises or consists of an antigen-binding domain directed to a senescent cell-associated antigen, which recognizes and is capable of binding to a senescent cell-associated antigen, as defined hereinabove.

In one embodiment, the senescent cell-associated antigen is selected from the group comprising or consisting of DEP1 and DPP4. Hence, in one embodiment, the at least one extracellular binding domain of the CAR of the invention recognizes and is capable of binding to DEP1 and/or DPP4. In one embodiment, the extracellular binding domain comprises or consists of an antigen-binding domain directed to DEP1 and/or DPP4, which recognizes and is capable of binding to DEP1 and/or DPP4, as defined hereinabove.

In one embodiment, the at least one extracellular binding domain in the CAR of the invention recognizes and is capable of binding to DEP1, such as, e.g., human DEP1, or orthologs thereof, including murine and rat DEP1. In one embodiment, the at least one extracellular binding domain in the CAR of the invention recognizes and is capable of binding to human DEP1 (hDEP1) with SEQ ID NO: 1. In one embodiment, the at least one extracellular binding domain in the CAR of the invention recognizes and is capable of binding to the extracellular domain of human DEP1 (hDEP1) comprising or consisting of amino acid residues 36-975 of SEQ ID NO: 1. In one embodiment, the extracellular binding domain comprises or consists of a DEP1-binding domain, as defined hereinabove. Hence, the CAR of the invention is an "anti-DEP1 chimeric antigen receptor (CAR)".

In one embodiment, the at least one extracellular binding domain in the CAR of the invention recognizes and is capable of binding to DPP4, such as, e.g., human DPP4 or orthologs thereof, including murine and rat DPP4. In one embodiment, the at least one extracellular binding domain in the CAR of the invention recognizes and is capable of binding to human DPP4 (hDPP4) with SEQ ID NO: 101. In one embodiment, the at least one extracellular binding domain in the CAR of the invention recognizes and is capable of binding to the extracellular domain of human DPP4 (hDPP4) comprising or consisting of amino acid residues 29-766 of SEQ ID NO: 101. In one embodiment, the extracellular binding domain comprises or consists of a DPP4-binding domain, as defined hereinabove. Hence, the CAR of the invention is an "anti-DDP4 chimeric antigen receptor (CAR)".

In one embodiment, the at least one extracellular binding domain in the CAR of the invention comprises an antigen-binding domain, as described hereinabove.

In one embodiment, the extracellular binding domain of the anti-DEP1 chimeric antigen receptor (CAR) of the invention comprises a DEP1-binding domain, as described hereinabove.

In one embodiment, the extracellular binding domain of the anti-DEP1 chimeric antigen receptor (CAR) of the invention comprises a DEP1-binding domain comprising a combination of (i) at least one, preferably at least two, more preferably three HCVR's CDRs and (ii) at least one, preferably at least two, more preferably three LCVR's CDRs, said combination being as defined in Table 1.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being as defined in Table 1.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of any one of the following clones as defined in Table 1: 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-C1 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-D3 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R4A-D1 1 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R3A-F5 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R4A-F11 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-H3 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R2A-H4 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R4A-H9 as defined in Table 1. In one embodiment, the extracellular binding domain of the anti-DEP1 chimeric antigen receptor (CAR) of the invention comprises a DEP1-binding domain comprising a combination of (i) three HCVR's CDRs and (ii) three LCVR's CDRs, said combination being that of clone 5738-13-R4A-H11 as defined in Table 1.

In one embodiment, the extracellular binding domain of the anti-DEP1 chimeric antigen receptor (CAR) of the invention comprises a DEP1-binding domain comprising a combination of (i) a HCVR and (ii) a LCVR, said combination being as defined in Table 2.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-10-R4A-G12, 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of any one of the following clones as defined in Table 2: 5738-13-R4A-D11, and 5738-13-R2A-H4.

In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-C1 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-D3 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-D11 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R3A-F5 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-F11 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-H3 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R2A-H4 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-H9 as defined in Table 2. In one embodiment, the extracellular binding domain of the anti-DEP1 chimeric antigen receptor (CAR) of the invention comprises a DEP1-binding domain comprising a combination of (i) a HCVR and (ii) a LCVR, combination being that of clone 5738-13-R4A-H11 as defined in Table 2.

In one embodiment, the extracellular binding domain of the anti-DPP4 chimeric antigen receptor (CAR) of the invention comprises a DPP4-binding domain, as described hereinabove.

In one embodiment, the extracellular binding domain of the anti-DPP4 chimeric antigen receptor (CAR) of the invention comprises a DPP4-binding domain comprising a combination of (i) at least one, preferably at least two, more preferably three HCVR's CDRs and (ii) at least one, preferably at least two, more preferably three LCVR's CDRs, said combination being as defined in Table 3.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being as defined in Table 3.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of any one of the following clones as defined in Table 3: 5826-8-R6A-E10, 5826-8-R5A-G8, 5826-8-R6A-H11, 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-A10 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-B1 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-B3 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-D5 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R3A-D6 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-E2 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-E6 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-E9 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-F10 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-G11 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-G12 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H1 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H2 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H3 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H4 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H5 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H6 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H9 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H10 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H11 as defined in Table 3. In one embodiment, the extracellular binding domain of the anti-DPP4 chimeric antigen receptor (CAR) of the invention comprises a DPP4-binding domain comprising a combination of (i) three HCVR's CDRs and (ii) three LCVR's CDRs, said combination being that of clone 5826-13-R4A-H12 as defined in Table 3.

In one embodiment, the extracellular binding domain of the anti-DPP4 chimeric antigen receptor (CAR) of the invention comprises a DPP4-binding domain comprising a combination of (i) a HCVR and (ii) a LCVR, said combination being as defined in Table 4.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-GT 1, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12.

In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-A10 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-B1 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-B3 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-D5 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R3A-D6 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-E2 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-E6 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-E9 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-F10 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-G11 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-G12 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H1 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H2 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H3 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H4 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H5 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H6 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H9 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H10 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H11 as defined in Table 4. In one embodiment, the extracellular binding domain of the anti-DPP4 chimeric antigen receptor (CAR) of the invention comprises a DPP4-binding domain comprising a combination of (i) a HCVR and (ii) a LCVR, combination being that of clone 5826-13-R4A-H12 as defined in Table 4.

In one embodiment, the extracellular binding domain of the CAR of the invention comprises or consists a single chain variable region (scFv) or a Fab fragment, preferably a scFv, comprising an one antigen-binding domain as defined hereinabove.

In one embodiment, the CAR of the invention comprises more than one extracellular binding domain, such as 2 extracellular binding domains, 3 extracellular binding domains or more. Such CARs are called "tandem CARs" or "multispecific CARs", such as bispecific, trispecific, etc.

In this embodiment, the CAR of the invention is multispecific and comprises extracellular binding domains, wherein at least one of the extracellular binding domains recognizes and is capable of binding to a senescent cell-associated antigen.

In one embodiment, the CAR of the invention is multispecific and comprises extracellular binding domains, each of which recognizes and is capable of binding to a different senescent cell-associated antigen.

In one embodiment, the CAR of the invention is multispecific and comprises extracellular binding domains, wherein one extracellular binding domain recognizes and is capable of binding to either of DEP1 or DPP4, and at least one other extracellular binding domain recognizes and is capable of binding to another senescent cell-associated antigen.

In one embodiment, the CAR of the invention is multispecific and comprises extracellular binding domains, wherein one extracellular binding domain recognizes and is capable of binding to DEP1, and at least one other extracellular binding domain recognizes and is capable of binding to DPP4.

In one embodiment, the CAR of the invention is bispecific and comprises two extracellular binding domains, wherein one extracellular binding domain recognizes and is capable of binding to DEP1, and the other extracellular binding domain recognizes and is capable of binding to DPP4.

In this embodiment, a) one extracellular binding domain of the bispecific CAR of the invention comprises a DEP1-binding domain comprising a combination of (i) at least one, preferably at least two, more preferably three HCVR's CDRs and (ii) at least one, preferably at least two, more preferably three LCVR's CDRs, said combination being as defined in Table 1; and
b) one extracellular binding domain of the bispecific CAR of the invention comprises a DPP4-binding domain comprising a combination of (i) at least one, preferably at least two, more preferably three HCVR's CDRs and (ii) at least one, preferably at least two, more preferably three LCVR's CDRs, said combination being as defined in Table 3, as described and defined hereinabove.

In this embodiment, a) one extracellular binding domain of the bispecific CAR of the invention comprises a DEP1-binding domain comprising a combination of (i) three HCVR's CDRs and (ii) three LCVR's CDRs, said combination being as defined in Table 1; and
b) one extracellular binding domain of the bispecific CAR of the invention comprises a DPP4-binding domain comprising a combination of (i) three HCVR's CDRs and (ii) three LCVR's CDRs, said combination being as defined in Table 3, as described and defined hereinabove.

In this embodiment, a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11; and
b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12, as described and defined hereinabove.

In this embodiment, a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-10-R3A-C6, 5738-10-R3A-D5, 5738-10-R4A-G12, 5738-13-R4A-D11, and 5738-13-R2A-H4; and b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-8-R6A-E10, 5826-8-R5A-G8, 5826-8-R6A-H11, 5826-13-R3A-D5, 5826-13-R4A-H5, and 5826-13-R4A-H12, as described and defined hereinabove.

In this embodiment, a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-10-R4A-G12, 5738-13-R4A-D11, and 5738-13-R2A-H4; and b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12, as described and defined hereinabove.

In this embodiment, a) one extracellular binding domain of the bispecific CAR of the invention comprises a DEP1-binding domain comprising a combination of (i) three HCVR's CDRs and (ii) three LCVR's CDRs, said combination being that of any one of the following clones as defined in Table 1: 5738-13-R4A-D11, and 5738-13-R2A-H4; and b) one extracellular binding domain of the bispecific CAR of the invention comprises a DPP4-binding domain comprising a combination of (i) three HCVR's CDRs and (ii) three LCVR's CDRs, said combination being that of any one of the following clones as defined in Table 3: 5826-13-R3A-D5, 5826-13-R4A-H5, and 5826-13-R4A-H12, as described and defined hereinabove.

In this embodiment, a) one extracellular binding domain of the bispecific CAR of the invention comprises a DEP1-binding domain comprising a combination of (i) a HCVR and (ii) a LCVR, said combination being as defined in Table 2; and b) one extracellular binding domain of the bispecific CAR of the invention comprises a DPP4-binding domain comprising a combination of (i) a HCVR and (ii) a LCVR, said combination being as defined in Table 4, as described and defined hereinabove.

In this embodiment, a) one extracellular binding domain of the bispecific CAR of the invention comprises a DEP1-binding domain comprising a combination of (i) a HCVR and (ii) a LCVR, combination being that of any one of the following clones as defined in Table 2: 5738-13-R2A-C1, 5738-13-R2A-D3, 5738-13-R4A-D11, 5738-13-R3A-F5, 5738-13-R4A-F11, 5738-13-R2A-H3, 5738-13-R2A-H4, 5738-13-R4A-H9, and 5738-13-R4A-H11; and b) one extracellular binding domain of the bispecific CAR of the invention comprises a DPP4-binding domain comprising a combination of (i) a HCVR and (ii) a LCVR, combination being that of any one of the following clones as defined in Table 4: 5826-13-R3A-A10, 5826-13-R3A-B1, 5826-13-R3A-B3, 5826-13-R3A-D5, 5826-13-R3A-D6, 5826-13-R4A-E2, 5826-13-R4A-E6, 5826-13-R4A-E9, 5826-13-R4A-F10, 5826-13-R4A-G11, 5826-13-R4A-G12, 5826-13-R4A-H1, 5826-13-R4A-H2, 5826-13-R4A-H3, 5826-13-R4A-H4, 5826-13-R4A-H5, 5826-13-R4A-H6, 5826-13-R4A-H9, 5826-13-R4A-H10, 5826-13-R4A-H11, and 5826-13-R4A-H12, as described and defined hereinabove.

In this embodiment, a) one extracellular binding domain of the bispecific CAR of the invention comprises a DEP1-binding domain comprising a combination of (i) a HCVR and (ii) a LCVR, combination being that of any one of the following clones as defined in Table 2: 5738-10-R3A-C6, 5738-10-R3A-D5, 5738-10-R4A-G12, 5738-13-R4A-D11, and 5738-13-R2A-H4; and b) one extracellular binding domain of the bispecific CAR of the invention comprises a DPP4-binding domain comprising a combination of (i) a HCVR and (ii) a LCVR, combination being that of any one of the following clones as defined in Table 4: 5826-8-R6A-E10, 5826-8-R5A-G8, 5826-8-R6A-H11, 5826-13-R3A-D5, 5826-13-R4A-H5, and 5826-13-R4A-H12, as described and defined hereinabove.

In this embodiment, a) one extracellular binding domain of the bispecific CAR of the invention comprises a DEP1-binding domain comprising a combination of (i) a HCVR and (ii) a LCVR, combination being that of any one of the following clones as defined in Table 2: 5738-10-R4A-G12, 5738-13-R4A-D11, and 5738-13-R2A-H4; and b) one extracellular binding domain of the bispecific CAR of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12, as described and defined hereinabove.

In this embodiment, a) one extracellular binding domain of the bispecific CAR of the invention comprises a DEP1-binding domain comprising a combination of (i) a HCVR and (ii) a LCVR, combination being that of any one of the following clones as defined in Table 2: 5738-13-R4A-D11, and 5738-13-R2A-H4; and b) one extracellular binding domain of the bispecific CAR of the invention comprises a DPP4-binding domain comprising a combination of (i) a HCVR and (ii) a LCVR, combination being that of any one of the following clones as defined in Table 4: 5826-13-R3A-D5, 5826-13-R4A-H5, and 5826-13-R4A-H12, as described and defined hereinabove.

Additionally or alternatively, the CAR of the invention is multispecific and comprises extracellular binding domains, wherein at least two extracellular binding domains recognize and are capable of binding to the same senescent cell-associated antigen, but on different epitopes of said senescent cell-associated antigen.

Such multispecific CARs typically comprise:

(i) two of more extracellular binding domains, as defined hereinabove, (ii) one extracellular spacer domain, (iii) one transmembrane domain, (iv) optionally, at least one costimulatory domain, and (v) at least one intracellular signaling domain.

In a multispecific CAR, each extracellular binding domain comprises or consists of a single chain variable region (scFv) or a Fab fragment. preferably a scFv, comprising the antigen-binding domain as defined hereinabove.

In one embodiment, the extracellular binding domains in the multispecific CAR of the invention are linked or fused together through a flexible peptidic linker, enabling each extracellular binding domain to form the desired structure for antigen binding (Pluckthun, 1994. "Antibodies from *Escherichia coli*". In Rosenberg & Moore (Eds.), *The pharmacology of monoclonal antibodies*. Handbook of Experimental Pharmacology, 113:269-315. Springer: Berlin, Heidelberg). Flexible peptidic linkers are generally composed of small, non-polar (e.g., glycine, Gly, G) or polar (e.g., serine, Ser, S; or threonine, Thr, T) amino acids, as suggested by Argos (1990. *J Mol Biol.* 211(4):943-958). The small size of these amino acids provides flexibility, and allows for mobility of the connecting functional domains, such as the extracellular binding domains. In one embodiment, the flexible peptidic linker may be a short oligo- or polypeptide, preferably having a length ranging from 2 to 30 amino acids. In one embodiment, the flexible peptidic linker comprises glycine-serine repeats. In one embodiment, the flexible peptidic linker comprises one, or several repeats of, such as 2, 3, 4, 5 or more repeats of, GS linker(s) (i.e., a sequence of one Gly and one Ser), G2S linker(s) (i.e., a sequence of two Gly and one Ser), G3S linker(s) (i.e., a sequence of three Gly and one Ser), G4S linker(s) (i.e., a sequence of four Gly and one Ser), or G5S linker(s) (i.e., a sequence of five Gly and one Ser).

In one embodiment, the CAR of the invention comprises an extracellular spacer domain (also called hinge domain).

In one embodiment, the at least one extracellular binding domain is connected to one transmembrane domain through one extracellular spacer domain.

The extracellular spacer domain typically facilitates proper protein folding, provides flexibility to the at least one extracellular binding domain and helps avoiding steric hindrance. It typically comprises a hydrophilic region linking the at least one extracellular binding domain and the transmembrane domain.

Extracellular spacer domains may include, but are not limited to, Fc fragments of antibodies or fragments or derivatives thereof, hinge regions of antibodies or fragments or derivatives thereof, $C_H2$ regions of antibodies, $C_H3$ regions antibodies, artificial spacer sequences or combinations thereof.

Examples of extracellular spacer domains include, but are not limited to, CD8α hinge; CD28 hinge; flexible peptidic linkers (such as, e.g., Gly3); or hinge region, $C_H1$, $C_H2$ and/or $C_H3$ domains of IgG's (such as human IgG4).

In one embodiment, the extracellular spacer domain is selected from the group comprising or consisting of (i) a hinge region, $C_H2$ domain and $C_H3$ domain of IgG4, (ii) a hinge region of IgG4, (iii) a hinge region and $C_H2$ domain of IgG4, (iv) a hinge region of CD8α, (v) a hinge region, $C_H2$ domain and $C_H3$ domain of IgG1, (vi) a hinge region of IgG1 (vii) a hinge region and $C_H2$ domain of IgG1, and (viii) a hinge region of CD28; and combinations thereof.

Additional extracellular spacer domains will be apparent to those skilled in the art and may be used in connection with alternate embodiments of the invention.

In one embodiment, the CAR of the invention comprises a transmembrane domain.

In one embodiment, the transmembrane domain comprises an amino acid sequence derived from the transmembrane domain of any protein which has such transmembrane domain, including any of the type I, type II or type III transmembrane proteins.

In one embodiment, the transmembrane domain may also comprise an artificial hydrophobic sequence.

Examples of transmembrane domains that are suitable in the CAR of the invention include, but are not limited to, transmembrane domains of an α, β or ζ chain of a T cell receptor, or of CD28, CD3γ, CD3δ, CD3ε, CD3ζ, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR (CD357), CD40, BAFFR, HVEM (LIGHTR), SLAMF7, NKp80 (KLRF1), CD160, CD19, IL2Rβ, IL2Rγ, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, PD1, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM (CD355), Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D or NKG2C.

In one embodiment, the transmembrane domain comprises an amino acid sequence derived from the transmembrane domain of CD28 or CD3ζ.

Additional transmembrane domains will be apparent to those skilled in the art and may be used in connection with alternate embodiments of the invention.

In one embodiment, the transmembrane domain may be recombinant, in which case it will comprise predominantly hydrophobic amino acids, such as, e.g., valine, Val, V or leucine, Leu, L.

In one embodiment, the CAR of the invention can optionally comprise one or several costimulatory domain(s).

Costimulatory domains enhance cell proliferation, cell survival and development of memory cells.

Examples of costimulatory domains that are suitable in the CAR of the invention include, but are not limited to, costimulatory domains of any of the members of the TNFR super family, CD28, CD137 (4-1BB), CD134 (OX40), Dap10, CD27, CD2, CD5, ICAM-1, Lck, TNFR-1, TNFR-II, Fas, CD30, CD40, CTLA-4, ICOS, PD-1, and combinations thereof.

Costimulatory domains from other proteins may also be used with the CARs of the invention. Additional costimulatory domains will be apparent to those skilled in the art and may be used in connection with alternate embodiments of the invention.

If the CAR of the invention comprises more than one costimulatory domain, these domains may be arranged in tandem, optionally separated by a linker, such as a flexible peptidic linker as has been described above.

In one embodiment, the costimulatory domain comprises a T cell costimulatory molecule, or a sequence derived therefrom.

In one embodiment, the CAR of the invention comprises at least one costimulatory domain selected from the group comprising or consisting of 4-1BB, ICOS, CD27, OX40, CD28, CTLA4 and PD-1.

In one embodiment, the CAR of the invention comprises at least one intracellular signaling domain (also called endodomain).

The intracellular signaling domain is cytoplasmic, and allows to transduce the effector function signal and direct the cell to perform its specialized function upon binding of the extracellular binding domain to its antigen.

Examples of intracellular signaling domains that are suitable in the CAR of the invention include, but are not limited to, ζ chain of the T cell receptor or any of its homologs (such as, e.g., η chain, FcεR1γ and β chains, MB1 (Igα) chain, B29 (Igβ) chain, etc.), CD3 polypeptides (such as, e.g., Δ, δ and ε), syk family tyrosine kinases (such as, e.g., Syk, ZAP 70, etc.), src family tyrosine kinases (such as, e.g., Lck, Fyn, Lyn, etc.) and other molecules involved in T cell transduction, such as, e.g., CD2, CD5 and CD28.

In one embodiment, the intracellular signaling domain may be human CD3 chain, FcγRIII, FcεRI, cytoplasmic tails of Fc receptors, immunoreceptor tyrosine-based activation motif (ITAM) bearing cytoplasmic receptors or combinations thereof. Additional intracellular signaling domains will be apparent to those skilled in the art and may be used in connection with alternate embodiments of the invention.

In one embodiment, the at least one intracellular signaling domain may comprise the entire intracellular portion, or the entire native intracellular signaling domain, of the molecule from which it is derived, or a functional fragment or derivative thereof.

In one embodiment, the at least one intracellular signaling domain comprises or consists of a T cell primary signaling domain (or a sequence derived therefrom).

In one embodiment, the T cell primary signaling domain comprises or consists of a signaling domain of a protein selected in the group of CD3ζ, CD3γ, CD3δ, CD3ε, common FcRγ (FCER1G), FcRε (Fc Epsilon Rib), CD79a, CD79b, FcγRIIa, DAP10, DAP12, and sequences derived therefrom.

In one embodiment, the T cell primary signaling domain comprises or consists of a functional signaling domain of CD3ζ.

T cell primary signaling domains that act in a stimulatory manner may comprise signaling motifs known as immunoreceptor tyrosine-based activation motifs (ITAMS).

Examples of ITAM containing T cell primary intracellular signaling domains that are of particular use in the invention include, but are not limited to, those of (or derived from) CD3ζ, common FcRγ (FCER1G), FcγRIIa, FcRβ (FcεFR1b), CD3γ, CD3δ, CD3ε, CD5, CD22, CD66b, CD79a, CD79b, DAP10, and DAP12.

In one embodiment, the T cell primary signaling domain comprises a modified ITAM domain (e.g., a mutated ITAM domain which has altered e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In one embodiment, a primary signaling domain comprises one, two, three, four or more ITAM motifs.

In one embodiment, the at least one intracellular signaling domain and the at least one costimulatory domain, if present, may be linked to each other in tandem, in a random or in a specified order.

Optionally, a linker, such as a flexible peptidic linker as has been described above, may form the linkage between distinct intracellular signaling domains, and/or between a costimulatory domain and an intracellular signaling domain. Besides flexible peptidic linkers described above, a single amino acid (such as, e.g., alanine, Ala, A or glycine, Gly, G) may also be a suitable linker.

In one embodiment, the CAR of the invention comprises more than one intracellular signaling domain, such as 2, 3, 4, 5, or more, intracellular signaling domains.

In one embodiment, the CAR of the invention may further comprise a tag, such as, e.g., a tag for quality control, enrichment, tracking in vivo and the like.

In one embodiment, said tag is localized N-terminally, C-terminally and/or internally.

Examples of tags that that are suitable in the CAR of the invention include, but are not limited to, hemagglutinin tag, poly-arginine tag, poly-histidine tag, Myc tag, strep tag, S-tag, HAT tag, 3×Flag tag, calmodulin-binding peptide (CBP) tag, SBP tag, chitin binding domain (CBD) tag, GST tag, maltose-binding protein (MBP) tag, fluorescent protein tag, T7 tag, V5 tag and Xpress tag.

The CAR of the invention may be a first-generation, second-generation or third-generation CAR.

The first generation of CARs was developed more than 30 years ago (Kuwana et al., 1987. *Biochem Biophys Res Commun.* 149(3):960-968; Gross et al., 1989. *Transplant Proc.* 21(1 Pt 1):127-130; Gross et al., 1989. *Proc Natl Acad Sci USA.* 86(24):10024-10028).

In one embodiment, the CAR of the invention is a first-generation CAR and comprises:

(i) at least one extracellular binding domain,
(ii) an extracellular spacer domain,
(iii) a transmembrane domain, and
(iv) one or more intracellular signaling domain(s).

A first-generation CAR can be, for example, a CAR in which signaling is provided by CD3ζ, i.e., the intracellular signaling domain is CD3ζ.

Second-generation CARs add a co-stimulatory domain, such as, e.g., CD28 or 4-1BB.

The involvement of these intracellular signaling domains improve T cell proliferation, cytokine secretion, resistance to apoptosis, and in vivo persistence.

In one embodiment, the CAR of the invention is a second-generation CAR and comprises:

(i) at least one extracellular binding domain,
(ii) an extracellular spacer domain,
(iii) a transmembrane domain,
(iv) a costimulatory domain(s), and
(v) one or more intracellular signaling domain(s).

Third-generation CARs combine multiple co-stimulatory domains, such as, e.g., CD28-4-1BB or CD28-OX40, to increase T cell activity.

In one embodiment, the CAR of the invention is a third-generation CAR and comprises:

(i) at least one extracellular binding domain, (ii) an extracellular spacer domain, (iii) a transmembrane domain, (iv) at least two costimulatory domains, and (v) one or more intracellular signaling domain(s).

Another object of the present invention is a nucleic acid encoding the CAR of the invention.

Another object of the present invention is a vector comprising the nucleic acid encoding the CAR of the invention.

In one embodiment, the nucleic acid or vector of the invention comprises a nucleic acid sequence of the extracellular binding domain(s) operably linked to the nucleic acid sequence of an extracellular spacer domain, operably linked to the nucleic acid sequence of a transmembrane domain, operably linked to the nucleic acid sequence of a cytoplasmic domain (i.e., at least one intracellular signaling domain and optionally, at least one costimulatory domain).

The nucleic acid or the vector of the invention can be prepared in conventional ways (e.g., recombinant methods), where the genes and regulatory regions may be isolated, as appropriate, ligated, and cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. Alternatively, the gene of interest can be produced synthetically, rather than cloned.

In one embodiment, the vector comprises a first nucleic acid encoding a CAR of the invention, and further comprises a second nucleic acid encoding an antibody or antigen-binding fragment thereof, a bispecific antibody (e.g., a BiTE), a cytokine or a costimulatory ligand. In one embodiment, the first nucleic acid and the second nucleic acid are each operably linked to a promoter. In one embodiment, the first nucleic acid is operably linked to a first promoter and the second nucleic acid is operably linked to a second promoter. The promoter can be a constitutively-expressed promoter (e.g., an EF1a promoter) or an inducibly-expressed promoter (e.g., a NFAT promoter).

In one embodiment, expression of the CAR and expression of the antibody or antigen-binding fragment thereof, bispecific antibody (e.g., a BiTE), cytokine or costimulatory ligand are driven by the same promoter, e.g., a constitutively expressed promoter (e.g., an EF1a promoter). In one embodiment, expression of the CAR and expression of the antibody or antigen-binding fragment thereof, bispecific antibody (e.g., a BiTE), cytokine or costimulatory ligand are driven by different promoters.

In one embodiment, the nucleic acid encoding the CAR can be located upstream or downstream of the second nucleic acid encoding the antibody or antigen-binding fragment thereof, the bispecific antibody (e.g., a BiTE), the cytokine or the costimulatory ligand.

Another object of the present invention is an immune cell, preferably an isolated immune cell engineered to express the chimeric antigen receptor (CAR) of the invention at its surface.

In one embodiment, the immune cell of the invention expresses at its cell surface a CAR comprising an extracellular binding domain comprising or consisting of an antigen-binding domain directed to a senescent cell-associated antigen, which recognizes and is capable of binding to a senescent cell-associated antigen, as defined hereinabove.

In one embodiment, the immune cell of the invention expresses at its cell surface an anti-DEP1 chimeric antigen receptor (CAR), as defined hereinabove.

In one embodiment, the immune cell of the invention expresses at its cell surface an anti-DPP4 chimeric antigen receptor (CAR), as defined hereinabove.

In one embodiment, the immune cell of the invention expresses at its cell surface at least two CARs, wherein the first CAR and the second CAR recognize two different senescent cell-associated antigens.

In one embodiment, the immune cell of the invention expresses at its cell surface at least two CARs, wherein the first CAR is an anti-DEP1 chimeric antigen receptor, and the second CAR is an anti-DPP4 chimeric antigen receptor, as defined hereinabove.

In one embodiment, the immune cell of the invention expresses at its cell surface a multispecific CAR, as defined hereinabove.

In one embodiment, the immune cell of the invention expresses at its cell surface a bispecific CAR, comprising two extracellular binding domains, wherein one extracellular binding domain recognizes and is capable of binding to DEP1, and the other extracellular binding domain recognizes and is capable of binding to DPP4, as defined hereinabove.

In one embodiment, the immune cell of the invention further expresses at its cell surface a bispecific T cell engager (BiTE).

In one embodiment, the BiTE binds to at least one senescent cell-associated antigen and at least one non-senescent cell-associated antigen, as defined hereinabove.

In one embodiment, the immune cell of the invention is a T cell, preferably an isolated T cell. In one embodiment, the immune cell is a $CD8^+$ T cell, a $CD4^+$ T cells, a natural killer (NK) cell or an NKT cell.

In one embodiment, the immune cell of the invention is a cytotoxic T cell (also known as TC, cytotoxic T lymphocyte, CTL, T-killer cell, cytolytic T cell, $CD8^+$ T cells or killer T cell). NK cells and NKT cells are also encompassed in the invention.

In one embodiment, the T cell is a $CD8^+$ T cytotoxic lymphocyte cell selected from the group comprising or consisting of naive $CD8^+$ T cells, $CD8^+$ memory T cells, central memory $CD8^+$ T cells, regulatory $CD8^+$ T cells, IPS-derived $CD8^+$ T cells, effector memory $CD8^+$ T cells and bulk $CD8^+$ T cells.

In one embodiment, the T cell is a $CD4^+$ T helper lymphocyte cell selected from the group comprising or consisting of naive $CD4^+$ T cells, CD4+ memory T cells, central memory $CD4^+$ T cells, regulatory $CD4^+$ T cells, IPS-derived $CD4^+$ T cells, effector memory CD4+ T cells and bulk $CD4^+$ T cells.

In one embodiment, the immune cell of the invention is cytotoxic for cells expressing at their surface the senescent cell-associated antigen recognized by the CAR (such as, e.g., DEP1 and/or DPP4). In one embodiment, the immune cell of the invention is not cytotoxic for cells expressing at their surface the senescent cell-associated antigen recognized by the CAR (such as, e.g, DEP1 and/or DPP4).

In one embodiment, the immune cell of the invention is a phagocytic cell.

In one embodiment, the immune cell of the invention is a phagocytic cell selected from the group comprising or consisting of macrophages, monocytes, histiocytes, Kupffer cells, alveolar macrophages, microglial cells and dendritic cells.

In one embodiment, the immune cell of the invention is a mammal immune cell, preferably a human immune cell.

In one embodiment, the immune cells of the invention is an autologous cell, a syngeneic cell, an allogenic cell, or a xenogeneic cell.

Another object of the present invention is a population of immune cells, comprising a plurality of immune cells of the invention.

In one embodiment, the population of immune cells may be homogeneous, i.e., composed at more than 50%, such as more than 60%, 70%, 80%, 90%, 95% or more of the same immune cells, i.e., immune cells of same nature, origin, and/or expressing the same CAR at their cell surface.

In one embodiment, the population of immune cells may be heterogeneous, i.e., composed of a mix of different immune cells, i.e., immune cells of different nature, origin, and/or expressing a different CAR at their cell surface.

Another object of the present invention is a method of obtaining an immune cell expressing the CAR of the invention at its surface, or a population of such immune cells.

Means and methods to obtain immune cells expressing the CAR of the invention at its surface, or a population of such immune cells, are well known in the art.

In one embodiment, the method for obtaining an immune cell expressing the CAR of the invention at its surface, or a population of such immune cells, comprises one or several of:

- a step of isolating an immune cell or population of immune cells (e.g., T cells or phagocytic cells) from a sample obtained from a subject,
- optionally, a step of selecting a specific subpopulation of immune cells,
- a step of transducing the immune cell or population of immune cells with a nucleic acid encoding the CAR of the invention,
- optionally, a step of expanding the transduced immune cell or population of immune cells,
- optionally, a step of washing the immune cell or population of immune cells,
- optionally, a step of cryopreserving the immune cell or population of immune cells.

Prior to transduction and expansion of the immune cell of the invention, a source of immune cells (e.g., T cells or phagocytic cells) is obtained from a subject. Thus, in one embodiment, the immune cell or the population of immune cells of the invention is isolated and/or substantially purified.

T cells and/or phagocytic cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In one embodiment, any number of T cell and/or phagocytic cells lines available in the art may be used.

In one embodiment, T cells and/or phagocytic cells can be obtained from a unit of blood collected from a subject using any number of techniques known to those skilled in the art, such as Ficoll™ separation.

In one embodiment, cells from the circulating blood of a subject are obtained by apheresis. The apheresis product typically contains lymphocytes, including T cells, monocytes, granulocytes, B cells, other nucleated white blood cells, red blood cells, and platelets.

In one embodiment, cells from the circulating blood of a subject are obtained by leukapheresis. In one embodiment, cells collected by leukapheresis may be washed to remove the plasma fraction and to place the cells in an appropriate buffer or media for subsequent processing steps. In one embodiment of the invention, the cells are washed with phosphate buffered saline (PBS). In one embodiment, the wash solution lacks calcium, and may lack magnesium or many if not all divalent cations. After washing, the cells may be resuspended in a variety of biocompatible buffers, such as, e.g., $Ca^{2+}$-free, $Mg^{2+}$-free PBS, PlasmaLyte A, or other saline solution with or without buffer. Alternatively, the undesirable components of the leukapheresis sample may be removed and the cells directly resuspended in culture media.

In one embodiment, T cells and/or phagocytic cells are isolated from peripheral blood lymphocytes by lysing the red blood cells and depleting the monocytes, e.g., by centrifugation through a PERCOLL™ gradient or by counterflow centrifugal elutriation. A specific subpopulation of T cells can be further isolated by positive or negative selection techniques. Those skilled in the art would recognize that multiple rounds of selection can also be used in the context of this invention.

In one embodiment, it may be desirable to perform the selection procedure and use the "unselected" cells in the activation and expansion process. "Unselected" cells can also be subjected to further rounds of selection. Enrichment of a T cell population by negative selection can be accomplished with a combination of antibodies directed to surface markers unique to the negatively selected cells. One method is cell sorting and/or selection via negative magnetic immuno-adherence or flow cytometry that uses a cocktail of monoclonal antibodies directed to cell surface markers present on the cells negatively selected.

For example, to enrich CD4+ cells by negative selection, a monoclonal antibody cocktail typically includes antibodies directed to CD14, CD20, CD11b, CD16, HLA-DR, and CD8. To deplete T regulatory cells, anti-CD25 conjugated beads or other similar method of selection can be used. To enrich a population of monocytes, macrophages and/or dendritic cells by negative selection, a monoclonal antibody cocktail typically includes antibodies to CD34, CD3, CD4, CD8, CD14, CD19 or CD20. Those skilled in the art are familiar with such means and methods.

In one embodiment, the immune cell or population of immune cells of the invention is transduced with a nucleic acid encoding the CAR of the invention, or with a vector comprising the nucleic acid encoding the CAR of the invention, and optionally expanded.

Methods for transfecting eukaryotic cells and tissues removed from an organism in an ex vivo method are known to those skilled in the art. In one embodiment, the method is an ex vivo method. Thus, it is contemplated that cells or tissues may be removed and transfected ex vivo using nucleic acids or vectors of the invention. In one embodiment, the transplanted cells or tissues may be placed into an organism. In one embodiment, a nucleic acid is expressed in the transplanted immune cell population.

The nucleic acid encoding the CAR of the invention, once completed and demonstrated to have the appropriate sequences, may be introduced into the immune cell by any convenient means, including, but not limited to, by fusion, electroporation, biolistics, transfection, lipofection, or the like. Alternatively, the nucleic acid encoding the CAR of the invention may also be integrated and packaged into non-replicating, defective viral genomes like adenovirus, adeno-associated virus (AAV), or herpes simplex virus (HSV) or others, including retroviral vectors or lentiviral vectors, for infection or transduction into cells. The nucleic acid encoding the CAR of the invention may include viral sequences for transfection, if desired. The engineered cells may be grown and expanded in culture before introduction of the construct(s), followed by the appropriate treatment for introduction of the construct(s) and integration of the construct(s). The engineered cells are then expanded and screened by virtue of a marker present in the construct. Various markers that may be used successfully include hprt, neomycin resistance, thymidine kinase, hygromycin resistance, etc.

In one embodiment, one may have a target site for homologous recombination, where it is desired that a nucleic acid be integrated at a particular locus. For example, one can knock-out an endogenous gene and replace it (at the same locus or elsewhere) with the gene encoded for by the construct using materials and methods as are known in the art for homologous recombination. For homologous recombination, one may use either OMEGA or O-vectors. See, e.g., Thomas & Capecchi, 1987. *Cell.* 51(3):503-12; Mansour et al., 1988. *Nature.* 336(6197):348-352; and Joyner et al., 1989. *Nature.* 338(6211):153-156.

The nucleic acid encoding the CAR of the invention may be introduced as a single DNA molecule encoding at least the CAR of the invention and optionally another gene, or different DNA molecules having one or more genes. Other genes include genes that encode therapeutic molecules or suicide genes, for example. The constructs may be introduced simultaneously or consecutively, each with the same or different markers.

In one embodiment, suicide gene technology may be used. Different suicide gene technologies are described in the art depending on their mechanism of action (Jones et al., 2014. *Front Pharmacol.* 5:254). Examples of gene-directed enzyme prodrug therapy (GDEPT) converting a nontoxic drug to a toxic drug include herpes simplex virus thymidine kinase (HSV-TK) and cytosine deaminase (CD). Other examples are chimeric proteins composed of a drug binding domain linked to apoptotic components such as for example the inducible Fas (iFas) or the inducible Caspase 9 (iCasp9) systems. Other examples include systems mediated by therapeutic antibodies such as inducing overexpression of c-myc at the surface of the engineered cell to induce their deletion by administration of an anti-c-myc antibody. The use of EGFR is described as a similar system compared to the c-myc system.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

In one embodiment, the step of transducing the immune cell or population of immune cells corresponds to a gene disruption step, a gene correction step or a gene addition step, preferably a gene addition step.

The immune cells that have been transduced with the nucleic acid encoding the CAR of the invention are then grown in culture under selective conditions, to retain only those cells which were successfully transduced.

In one embodiment, the immune cell or the population of immune cells of the invention is or comprises or consists of a genetically modified immune cell.

In one embodiment, the genetically modified immune cell or the population of immune cells of the invention can be or comprise or consist of an allogeneic immune cell. For example, the allogeneic immune cell can be an immune cell lacking expression of a functional human leukocyte antigen (HLA), e.g., HLA class I and/or HLA class II or a T cell receptor (TCR).

In one embodiment, the immune cell or the population of immune cells of the invention can be engineered such that the immune cell does not express a functional HLA and/or TCR on its surface. For example, an immune cell can be engineered such that cell surface expression HLA, e.g., HLA class 1 and/or HLA class II or non-classical HLA molecules, is downregulated.

Modified immune cells that lack expression of a functional HLA and/or TCR can be obtained by any suitable means, including a knock-out or knock-down of one or more subunit of HLA. For example, the immune cell can include a knock-down of HLA using siRNA, shRNA, clustered regularly interspaced short palindromic repeats (CRISPR) transcription-activator like effector nuclease (TALEN), zinc finger endonuclease (ZFN), meganuclease (mn, also known as homing endonuclease), or megaTAL (combining a TAL effector with a mn cleavage domain). Such systems are well known in the art.

In one embodiment, the nucleic acid encoding a CAR as described herein is inserted at a specific locus in the genome of an immune cell, such as, e.g., at the locus of a gene to be deleted. In one embodiment, the nucleic acid encoding a CAR as described herein is inserted within an HLA locus, thereby resulting in the inhibition of HLA expression.

In one embodiment, the CAR of the invention, when expressed by a T cell or phagocytic cell, confers to the T cell or phagocytic cell the ability to bind to cells expressing DEP1 and/or DPP4 on their cell surface and be activated by DEP1 and/or DPP4, differently from the antigen that the T cells or phagocytic cell are or would have been specific or activated by.

The immune cell population of the invention may thus be defined as a redirected immune cell population. The term "redirected" refers to such immune cells, e.g., a T cell or phagocytic cell, which carries a CAR as described herein, conferring to the immune cell the ability to bind to and be activated by a ligand that is different from the one the immune cell is or would have been specific or be activated by.

In one embodiment, the immune cell or population of immune cell of the invention can express certain gene products that can kill the modified cells under controlled conditions, such as inducible suicide genes.

In one embodiment, the immune cell or the population of immune cells of the invention is cultured for expansion. In one embodiment, the immune cell or the population of immune cells of the invention comprises or consists of progenitor cells, which are cultured for differentiation and expansion of the immune cells or population of immune cells as described herein.

Whether prior to or after transduction of the immune cells (i.e., T cells or phagocytic cells) to express a desirable CAR as described herein, the immune cells (i.e., T cells and/or phagocytic cells) can be activated and expanded generally using methods as described, e.g., in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and 7,572,631.

In one embodiment, immune cells may be cryopreserved, either after isolation and optionally, selection, and/or after transduction and expansion.

In one embodiment, cryopreserved cells are thawed and washed as described herein and allowed to rest for one hour at room temperature prior to activation.

Also contemplated in the context of the invention is the collection of blood samples or leukapheresis product from a subject at a time period prior to when the expanded cells as described herein might be needed. As such, the source of the cells to be expanded can be collected at any time point necessary, and desired cells, such as T cells and/or phagocytic cells, isolated and frozen for later use in cell therapy for any number of diseases or conditions that would benefit from cell therapy, such as those described herein.

In one embodiment, a blood sample or a leukapheresis product is taken from a generally healthy subject. In one embodiment, a blood sample or a leukapheresis product is taken from a healthy subject who is at risk of developing a disease, but who has not yet developed said disease, and the cells of interest are isolated and cryopreserved for later use. In one embodiment, the T cells and/or phagocytic cells may be expanded, frozen, and used at a later time.

Another object of the invention is a composition comprising, consisting of or consisting essentially of:

- an antigen-binding domain, as described above;
- an antibody or antigen-binding fragment thereof, as described above;
- a nucleic acid encoding the antigen-binding domain, the antibody or the antigen-binding fragment thereof, as described above;
- a vector comprising the nucleic acid encoding the antigen-binding domain, the antibody or the antigen-binding fragment thereof, as described above;
- a CAR, as described above;
- a nucleic acid encoding the CAR, as described above;
- a vector comprising the nucleic acid encoding the CAR, as described above;
- an immune cell engineered to express the CAR at its cell surface, as described above;
- a population of immune cells engineered to express the CAR at their cell surface, as described above.

In one embodiment, the composition comprises, consists of or consists essentially of:

- a DEP1-binding domain, as described above;
- an anti-DEP1 antibody or antigen-binding fragment thereof, as described above;
- a nucleic acid encoding the DEP1-binding domain, the anti-DEP1 antibody or the antigen-binding fragment thereof, as described above;
- a vector comprising the nucleic acid encoding the DEP1-binding domain, the anti-DEP1 antibody or the antigen-binding fragment thereof, as described above;
- an anti-DEP1 CAR, as described above;
- a nucleic acid encoding the anti-DEP1 CAR, as described above;
- a vector comprising the nucleic acid encoding the anti-DEP1 CAR, as described above;
- an immune cell engineered to express the anti-DEP1 CAR at its cell surface, as described above;
- a population of immune cells engineered to express the anti-DEP1 CAR at their cell surface, as described above.

In one embodiment, the composition comprises, consists of or consists essentially of:

- a DPP4-binding domain, as described above;
- an anti-DPP4 antibody or antigen-binding fragment thereof, as described above;
- a nucleic acid encoding the DPP4-binding domain, the anti-DPP4 antibody or the antigen-binding fragment thereof, as described above;
- a vector comprising the nucleic acid encoding the DPP4-binding domain, the anti-DPP4 antibody or the antigen-binding fragment thereof, as described above;
- an anti-DPP4 CAR, as described above;
- a nucleic acid encoding the anti-DPP4 CAR, as described above;
- a vector comprising the nucleic acid encoding the anti-DPP4 CAR, as described above;
- an immune cell engineered to express the anti-DPP4 CAR at its cell surface, as described above;
- a population of immune cells engineered to express the anti-DPP4 CAR at their cell surface, as described above.

In one embodiment, the composition comprises, consists of or consists essentially of:

- a DEP1-binding domain and a DPP4-binding domain, as described above;
- an anti-DEP1 antibody or antigen-binding fragment thereof and an anti-DPP4 antibody or antigen-binding fragment thereof, as described above;
- an anti-DEP1/anti-DPP4 bispecific antibody;
- a nucleic acid encoding the DEP1-binding domain, the anti-DEP1 antibody or the antigen-binding fragment thereof and a nucleic acid encoding the DPP4-binding domain, the anti-DPP4 antibody or the antigen-binding fragment thereof, as described above;
- a nucleic acid encoding the anti-DEP1/anti-DPP4 bispecific antibody, as described above;
- a vector comprising the nucleic acid encoding the DEP1-binding domain, the anti-DEP1 antibody or the antigen-binding fragment thereof and a vector comprising the nucleic acid encoding the DPP4-binding domain, the anti-DPP4 antibody or the antigen-binding fragment thereof, as described above;
- a vector comprising the nucleic acid encoding the DEP1-binding domain, the anti-DEP1 antibody or the antigen-binding fragment thereof and the nucleic acid encoding the DPP4-binding domain, the anti-DPP4 antibody or the antigen-binding fragment thereof, as described above;
- a vector comprising the nucleic acid the anti-DEP1/anti-DPP4 bispecific antibody, as described above;
- an anti-DEP1 CAR and an anti-DPP4 CAR, as described above;
- an anti-DEP1/anti-DPP4 bispecific CAR, as described above;
- a nucleic acid encoding the anti-DEP1 CAR and the anti-DPP4 CAR, as described above;
- a nucleic acid encoding the anti-DEP1/anti-DPP4 bispecific CAR, as described above;
- a vector comprising a nucleic acid encoding the anti-DEP1 CAR and a vector comprising the nucleic acid encoding the anti-DPP4 CAR, as described above;
- a vector comprising a nucleic acid encoding the anti-DEP1 CAR and the nucleic acid encoding the anti-DPP4 CAR, as described above;
- a vector comprising a nucleic acid encoding the anti-DEP1/anti-DPP4 bispecific CAR, as described above;
- an immune cell engineered to express the anti-DEP1 CAR and an immune cell engineered to express the anti-DPP4 CAR, as described above;
- an immune cell engineered to express the anti-DEP1 CAR and the anti-DPP4 CAR, as described above;

- an immune cell engineered to express the anti-DEP1/anti-DPP4 bispecific CAR, as described above;
- a population of immune cells engineered to express the anti-DEP1 CAR and a population of immune cells engineered to express the anti-DPP4 CAR, as described above;
- a population of immune cells engineered to express the anti-DEP1 CAR and the anti-DPP4 CAR, as described above;
- a population of immune cells engineered to express the anti-DEP1/anti-DPP4 bispecific CAR, as described above.

In one embodiment, the composition has been frozen and thawed. In one embodiment, the composition is lyophilized.

In one embodiment, the compositions of the invention are pharmaceutical compositions and further comprise at least one pharmaceutically acceptable excipient.

The term "pharmaceutically acceptable excipient" includes any and all solvents, dispersion media, coatings, antibacterial and antifungal agents, isotonic and absorption delaying agents and the like. Said excipient does not produce an adverse, allergic or other untoward reaction when administered to an animal, preferably a human. For human administration, preparations should meet sterility, pyrogenicity, and general safety and purity standards as required by regulatory offices, such as, for example, FDA Office or EMA.

Pharmaceutically acceptable excipients that may be used in the pharmaceutical composition of the invention include, without being not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In one embodiment, the compositions according to the present invention are medicaments.

As used herein, the term "consisting essentially of", with reference to a composition, pharmaceutical composition or medicament, means that the antigen-binding domain, antibody or antigen-binding fragment thereof, nucleic acid, vector, CAR, immune cell or population of immune cells of the invention is/are the only therapeutic agent, or agent with a biologic activity, within said composition, pharmaceutical composition or medicament.

Such compositions and medicaments may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Since the present invention selectively target senescent cells, it is contemplated that the compositions according to the present invention may be cosmetic compositions, and further comprise at least one dermatologically acceptable excipient.

The term "dermatologically acceptable excipient" refers to excipient which are suitable for external topical application. Examples of dermatologically acceptable excipients include, but are not limited to, sebum-regulating agents, antibacterial agents, antifungal agents, keratolytic agents, keratoregulating agents, astringents, anti-inflammatory agents, anti-irritants, antioxidants, free-radical scavengers, cicatrizing agents, anti-aging agents and moisturizing agents.

The administration of the composition, pharmaceutical composition, medicament or cosmetic composition of the invention may be carried out in any convenient manner, including by injection, aerosol inhalation, topical delivery (such as, for example, by transdermal delivery), oral delivery, rectal delivery, nasal delivery, or vaginal delivery.

In one embodiment, the composition, pharmaceutical composition, medicament or cosmetic composition of the present invention is in a form adapted for injection, such as, e.g., for trans-arterial, intravenous (i.v.), intramuscular, intraperitoneal (i.p.), intrapleural, intradermal, subcutaneous, transdermal injection or infusion.

Examples of forms suitable for injectable use include, but are not limited to, sterile solutions or dispersions and sterile powders for the extemporaneous preparation of sterile injectable solutions or dispersions. The prevention against contamination by microorganisms can be brought about by adding in the composition preservatives such as, e.g., various antibacterial and antifungal agents (e.g., parabens, chlorobutanol, phenol, sorbic acid, thimerosal and the like). In one embodiment, it may be preferable to include isotonic agents, e.g., sugars or sodium chloride, to reduce pain during injection. In one embodiment, prolonged absorption of the injectable compositions can be brought about by the use in the compositions of agents delaying absorption, e.g., aluminum monostearate and gelatin.

In one embodiment, the composition, pharmaceutical composition, medicament or cosmetic composition of the present invention is in an adapted form for a parenteral administration. Thus, in one embodiment, the composition, pharmaceutical composition, medicament or cosmetic composition of the invention is to be administered parenterally.

In one embodiment, the composition, pharmaceutical composition, medicament or cosmetic composition of the invention is in an adapted form for an intravenous administration. Thus, in one embodiment, the composition, pharmaceutical composition, medicament or cosmetic composition of the present invention is to be administered intravenously.

In one embodiment, the composition, pharmaceutical composition, medicament or cosmetic composition of the present invention may be injected directly into the site of the disease or disorder to be treated.

In one embodiment, a lyophilized composition, a lyophilized pharmaceutical composition, a lyophilized medicament or a lyophilized cosmetic composition of the invention is solubilized in water for injection and gently mixed, the mixture is gently mixed and charged into a suitable syringe. This invention thus also relates to a medical device, including a syringe filled or prefilled with a composition, pharmaceutical composition, medicament or cosmetic composition of the invention.

In one embodiment, the composition, pharmaceutical composition, medicament or cosmetic composition of the invention is formulated for topical administration. Thus, in one embodiment, the composition, pharmaceutical composition, medicament or cosmetic composition is to be administered topically.

Examples of forms adapted for topical administration include, without being limited to, liquid, paste or solid compositions, and more particularly aqueous solutions, drops, dispersions, sprays, microcapsules, micro- or nanoparticles, polymeric patch, or controlled-release patch, and the like.

In particular embodiments where the compositions of the invention comprise a CAR, an immune cell or a population of immune cells as described above, such compositions may be administered by intradermal or subcutaneous injection, such as by i.v. injection.

In one embodiment, the compositions comprising a CAR, an immune cell or a population of immune cells may be injected directly into a lymph node, site of infection, site of inflammation or site of tissue or organ rejection. In one embodiment, the compositions comprising a CAR, an immune cell or a population of immune cells may be injected directly into the site of the autoimmune and/or inflammatory disease.

In one embodiment, the subject is administered, or is to be administered, with autologous cells. In some embodiments, the subject is administered, or is to be administered, with allogenic cells.

In one embodiment, the subject may be a mammal. In one embodiment, the subject may be a human.

Another object of the present invention is the use of the composition, pharmaceutical composition or medicament described herein, as a medicament.

Another object of the present invention is the use of the composition, pharmaceutical composition or medicament described herein, in treating, preventing or alleviating senescence-related diseases or disorders.

Another object of the present invention is a method of treating, preventing or alleviating senescence-related diseases or disorders in a subject in need thereof, comprising administering to said subject the composition, pharmaceutical composition or medicament described herein.

As used herein, the term "senescence-associated", "senescence-related" or "age-related" diseases, disorders, or conditions refers to a physiological condition that presents with one or more symptoms or signs, wherein a subject having the condition needs or would benefit from a lessening of such symptoms or signs. The condition is senescence-associated if it is caused or mediated in part by senescent cells, which may be induced by multiple etiologic factors including age, DNA damage, oxidative stress, genetic defects, etc. Lists of senescence-associated disorders that can potentially be treated or managed using the methods and products taught in this disclosure include those discussed in this disclosure and the previous disclosures to which this application claims priority.

Non-limiting examples of senescence-related diseases include: fibrotic diseases, chronic inflammatory diseases (e.g., arthritis or arthrosis), cancer, premalignant lesions, atherosclerosis, osteoarthritis, diabetes, diabetic ulcers, kyphosis, scoliosis, hepatic insufficiency, cirrhosis, Hutchinson-Gilford progeria syndrome (HGPS), laminopathies, osteoporosis, dementia, (cardio)vascular diseases (e.g., angina, arrhythmia, atherosclerosis, cardiomyopathy, congestive heart failure, coronary artery disease (CAD), carotid artery disease, endocarditis, heart attack, coronary thrombosis, myocardial infarction, high blood pressure/hypertension, hypercholesterolemia/hyperlipidemia, mitral valve prolapsed, peripheral artery disease (PAD) and stroke), obesity, metabolic syndrome, acute myocardial infarction, emphysema, insulin sensitivity, boutonneuse fever, sarcopenia, neurodegenerative diseases (e.g., Alzheimer's, Huntington's or Parkinson's disease), cataract, anemia, hypertension, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

Another object of the present invention is the use of the composition, pharmaceutical composition or medicament described herein, in treating, preventing or alleviating fibrotic diseases, premalignant lesions, inflammatory diseases and cancers.

Another object of the present invention is a method of treating, preventing or alleviating fibrotic diseases, premalignant lesions, inflammatory diseases and cancers in a subject in need thereof, comprising administering to said subject the composition, pharmaceutical composition or medicament described herein.

Senescent cells are present in fibrosis of many tissues including, but not limited, to skin, liver, lung, pancreas and prostate.

Thus, in one embodiment, the senescence-related disease or disorder to be treated is a fibrotic disease. Exemplary fibrotic diseases which may be treated by the invention include but are not limited to eosinophilic esophagitis, hypereosinophilic syndromes (HES), Loeffler's endomyocarditis, endomyocardial fibrosis, idiopathic pulmonary fibrosis, and scleroderma.

In one embodiment, the pulmonary fibrotic disease to be treated, prevented or alleviated is selected from the group comprising idiopathic pulmonary fibrosis (IPF), chronic obstructive pulmonary disease (COPD) acute respiratory distress syndrome (ARDS), combined pulmonary fibrosis and emphysema (CPFR), pulmonary edema, Loffler's syndrome, eosinophilic pneumonia, respiratory hypersensitivity, allergic bronchopulmonary aspergillosis (ABPA), Hamman-Rich syndrome, sarcoidosis, pneumoconiosis, and hypersensitivity pneumonitis (HP).

In one embodiment, the pulmonary fibrotic disease to be treated, prevented or alleviated is chronic obstructive pulmonary disease (COPD) or idiopathic pulmonary fibrosis.

In one embodiment, the senescence-related disease or disorder to be treated is a premalignant lesion.

As used herein, the phrase "premalignant lesion" refers to a mass of cells and/or tissue having increased probability of transforming into a malignant tumor.

Examples of premalignant lesions include, but are not limited to, adenomatous polyps, Barrett's esophagus, pancreatic intraepithelial neoplasia (PanIN), IPMN (intraductal papillary mucinus neoplasia), DCIS (ductal carcinoma in situ) in the breast, leukoplakia and erythroplakia. Thus, the premalignant lesion to be treated by the invention can transform into a malignant solid or non-solid (e.g., hematological malignancies) cancer (or tumor).

In one embodiment, the premalignant lesion which is to be treated is an adenomatous polyp of the colon, an adenomatous polyp of the rectum, an adenomatous polyp of the small bowel or Barrett's esophagus.

As used herein, the term "inflammatory diseases" refers to any abnormality associated with inflammation, such as, for example, chronic inflammatory diseases, acute inflammatory diseases.

Examples of inflammatory disorders include, but are not limited to, rheumatic diseases, neurological diseases, cardiovascular diseases, uro-gynecological diseases, eye and ear diseases, mucocutaneous diseases, infectious diseases, graft rejection diseases and allergic diseases.

Examples of rheumatic diseases include, but are not limited to, arthritis, osteoarthritis, rheumatoid arthritis, osteoporosis, fibromyalgia, lupus, systemic lupus erythematosus and scleroderma.

Examples of neurological diseases include, but are not limited to, multiple sclerosis, Alzheimer's disease, Parkinson's disease, Huntington's disease, stroke, traumatic brain injury, spinal cord injury, dystonia, chronic regional pain syndrome, motor neuron disease/amyotrophic lateral sclerosis, Guillain-Barre syndrome, muscular dystrophy, cerebral palsy, neuropathy and myositis.

Examples of cardiovascular diseases include, but are not limited to, coronary heart disease, stroke, hypertensive heart disease, inflammatory heart disease, rheumatic heart disease, aortic aneurysm and dissection, congenital heart disease, deep vein thrombosis and pulmonary embolism and atherosclerosis.

Examples of uro-gynecological diseases include, but are not limited to, glomerulonephritis, urinary incontinence and prolapse.

Examples of eye and ear diseases include, but are not limited to, cataract, glaucoma, age-related macular degeneration (AMD), presbyopia, dry eyes, corneal diseases, diabetic retinopathy, vertigo, tinnitus and Meniere's disease.

Examples of mucocutaneous diseases include, but are not limited to, eczema, xeroderma pigmentosum, oral lichen planus, mucous membrane pemphigoid and pemphigus vulgaris.

Examples of infectious diseases include, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases.

Examples of diseases associated with transplantation of a graft include, but are not limited to, graft rejection, chronic graft rejection, subacute graft rejection, hyperacute graft rejection, acute graft rejection and graft versus host disease.

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

In one embodiment, the senescence-related disease or disorder to be treated is cancer.

Non-limiting examples of cancers which may be treated according to this aspect of the present invention include, but are not limited to, adenocarcinoma, adrenal gland tumor, ameloblastoma, anaplastic, anaplastic carcinoma of the thyroid, angiofibroma, angioma, angiosarcoma, apudoma, argentaffmoma, arrhenoblastoma, ascites tumor cell, ascitic tumor, astroblastoma, astrocytoma, ataxia-telangiectasia, atrial myxoma, a basal cell carcinoma cell, bone cancer, brainstem glioma, brain tumor, breast cancer, Burkitt's lymphoma, cerebellar astrocytoma, cervical cancer, cherry angioma, cholangiocarcinoma, cholangioma, chondroblastoma, chondroma, chondrosarcoma, chorioblastoma, choriocarcinoma, colon cancer, common acute lymphoblastic leukemia, craniopharyngioma, cystocarcinoma, cystofbroma, cystoma, ductal carcinoma in situ, ductal papilloma, dysgerminoma, encephaloma, endometrial carcinoma, endothelioma, ependymoma, epithelioma, erythroleukemia, Ewing's sarcoma, extra nodal lymphoma, feline sarcoma, fibro adenoma, fibro sarcoma, follicular cancer of the thyroid, ganglioglioma, gastrinoma cell, glioblastoma multiform, glioma, gonadoblastoma, haemangioblastoma, haemangioendothelioblastoma, haemangioendothelioma, haemangiopericytoma, haematolymphangioma, haemocytoblastoma, haemocytoma, hairy cell leukemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angioforoma, Kaposi sarcoma, kidney tumor, large cell lymphoma, leukemia, a leukemia, acute leukemia, lipoma, liver cancer, liver metastases, Lucke carcinoma, lymphadenoma, lymphangioma, lymphocytic leukemia, lymphocytic lymphoma, lymphoeytoma, lymphoedema, lymphoma, lung cancer, malignant mesothelioma, malignant teratoma, mastocytoma, medulloblastome, melanoma, meningioma, mesothelioma, Morton's neuroma, multiple myeloma, myeloblastoma, myeloid leukemia, myelolipoma, myeloma, myoblastoma, myxoma, nasopharyngeal carcinoma, neoplastic, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheoehromocytoma, plasmacytoma, primary brain tumor, progonoma, prolactinoma, renal cell carcinoma, retinoblastoma, rhabdomyosarcoma, rhabdo sarcoma, a solid tumor, sarcoma, a secondary tumor, seminoma, skin cancer, small cell carcinoma, squamous cell carcinoma, strawberry haemangioma, T cell lymphoma, teratoma, testicular cancer, thymoma, trophoblastic tumor, and Wilm's tumor.

In one embodiment, the composition, pharmaceutical composition or medicament described herein is used alone. In one embodiment, the composition, pharmaceutical composition, or medicament described herein is used in combination with at least one anti-cancer agent.

Indeed, many of existing and potential anti-cancer agents induce senescence of cancer cells, therefore the present invention can be used in combination with these agents to increase the efficacy of an anti-cancer treatment. Treatment by these agents can also reduce side effects of radiotherapy or chemotherapy with DNA-damaging agents.

Thus, the composition, pharmaceutical composition or medicament described herein can be used as an adjuvant therapy along with other treatment modalities for cancers, which are selected based on cancer type, location, the cell type and the grade of malignancy. Conventional therapies include surgery, radiation therapy, and chemotherapy.

Exemplary anti-cancer drugs that can be co-administered with the composition, pharmaceutical composition or medicament described herein include, but are not limited to, acivicin, aclarubicin, acodazole hydrochloride, acronine, adriamycin, adozelesin, aldesleukin, altretamine, ambomycin, ametantrone acetate, aminoglutethimide, amsacrine, anastrozole, anthramycin, asparaginase, asperlin, azacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interferon alfa-2a, interferon alfa-2b, interferon alfa-n1, interferon alfa-n3, interferon beta-1a, interferon gamma-1b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, taxol, tecogalan sodium, tegafur, teloxantrone hydrochloride, temoporfin, teniposide, teroxirone, testolactone, thiamiprine, thioguanine, thiotepa, tiazofuirin, tirapazamine, topotecan hydrochloride, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, and zorubicin hydrochloride.

Additional antineoplastic agents include those disclosed in Chabner et al., 2001. "Antineoplastic agents". In Goodman et al. (Eds.), Goodman & Gilman's The pharmacological basis of therapeutics ($10^{th}$ ed., pp. 1315-1404). New York, NY: McGraw-Hill.

Another object of the present invention is the use of the cosmetic composition described herein, as cosmetics.

Indeed, since the present invention selectively target senescent cells, it is contemplated that the present invention can be used for skin care, skin anti-aging and/or skin rejuvenation.

Another object of the present invention is thus a method for rejuvenating the skin in a subject in need thereof, comprising administering to the subject the cosmetic composition described herein.

Because senescent cells drive age-related pathologies, a selective elimination of these cells can prevent or delay age-related deterioration. Thus, senescent cells may be therapeutic targets in the treatment of aging and age-related disease. As such, removal of senescent cells may delay tissue dysfunction and extend health span. Clearance of senescent cells is expected to improve tissue milieu, thereby improving the function of the remaining non-senescent cells.

Another object of the present invention is thus the use of the composition, pharmaceutical composition or medicament described herein, for depleting and/or killing senescent cells.

Another object of the present invention is thus a method for depleting and/or killing senescent cells in a subject, comprising administering to the subject the composition, pharmaceutical composition or medicament described herein.

In one embodiment, the composition, pharmaceutical composition, medicament or cosmetic composition described herein is to be administered to a subject in need thereof in a therapeutically effective amount.

It will be however understood that the total daily usage of the composition, pharmaceutical composition, medicament or cosmetic composition described herein will be decided by the attending physician within the scope of sound medical judgment. The specific therapeutically effective dose level for any particular patient will depend upon a variety of factors including the disease being treated and the severity of the disease; activity of the therapeutic agent in the composition, pharmaceutical composition, medicament or cosmetic composition (antigen-binding domain, antibody or antigen-binding fragment thereof, nucleic acid, vector, CAR, immune cell or population of immune cells of the invention) employed; the age, body weight, general health, sex and diet of the subject; the time of administration, route of administration, and rate of excretion of the specific composition, pharmaceutical composition, medicament or cosmetic composition employed; the duration of the treatment; drugs used in combination or coincidental with the composition, pharmaceutical composition, medicament or cosmetic composition employed; and like factors well known in the medical arts. For example, it is well within the skill of the art to start doses of the compound at levels lower than those required to achieve the desired therapeutic effect and to gradually increase the dosage until the desired effect is achieved. The total dose required for each treatment may be administered by multiple doses or in a single dose.

Disclosed herein is a chimeric antigen receptor (CAR) comprising:

(i) at least one extracellular binding domain, comprising at least one antigen-binding domain directed to a senescent cell-associated antigen, preferably to DEP1 and/or DPP4,
(ii) an extracellular spacer domain,
(iii) a transmembrane domain,
(iv) optionally at least one costimulatory domain, and
(v) at least one intracellular signaling domain.

In one embodiment, said at least one antigen-binding domain is directed to DEP1.

In one embodiment, said at least one antigen-binding domain is directed to DPP4.

In one embodiment, said CAR is a bispecific CAR comprising two antigen-binding domains.

In one embodiment, each of the at least two antigen-binding domains binds to a different antigen, preferably to DEP1 and DPP4.

Also disclosed herein is an isolated immune cell population expressing at least one CAR according to the present disclosure, preferably the isolated immune cell population expresses:

at least one CAR directed to DEP1 and at least one CAR directed to DPP4; or at least one bispecific CAR comprising two antigen-binding domains, preferably wherein each of the at least two antigen-binding domains binds to a different antigen, preferably to DEP1 and DPP4.

In one embodiment, the isolated immune cell population according to the present disclosure comprises immune cells selected from the group comprising T cells, natural killer (NK) cells, or a combination thereof.

Also disclosed herein is an isolated bispecific antibody or a fragment thereof, comprising at least two antigen binding domains directed to at least two senescent cell-associated antigens, preferably the at least two senescent cell-associated antigens are DEP1 and DPP4.

In one embodiment, the isolated bispecific antibody or fragment thereof according to the present disclosure comprises:

(i) an antigen-binding domain of an anti-human DEP1 antibody or a fragment thereof; and (ii) an antigen-binding domain of an anti-human DPP4 antibody or a fragment thereof.

Also disclosed herein is a composition comprising:

the isolated immune cell population according to the present disclosure;

the isolated bispecific antibody or fragment thereof according to the present disclosure; or a mixture of an isolated anti-human DEP1 antibody or a fragment thereof and an isolated anti-human DPP4 antibody or a fragment thereof.

In one embodiment, the composition according to the present disclosure is a pharmaceutical composition and further comprises at least one pharmaceutically acceptable excipient.

In one embodiment, the composition or pharmaceutical composition according to the present disclosure is for use as a medicament.

In one embodiment, the composition or pharmaceutical composition according to the present disclosure is:

for use in treating, preventing or alleviating senescence-related diseases or disorders; or for depleting and/or killing senescent cells.

In one embodiment, senescence-related diseases or disorders are selected from the group comprising fibrotic diseases, premalignant lesions, inflammatory diseases and cancers.

BRIEF DESCRIPTION OF THE DRAWINGS

FIG. 9A: staining with monoclonal antibody (Creative Biolabs);

FIG. 9B: staining with 5826-13-R3A-D5;

FIG. 9C: staining with 5826-13-R4A-H5.

FIG. 10A: staining with monoclonal antibody (AbCam)
FIG. 10B: staining with 5738-10-R3A-D5;
FIG. 10C: staining with 5738-13-R4A-D11;
FIG. 10D: staining with 5738-13-R2A-H4.

EXAMPLES

The present invention is further illustrated by the following examples.

Example 1—DPP4 is Expressed on the Surface of Senescent Cells

Materials and Methods

Expression of DPP4 (rhuMAB 41) Antibody and Antigen

The full-length of the antigen was synthesized and subcloned into an expression vector. The insert was confirmed by Sanger sequencing. After the vector was verified by sequencing, the vector was expressed in CHO-S cell line with chemically defined culture media. After 9 days cultivation, the protein was purified by Nickel columns, ultrafiltration and then subjected to 0.2-micron sterile filtration to get the bulk of high purity.

The heavy chain and light chain of the rhuMAB 41 antibody (Creative Biolabs) were synthesized and subcloned into Creative Biolabs property expression vector, respectively. The insert was confirmed by Sanger sequencing. After the vectors were verified by sequencing, they were expressed in HEK293 cell line with chemically defined culture media. After 9 days of cultivation, the protein was purified by Protein A affinity chromatography, ultrafiltration and then subjected to 0.2-micron sterile filtration to get the bulk of high purity.

Expression of DPP4 (rhuMAB 41) scFv

The scFv consists of variable regions of heavy and light chains that are joined together by a flexible peptide linker. In the scFv, the order of the domains can be either VH-linker-VL or VL-linker-VH. The affinity of the two construction types to the target might be different. Hence, the two construction types can lead to secretory expression in different level.

The scFv(s) were expressed and tested by flow cytometry to evaluate the binding affinity to target cells. $5\times10^5$ WI-38 cells were co-cultured with rhuMAB 41 antibody (humanized antibody), VL-Linker-VH antibody and VH-Linker-VL antibody (1 μg/tube), respectively, and then analyzed by using PE-anti-human IgG Fc as secondary antibody.

The results indicated that VH-linker-VL antibody has higher affinity for target cell WI-38 and was chosen for CAR development.

CAR-T Cell Preparation and Construction

Primary human T cells were used for CAR-T generation. Human primary T cells were isolated from PBMCs of healthy donors by magnetic beads and stimulated in growth medium supplemented with IL-2. Activated T cells were then transduced with lentivirus expressing customized chimeric antigen receptor. After CAR-T cell expansion, CAR-transduction efficiency was examined by FACS and qPCR.

Figure 1:
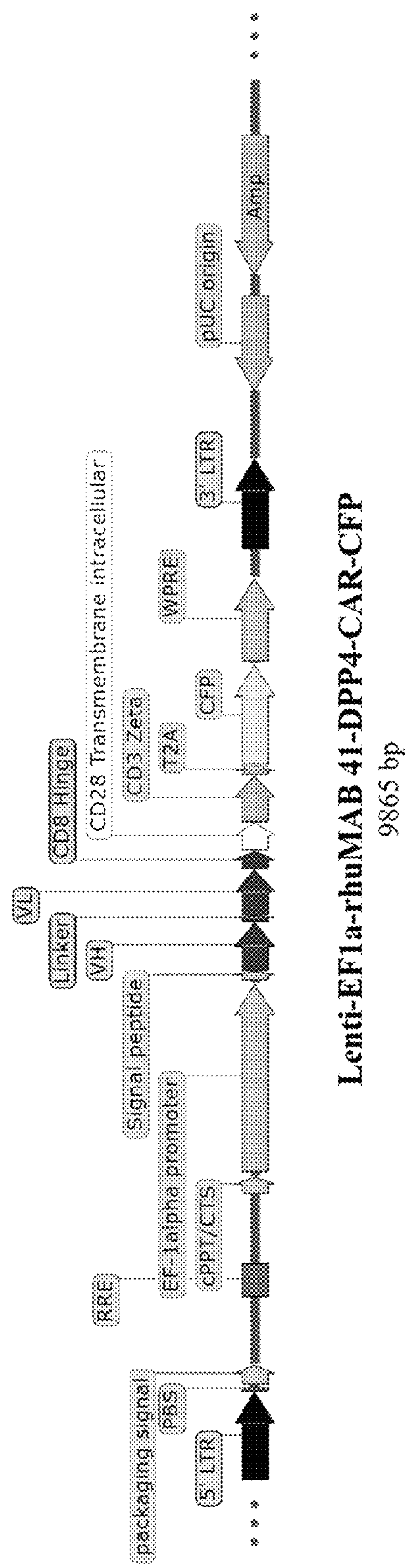
FIG. 1—'The structure of CAR vector'—is a schema illustrating the construction of the full-length CAR expression cassette, subcloned into Lenti-EF1a-rhuMAB 41-VH-Linker-VL-CFPCART, pCDCAR1. The full length of chimeric antigen receptor was synthesized and subcloned into lentivirus vector. The insert was confirmed by Sanger sequencing and is schematically illustrated in the figure. This CAR vector was used in the CAR-T assays for the proof-of-concept experiments.

The full-length of chimeric antigen receptor was synthesized and subcloned into lentivirus vector. The insert was confirmed by Sanger sequencing. The structure of CAR vector is schematically illustrated in FIG. 1.

Lentiviral vectors, which were derived from immunodeficiency viruses, were used for their relatively high efficiency for T cell transduction and their ability of infection of the non-proliferating cells. A second generation of the packaging system was utilized to generate transduction-ready pseudoviral particles in HEK293T cells. The titer of the lentivirus particle was determined by qPCR and cell-based titration assay. The results of lentivirus titration showed that prepared virus stock was at a high titer of $3.27\times10^8$ TU/mL.

Primary Human T Lymphocytes Preparation and CAR-T Preparation

PBMC from a healthy human donor was stimulated with anti-CD3/CD28 magnetic beads and the T cells were isolated using magnetic cell separation system. To generate CAR-T cells, the lentivirus particles with DPP4-CAR coding gene were incubated with the T cells in the presence of polybrene. After T cell expansion, the CAR-T cells were used for in vitro cytotoxicity assays.

Target Cell Preparation

WI-38 target cells were obtained at population doubling 19 (PD19) and passaged until they stopped proliferating. They were further analyzed by FACS for the detection of their surface antigen DPP4 and by qRT-PCT for the detection of their relative DPP4 mRNA expression level.

Cellular senescence induced by DNA damage was also induced in GM21808 fibroblasts by adding etoposide, as previously described (Robles et al., 1999. *Biochem Pharmacol.* 58(4):675-685; Gey & Seeger, 2013. *Mech Ageing Dev.* 134(3-4):130-138). Untreated (control) and treated cells were further analyzed by qRT-PCT for the detection of their relative DPP4 mRNA expression level.

Natural Killer (NK) Cell Preparation

Effector cells (NK cells) were freshly prepared before the ADCC assay. By using EasySep™ Human NK Cell Isolation Kit (STEMCELL, Catalog:17955), NK cells were isolated from a healthy human donor and resuspended in RPMI 1640 medium at $5\times10^6$/ML.

ADCC Assay

The target cells (WI-38), i.e., the senescent cells and proliferating cells, were plated into a 24-well plate at $1\times10^5$ cell/well in 100 μL RPMI-1640 supplied with 5% FBS 24 hour and cultured overnight. On the day of the assay, anti-DPP4 antibody (rhuMAB 41) was added into each well at a final concentration of 0 μg/mL, 0.05 μg/mL, and 0.5 μg/mL. After 30 minutes of incubation at 37° C. with 5% $CO_2$, 100 μL NK cells ($5\times10^5$ cell/well) were added to each well at E/T=5:1. After incubation for 6 hours at 37° C. with 5% $CO_2$, the cells were stained with eBioscience™ Annexin V Apoptosis Detection Kit PE (Invitrogen, Catalog: 88-8102-74) with 7-AAD and analyzed by flow cytometry.

In Vitro CAR-T Activity Assay by FACS

In vitro analysis was used for evaluation of the targeting effect of DPP4-CAR-T. The target cells (WI-38 or GM21808), i.e., the senescent cells and proliferating cells, were plated into a 24-well plate at $1\times10^5$ cell/well in 100 μL RPMI-1640 supplied with 5% FBS and cultured overnight. On the day of the assay, effector cells ($5\times10^5$ cell/well) were added to each well at E/T=5:1. After incubation for 6 hours at 37° C. with 5% $CO_2$, the cells were stained with eBioscience™ Annexin V Apoptosis Detection Kit PE (Invitrogen, Catalog: 88-8102-74) with 7-AAD and analyzed by flow cytometry. The relative percentage was quantified by normalizing the results to control CAR-T.

Results

Assessment of Senescent State and DPP4 Levels in Target Cells

Figure 2:
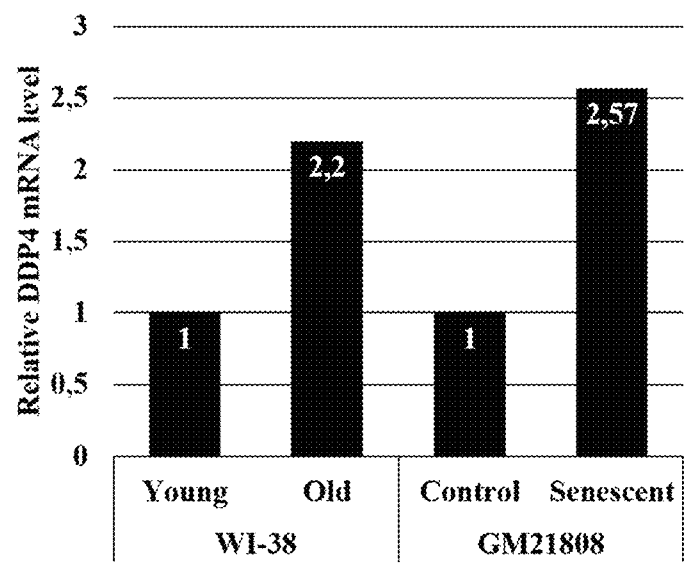
FIG. 2—'The assessment of senescent state and DPP4 levels in target cells'—is a graph showing the senescent state of WI-38 and GM21808 cells, confirmed by senescence associated β-galactosidase activity. Representative results of control versus senescent fibroblasts are shown. DPP4 levels of the cells were monitored by quantitative RT-PCR. Relative quantities of DPP4 in young WI-38 (low passage number: PDL<20) or old WI-38 (high passage number: PDL>50) and in GM21808 cells, untreated or cultured with DNA-damaging agent etoposide (adding etoposide every two days for fourteen days) were calculated. Fold-change, or relative quantity, of DPP4 in each sample was calculated relative to young WI-38 or untreated GM21808.

The senescent state of the cells was confirmed by senescence associated β-galactosidase activity. DPP4 levels were monitored by quantitative RT-PCR. FIG. 2 shows that DPP4 is expressed selectively in senescent cells, but not in proliferating human diploid fibroblasts or healthy foreskin fibroblasts.

ADCC Assay

In vitro Antibody-Dependent Cell-Mediated Cytotoxicity (ADCC) assays are common tools for immunotherapeutic drug discovery and biosimilar development. For this experiment, cytotoxicity is defined as apoptosis monitored by annexin-V positive and 7-ADD negative cells counted.

Figure 3:
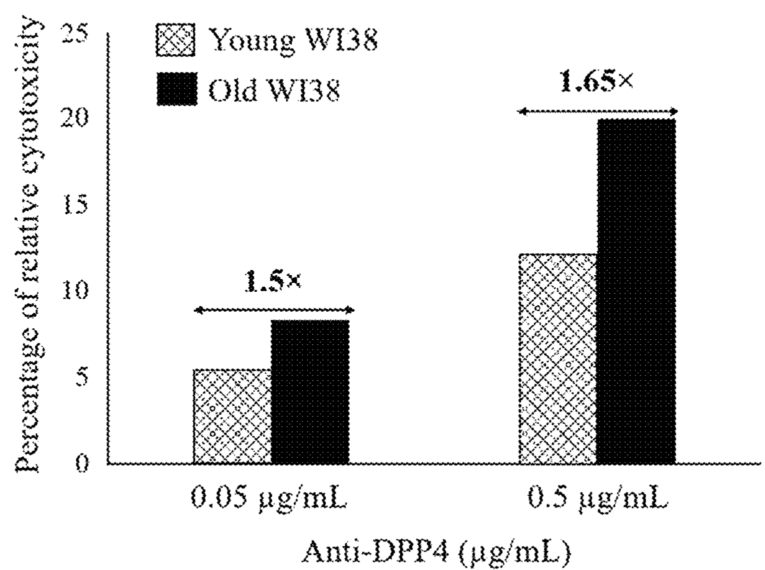
FIG. 3—'The ADCC Assay'—is a graph showing the relative toxicity in young and old fibroblast cells (WI-38 cells), using 0.05 μg/mL or 0.5 μg/ml of anti-DPP4 antibody.

Results of a standard ADCC assay are shown in FIG. 3. This experiment depicts a difference between young and old fibroblast cells at indicated antibody concentration as listed 1.5 and 1.65-fold, respectively.

Our results show that high abundance of DPP4 on the surface of senescent cells lead to a 1.5-fold selective elimination of senescent cells using anti-DPP4 antibody under optimal conditions.

DPP4-CAR-T Assay

Figure 4:
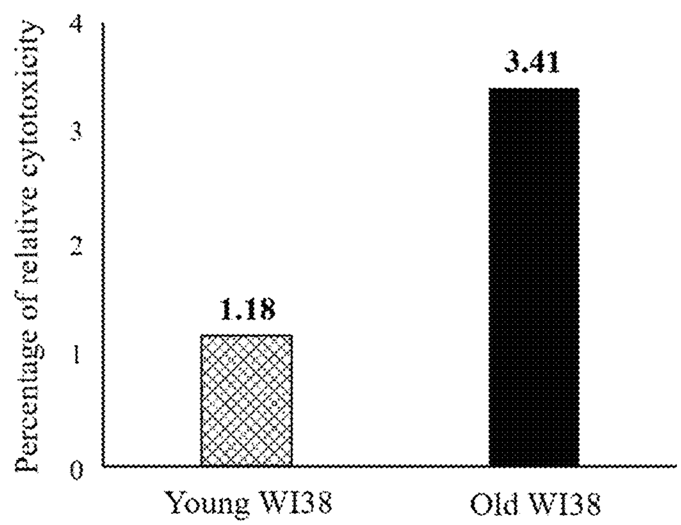
FIG. 4—'The CAR-T assay'—is a graph showing the results of selective elimination of senescent cells by engineered CAR-T against DPP4.
Figure 5:
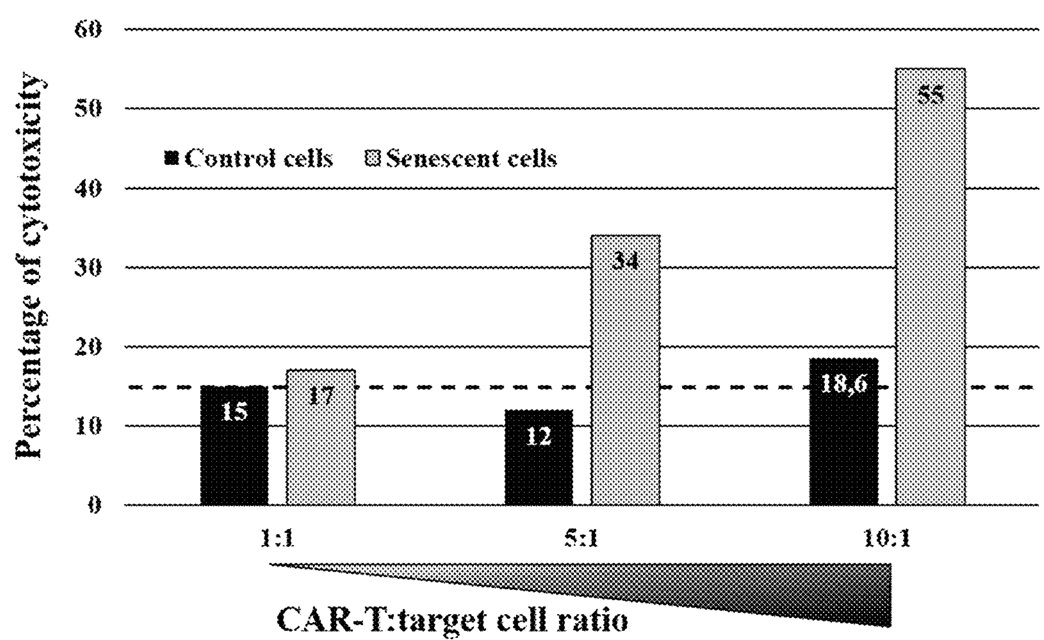
FIG. 5—'The quantification of experimental CAR-T assay results'—is a graph showing the results of the CAR-T assay on control (WI-38/GM21808) versus senescent cells. Cells were incubated with increasing ratios of CAR-T to target cells (1:1, 5:1 and 10:1).

When we used the same cells with control and DPP4-CAR-T cells, we observe a 3-fold selective elimination of old senescent cells with respect to the young ones. CAR-T cells engineered against DPP4 show high specificity against DPP4-bearing senescent cells (FIG. 4). The quantification of experimental results also shows that increasing CAR-T levels are only cytotoxic to senescent cells, but not to control cells (FIG. 5). This indicates that the CAR-T assay selectively eliminates target cells, i.e., senescent cells.

Conclusion

DPP4 is a novel senescent surface marker identified in human fibroblasts both in replicative and oncogene-induced (RAS) senescence. DPP4 is robustly upregulated on the plasma membrane of senescent cells.

DPP4 is expressed selectively in senescent cells, but not proliferating human diploid fibroblasts, making it a suitable target for senolytic therapy (FIG. 2). We showed that, upon two different senescent-inducing stimuli in two different types of fibroblasts, CAR-T cell therapy against DPP4 selectively eliminates DPP4-positive senescent cells (FIG. 5).

Example 2—Development of scFv Against Human DEP1

Materials

Rat Immunization and Splenectomy

- "hDEP1 Peptide #1": amino acid residues 36-48 of SEQ ID NO: 1, conjugated to BSA
- "hDEP1 Peptide #2": amino acid residues 436-452 of SEQ ID NO: 1, conjugated to BSA
- "hDEP1 Peptide #3": amino acid residues 728-741 of SEQ ID NO: 1, conjugated to BSA
- "hDEP1 Peptide #4": amino acid residues 864-881 of SEQ ID NO: 1, conjugated to BSA
- "hDEP1-ECD-Fc": amino acid residues 621-969 of SEQ ID NO: 1 conjugated to an IgG1 Fc domain (SEQ ID NO: 2), produced recombinantly in CHO cells and purified on protein A resin
- "hDEP1-ECD-His": amino acid residues 621-969 of SEQ ID NO: 1 conjugated to a 6×His tag through a linker (SEQ ID NO: 3), produced recombinantly in CHO cells and purified on Ni-NTA resin
- BSA (NEB)
- Freund's complete and incomplete adjuvants (Sigma, F5881 and F5506)
- Standard ELISA material
- Fc-specific polyclonal anti-rat immunoglobulin G (IgG) (Jackson 112-036-071; 1/5000)

RNA Extraction

- RNAse AWAY (Molecular Bio-products, Cat. no. 7002)
- Tri reagent (Molecular research center Inc, Cat. no. TR118)
- BCP (Molecular research center Inc, Cat. no. BP-ISI)
- Isopropanol, ethanol 75% (molecular grade)

RT-PCR, Library Pre-Cloning

- SuperScript Reverse Transcriptase (Invitrogen, Cat. no. 18064-014)
- Murine Primers set
- Taq DNA polymerase, recombinant (Invitrogen, Cat. 10342-020)
- pGemT Vector System (Promega, Cat. A3600)
- Electroporation device and material
- Electrocompetent Sure bacteria (*E. coli*) (Stratagene, Cat. 200227)
- Nucleobond AX (Macherey-Nagel, Cat. 740 573-100)

Amplifying VH and VL

- Red Taq (Sigma, Hamburg)+10×buffer
- dNTP mix (10 mM each)
- Oligonucleotide primer
- Agarose (Serva, Heidelberg)
- TAE-buffer 50× (2 M TrisHCl, 1 M acetic acid, 0.05 M EDTA pH 8)
- Nucleospin Extract 2 Kit (Macherey-Nagel, Duren)

Cloning VH and VL

- NotI, MluI, NcoI, HindIII (NEB)
- Buffer 2, Buffer 3 (NEB)
- BSA (NEB)
- Calf intestine phosphatase (CIP) (MBI Fermentas, St. Leon-Rot)
- T4 ligase (Promega, Mannheim)
- 3 M sodium acetate pH 5.2
- *E. coli* XL1-Blue MRF (Stratagene, Amsterdam), genotype: Δ(mcrA)183 Δ(mcrCB-hsdSMR-mrr)173 endA1 supE44 thi-1 recA1 gyrA96 relA1 lac [F' proAB lacIqZΔM15 Tn10 (Tetr)]
- Electroporator MicroPulser (BIO-RAD, München)
- 2 M glucose (sterile filtered)
- 2 M magnesium solution (1 M MgCl, 1 M MgSO4)
- SOC medium pH 7.0 (2% w/v tryptone, 0.5% w/v yeast extract, 0.05% w/v NaCl, 20 mM Mg solution, 20 mM glucose)
- 2×YT-medium pH 7.0 (1.6% w/v tryptone, 1% w/v yeast extract, 0.5% w/v NaCl)
- 2×YT-GAT (2×YT+100 mM glucose+100 μg/mL ampiciline+20 μg/mL tetracycline)
- Ampiciline (100 mg/mL stock)
- Tetracycline (10 mg/mL stock)
- 9 cm-Petrie dishes
- 25 cm-square Petri dishes ("pizza plates")
- 2×YT-GAT agar plates (2×YT-GAT, 1.5% w/v agar-agar)
- Nucleobond Plasmid Midi Kit (Macherey-Nagel)
- Glycerol 99.5% (Roth, Karlsruhe)

Library Packaging

- 2×YT-medium pH 7.0 (1.6% w/v tryptone, 1% w/v yeast extract, 0.5% w/v NaCl)
- 2×TY-GA (2×TY, 100 mM glucose, 100 μg/mL ampicillin)
- M13K07 Helperphage for monovalent display (Stratagene)

2×TY-AK (2×TY+100 μg/mL ampicillin+50 μg/mL kanamycin)

Sorval Centrifuge RC5B Plus, rotor GS3 and SS34 (Thermo Scientific, Waltham)

Polyethylenglycol (PEG) solution (20% w/v PEG 6000, 2.5 M NaCl)

Phage dilution buffer (10 mM Tris-HCl pH 7.5, 20 mM NaCl, 2 mM EDTA)

Library Screening

Microtiter plate (Nunc Maxisorp)

3% BSA in TBS (50 mM Tris; 137 mM NaCl; 2.7 mM KCl; pH adjusted to 8.0)

TBS supplemented with 0.1% Tween20

*E. coli* (SURE strain, Stratagene)

SB (super broth) supplemented with tetracycline (10 μg/mL) and carbenicillin (50 μg/mL).

SB supplemented with tetracycline (10 μg/mL), carbenicillin (50 μg/mL) and kanamycin (70 μg/mL)

Polyethylenglycol (PEG) solution (20% w/v PEG 6000, 2.5 M NaCl)

Sorval Centrifuge RC5B Plus, rotor GS3 and SS34 (Thermo Scientific, Waltham)

scFv Production and Purification

*E. coli* strain HB2151

SB (super broth) supplemented with carbenicillin (50 μg/mL) and 1% glucose 1 mM IPTG Polymyxin B sulfate His-Trap column (GE Healthcare, Buckinghamshire, UK)

Methods

Rat Immunization 12 rats were immunized with i.p. injections of 50 μg of hDEP1 Peptide #1, Peptide #2, Peptide #3 or Peptide #4 (3 rats/peptide). In parallel, 5 rats were immunized with i.p. injections of 50 μg of hDEP1-ECD-Fc.

The three first injections were administered at 14 days intervals (DO, D14 and D28). A fourth injection was administered after animal selection according to the titer reached.

The first injection at DO was mixed with complete Freund's adjuvant. The remaining injections were carried out with incomplete Freund's adjuvant.

The rat immune response was evaluated by ELISA performed in 96-well microtiter plates using hDEP1 Peptide #1, Peptide #2, Peptide #3, Peptide #4, hDEP1-ECD-His, or BSA. Pre-immune serum was used as a negative control. For detection, Fc-specific polyclonal anti-rat IgG was used and the titer was measured as the reciprocal of the highest dilution of immune serum giving a signal at 50% of the highest OD.

RNA Extraction, RT-PCR, Library Pre-Cloning

After the fourth injection, RNA was isolated with Tri Reagent/BCP method from the spleen of the immunized rats and used for reverse transcription. Oligonucleotides sets were used for amplification of the DNA encoding the κ and λ light chain and to amplify the DNA encoding Fd fragments of the heavy γ chain. To obtain two sub-libraries encoding the Fd fragment and light chain, the corresponding PCR products were pooled and sub-cloned into the pGEMT vector.

Library Construction

The final library was constructed starting from these two sub-libraries. The DNA encoding the Fd fragment and the light chain was re-amplified with two individual oligonucleotide sets introducing the required restrictions sites for library-cloning using the pTH1 vector. First the pTH1 vector and the VL-amplified repertoire were digested with MluI and NotI. Afterwards, the enzyme reaction was terminated and the vector was dephosphorylated with calf intestinal phosphatase. The vector and the VL-repertoire were purified using NucleoSpinII Gel and PCR Clean-up Kit (Macherey-Nagel) and 270 ng of the VL-repertoire was cloned into 1 μg of dephosphorylated vector using T4 DNA-ligase. The pellet was washed twice with 70% ethanol and resuspended in 30 μL $H_2O$ before it was used for electroporation (1.7 kV) with 25 μL of XL1-BlueMRF'. The transformed bacteria were cultured on 2×YT agar plates supplemented with 100 μg/mL ampicillin, 20 μg/mL tetracycline and 100 mM glucose. The colonies were harvested by resuspension in 40 mL of 2×YT medium with a Drigalsky spatula and plasmids were isolated with the Nucleobond Plasmid Midi Kit. Following this, the VL-library and the VH-repertoire were digested with SfiI and HindIII, ligated and electroporated as described for VL, but this time 250 ng of the digested and purified VH-repertoire was inserted into 1 μg of the VL-library. The harvested bacteria of the final scFv antibody gene library were pooled, aliquoted and stored at −80° C. The library was packaged with M13K07.

Library Packaging

To package the library, inoculate 400 mL 2×TY-GA in a 1 L Erlenmeyer flask with 1 mL antibody gene library stock and then infect 25 mL bacteria culture (~$1.25\times10^{10}$ cells) with $2.5\times10^{11}$ colony forming units (cfu) of the helper phage M13K07.

Produce scFv-phage overnight at 250 rpm and 30° C. Pellet the bacteria by centrifugation for 10 minutes at 10000 g. Precipitate the phage from the supernatant by adding ⅕ volume PEG solution. Incubate for 1 hour at 4° C. with gentle shaking, followed by centrifugation for 1 hour at 10000 g. Discard the supernatant, resolve each pellet in 10 mL phage dilution buffer and add ⅕ volume PEG solution. Incubate on ice for 20 minutes and pellet the phage by centrifugation for 30 minutes at 10000 g. Discard the supernatant and put the open tubes upside down on tissue paper. Let the viscous PEG solution move out completely. Resuspend the phage pellet in 1 mL phage dilution buffer.

Library Screening

For isolation of anti-DEP1 specific scFv, microtiter plates were coated overnight with hDEP1-ECD-His or Peptide #4 at 10 μg/mL in PBS at 4° C. The plates were then blocked with 3% BSA in TBS for 2 hours at 37° C. After a washing step, the antibody phage display library was added and incubated for an additional 2 hours at 37° C.

During the first round of panning, the plates were washed 5 times with TBS supplemented with 0.1% Tween20. The plates were finally rinsed with sterile PBS and phage were eluted with trypsin (1 mg/mL in TBS) for 30 minutes at 37° C. The eluted phages were used to infect *E. coli* cultured in SB supplemented with tetracycline and carbenicillin.

For the production of new phage particles, infected *E. coli* were co-infected with M13K07 and cultured overnight at 37° C. in SB supplemented with tetracycline, carbenicillin and kanamycin. Phage particles were precipitated in PEG/NaCl (4% w/v PEG8000, 3% w/v NaCl) and used for the next round of panning. This was performed as described above, with the exception that the plates were washed with increasing stringency.

The infected *E. coli* of the last round of panning were grown on SB media in petri dishes and used for screening by ELISA using hDEP1-ECD-His or Peptide #4.

scFv Production and Purification

For expression of soluble scFv, the DNA encoding the selected scFv was used to transform the non-suppressor *E. coli* strain HB2151. Transformed *E. coli* were then used to inoculate 500 mL of SB medium and cultivated at 30° C.

until $OD_{600}$≈1.5. Then, 1 mM IPTG was added to induce the expression of scFv and the culture was incubated overnight at 22° C. After harvesting by centrifugation at 2500 g for 15 minutes at 4° C., scFv were extracted with polymyxin B sulfate and purified using a His-Trap column according to the manufacturer's instructions. Purified scFv were quantified by $OD_{280}$ and controlled by SDS-PAGE analysis.

Confirmation of Selected scFv by ELISA Against Screening Peptide

The soluble anti-DEP1 scFv were tested in indirect ELISA for reactivities against the 4 peptides (Peptide #1, Peptide #2, Peptide #3, and Peptide #4), against hDEP1-ECD-His and its murine counterpart with SEQ ID NO: 4; and against BSA as negative control. Reactivity was assessed by $OD_{450}$, in serial dilutions.

Results

Serum of the 17 rats was collected on D38 (after the third immunization, on D28) and Fc-specific polyclonal anti-rat IgG was used to measure the titer at 50% of maximum signal. Results are given in Table 5.

TABLE 5

| | | hDEP1 Peptide #1 | hDEP1 Peptide #2 | hDEP1 Peptide #3 | hDEP1 Peptide #4 | hDEP1-ECD-His | BSA |
|---|---|---|---|---|---|---|---|
| hDEP1 | Rat 1 | 380000 | ND | ND | ND | ND | ND |
| Peptide | Rat 2 | 55000 | ND | ND | ND | ND | ND |
| #1 | Rat 3 | 11000 | ND | ND | ND | ND | ND |
| hDEP1 | Rat 4 | ND | 27000 | ND | ND | ND | ND |
| Peptide | Rat 5 | ND | 23000 | ND | ND | ND | ND |
| #2 | Rat 6 (dead) | ND | 170000 | ND | ND | ND | ND |
| hDEP1 | Rat 7 | ND | ND | 12000 | ND | 500 | ND |
| Peptide | Rat 8 | ND | ND | 18000 | ND | 500 | ND |
| #3 | Rat 9 | ND | ND | 22000 | ND | 500 | ND |
| hDEP1 | Rat 10 | ND | ND | ND | 113000 | 6000 | ND |
| Peptide | Rat 11 | ND | ND | ND | 110000 | 4500 | ND |
| #4 | Rat 12 | ND | ND | ND | 113000 | 5000 | 500 |
| hDEP1- | Rat 13 | 500 | 500 | 500 | ND | 321000 | ND |
| ECD-Fc | Rat 14 | ND | ND | 500 | ND | 64000 | 500 |
| | Rat 15 | ND | ND | 500 | ND | 180000 | 500 |
| | Rat 16 | 500 | 500 | 500 | 500 | 82000 | ND |
| | Rat 17 | ND | ND | 500 | ND | 40000 | ND |

High titers were harvested against each immunogenic peptide.

Peptides #1 and #4 appeared to be more immunogenic than Peptides #2 and #3, allowing better immune responses. Rats immunized with Peptide #4 also presented a positive immune response for the recombinant hDEP1-ECD-His protein, while rats immunized with Peptides #1 and #2 did not present such positive immune response. Overall, rat 10 seemed to be the best candidate among rats 1 to 12.

High titers were also harvested against the recombinant protein hDEP1-ECD-His, ranging from 1/40000 to 1/321000. Overall, rat 13 seemed to be the best candidate among rats 13 to 17.

A splenectomy was carried out on rats 10 and 13. RNA were extracted from the spleens, and total RNA was quantified (Table 6) and controlled on agarose gel (not shown).

TABLE 6

| Sample | Concentration (μg/mL) | $A_{260nm}$ | $A_{280nm}$ | $A_{260nm}/A_{280nm}$ | $A_{260nm}/A_{230nm}$ |
|---|---|---|---|---|---|
| Rat 10 | 2108.9 | 52.7 | 29.5 | 1.78 | 1.55 |
| Rat 13 | 2370.77 | 59.3 | 33.4 | 1.77 | 1.42 |

The first step of the library construction consisted of the VL fragments cloning in a phagemid vector, and then the VH fragments were inserted into the vector containing the VL repertoire. The vector format VH/VL-6×His-Flag was selected for constructions.

Rat 10

The final scFv library consisted of $1\times10^7$ independent clones with a full-size insert rate of 92% (by colony-PCR) and was finally packaged in M13K07 phage.

Figure 6:
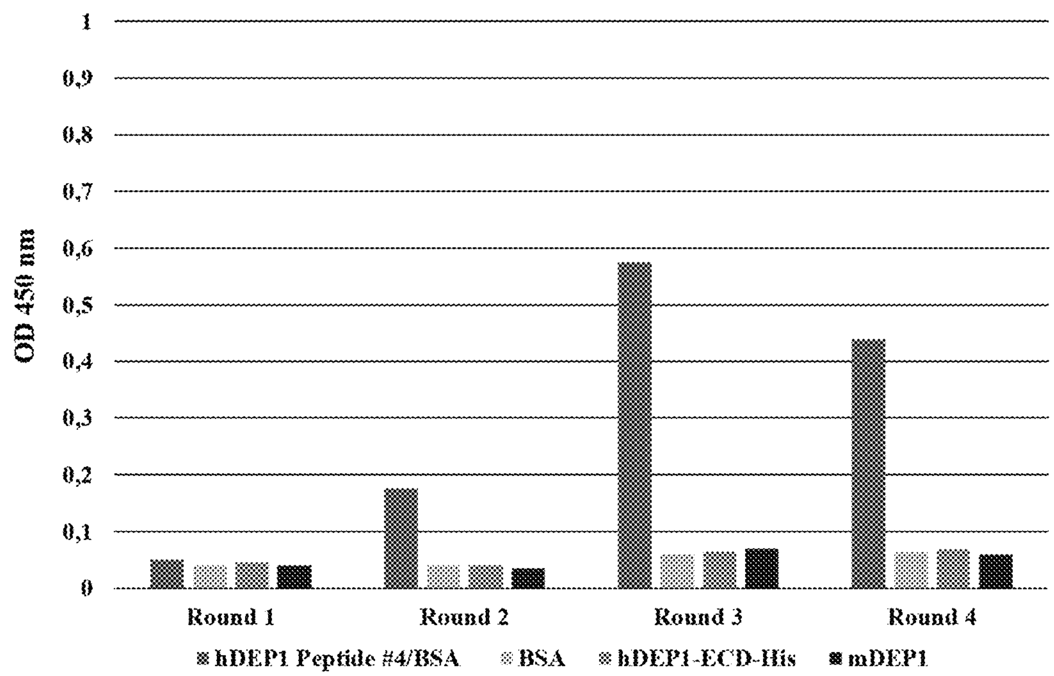
FIG. 6—'scFv library screening by phage display'—is a graph showing the panning using hDEP1 Peptide #4/BSA as target and standard elution strategy. Four rounds were carried out in order to isolate specific binders. The reactivity of phages eluted after each round against the targeted peptide was assessed in phage-ELISA.

The panning was performed using hDEP1 Peptide #4/BSA as target and standard elution strategy. Four rounds were carried out in order to isolate specific binders. After each round, only the phages having interacted with hDEP1 Peptide #4/BSA were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 3 and 4 (FIG. 6).

96 isolated clones from the second, third and fourth rounds of panning were hand-picked and used to produce the respective soluble scFv in microtiter plate. Each clone was then tested in ELISA against hDEP1 Peptide #4/BSA.

48 isolated clones showing a specific signal against hDEP1 Peptide #4/BSA compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Twelve sequences corresponding to non-recombined and non-redundant scFv sequences were identified, grouped into two clusters (Table 7).

TABLE 7

HCVR and LCVR column indicate the amino acid sequence of the heavy chain and light chain variable regions, respectively.

| Cluster | Clone's name | Redundancy | HCVR | LCVR |
|---|---|---|---|---|
| Cluster 1 | 5738-10-R3A-C6 | 2 | 56 | 76 |
| | 5738-10-R3A-D8 | 1 | 59 | 79 |
| Cluster 2 | 5738-10-R3A-B2 | 1 | 55 | 75 |
| | 5738-10-R3A-D1 | 1 | 57 | 77 |
| | 5738-10-R3A-D5 | 1 | 58 | 78 |
| | 5738-10-R3A-D11 | 3 | 60 | 80 |
| | 5738-10-R4A-E7 | 1 | 61 | 81 |
| | 5738-10-R4A-E9 | 1 | 60 | 82 |
| | 5738-10-R4A-F12 | 5 | 62 | 83 |
| | 5738-10-R4A-G4 | 2 | 63 | 84 |
| | 5738-10-R4A-G11 | 7 | 64 | 85 |
| | 5738-10-R4A-G12 | 18 | 65 | 86 |

According to sequence and redundancy analysis, the following clones were selected:

5738-10-R3A-C6 (cluster 1)

5738-10-R3A-D5 (cluster 2)

5738-10-R4A-G12 (cluster 2)

After transformation of the 3 selected clones DNA in an *E. coli* strain dedicated to production, the clones were expressed as soluble scFv and purified using the His tag on an Ni-NTA column. These soluble anti-hDEP1 scFv were tested in indirect ELISA for reactivities against the 4 peptides and DEP1 proteins (human and murine) and against the negative control (BSA only).

All three scFv were reactive against hDEP1 Peptide #4, as expected, especially the two scFv of cluster 2. No reactivity could be observed against the 3 other peptides. Only clone 5738-10-R4A-G12 showed a reactivity against hDEP1, with no response for the mDEP1 or the negative control.

Rat 13

The final scFv library consisted of $1\times10^7$ independent clones with a full-size insert rate of 88% (by colony-PCR) and was finally packaged in M13K07 phage.

Figure 7:
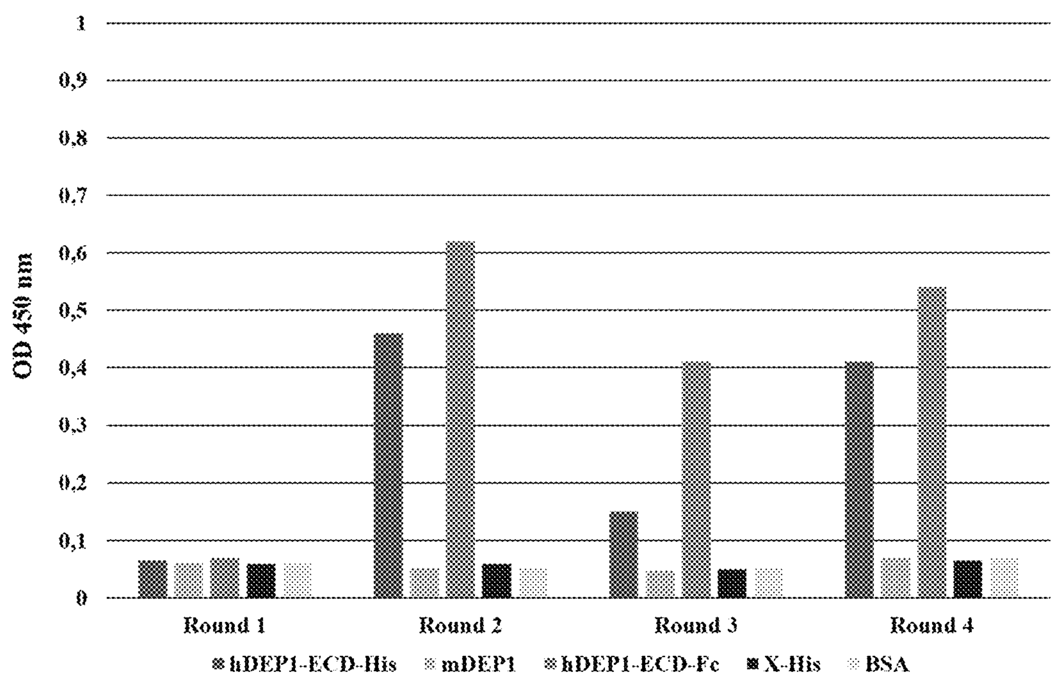
FIG. 7—'scFv library screening by phage display'—is a graph showing the panning using hDEP1-ECD-His as target and standard elution strategy. Four rounds were carried out in order to isolate specific binders. The reactivity of phages eluted after each round against the targeted peptide was assessed in phage-ELISA.

The panning was performed using hDEP1-ECD-His as target and standard elution strategy. Four rounds were carried out in order to isolate specific binders. After each round, only the phages having interacted with hDEP1-ECD-His were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 2, 3 and 4 (FIG. 7).

96 isolated clones from the second, third and fourth rounds of panning were hand-picked and used to produce the respective soluble scFv in microtiter plate. Each clone was then tested in ELISA against hDEP1-ECD-His.

48 isolated clones showing a specific signal against hDEP1-ECD-His compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Nine sequences corresponding to non-recombined and non-redundant scFv sequences were identified, grouped into two clusters (Table 8).

TABLE 8

HCVR and LCVR column indicate the amino acid sequence of the heavy chain and light chain variable regions, respectively.

| Cluster | Clone's name | Redundancy | HCVR | LCVR |
|---|---|---|---|---|
| Cluster 1 | 5738-13-R2A-C1 | 1 | 66 | 87 |
| | 5738-13-R4A-D11 | 1 | 68 | 89 |
| Cluster 2 | 5738-13-R2A-D3 | 1 | 67 | 88 |
| | 5738-13-R3A-F5 | 1 | 69 | 90 |
| | 5738-13-R4A-F11 | 1 | 70 | 91 |
| | 5738-13-R2A-H3 | 3 | 71 | 92 |
| | 5738-13-R2A-H4 | 21 | 72 | 93 |
| | 5738-13-R4A-H9 | 2 | 73 | 94 |
| | 5738-13-R4A-H11 | 15 | 74 | 94 |

According to sequence and redundancy analysis, the following clones were selected:

5738-13-R4A-D11 (cluster 1)

5738-13-R2A-H4 (cluster 2)

After transformation of the 2 selected clones DNA in an *E. coli* strain dedicated to production, the clones were expressed as soluble scFv and purified using the His tag on an Ni-NTA column. These soluble anti-hDEP1 scFv were tested in indirect ELISA for reactivities against the 4 peptides and DEP1 proteins (human and murine) and against the negative control (BSA only).

The two scFv were reactive against hDEP1, as expected. No reactivity could be observed against any of the 4 peptides, the mDEP1 or the negative control.

Example 3—Development of scFv Against Human DPP4

Materials

Rat Immunization and Splenectomy

- "hDPP4 Peptide P2": amino acid residues 170-191 of SEQ ID NO: 101, conjugated to BSA
- "hDPP4 Peptide P3": amino acid residues 235-254 of SEQ ID NO: 101, conjugated to BSA
- "hDPP4 Peptide P5": amino acid residues 492-517 of SEQ ID NO: 101, conjugated to BSA
- "hDPP4 Peptide P6": amino acid residues 533-551 of SEQ ID NO: 101, conjugated to BSA
- "hDPP4-ECD-His": SEQ ID NO: 102
- "mDPP4": murine DDP with SEQ ID NO: 103 (Uniprot accession number P28843-1; Last modified: Feb. 1, 1996 (version 3))
- BSA (NEB)
- Freund's complete and incomplete adjuvants (Sigma, F5881 and F5506)
- Standard ELISA material
- Fc-specific polyclonal anti-rat immunoglobulin G (IgG) (Jackson 112-036-071; 1/5000)

RNA Extraction

- RNAse AWAY (Molecular Bio-products, Cat. no. 7002)
- Tri reagent (Molecular research center Inc, Cat. no. TR118)
- BCP (Molecular research center Inc, Cat. no. BP-ISI)
- Isopropanol, ethanol 75% (molecular grade)

RT-PCR, Library Pre-Cloning

- SuperScript Reverse Transcriptase (Invitrogen, Cat. no. 18064-014)
- Murine Primers set
- Taq DNA polymerase, recombinant (Invitrogen, Cat. 10342-020)
- pGemT Vector System (Promega, Cat. A3600)
- Electroporation device and material
- Electrocompetent Sure bacteria (*E. coli*) (Stratagene, Cat. 200227)
- Nucleobond AX (Macherey-Nagel, Cat. 740 573-100)

Amplifying VH and VL

- Red Taq (Sigma, Hamburg)+10×buffer
- dNTP mix (10 mM each)
- Oligonucleotide primer
- Agarose (Serva, Heidelberg)
- TAE-buffer 50× (2 M TrisHCl, 1 M acetic acid, 0.05 M EDTA pH 8)
- Nucleospin Extract 2 Kit (Macherey-Nagel, Düren)

Cloning VH and VL

- NotI, MluI, NeoI, HindIII (NEB)
- Buffer 2, Buffer 3 (NEB)
- BSA (NEB)
- Calf intestine phosphatase (CIP) (MBI Fermentas, St. Leon-Rot)
- T4 ligase (Promega, Mannheim)
- 3 M sodium acetate pH 5.2
- *E. coli* XL1-Blue MRF (Stratagene, Amsterdam), genotype: Δ(mcrA)183 Δ(mcrCB-hsdSMR-mrr)173 endA1 supE44 thi-1 recA1 gyrA96 relA1 lac [F' proAB lacIqZΔM15 Tn10 (Tetr)]
- Electroporator MicroPulser (BIO-RAD, München)
- 2 M glucose (sterile filtered)
- 2 M magnesium solution (1 M MgCl, 1 M MgSO4)
- SOC medium pH 7.0 (2% w/v tryptone, 0.5% w/v yeast extract, 0.05% w/v NaCl, 20 mM Mg solution, 20 mM glucose)

2×YT-medium pH 7.0 (1.6% w/v tryptone, 1% w/v yeast extract, 0.5% w/v NaCl)
2×YT-GAT (2×YT+100 mM glucose+100 μg/mL ampiciline+20 μg/mL tetracycline)
Ampiciline (100 mg/mL stock)
Tetracycline (10 mg/mL stock)
9 cm-Petrie dishes
25 cm-square Petri dishes ("pizza plates")
2×YT-GAT agar plates (2×YT-GAT, 1.5% w/v agar-agar)
Nucleobond Plasmid Midi Kit (Macherey-Nagel)
Glycerol 99.5% (Roth, Karlsruhe)

Library Packaging

2×YT-medium pH 7.0 (1.6% w/v tryptone, 1% w/v yeast extract, 0.5% w/v NaCl)
2×TY-GA (2×TY, 100 mM glucose, 100 μg/mL ampicillin)
M13K07 Helperphage for monovalent display (Stratagene)
2×TY-AK (2×TY+100 μg/mL ampicillin+50 μg/mL kanamycin)
Sorval Centrifuge RC5B Plus, rotor GS3 and SS34 (Thermo Scientific, Waltham)
Polyethylenglycol (PEG) solution (20% w/v PEG 6000, 2.5 M NaCl)
Phage dilution buffer (10 mM Tris-HCl pH 7.5, 20 mM NaCl, 2 mM EDTA)

Library Screening

Microtiter plate (Nunc Maxisorp)
3% BSA in TBS (50 mM Tris; 137 mM NaCl; 2.7 mM KCl; pH adjusted to 8.0)
TBS supplemented with 0.1% Tween20
*E. coli* (SURE strain, Stratagene)
SB (super broth) supplemented with tetracycline (10 μg/mL) and carbenicillin (50 μg/mL).
SB supplemented with tetracycline (10 μg/mL), carbenicillin (50 μg/mL) and kanamycin (70 μg/mL)
Polyethylenglycol (PEG) solution (20% w/v PEG 6000, 2.5 M NaCl)
Sorval Centrifuge RC5B Plus, rotor GS3 and SS34 (Thermo Scientific, Waltham)

scFv Production and Purification

*E. coli* strain HB2151
SB (super broth) supplemented with carbenicillin (50 μg/mL) and 1% glucose
1 mM IPTG
Polymyxin B sulfate
His-Trap column (GE Healthcare, Buckinghamshire, UK)

Methods

Rat Immunization 12 rats were immunized with i.p. injections of 50 μg of hDDP4 Peptide P1, Peptide P3, Peptide P5 or Peptide P6 (3 rats/peptide). In parallel, 5 rats were immunized with i.p. injections of 50 μg of hDDP4-ECD-His.

The three first injections were administered at 14 days intervals (DO, D14 and D28). A fourth injection was administered after animal selection according to the titer reached.

The first injection at DO was mixed with complete Freund's adjuvant. The remaining injections were carried out with incomplete Freund's adjuvant.

The rat immune response was evaluated by ELISA performed in 96-well microtiter plates using hDDP4 Peptide P1, Peptide P3, Peptide P5, Peptide P6, hDPP4-ECD-His, mDPP4, or BSA.

Pre-immune serum was used as a negative control. For detection, Fc-specific polyclonal anti-rat IgG was used and the titer was measured as the reciprocal of the highest dilution of immune serum giving a signal at 50% of the highest OD.

RNA Extraction, RT-PCR, Library Pre-Cloning

After the fourth injection, RNA was isolated with Tri Reagent/BCP method from the spleen of the immunized rats and used for reverse transcription. Oligonucleotides sets were used for amplification of the DNA encoding the κ and λ light chain and to amplify the DNA encoding Fd fragments of the heavy γ chain. To obtain two sub-libraries encoding the Fd fragment and light chain, the corresponding PCR products were pooled and sub-cloned into the pGEMT vector.

Library Construction

The final library was constructed starting from these two sub-libraries. The DNA encoding the Fd fragment and the light chain was re-amplified with two individual oligonucleotide sets introducing the required restrictions sites for library-cloning using the pTH1 vector. First the pTH1 vector and the VL-amplified repertoire were digested with MluI and NotI. Afterwards, the enzyme reaction was terminated and the vector was dephosphorylated with calf intestinal phosphatase. The vector and the VL-repertoire were purified using NucleoSpinII Gel and PCR Clean-up Kit (Macherey-Nagel) and 270 ng of the VL-repertoire was cloned into 1 μg of dephosphorylated vector using T4 DNA-ligase. The pellet was washed twice with 70% ethanol and resuspended in 30 μL $H_2O$ before it was used for electroporation (1.7 kV) with 25 μL of XL1-BlueMRF'. The transformed bacteria were cultured on 2×YT agar plates supplemented with 100 μg/mL ampicillin, 20 μg/mL tetracycline and 100 mM glucose. The colonies were harvested by resuspension in 40 mL of 2×YT medium with a Drigalsky spatula and plasmids were isolated with the Nucleobond Plasmid Midi Kit. Following this, the VL-library and the VH-repertoire were digested with SfiI and HindIII, ligated and electroporated as described for VL, but this time 250 ng of the digested and purified VH-repertoire was inserted into 1 μg of the VL-library. The harvested bacteria of the final scFv antibody gene library were pooled, aliquoted and stored at −80° C. The library was packaged with M13K07.

Library Packaging

To package the library, inoculate 400 mL 2×TY-GA in a 1 L Erlenmeyer flask with 1 mL antibody gene library stock and then infect 25 mL bacteria culture (~$1.25\times10^{10}$ cells) with $2.5\times10^{11}$ colony forming units (cfu) of the helper phage M13K07.

Produce scFv-phage overnight at 250 rpm and 30° C. Pellet the bacteria by centrifugation for 10 minutes at 10000 g. Precipitate the phage from the supernatant by adding ⅕ volume PEG solution. Incubate for 1 hour at 4° C. with gentle shaking, followed by centrifugation for 1 hour at 10000 g. Discard the supernatant, resolve each pellet in 10 mL phage dilution buffer and add ⅕ volume PEG solution. Incubate on ice for 20 minutes and pellet the phage by centrifugation for 30 minutes at 10000 g. Discard the supernatant and put the open tubes upside down on tissue paper. Let the viscous PEG solution move out completely. Resuspend the phage pellet in 1 mL phage dilution buffer.

Library Screening

For isolation of anti-DPP4 specific scFv, microtiter plates were coated overnight with hDPP4-ECD-His or Peptide P5 at 10 μg/mL in PBS at 4° C. The plates were then blocked with 3% BSA in TBS for 2 hours at 37° C. After a washing step, the antibody phage display library was added and incubated for an additional 2 hours at 37° C.

During the first round of panning, the plates were washed 5 times with TBS supplemented with 0.1% Tween20. The plates were finally rinsed with sterile PBS and phage were eluted with trypsin (1 mg/mL in TBS) for 30 minutes at 37° C. The eluted phages were used to infect *E. coli* cultured in SB supplemented with tetracycline and carbenicillin. For the production of new phage particles, infected *E. coli* were co-infected with M13K07 and cultured overnight at 37° C. in SB supplemented with tetracycline, carbenicillin and kanamycin. Phage particles were precipitated in PEG/NaCl (4% w/v PEG8000, 3% w/v NaCl) and used for the next round of panning. This was performed as described above, with the exception that the plates were washed with increasing stringency.

The infected *E. coli* of the last round of panning were grown on SB media in petri dishes and used for screening by ELISA using hDPP4-ECD-His or Peptide P5.

scFv Production and Purification

For expression of soluble scFv, the DNA encoding the selected scFv was used to transform the non-suppressor *E. coli* strain HB2151. Transformed *E. coli* were then used to inoculate 500 mL of SB medium and cultivated at 30° C. until $OD_{600}$≈1.5. Then, 1 mM IPTG was added to induce the expression of scFv and the culture was incubated overnight at 22° C. After harvesting by centrifugation at 2500 g for 15 minutes at 4° C., scFv were extracted with polymyxin B sulfate and purified using a His-Trap column according to the manufacturer's instructions. Purified scFv were quantified by $OD_{280}$ and controlled by SDS-PAGE analysis.

Confirmation of Selected scFv by ELISA Against Screening Peptide

The soluble anti-DPP4 scFv were tested in indirect ELISA for reactivities against the 4 peptides (Peptide P2, Peptide P3, Peptide P5, and Peptide P6), against hDPP4-ECD-His and its murine counterpart mDPP4 with SEQ ID NO: 103; and against BSA as negative control. Reactivity was assessed by $OD_{450}$, in serial dilutions.

Results

Serum of the 17 rats was collected on D38 (after the third immunization, on D28) and Fc-specific polyclonal anti-rat IgG was used to measure the titer at 50% of maximum signal. Results are given in Table 9.

TABLE 9

| | | hDEP4 Peptide P2 | hDEP4 Peptide P3 | hDEP4 Peptide P5 | hDEP4 Peptide P6 | hDEP4-ECD-His | mDPP4 |
|---|---|---|---|---|---|---|---|
| hDPP4 | Rat 1 | 10045 | ND | ND | ND | 3663 | ND |
| Peptide | Rat 2 | 5023 | ND | ND | ND | <423 | ND |
| P2 | Rat 3 | 3949 | <380 | ND | ND | 820 | ND |
| hDPP4 | Rat 4 | ND | <1545 | ND | ND | <950 | <515 |
| Peptide | Rat 5 | ND | <1456 | ND | ND | 1423 | <606 |
| P3 | Rat 6 | ND | <677 | ND | ND | <429 | ND |
| hDPP4 | Rat 7 | ND | ND | 38114 | ND | <954 | <1238 |
| Peptide | Rat 8 | ND | ND | 54322 | ND | 2363 | <1591 |
| P5 | Rat 9 | ND | ND | 6844 | ND | <532 | <584 |
| hDPP4 | Rat 10 | ND | ND | ND | <634 | ND | ND |
| Peptide | Rat 11 | ND | ND | ND | <1252 | ND | ND |
| P6 | Rat 12 | ND | ND | ND | 3183 | <506 | <578 |
| | Rat 13 | ND | ND | <1887 | ND | 278332 | <1497 |

TABLE 9-continued

| | | hDEP4 Peptide P2 | hDEP4 Peptide P3 | hDEP4 Peptide P5 | hDEP4 Peptide P6 | hDEP4-ECD-His | mDPP4 |
|---|---|---|---|---|---|---|---|
| hDPP4- | Rat 14 | ND | ND | <1503 | ND | 22112 | <468 |
| ECD- | Rat 15 | ND | <526 | 4592 | ND | 69570 | <708 |
| His | Rat 16 | ND | <537 | 2737 | ND | 198247 | <1719 |
| | Rat 17 | ND | <763 | <647 | ND | 40687 | <1635 |

Relatively low titers were harvested against each immunogenic peptide. Peptide P5 however appeared to be more immunogenic than Peptides P2, P3 and P6, allowing better immune responses. Overall, rat 8 seemed to be the best candidate among rats 1 to 12.

High titers were harvested against the recombinant protein hDPP4-ECD-His, ranging from 1/22000 to 1/278000. Overall, rat 13 seemed to be the best candidate among rats 13 to 17.

A splenectomy was carried out on rats 8 and 13. RNA were extracted from the spleens, and total RNA was quantified (Table 10) and controlled on agarose gel (not shown).

TABLE 10

| Sample | Concentration (μg/mL) | $A_{260nm}$ | $A_{280nm}$ | $A_{260nm}/A_{280nm}$ | $A_{260nm}/A_{230nm}$ |
|---|---|---|---|---|---|
| Rat 8 | 2051 | 51.2 | 29.0 | 1.78 | 1.29 |
| Rat 13 | 2107 | 52.7 | 29.8 | 1.77 | 1.29 |

The first step of the library construction consisted of the VL fragments cloning in a phagemid vector, and then the VH fragments were inserted into the vector containing the VL repertoire. The vector format VH/VL-6×His-Flag was selected for constructions.

Rat 8

The final scFv library consisted of $5.2\times10^7$ independent clones with a full-size insert rate of 75% (by colony-PCR) and was finally packaged in M13K07 phage.

The panning was performed using hDPP4 Peptide P5/BSA as target and standard elution strategy. Six rounds were carried out in order to isolate specific binders. After each round, only the phages having interacted with hDPP4 Peptide P5/BSA were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 4, 5 and 6.

96 isolated clones from the second, third and fourth rounds of panning were hand-picked and used to produce the respective soluble scFv in microtiter plate. Each clone was then tested in ELISA against hDPP4 Peptide P5/BSA.

48 isolated clones showing a specific signal against hDPP4 Peptide P5/BSA compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Nine sequences corresponding to non-recombined and non-redundant scFv sequences were identified, grouped into two clusters (Table 11).

TABLE 11

HCVR and LCVR column indicate the amino acid sequence of the heavy chain and light chain variable regions, respectively.

| Cluster | Clone's name | HCVR | LCVR |
|---|---|---|---|
| Cluster 1 | 5826-8-R6A-D12 | 176 | 204 |
| | 5826-8-R6A-H11 | 176 | 208 |
| Cluster 2 | 5826-8-R6A-A10 | 174 | 202 |
| | 5826-8-R6A-B11 | 175 | 203 |
| | 5826-8-R6A-E10 | 177 | 205 |
| | 5826-8-R5A-G6 | 178 | 203 |
| | 5826-8-R5A-G8 | 179 | 206 |
| | 5826-8-R6A-H9 | 180 | 207 |
| | 5826-8-R6A-H12 | 181 | 209 |

According to sequence and redundancy analysis, the following clones were selected:

5826-8-R6A-H11 (cluster 1)

5826-8-R6A-E10 (cluster 2)

5826-8-R5A-G8 (cluster 2)

After transformation of the 3 selected clones DNA in an *E. coli* strain dedicated to production, the clones were expressed as soluble scFv and purified using the His tag on an Ni-NTA column. These soluble anti-hDPP4 scFv were tested in indirect ELISA for reactivities against the 4 peptides and DPP4 proteins (human and murine) and against the negative control (BSA only).

All three scFv were reactive against hDPP4 Peptide P5, as expected. No reactivity could be observed against the 3 other peptides, the DPP4 proteins (human or murine) or the negative control.

Rat 13

The final scFv library consisted of $4\times10^7$ independent clones with a full-size insert rate of 88% (by colony-PCR) and was finally packaged in M13K07 phage.

The panning was performed using hDPP4-ECD-His as target and standard elution strategy. Four rounds were carried out in order to isolate specific binders. After each round, only the phages having interacted with hDEP1-ECD-His were eluted. Between the first and the last round of panning, the number of eluted phages increased, indicating that amplification/selection of reactive phages was expected from this panning. The reactivity of the phages eluted after each round against the targeted peptide was assessed in phage-ELISA and confirmed that potential binders were eluted in rounds 2, 3 and 4.

96 isolated clones from the second, third and fourth rounds of panning were hand-picked and used to produce the respective soluble scFv in microtiter plate. Each clone was then tested in ELISA against hDPP4-ECD-His.

48 isolated clones showing a specific signal against hDPP4-ECD-His compared to negative control (BSA) were selected. Their DNA was extracted and sequenced. Sequences with an early stop codon or with an incorrect size were considered as recombined. The non-recombined sequences were aligned for redundancy analysis in order to identify the identical sequences (referred to as "redundant" sequences).

Twenty-one sequences corresponding to non-recombined and non-redundant scFv sequences were identified, grouped into three clusters (Table 12).

TABLE 12

HCVR and LCVR column indicate the amino acid sequence of the heavy chain and light chain variable regions, respectively.

| Cluster | Clone's name | HCVR | LCVR |
|---|---|---|---|
| Cluster 1 | 5826-13-R3A-A10 | 182 | 210 |
| | 5826-13-R4A-E6 | 188 | 216 |
| | 5826-13-R4A-H1 | 193 | 221 |
| | 5826-13-R4A-H4 | 196 | 224 |
| | 5826-13-R4A-H10 | 200 | 224 |
| | 5826-13-R4A-H11 | 201 | 224 |
| | 5826-13-R4A-H12 | 200 | 227 |
| Cluster 2 | 5826-13-R3A-D5 | 185 | 213 |
| Cluster 3 | 5826-13-R3A-B1 | 183 | 211 |
| | 5826-13-R3A-B3 | 184 | 212 |
| | 5826-13-R3A-D6 | 186 | 214 |
| | 5826-13-R4A-E2 | 187 | 215 |
| | 5826-13-R4A-E9 | 189 | 217 |
| | 5826-13-R4A-F10 | 190 | 218 |
| | 5826-13-R4A-G11 | 191 | 219 |
| | 5826-13-R4A-G12 | 192 | 220 |
| | 5826-13-R4A-H2 | 194 | 222 |
| | 5826-13-R4A-H3 | 195 | 223 |
| | 5826-13-R4A-H5 | 197 | 212 |
| | 5826-13-R4A-H6 | 198 | 225 |
| | 5826-13-R4A-H9 | 199 | 226 |

According to sequence and redundancy analysis, the following clones were selected:

5826-13-R4A-H12 (cluster 1)

5826-13-R3A-D5 (cluster 2)

5826-13-R4A-H5 (cluster 3)

After transformation of the 3 selected clones DNA in an *E. coli* strain dedicated to production, the clones were expressed as soluble scFv and purified using the His tag on an Ni-NTA column. These soluble anti-hDPP4 scFv were tested in indirect ELISA for reactivities against the 4 peptides and DPP4 proteins (human and murine) and against the negative control (BSA only).

The three scFv were reactive against hDPP4, as expected. No reactivity could be observed against any of the 4 peptides, the mDPP4 protein or the negative control.

Example 4—Antibody Screening in Fibroblasts

Material and Methods

Screening of scFv Against Human DPP4

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 μM etoposide and cultured for a further 15 days to instigate chemical-induced senescence, or left untreated. WI-38 is a diploid human cell line composed of fibroblasts derived from lung tissue and GM21808 is a healthy human foreskin fibroblast line. Senescence can be induced in both of these cell lines, by two different methods: replicative senescence via repeated passaging for WI-38 and damage-induced senescence via etoposide treatment for GM21808.

Cultures of expanding fibroblasts were gently detached using a cell scraper and harvested for staining with the following panel of anti-DPP4 antibodies:

commercial mAb (Creative Biolabs);

5826-13-R3A-D5, comprising a $V_H$-CDR1 with SEQ ID NO: 109, a $V_H$-CDR2 with SEQ ID NO: 122, a $V_H$-CDR3 with SEQ ID NO: 139, a $V_L$-CDR1 with SEQ ID NO: 148, a $V_L$-CDR2 with SEQ ID NO: 160 and a $V_L$-CDR3 with SEQ ID NO: 172; and 5826-13-R4A-H5, comprising a $V_H$-CDR1 with SEQ ID NO: 108, a $V_H$-CDR2 with SEQ ID NO: 127, a $V_H$-CDR3 with SEQ ID NO: 138, a $V_L$-CDR1 with SEQ ID NO: 147, a $V_L$-CDR2 with SEQ ID NO: 159 and a $V_L$-CDR3 with SEQ ID NO: 171.

Briefly, cells were incubated with a fixable viability dye (eF780, eBioscience) in a protein-free solution at 4° C. for 15 minutes. Samples were then washed once before addition of Fc block (Miltenyi Biotec) for 5 minutes at 4° C. Each test antibody or ScFV recognizing DPP4 was then added (0.5 μg per test) and staining was performed for 30 minutes at 4° C. Samples were then washed and stained with a secondary anti-human-PE antibody (Biolegend) for the monoclonal antibody, or with an anti-6×His tag PE antibody (R&D systems) for 5826-13-R3A-D5 and 5826-13-R4A-H5.

At the end of the incubation, cells were washed and fixed with 1% PFA before analysis using a BD LSR-Fortessa cytometer (Becton Dickinson). Data was analyzed using FlowJo software (Treestar) and was presented as percentage binding of anti-DPP4 antibody versus binding of secondary antibody.

Screening of scFv Against Human DEP1

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 μM etoposide and cultured for a further 15 days to instigate chemical-induced senescence, or left untreated. WI-38 is a diploid human cell line composed of fibroblasts derived from lung tissue and GM21808 is a healthy human foreskin fibroblast line. Senescence can be induced in both of these cell lines, by two different methods: replicative senescence via repeated passaging for WI-38 and damage-induced senescence via etoposide treatment for GM21808.

Cultures of expanding fibroblasts were gently detached using a cell scraper and harvested for staining with the following panel of anti-DEP1 antibodies:

commercial mAb (AbCam);

5738-10-R3A-D5, comprising a $V_H$-CDR1 with SEQ ID NO: 5, a $V_H$-CDR2 with SEQ ID NO: 12, a $V_H$-CDR3 with SEQ ID NO: 29, a $V_L$-CDR1 with SEQ ID NO: 33, a $V_L$-CDR2 with SEQ ID NO: 40 and a $V_L$-CDR3 with SEQ ID NO: 49;

5738-13-R4A-D11, comprising a $V_H$-CDR1 with SEQ ID NO: 10, a $V_H$-CDR2 with SEQ ID NO: 21, a $V_H$-CDR3 with SEQ ID NO: 30, a $V_L$-CDR1 with SEQ ID NO: 37, a $V_L$-CDR2 with SEQ ID NO: 44 and a $V_L$-CDR3 with SEQ ID NO: 53; and 5738-13-R2A-H4, comprising a $V_H$-CDR1 with SEQ ID NO: 11, a $V_H$-CDR2 with SEQ ID NO: 25, a $V_H$-CDR3 with SEQ ID NO: 32, a $V_L$-CDR1 with SEQ ID NO: 38, a $V_L$-CDR2 with SEQ ID NO: 46 and a $V_L$-CDR3 with SEQ ID NO: 52.

Briefly, cells were incubated with a fixable viability dye (eF780, eBioscience) in a protein-free solution at 4° C. for 15 minutes. Samples were then washed once before addition of Fc block (Miltenyi Biotec) for 5 minutes at 4° C. Each test antibody or ScFV recognizing DEP1 was then added (0.5 μg per test) and staining was performed for 30 minutes at 4° C. Samples were then washed and stained with a secondary anti-human-PE antibody (Biolegend) for the monoclonal antibody, or with an anti-6×His tag PE antibody (R&D systems) for 5738-10-R3A-D5, 5738-13-R4A-D11 and 5738-13-R2A-H4.

At the end of the incubation, cells were washed and fixed with 1% PFA before analysis using a BD LSR-Fortessa cytometer (Becton Dickinson). Data was analyzed using FlowJo software (Treestar) and was presented as percentage binding of anti-DEP1 antibody versus binding of secondary antibody.

Results

Both DPP4 and DEP1 are Specifically Increased in Lung Fibrosis Cells

Figure 8:
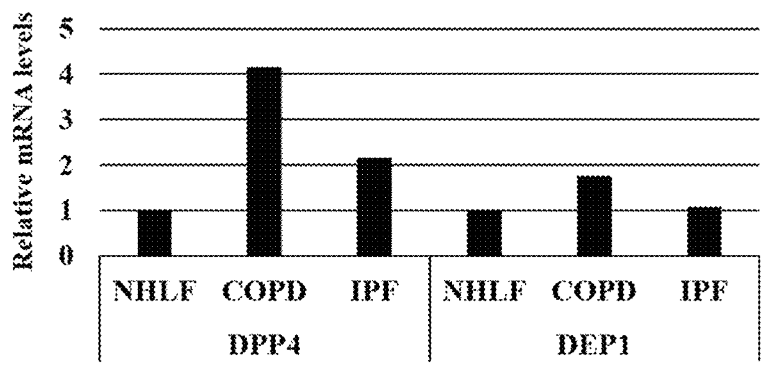
FIG. 8—'DPP4 and DEP1 mRNA levels in normal and diseased primary human lung fibroblasts'—is a graph showing the relative quantity of DPP4 and DEP-1 in normal and diseased human lung fibroblasts. Expression levels in NHLF (normal human lung fibroblast), idiopathic pulmonary fibroblast (IPF) and chronic obstructive pulmonary disease (COPD) human fibroblast cells were calculated relative to NHLF.

As seen in FIG. 8, DPP4, but also DEP1, another novel surface antigen, are specifically increased in lung fibrosis cells with respect to normal lung cells.

DPP4/DEP1 Staining in Fibroblasts

Figure 9A:
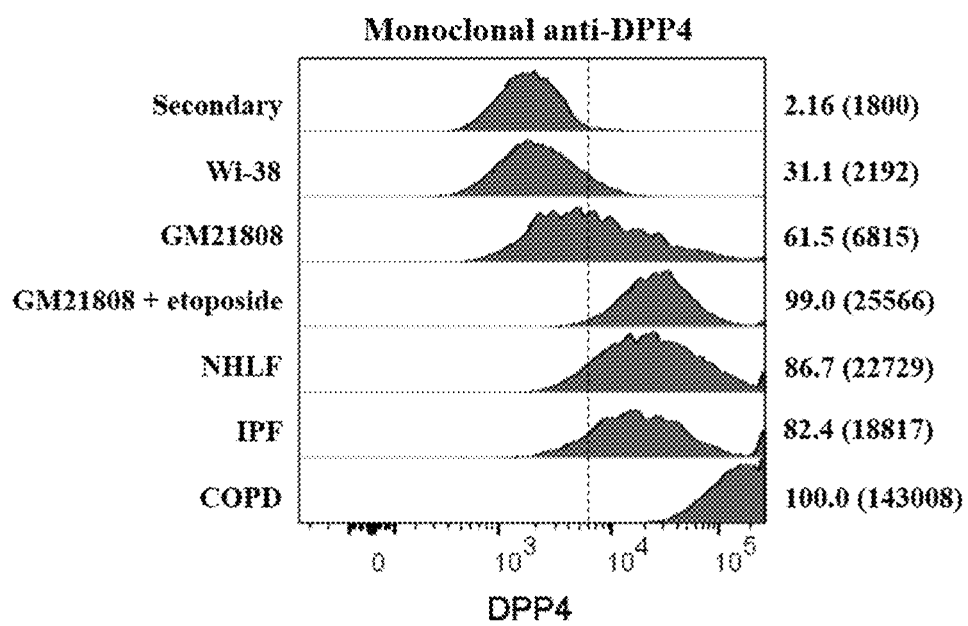
FIGS. 9A-C—'DPP4 staining infibroblasts' are three graphs showing the staining of various primary human fibroblasts and different senescence-stressors in terms of DPP4 surface antigen presentation in target senescent cells versus normal/young cells. The data also include normal human cells versus human lung fibrosis disease cells. WI-38 (PDL<20), GM21808 (±etoposide), normal human lung fibroblast (NHLF), idiopathic pulmonary fibroblast (IPF) and chronic obstructive pulmonary disease (COPD) human fibroblast cells were stained with anti-DPP4 antibodies or scFv. Control staining comprising secondary antibody only was included for all cell types, but only the control staining for NHLF cells is shown for illustration. Percentage of positive cells is indicated on the right side, with MFI indicated in parenthesis.
Figure 9B:
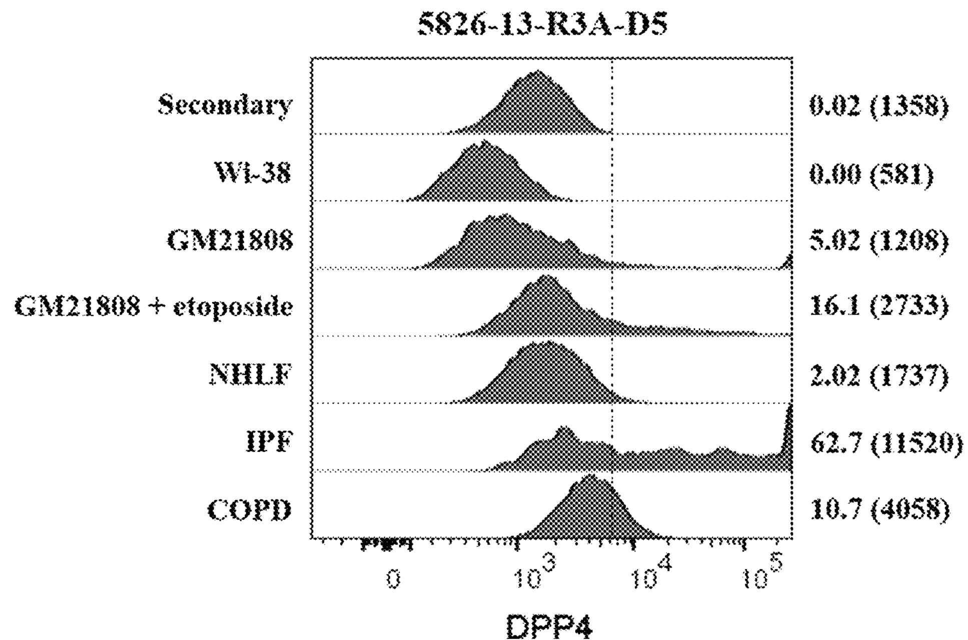
Figure 9C:
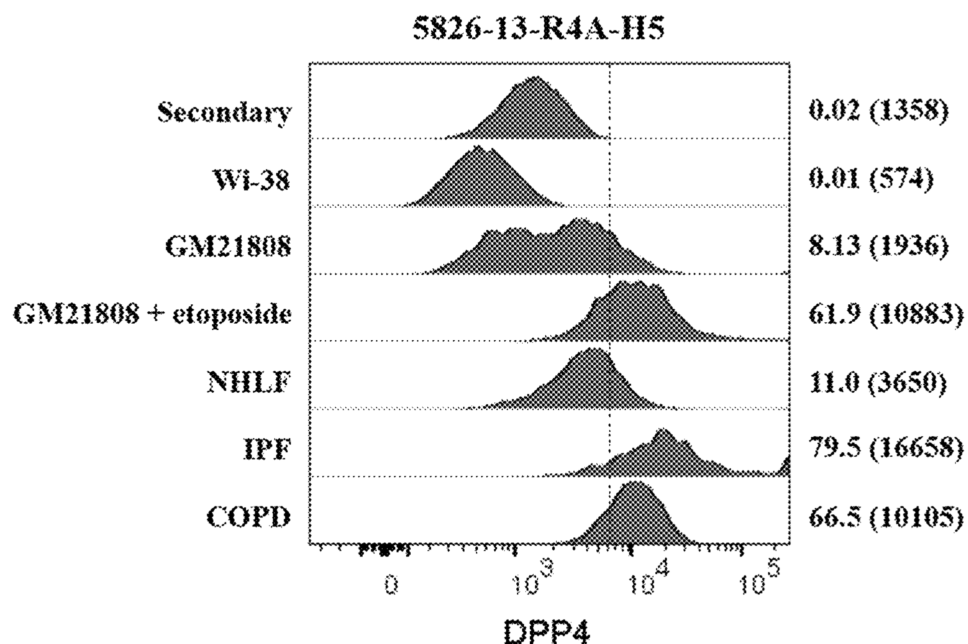
Figure 10A:
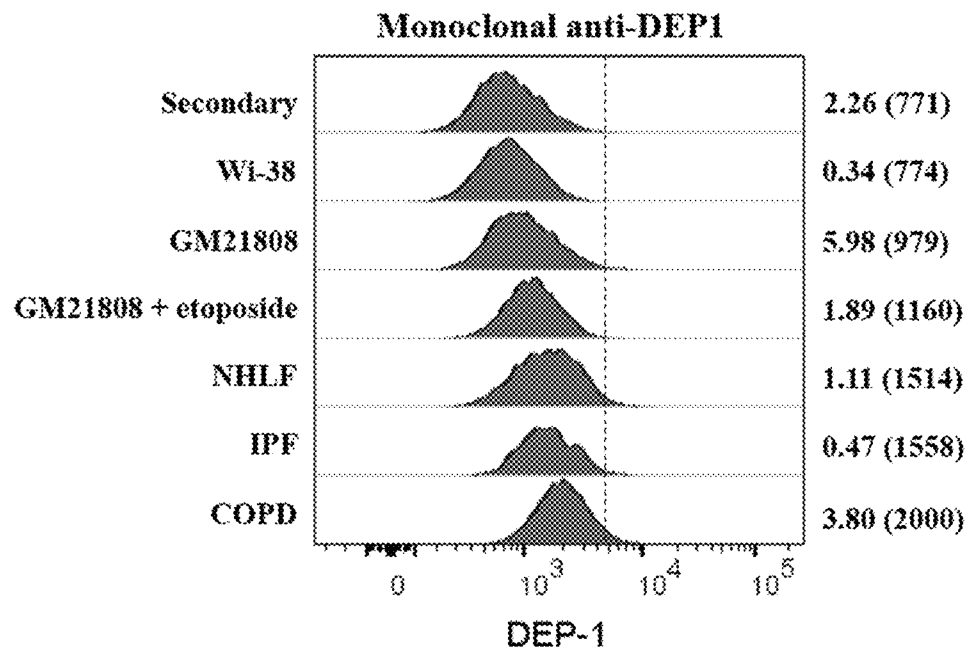
FIGS. 10A-D—'DEP1 staining infibroblasts' are four graphs showing the staining of various primary human fibroblasts and different senescence-stressors in terms of DEP1 surface antigen presentation in target senescent cells versus normal/young cells. The data also include normal human cells versus human lung fibrosis disease cells. WI-38 (PDL<20), GM21808 (±etoposide), normal human lung fibroblast (NHLF), idiopathic pulmonary fibroblast (IPF) and chronic obstructive pulmonary disease (COPD) human fibroblast cells were stained with anti-DEP1 antibodies or scFv. Control staining comprising secondary antibody only was included for all cell types, but only the control staining for NHLF cells is shown for illustration. Percentage of positive cells is indicated on the right side, with MFI indicated in parenthesis.
Figure 10B:
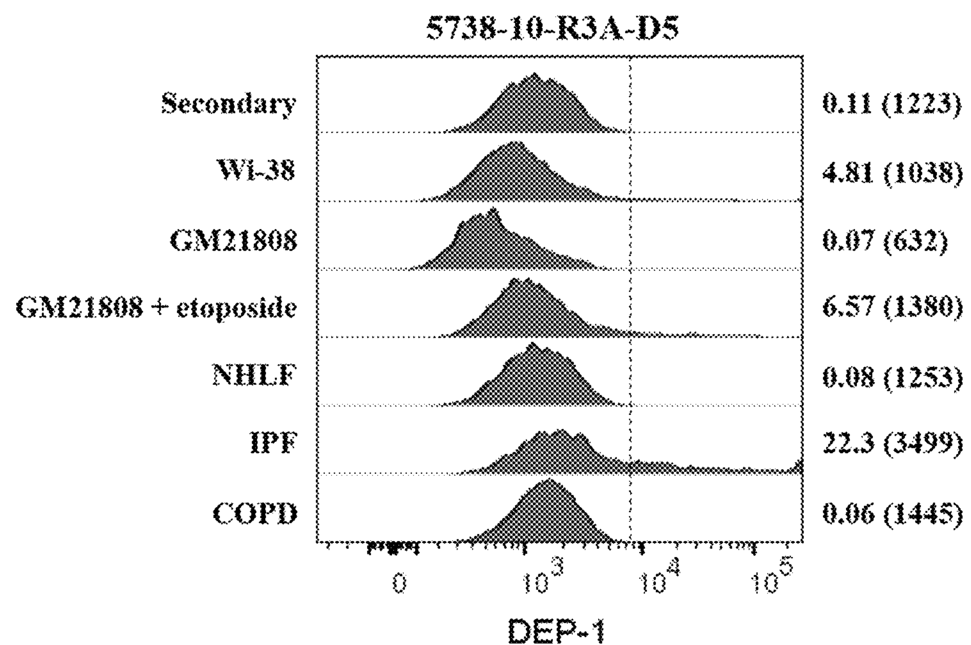
Figure 10C:
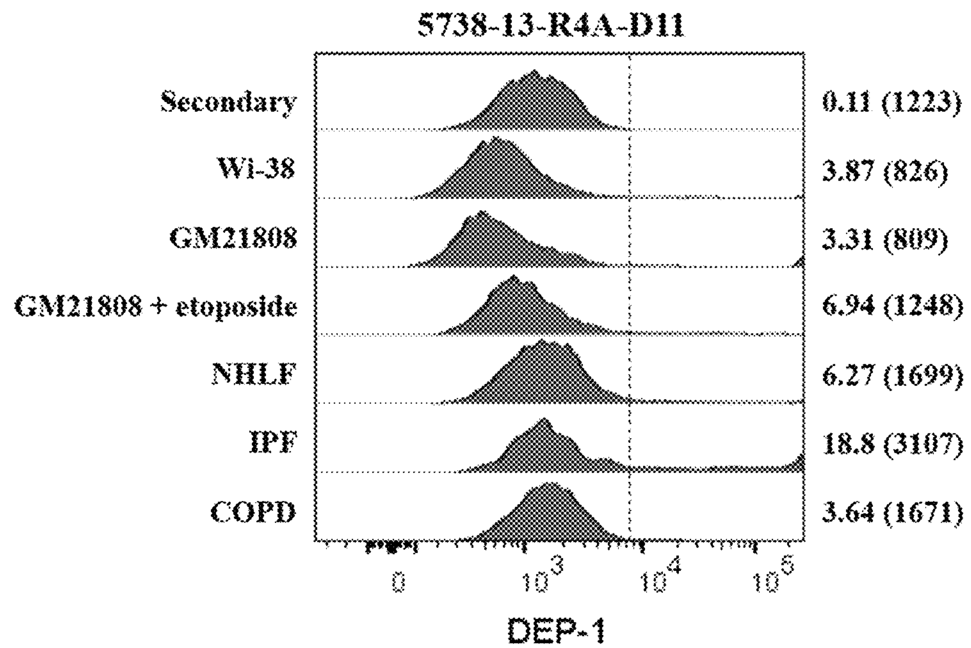
Figure 10D:
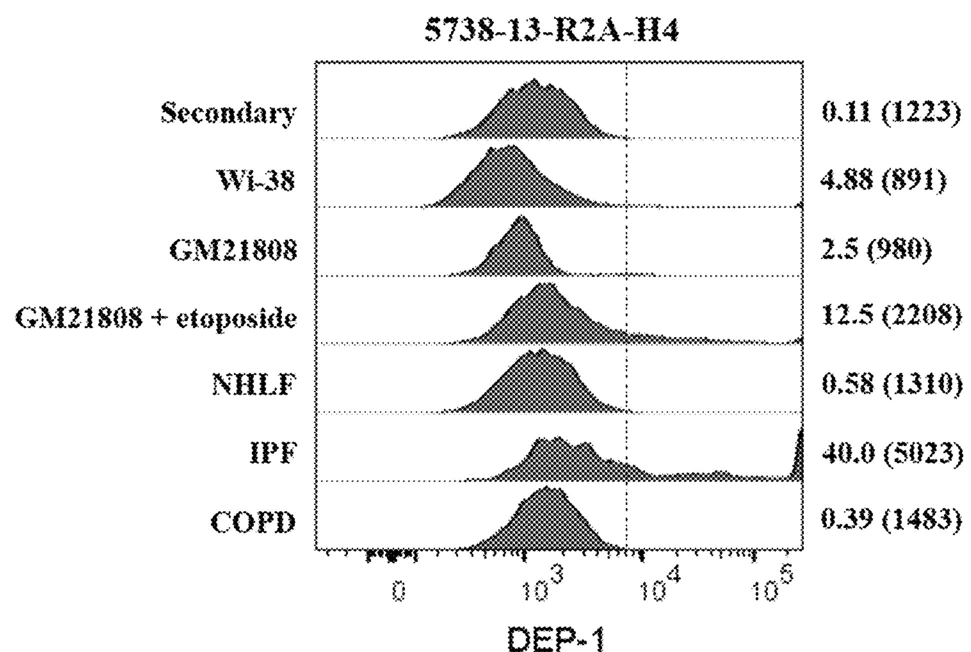

The anti-DPP4 scFv described herein detect the DPP4 surface antigen in both disease human lung fibroblasts cells (COPD and IPF) with less background than the commercial antibody (see for comparison, staining in young WI-38, untreated GM21808 and NHLF cells) (FIGS. 9A to 9C).

The anti-DEP1 scFv described herein also performed substantially better at detecting the DEP1 surface antigen in disease human lung fibroblasts cells than the commercial antibody (FIGS. 10A to 10D).

Conclusion

Fibroblasts are key effector cells in the progression of fibrotic diseases. CAR-T cell-based immunotherapy approach using specific surface markers to target senescent cells in lung fibrosis disease state has a significant potential for the exploration of novel anti-fibrotic strategies.

Example 5—Analysis of DPP4 and DEP1 Expression by qPCR

Material and Methods

Analysis of DPP4 Expression by qPCR

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 μM etoposide and cultured for a further 15 days to instigate chemical-induced senescence, or left untreated.

RNA was isolated using a RNeasy plus kit (Qiagen) following manufacturer's instructions. RNA was quantified using a NanoDrop One (Thermofisher Scientific) by measuring absorbance at 260 nm. 100-500 ng of RNA was reversed-transcribed using QuantiTect Reverse Transcription kit (Qiagen) in a final reaction volume of 20 μL following manufacturer's instructions.

Gene expression of DPP4 in each cell type was determined by qPCR using a SYBR green assay. Briefly, 10 ng cDNA (5 μl) from each cell type was mixed in a BrightWhite qPCR 96-well plate with 15 μL master mix containing PrecisionFAST SYBR master mix (PrimerDesign), DPP4 SYBR green forward and reverse primers (300 nM each; Integrated DNA technologies) and PCR water.

Expression of GAPDH was also assessed as a housekeeping gene using a TaqMan assay. Briefly, 10 ng cDNA (5 μL) from each cell type was mixed in a BrightWhite qPCR 96-well plate with 15 μL master mix containing TaqMan Fast Advanced master mix, 300 nM GAPDH TaqMan gene expression assays and PCR water, all sourced from ThermoFisher Scientific.

The plate was then sealed with an optical seal and amplification was performed on a QuantStudio 3 Real-Time system using the following protocols:

for DPP4 SYBR green gene expression assays: initial denaturation at 95° C. for 20 seconds; followed by 40 cycles of (i) denaturation at 95° C. for 3 seconds and (ii) annealing/extension at 54.5° C. for 30 seconds; followed by a step of melt curve comprising (i) a denaturation step at 95° C. for 1 second and (ii) a ramp from 95° C. to 60° C. with a 0.15° C. decrease per second.

for GAPDH TaqMan expression assays: initial denaturation at 95° C. for 2 minutes; followed by 40 cycles of (i) denaturation at 95° C. for 5 seconds and (ii) annealing/extension at 60° C. for 20 seconds.

Data was analyzed using the $2^{-\Delta\Delta Ct}$ method. The signal from DPP4 was normalized against the GAPDH reference gene. These values for each cell type were then further normalized against the level of expression in the WI-38 sample to give a relative quantification (RQ) value.

Analysis of DEP1 Expression by qPCR

WI-38 and GM21808 fibroblast cell lines and primary fibroblasts from healthy and diseased patients (COPD subjects—chronic obstructive pulmonary disease; and IPF subjects—idiopathic pulmonary fibrosis) were purchased from ethically sourced suppliers. GM21808 cells were treated with 20 μM etoposide and cultured for a further 15 days to instigate chemical-induced senescence, or left untreated.

RNA was isolated using a RNeasy plus kit (Qiagen) following manufacturer's instructions. RNA was quantified using a NanoDrop One (Thermofisher Scientific) by measuring absorbance at 260 nm. 100-500 ng of RNA was reversed-transcribed using QuantiTect Reverse Transcription kit (Qiagen) in a final reaction volume of 20 μL following manufacturer's instructions.

Gene expression of DEP1 and GAPDH in each cell type was determined by qPCR using a TaqMan assay. Briefly, 10 ng cDNA (5 μl) from each cell type was mixed in a BrightWhite qPCR 96-well plate with 15 μL master mix containing TaqMan Fast Advanced master mix, 300 nM GAPDH/DEP1 TaqMan gene expression assays and PCR water, all sourced from ThermoFisher Scientific.

The plate was then sealed with an optical seal and amplification was performed on a QuantStudio 3 Real-Time system using the following protocol: initial denaturation at 95° C. for 2 minutes; followed by 40 cycles of (i) denaturation at 95° C. for 5 seconds and (ii) annealing/extension at 60° C. for 20 seconds.

The signal from DEP1 was normalized against the GAPDH reference gene. These values for each cell type were then further normalized against the level of expression in the WI-38 sample to give a relative quantification (RQ) value.

The invention claimed is:

1. A method of treating or alleviating a senescence-related disease or disorder in a subject in need thereof, wherein said senescence-related disease or disorder is a cancer comprising DPP4-expressing cells or a fibrotic disease comprising DPP4-expressing cells, the method comprising administering to the subject a composition comprising:

an isolated antibody or antigen-binding fragment thereof comprising a DPP4-binding domain; and/or an immune cell engineered to express at its surface a chimeric antigen receptor (CAR) comprising:

at least one extracellular binding domain, comprising said DPP4-binding domain, an extracellular spacer domain, a transmembrane domain, optionally, at least one costimulatory domain, and at least one intracellular signaling domain; and/or a population of immune cells comprising a plurality of said engineered immune cells, wherein said DPP4-binding domain comprises a combination of three heavy chain variable region (HCVR)'s complementary-determining regions (CDRs) and three light chain variable region (LCVR)'s CDRs, said combination being as defined in any row of the table below, wherein the CDRs are defined by their SEQ ID NO:

| Clone's name | $V_H$-CDR1 | $V_H$-CDR2 | $V_H$-CDR3 | $V_L$-CDR1 | $V_L$-CDR2 | $V_L$-CDR3 |
|---|---|---|---|---|---|---|
| 5826-13-R3A-A10 | 107 | 119 | 137 | 146 | 157 | 170 |
| 5826-13-R3A-B1 | 108 | 120 | 138 | 147 | 158 | 171 |
| 5826-13-R3A-B3 | 108 | 121 | 138 | 147 | 159 | 171 |
| 5826-13-R3A-D5 | 109 | 122 | 139 | 148 | 160 | 172 |
| 5826-13-R3A-D6 | 108 | 123 | 138 | 149 | 159 | 171 |
| 5826-13-R4A-E2 | 108 | 124 | 138 | 147 | 159 | 171 |
| 5826-13-R4A-E6 | 110 | 125 | 140 | 146 | 161 | 170 |
| 5826-13-R4A-E9 | 108 | 126 | 141 | 149 | 159 | 171 |
| 5826-13-R4A-F10 | 108 | 126 | 138 | 150 | 159 | 171 |
| 5826-13-R4A-G11 | 108 | 126 | 138 | 150 | 159 | 171 |
| 5826-13-R4A-G12 | 111 | 127 | 138 | 151 | 159 | 171 |
| 5826-13-R4A-H1 | 110 | 128 | 140 | 146 | 162 | 170 |
| 5826-13-R4A-H2 | 108 | 126 | 141 | 149 | 159 | 171 |
| 5826-13-R4A-H3 | 108 | 126 | 138 | 149 | 159 | 173 |
| 5826-13-R4A-H4 | 112 | 125 | 140 | 146 | 162 | 170 |
| 5826-13-R4A-H5 | 108 | 127 | 138 | 147 | 159 | 171 |
| 5826-13-R4A-H6 | 108 | 127 | 142 | 147 | 159 | 171 |
| 5826-13-R4A-H9 | 108 | 123 | 138 | 149 | 159 | 171 |
| 5826-13-R4A-H10 | 110 | 125 | 140 | 146 | 162 | 170 |
| 5826-13-R4A-H11 | 110 | 128 | 140 | 146 | 162 | 170 |
| 5826-13-R4A-H12 | 110 | 125 | 140 | 146 | 163 | 170 |

2. The method according to claim 1, wherein the senescence-related disease or disorder is selected from the group consisting of idiopathic pulmonary fibrosis (IPF), chronic obstructive pulmonary disease (COPD), acute respiratory distress syndrome (ARDS), combined pulmonary fibrosis and emphysema (CPFR), pulmonary edema, Löffler's syndrome, eosinophilic pneumonia, respiratory hypersensitivity, allergic bronchopulmonary aspergillosis (ABPA), Hamman-Rich syndrome, sarcoidosis, pneumoconiosis, and hypersensitivity pneumonitis (HP).

3. The method according to claim 1, wherein the senescence-related disease or disorder is selected from the group consisting of idiopathic pulmonary fibrosis (IPF) and chronic obstructive pulmonary disease (COPD).

4. The method according to claim 1, wherein said DPP4-binding domain comprises:

a HCVR which comprises the following three CDRs:

$V_H$-CDR1 selected from the group consisting of SEQ ID NO: 109, 108, and 110;

$V_H$-CDR2 selected from the group consisting of SEQ ID NO: 122, 127, and 125;

$V_H$-CDR3 selected from the group consisting of SEQ ID NO: 139, 138, and 140;

a LCVR which comprises the following three CDRs:

$V_L$-CDR1 selected from the group consisting of SEQ ID NO: 148, 147, and 146;

$V_L$-CDR2 selected from the group consisting of SEQ ID NO: 160, 159, and 163;

$V_L$-CDR3 selected from the group consisting of SEQ ID NO: 172, 171, and 170.

5. The method according to claim 1, wherein said DPP4-binding domain is selected from the group consisting of:

a DPP4-binding domain comprising a $V_H$-CDR1 with SEQ ID NO: 109, a $V_H$-CDR2 with SEQ ID NO: 122, a $V_H$-CDR3 with SEQ ID NO: 139, a $V_L$-CDR1 with SEQ ID NO: 148, a $V_L$-CDR2 with SEQ ID NO: 160 and a $V_L$-CDR3 with SEQ ID NO: 172;

a DPP4-binding domain comprising a $V_H$-CDR1 with SEQ ID NO: 108, a $V_H$-CDR2 with SEQ ID NO: 127, a $V_H$-CDR3 with SEQ ID NO: 138, a $V_L$-CDR1 with SEQ ID NO: 147, a $V_L$-CDR2 with SEQ ID NO: 159 and a $V_L$-CDR3 with SEQ ID NO: 171, and a DPP4-binding domain comprising a $V_H$-CDR1 with SEQ ID NO: 110, a $V_H$-CDR2 with SEQ ID NO: 125, a $V_H$-CDR3 with SEQ ID NO: 140, a $V_L$-CDR1 with SEQ ID NO: 146, a $V_L$-CDR2 with SEQ ID NO: 163 and a $V_L$-CDR3 with SEQ ID NO: 170.

6. The method according to claim 1, wherein said DPP4-binding domain is selected from the group consisting of:

a DPP4-binding domain comprising a HCVR with a sequence sharing at least 80% of sequence identity with the non-CDR regions of SEQ ID NO: 185 and a LCVR with a sequence sharing at least 80% of sequence identity with the non-CDR regions of SEQ ID NO: 213;

a DPP4-binding domain comprising a HCVR with a sequence sharing at least 80% of sequence identity with the non-CDR regions of SEQ ID NO: 197 and a LCVR with a sequence sharing at least 80% of sequence identity with the non-CDR regions of SEQ ID NO: 212212, and a DPP4-binding domain comprising a HCVR with a sequence sharing at least 80% of sequence identity with the non-CDR regions of SEQ ID NO: 200 and a LCVR with a sequence sharing at least 80% of sequence identity with the non-CDR regions of SEQ ID NO: 227.

7. The method according to claim 1, wherein said isolated antibody or antigen-binding fragment thereof is a bispecific antibody comprising said DPP4-binding domain and an antigen-binding domain to a non-senescent cell-associated antigen.

8. The method according to claim 1, wherein said isolated antibody or antigen-binding fragment thereof is a bispecific antibody comprising said DPP4-binding domain and an antigen-binding domain to another senescent cell-associated antigen.

9. The method according to claim 1, wherein said CAR is multispecific and comprises said DPP4-binding domain and at least one antigen-binding domain to a non-senescent cell-associated antigen.

10. The method according to claim 1, wherein said CAR is multispecific and comprises said DPP4-binding domain and at least one antigen-binding domain to another senescent cell-associated antigen.

11. The method according to claim 1, wherein said composition is a pharmaceutical composition further comprising at least one pharmaceutically acceptable excipient.

12. The method according to claim 1, wherein said isolated antibody or antigen-binding fragment thereof is an antibody drug conjugate (ADC).

* * * * *

SEQUENCE LISTING

```
Sequence total quantity: 227
SEQ ID NO: 1             moltype = AA  length = 1337
FEATURE                  Location/Qualifiers
DOMAIN                   1..35
                         note = Signal peptide
REGION                   1..1337
                         note = hDEP1
SITE                     36..48
                         note = hDEP1 Peptide #1
DOMAIN                   36..975
                         note = Extracellular domain
SITE                     436..452
                         note = hDEP1 Peptide #2
SITE                     728..741
                         note = hDEP1 Peptide #3
SITE                     864..881
                         note = hDEP1 Peptide #4
DOMAIN                   976..996
                         note = Transmembrane domain
DOMAIN                   997..1337
                         note = Cytoplasmic domain
source                   1..1337
                         mol_type = protein
                         organism = Homo sapiens
SEQUENCE: 1
MKPAAREARL PPRSPGLRWA LPLLLLLLRL GQILCAGGTP SPIPDPSVAT VATGENGITQ  60
ISSTAESFHK QNGTGTPQVE TNTSEDGESS GANDSLRTPE QGSNGTDGAS QKTPSSTGPS  120
PVFDIKAVSI SPTNVILTWK SNDTAASEYK YVVKHKMENE KTITVVHQPW CNITGLRPAT  180
SYVFSITPGI GNETWGDPRV IKVITEPIPV SDLRVALTGV RKAALSWSNG NGTASCRVLL  240
ESIGSHEELT QDSRLQVNIS GLKPGVQYNI NPYLLQSNKT KGDPLGTEGG LDASNTERSR  300
AGSPTAPVHD ESLVGPVDPS SGQQSRDTEV LLVGLEPGTR YNATVYSQAA NGTEGQPQAI  360
EFRTNAIQVF DVTAVNISAT SLTLIWKVSD NESSSNYTYK IHVAGETDSS NLNVSEPRAV  420
IPGLRSSTFY NITVCPVLGD IEGTPGFLQV HTPPVPVSDF RVTVVSTTEI GLAWSSHDAE  480
SFQMHITQEG AGNSRVEITT NQSIIIGGLF PGTKYCFEIV PKGPNGTEGA SRTVCNRTVP  540
SAVFDIHVVY VTTTEMWLDW KSPDGASEYV YHLVIESKHG SNHTSTYDKA ITLQGLIPGT  600
LYNITISPEV DHVWGDPNST AQYTRPSNVS NIDVSTNTTA ATLSWQNFDD ASPTYSYCLL  660
IEKAGNSSNA TQVVTDIGIT DATVTELIPG SSYTVEIFAQ VGDGIKSLEP GRKSFCTDPA  720
SMASFDCEVV PKEPALVLKW TCPPGANAGF ELEVSSGAWN NATHLESCSS ENGTEYRTEV  780
TYLNFSTSYN ISITTVSCGK MAAPTRNTCT TGITDPPPPD GSPNITSVSH NSVKVKFSGF  840
EASHGPIKAY AVILTTGEAG HPSADVLKYT YEDFKKGASD TYVTYLIRTE EKGRSQSLSE  900
VLKYEIDVGN ESTTLGYYNG KLEPLGSYRA CVAGFTNITF HPQNKGLIDG AESYVSFSRY  960
SDAVSLPQDP GVICGAVFGC IFGALVIVTV GGFIFWRKKR KDAKNNEVSF SQIKPKKSKL  1020
IRVENFEAYF KKQQADSNCG FAEEYEDLKL VGISQPKYAA ELAENRGKNR YNNVLPYDIS  1080
RVKLSVQTHS TDDYINANYM PGYHSKKDFI ATQGPLPNTL KDFWRMVWEK NVYAIIMLTK  1140
CVEQGRTKCE EYWPSKQAQD YGDITVAMTS EIVLPEWTIR DFTVKNIQTS ESHPLRQFHF  1200
TSWPDHGVPD TTDLLINFRY LVRDYMKQSP PESPILVHCS AGVGRTGTFI AIDRLIYQIE  1260
NENTVDVYGI VYDLRMHRPL MVQTEDQYVF LNQCVLDIVR SQKDSKVDLI YQNTTAMTIY  1320
```

```
ENLAPVTTFG KTNGYIA                                              1337

SEQ ID NO: 2            moltype = AA  length = 583
FEATURE                 Location/Qualifiers
REGION                  1..583
                        note = hDEP1-ECD-Fc (Amino acid residues 621-969 of SEQ ID
                         NO: 1 + Fc domain)
source                  1..583
                        mol_type = protein
                        organism = synthetic construct
SEQUENCE: 2
AQYTRPSNVS NIDVSTNTTA ATLSWQNFDD ASPTYSYCLL IEKAGNSSNA TQVVTDIGIT  60
DATVTELIPG SSYTVEIFAQ VGDGIKSLEP GRKSFCTDPA SMASFDCEVV PKEPALVLKW  120
TCPPGANAGF ELEVSSGAWN NATHLESCSS ENGTEYRTEV TYLNFSTSYN ISITTVSCGK  180
MAAPTRNTCT TGITDPPPPD GSPNITSVSH NSVKVKFSGF EASHGPIKAY AVILTTGEAG  240
HPSADVLKYT YEDFKKGASD TYVTYLIRTE EKGRSQSLSE VLKYEIDVGN ESTTLGYYNG  300
KLEPLGSYRA CVAGFTNITF HPQNKGLIDG AESYVSFSRY SDAVSLPQDG SEPKSCDKTH  360
TCPPCPAPEL LGGPSVFLFP PKPKDTLMIS RTPEVTCVVV DVSHEDPEVK FNWYVDGVEV  420
HNAKTKPREE QYNSTYRVVS VLTVLHQDWL NGKEYKCKVS NKALPAPIEK TISKAKGQPR  480
EPQVYTLPPS RDELTKNQVS LTCLVKGFYP SDIAVEWESN GQPENNYKTT PPVLDSDGSF  540
FLYSKLTVDK SRWQQGNVFS CSVMHEALHN HYTQKSLSLS PGK                  583

SEQ ID NO: 3            moltype = AA  length = 359
FEATURE                 Location/Qualifiers
REGION                  1..359
                        note = hDEP1-ECD-6His (Amino acid residues 621-969 of SEQ
                         ID NO: 1 + Linker + 6His tag)
source                  1..359
                        mol_type = protein
                        organism = synthetic construct
SEQUENCE: 3
AQYTRPSNVS NIDVSTNTTA ATLSWQNFDD ASPTYSYCLL IEKAGNSSNA TQVVTDIGIT  60
DATVTELIPG SSYTVEIFAQ VGDGIKSLEP GRKSFCTDPA SMASFDCEVV PKEPALVLKW  120
TCPPGANAGF ELEVSSGAWN NATHLESCSS ENGTEYRTEV TYLNFSTSYN ISITTVSCGK  180
MAAPTRNTCT TGITDPPPPD GSPNITSVSH NSVKVKFSGF EASHGPIKAY AVILTTGEAG  240
HPSADVLKYT YEDFKKGASD TYVTYLIRTE EKGRSQSLSE VLKYEIDVGN ESTTLGYYNG  300
KLEPLGSYRA CVAGFTNITF HPQNKGLIDG AESYVSFSRY SDAVSLPQDV AAAHHHHHH   359

SEQ ID NO: 4            moltype = AA  length = 357
FEATURE                 Location/Qualifiers
REGION                  1..357
                        note = mDEP1-ECD-6His
source                  1..357
                        mol_type = protein
                        organism = synthetic construct
SEQUENCE: 4
TQYTRPSSVS HIEVNTTTTT AAIRWKNEDA ASASYAYSVL ILKTGDGSNV TSNFTKDPSI  60
LIPELIPGVS YTVKILTQVG DGTTSLVPGW NLFCTEPEPV TSFHCEVVPK EPALVLKWAC  120
PFGMYTGFEL GVRSDSWDNM TRLENCTSDD DTECRTEVAY LNFSTSYNIS IATLSCGKMA  180
LPAQNICTTG ITDPPTPDGS PNITSVSHNS VKVKFSGFEA SHGPIKAYAV ILTTGEAAQP  240
SADVLKYTYE DFKRGASDTY VTYLIRIEEK GQSQGLSEVL NYEIDVGNQS TTLGYYNGRL  300
EPLGSYRACV AGFTNITYNL QNDGLINGDE SYVSFSPYSE AVFLPQDVAA AHHHHHH     357

SEQ ID NO: 5            moltype = AA  length = 5
FEATURE                 Location/Qualifiers
REGION                  1..5
                        note = HCDR1
source                  1..5
                        mol_type = protein
                        organism = synthetic construct
SEQUENCE: 5
SYYIS                                                           5

SEQ ID NO: 6            moltype = AA  length = 5
FEATURE                 Location/Qualifiers
REGION                  1..5
                        note = HCDR1
source                  1..5
                        mol_type = protein
                        organism = synthetic construct
SEQUENCE: 6
NIAMY                                                           5

SEQ ID NO: 7            moltype = AA  length = 5
FEATURE                 Location/Qualifiers
REGION                  1..5
                        note = HCDR1
source                  1..5
                        mol_type = protein
```

```
                        organism = synthetic construct
SEQUENCE: 7
NYTIS                                                                5

SEQ ID NO: 8            moltype = AA  length = 5
FEATURE                 Location/Qualifiers
REGION                  1..5
                        note = HCDR1
source                  1..5
                        mol_type = protein
                        organism = synthetic construct
SEQUENCE: 8
SDSIS                                                                5

SEQ ID NO: 9            moltype = AA  length = 5
FEATURE                 Location/Qualifiers
REGION                  1..5
                        note = HCDR1
source                  1..5
                        mol_type = protein
                        organism = synthetic construct
SEQUENCE: 9
NYSIS                                                                5

SEQ ID NO: 10           moltype = AA  length = 5
FEATURE                 Location/Qualifiers
REGION                  1..5
                        note = HCDR1
source                  1..5
                        mol_type = protein
                        organism = synthetic construct
SEQUENCE: 10
DYNMA                                                                5

SEQ ID NO: 11           moltype = AA  length = 5
FEATURE                 Location/Qualifiers
REGION                  1..5
                        note = HCDR1
source                  1..5
                        mol_type = protein
                        organism = synthetic construct
SEQUENCE: 11
NYYMA                                                                5

SEQ ID NO: 12           moltype = AA  length = 17
FEATURE                 Location/Qualifiers
REGION                  1..17
                        note = HCDR2
source                  1..17
                        mol_type = protein
                        organism = synthetic construct
SEQUENCE: 12
YINTGSGGTN YNEKFKG                                                   17

SEQ ID NO: 13           moltype = AA  length = 19
FEATURE                 Location/Qualifiers
REGION                  1..19
                        note = HCDR2
source                  1..19
                        mol_type = protein
                        organism = synthetic construct
SEQUENCE: 13
HIRTKPHNFA TYYANSVKG                                                 19

SEQ ID NO: 14           moltype = AA  length = 17
FEATURE                 Location/Qualifiers
REGION                  1..17
                        note = HCDR2
source                  1..17
                        mol_type = protein
                        organism = synthetic construct
SEQUENCE: 14
YIYAGTGDTN YNEKFKG                                                   17

SEQ ID NO: 15           moltype = AA  length = 19
FEATURE                 Location/Qualifiers
REGION                  1..19
                        note = HCDR2
source                  1..19
```

```
                        mol_type = protein
                        organism = synthetic construct
SEQUENCE: 15
HIRTKPHNYA TYYADSVKG                                            19

SEQ ID NO: 16           moltype = AA  length = 17
FEATURE                 Location/Qualifiers
REGION                  1..17
                        note = HCDR2
source                  1..17
                        mol_type = protein
                        organism = synthetic construct
SEQUENCE: 16
YIHPGSGVTN YNEKFKG                                              17

SEQ ID NO: 17           moltype = AA  length = 17
FEATURE                 Location/Qualifiers
REGION                  1..17
                        note = HCDR2
source                  1..17
                        mol_type = protein
                        organism = synthetic construct
SEQUENCE: 17
YIHPGSGVTN YNEKFRG                                              17

SEQ ID NO: 18           moltype = AA  length = 17
FEATURE                 Location/Qualifiers
REGION                  1..17
                        note = HCDR2
source                  1..17
                        mol_type = protein
                        organism = synthetic construct
SEQUENCE: 18
YIYPGSGDTN YNEKFKG                                              17

SEQ ID NO: 19           moltype = AA  length = 17
FEATURE                 Location/Qualifiers
REGION                  1..17
                        note = HCDR2
source                  1..17
                        mol_type = protein
                        organism = synthetic construct
SEQUENCE: 19
TISYDDSRTY YRDSVKG                                              17

SEQ ID NO: 20           moltype = AA  length = 17
FEATURE                 Location/Qualifiers
REGION                  1..17
                        note = HCDR2
source                  1..17
                        mol_type = protein
                        organism = synthetic construct
SEQUENCE: 20
YITNSFGSAY YRDSVKG                                              17

SEQ ID NO: 21           moltype = AA  length = 17
FEATURE                 Location/Qualifiers
REGION                  1..17
                        note = HCDR2
source                  1..17
                        mol_type = protein
                        organism = synthetic construct
SEQUENCE: 21
TISYDDYRTY YRDSVKG                                              17

SEQ ID NO: 22           moltype = AA  length = 17
FEATURE                 Location/Qualifiers
REGION                  1..17
                        note = HCDR2
source                  1..17
                        mol_type = protein
                        organism = synthetic construct
SEQUENCE: 22
YITNSLGSAY YRDSVKG                                              17

SEQ ID NO: 23           moltype = AA  length = 17
FEATURE                 Location/Qualifiers
REGION                  1..17
                        note = HCDR2
```

```
source                  1..17
                        mol_type = protein
                        organism = synthetic construct
SEQUENCE: 23
YITNSFGSTY YRDSVKG                                                17

SEQ ID NO: 24           moltype = AA  length = 17
FEATURE                 Location/Qualifiers
REGION                  1..17
                        note = HCDR2
source                  1..17
                        mol_type = protein
                        organism = synthetic construct
SEQUENCE: 24
YITNGYGSTY YRDSVKG                                                17

SEQ ID NO: 25           moltype = AA  length = 17
FEATURE                 Location/Qualifiers
REGION                  1..17
                        note = HCDR2
source                  1..17
                        mol_type = protein
                        organism = synthetic construct
SEQUENCE: 25
YITNGFGSTY YRDSVKG                                                17

SEQ ID NO: 26           moltype = AA  length = 4
FEATURE                 Location/Qualifiers
REGION                  1..4
                        note = HCDR3
source                  1..4
                        mol_type = protein
                        organism = synthetic construct
SEQUENCE: 26
YFDY                                                              4

SEQ ID NO: 27           moltype = AA  length = 5
FEATURE                 Location/Qualifiers
REGION                  1..5
                        note = HCDR3
source                  1..5
                        mol_type = protein
                        organism = synthetic construct
SEQUENCE: 27
GFGDY                                                             5

SEQ ID NO: 28           moltype = AA  length = 4
FEATURE                 Location/Qualifiers
REGION                  1..4
                        note = HCDR3
source                  1..4
                        mol_type = protein
                        organism = synthetic construct
SEQUENCE: 28
YFDH                                                              4

SEQ ID NO: 29           moltype = AA  length = 5
FEATURE                 Location/Qualifiers
REGION                  1..5
                        note = HCDR3
source                  1..5
                        mol_type = protein
                        organism = synthetic construct
SEQUENCE: 29
DKWVD                                                             5

SEQ ID NO: 30           moltype = AA  length = 12
FEATURE                 Location/Qualifiers
REGION                  1..12
                        note = HCDR3
source                  1..12
                        mol_type = protein
                        organism = synthetic construct
SEQUENCE: 30
QGGIIRGVWF PY                                                     12

SEQ ID NO: 31           moltype = AA  length = 8
FEATURE                 Location/Qualifiers
REGION                  1..8
```

```
                        note = HCDR3
source                  1..8
                        mol_type = protein
                        organism = synthetic construct
SEQUENCE: 31
VPLGAFVY                                                    8

SEQ ID NO: 32           moltype = AA  length = 8
FEATURE                 Location/Qualifiers
REGION                  1..8
                        note = HCDR3
source                  1..8
                        mol_type = protein
                        organism = synthetic construct
SEQUENCE: 32
VPLGAFVS                                                    8

SEQ ID NO: 33           moltype = AA  length = 11
FEATURE                 Location/Qualifiers
REGION                  1..11
                        note = LCDR1
source                  1..11
                        mol_type = protein
                        organism = synthetic construct
SEQUENCE: 33
RASQDVGIYV N                                                11

SEQ ID NO: 34           moltype = AA  length = 16
FEATURE                 Location/Qualifiers
REGION                  1..16
                        note = LCDR1
source                  1..16
                        mol_type = protein
                        organism = synthetic construct
SEQUENCE: 34
KSSQSLKHSD GKTYLN                                           16

SEQ ID NO: 35           moltype = AA  length = 11
FEATURE                 Location/Qualifiers
REGION                  1..11
                        note = LCDR1
source                  1..11
                        mol_type = protein
                        organism = synthetic construct
SEQUENCE: 35
QASQDIGNNL I                                                11

SEQ ID NO: 36           moltype = AA  length = 16
FEATURE                 Location/Qualifiers
REGION                  1..16
                        note = LCDR1
source                  1..16
                        mol_type = protein
                        organism = synthetic construct
SEQUENCE: 36
RSSQSLKHSD GKTYLN                                           16

SEQ ID NO: 37           moltype = AA  length = 11
FEATURE                 Location/Qualifiers
REGION                  1..11
                        note = LCDR1
source                  1..11
                        mol_type = protein
                        organism = synthetic construct
SEQUENCE: 37
QASQDIGNWL A                                                11

SEQ ID NO: 38           moltype = AA  length = 11
FEATURE                 Location/Qualifiers
REGION                  1..11
                        note = LCDR1
source                  1..11
                        mol_type = protein
                        organism = synthetic construct
SEQUENCE: 38
LASEGISNYL A                                                11

SEQ ID NO: 39           moltype = AA  length = 11
FEATURE                 Location/Qualifiers
```

```
REGION                1..11
                      note = LCDR1
source                1..11
                      mol_type = protein
                      organism = synthetic construct
SEQUENCE: 39
LASEDIYSYL A                                                     11

SEQ ID NO: 40         moltype = AA  length = 7
FEATURE               Location/Qualifiers
REGION                1..7
                      note = LCDR2
source                1..7
                      mol_type = protein
                      organism = synthetic construct
SEQUENCE: 40
RATNLAD                                                          7

SEQ ID NO: 41         moltype = AA  length = 7
FEATURE               Location/Qualifiers
REGION                1..7
                      note = LCDR2
source                1..7
                      mol_type = protein
                      organism = synthetic construct
SEQUENCE: 41
QVSKLDS                                                          7

SEQ ID NO: 42         moltype = AA  length = 7
FEATURE               Location/Qualifiers
REGION                1..7
                      note = LCDR2
source                1..7
                      mol_type = protein
                      organism = synthetic construct
SEQUENCE: 42
YATNLAN                                                          7

SEQ ID NO: 43         moltype = AA  length = 7
FEATURE               Location/Qualifiers
REGION                1..7
                      note = LCDR2
source                1..7
                      mol_type = protein
                      organism = synthetic construct
SEQUENCE: 43
RATTLAD                                                          7

SEQ ID NO: 44         moltype = AA  length = 7
FEATURE               Location/Qualifiers
REGION                1..7
                      note = LCDR2
source                1..7
                      mol_type = protein
                      organism = synthetic construct
SEQUENCE: 44
GATTLAD                                                          7

SEQ ID NO: 45         moltype = AA  length = 7
FEATURE               Location/Qualifiers
REGION                1..7
                      note = LCDR2
source                1..7
                      mol_type = protein
                      organism = synthetic construct
SEQUENCE: 45
HANPLHD                                                          7

SEQ ID NO: 46         moltype = AA  length = 7
FEATURE               Location/Qualifiers
REGION                1..7
                      note = LCDR2
source                1..7
                      mol_type = protein
                      organism = synthetic construct
SEQUENCE: 46
YANPLHD                                                          7

SEQ ID NO: 47         moltype = AA  length = 9
```

```
FEATURE                 Location/Qualifiers
REGION                  1..9
                        note = LCDR3
source                  1..9
                        mol_type = protein
                        organism = synthetic construct
SEQUENCE: 47
LQYDEFPPT                                                                 9

SEQ ID NO: 48           moltype = AA  length = 9
FEATURE                 Location/Qualifiers
REGION                  1..9
                        note = LCDR3
source                  1..9
                        mol_type = protein
                        organism = synthetic construct
SEQUENCE: 48
CQGSYSPYT                                                                 9

SEQ ID NO: 49           moltype = AA  length = 9
FEATURE                 Location/Qualifiers
REGION                  1..9
                        note = LCDR3
source                  1..9
                        mol_type = protein
                        organism = synthetic construct
SEQUENCE: 49
LQYDEWPYT                                                                 9

SEQ ID NO: 50           moltype = AA  length = 9
FEATURE                 Location/Qualifiers
REGION                  1..9
                        note = LCDR3
source                  1..9
                        mol_type = protein
                        organism = synthetic construct
SEQUENCE: 50
LQYDEYPPT                                                                 9

SEQ ID NO: 51           moltype = AA  length = 9
FEATURE                 Location/Qualifiers
REGION                  1..9
                        note = LCDR3
source                  1..9
                        mol_type = protein
                        organism = synthetic construct
SEQUENCE: 51
QQTSSTPWT                                                                 9

SEQ ID NO: 52           moltype = AA  length = 9
FEATURE                 Location/Qualifiers
REGION                  1..9
                        note = LCDR3
source                  1..9
                        mol_type = protein
                        organism = synthetic construct
SEQUENCE: 52
QQGYKFPYT                                                                 9

SEQ ID NO: 53           moltype = AA  length = 9
FEATURE                 Location/Qualifiers
REGION                  1..9
                        note = LCDR3
source                  1..9
                        mol_type = protein
                        organism = synthetic construct
SEQUENCE: 53
QQASSAPWT                                                                 9

SEQ ID NO: 54           moltype = AA  length = 9
FEATURE                 Location/Qualifiers
REGION                  1..9
                        note = LCDR3
source                  1..9
                        mol_type = protein
                        organism = synthetic construct
SEQUENCE: 54
QQGYKFPYS                                                                 9
```

```
SEQ ID NO: 55           moltype = AA  length = 113
FEATURE                 Location/Qualifiers
REGION                  1..113
                        note = 5738-10-R3A-B2 HCVR
source                  1..113
                        mol_type = protein
                        organism = synthetic construct
SEQUENCE: 55
QVQLKQSGAE LAKPGSSVKI SCKASGYTFT SYYISWIKQT TGQGLEYIGY INTGSGGTNY  60
NEKFKGKATL TVDKSSSTAF MQLSSLTPDD SAVYYCARYF DYWGQGVMVT VSS         113

SEQ ID NO: 56           moltype = AA  length = 116
FEATURE                 Location/Qualifiers
REGION                  1..116
                        note = 5738-10-R3A-C6 HCVR
source                  1..116
                        mol_type = protein
                        organism = synthetic construct
SEQUENCE: 56
EVKLVESGGG LVQPKESLKI SCAASGFTFS NIAMYWVRQA PGKGLEWVAH IRTKPHNFAT  60
YYANSVKGRF TISRDDSKNM VYLQMDNLKP EDTAMYYCSV GFGDYWGQGV MVTVSS      116

SEQ ID NO: 57           moltype = AA  length = 113
FEATURE                 Location/Qualifiers
REGION                  1..113
                        note = 5738-10-R3A-D1 HCVR
source                  1..113
                        mol_type = protein
                        organism = synthetic construct
SEQUENCE: 57
EVQLQQSGAE LAKPGSSVKI SCKASGYTFT NYTISWIKQT TGQGLEYIGY IYAGTGDTNY  60
NEKFKGKATL TVDKSSNTAF MQLSSLTPDD SAVYYCARYF DHWGQGVMVT VSS         113

SEQ ID NO: 58           moltype = AA  length = 114
FEATURE                 Location/Qualifiers
REGION                  1..114
                        note = 5738-10-R3A-D5 HCVR
source                  1..114
                        mol_type = protein
                        organism = synthetic construct
SEQUENCE: 58
EVQLQQSGAE LAKPGSSVKI SCKASGYTFT SYYISWIKQT TGQGLEYIGY INTGSGGTNY  60
NEKFKGKATL TVDKSSSTAF MQLSSLTPDD SAVYYCARDK WVDWGQGVMV TVSS        114

SEQ ID NO: 59           moltype = AA  length = 116
FEATURE                 Location/Qualifiers
REGION                  1..116
                        note = 5738-10-R3A-D8 HCVR
source                  1..116
                        mol_type = protein
                        organism = synthetic construct
SEQUENCE: 59
EVQLEESGGG LVQPKESLKI SCAVSGFTFS NIAMYWVRQA PGKGLEWVGH IRTKPHNYAT  60
YYADSVKGRF TISRDDSNNM VYLEMDNLKP EDTAMYYCSV GFGDYWGQGV MVTVSS      116

SEQ ID NO: 60           moltype = AA  length = 113
FEATURE                 Location/Qualifiers
REGION                  1..113
                        note = 5738-10-R3A-D11 HCVR & 5738-10-R4A-E9 HCVR
source                  1..113
                        mol_type = protein
                        organism = synthetic construct
SEQUENCE: 60
QVQLKQSGAE LAKPGSSVKI SCKASGYTFT SYYISWIKQT TGQGLEYIGY IHPGSGVTNY  60
NEKFKGKATL TVDKSSSTAF MQLSSLTPDD SAIYYCARYF DYWGQGVMVT VSS         113

SEQ ID NO: 61           moltype = AA  length = 113
FEATURE                 Location/Qualifiers
REGION                  1..113
                        note = 5738-10-R4A-E7 HCVR
source                  1..113
                        mol_type = protein
                        organism = synthetic construct
SEQUENCE: 61
QVQLKQSGVE LAKPGSSVKI SCKASGYTFT SDSISWIKQT TGQGLEYIGY IHPGSGVTNY  60
NEKFKGKATL TVDKSSSTAF MQLSSLTPDD SAIYYCARYF DYWGQGVMVT VSS         113

SEQ ID NO: 62           moltype = AA  length = 113
FEATURE                 Location/Qualifiers
```

```
REGION                  1..113
                        note = 5738-10-R4A-F12 HCVR
source                  1..113
                        mol_type = protein
                        organism = synthetic construct
SEQUENCE: 62
EVQLQQSGVE LAKPGSSVKI SCKASGYTFT SDSISWIKQT TGQGLEYIGY IHPGSGVTNY  60
NEKFKGKATL TVDKSSSTAF MQLSSLTPDD SAIYYCARYF DYWGQGVMVT VSS         113

SEQ ID NO: 63           moltype = AA  length = 113
FEATURE                 Location/Qualifiers
REGION                  1..113
                        note = 5738-10-R4A-G4 HCVR
source                  1..113
                        mol_type = protein
                        organism = synthetic construct
SEQUENCE: 63
EVQLQQSGVE LAKPGSSVKI SCKASGYTFT SDSISWIKQT TGQGLEYIGY IHPGSGVTNY  60
NEKFRGKATL TVDKSSSTAF MQLSSLTPDD SAIYYCARYF DYWGQGVMVT VSS         113

SEQ ID NO: 64           moltype = AA  length = 113
FEATURE                 Location/Qualifiers
REGION                  1..113
                        note = 5738-10-R4A-G11 HCVR
source                  1..113
                        mol_type = protein
                        organism = synthetic construct
SEQUENCE: 64
QVQLQQPRAE LAKPGSSVKI SCKASGYTFT NYSISWIKQT TGQGLEYIGY IYPGSGDTNY  60
NEKFKGKATL TVDKSSSTAF MQLSSLTPDD SAVYYCARYF DHWGQGTLVT VSS         113

SEQ ID NO: 65           moltype = AA  length = 113
FEATURE                 Location/Qualifiers
REGION                  1..113
                        note = 5738-10-R4A-G12 HCVR
source                  1..113
                        mol_type = protein
                        organism = synthetic construct
SEQUENCE: 65
QVQLKESGAE LAKPGSSVKI SCKASGYTFT SDSISWIKQT TGQGLEYIGY IHPGSGVTNY  60
NEKFKGKATL TVDKSSSTAF MQLSSLTPDD SAIYYCARYF DYWGQGVMVT VSS         113

SEQ ID NO: 66           moltype = AA  length = 121
FEATURE                 Location/Qualifiers
REGION                  1..121
                        note = 5738-13-R2A-C1 HCVR
source                  1..121
                        mol_type = protein
                        organism = synthetic construct
SEQUENCE: 66
QVQLKESGGG LVQPGRSLKL SCAASGFTFS DYNMAWVRQA PKKGLEWVAT ISYDDSRTYY  60
RDSVKGRFAI SRDDAKGTLN LQMDSLRSED TATYYCARQG GIIRGVWFPY WGQGTLVTVS  120
S                                                                 121

SEQ ID NO: 67           moltype = AA  length = 117
FEATURE                 Location/Qualifiers
REGION                  1..117
                        note = 5738-13-R2A-D3 HCVR
source                  1..117
                        mol_type = protein
                        organism = synthetic construct
SEQUENCE: 67
EVKLVESGGG LVQPGGSLKL SCAASGFTFS NYYMAWVRQA PTKGLEWVAY ITNSFGSAYY  60
RDSVKGRFTI SRDNAKSTLY LQMDSLRSED TATYYCSTVP LGAFVYWGQG TLVTVSS     117

SEQ ID NO: 68           moltype = AA  length = 121
FEATURE                 Location/Qualifiers
REGION                  1..121
                        note = 5738-13-R4A-D11 HCVR
source                  1..121
                        mol_type = protein
                        organism = synthetic construct
SEQUENCE: 68
QVQLKESGGG LVQPGRSLKL SCAASGFSFG DYNMAWVRQA PKKGLEWVAT ISYDDYRTYY  60
RDSVKGRFTI SRDDAKATLY LQMDSLRSED TATYYCARQG GIIRGVWFPY WGQGTLVTVS  120
S                                                                 121

SEQ ID NO: 69           moltype = AA  length = 117
FEATURE                 Location/Qualifiers
```

```
REGION                  1..117
                        note = 5738-13-R3A-F5 HCVR
source                  1..117
                        mol_type = protein
                        organism = synthetic construct
SEQUENCE: 69
EVKLVESGGG LVQPGGSLKL SCAASGFTFS NYYMAWVRQA PTKGLEWVAY ITNSLGSAYY  60
RDSVKGRFTI SRDNAKSTLY LQMDSLRSED TATYYCSTVP LGAFVYWGQG TLVTVSS     117

SEQ ID NO: 70           moltype = AA  length = 117
FEATURE                 Location/Qualifiers
REGION                  1..117
                        note = 5738-13-R4A-F11 HCVR
source                  1..117
                        mol_type = protein
                        organism = synthetic construct
SEQUENCE: 70
EVKLVESGGG LVQPGGSLKL SCAASGFTFS NYYMAWVRQA PTKGLEWVAY ITNSFGSTYY  60
RDSVKGRFTI SRDNAKSTLY LQMDSLRSED TATYYCSTVP LGAFVYWGQG TLVTVSS     117

SEQ ID NO: 71           moltype = AA  length = 117
FEATURE                 Location/Qualifiers
REGION                  1..117
                        note = 5738-13-R2A-H3 HCVR
source                  1..117
                        mol_type = protein
                        organism = synthetic construct
SEQUENCE: 71
EVKLVESGGG LVQPGRSLKL SCAASGFTFS NYYMAWVRQA PTKGLEWVAY ITNGYGSTYY  60
RDSVKGRFTI SRDNAKSTLY LQMDSLRSED TATYYCSTVP LGAFVYWGQG TLVTVSS     117

SEQ ID NO: 72           moltype = AA  length = 117
FEATURE                 Location/Qualifiers
REGION                  1..117
                        note = 5738-13-R2A-H4 HCVR
source                  1..117
                        mol_type = protein
                        organism = synthetic construct
SEQUENCE: 72
EVKLVESGGG LVQPGRSLKL SCAASGFTFS NYYMAWVRQA PTKGLEWVAY ITNGFGSTYY  60
RDSVKGRFTI SRDNAKSTLY LQMDSLRSED TATYYCSTVP LGAFVSWGQG TLVTVSS     117

SEQ ID NO: 73           moltype = AA  length = 117
FEATURE                 Location/Qualifiers
REGION                  1..117
                        note = 5738-13-R4A-H9 HCVR
source                  1..117
                        mol_type = protein
                        organism = synthetic construct
SEQUENCE: 73
EVKLVESGGG LVQPGRSLKL SCAASGFTFS NYYMAWVRQA PTKGLEWVAY ITNGFGSTYY  60
RDSVKGRFTI SRDNAKSTLY LQMDSLRSED AATYYCSTVP LGAFVSWGQG TLVTVSS     117

SEQ ID NO: 74           moltype = AA  length = 117
FEATURE                 Location/Qualifiers
REGION                  1..117
                        note = 5738-13-R4A-H11 HCVR
source                  1..117
                        mol_type = protein
                        organism = synthetic construct
SEQUENCE: 74
EVKLVESGGG LVQPGGSLKL SCAASGFTFS NYYMAWVRQA PTKGLEWVAY ITNGFGSTYY  60
RDSVKGRFTI SRDNAKSTLY LQMDSLRSED TATYYCSTVP LGAFVSWGQG TLVTVSS     117

SEQ ID NO: 75           moltype = AA  length = 107
FEATURE                 Location/Qualifiers
REGION                  1..107
                        note = 5738-10-R3A-B2 LCVR
source                  1..107
                        mol_type = protein
                        organism = synthetic construct
SEQUENCE: 75
DIVMTQSPSS MSVSLGDTVT ITCRASQDVG IYVNWFQQKP GKPPRRMIYR ATNLADGVPS  60
RFSGTRSGSD YSLTISSLES EDVADYHCLQ YDEFPPTFGS GTKLDIK                107

SEQ ID NO: 76           moltype = AA  length = 112
FEATURE                 Location/Qualifiers
REGION                  1..112
                        note = 5738-10-R3A-C6 LCVR
```

```
source                  1..112
                        mol_type = protein
                        organism = synthetic construct
SEQUENCE: 76
DIVMTQAPLS LSVAIGQSAS ISCKSSQSLK HSDGKTYLNW IFQSPGQSPK RLIYQVSKLD  60
SGVPDRFSGT GSETDFTLKI SRVEAEDLGV YYCCQGSYSP YTFGAGTKLE LK          112

SEQ ID NO: 77           moltype = AA  length = 107
FEATURE                 Location/Qualifiers
REGION                  1..107
                        note = 5738-10-R3A-D1 LCVR
source                  1..107
                        mol_type = protein
                        organism = synthetic construct
SEQUENCE: 77
DILMTQSPSS MSASLGDRVT ITCQASQDIG NNLIWFQQKP GKSPRRMIYY ATNLANGVPS  60
RFSGSRSGSD YSLSISSLES EDVADYHCLQ YDEFPPTFGS GTKLEIK                107

SEQ ID NO: 78           moltype = AA  length = 107
FEATURE                 Location/Qualifiers
REGION                  1..107
                        note = 5738-10-R3A-D5 LCVR
source                  1..107
                        mol_type = protein
                        organism = synthetic construct
SEQUENCE: 78
DILMTQSPSS MSVSLGDTVT ITCRASQDVG IYVNWFQQKP GKPPRRMIYR ATNLADGVPS  60
RFSGSRSGSN YSLTIRSLES EDVADYHCLQ YDEWPYTFGA GTKLELK                107

SEQ ID NO: 79           moltype = AA  length = 112
FEATURE                 Location/Qualifiers
REGION                  1..112
                        note = 5738-10-R3A-D8 LCVR
source                  1..112
                        mol_type = protein
                        organism = synthetic construct
SEQUENCE: 79
DIVMTQAPLS LSVDIGQSAS ISCRSSQSLK HSDGKTYLNW VFQSPGQSPK RLIYQVSKLD  60
SGVPDRFSGS GSEADFTLKI SRVEAEDLGV YYCCQGSYSP YTFGAGTKLE LK          112

SEQ ID NO: 80           moltype = AA  length = 107
FEATURE                 Location/Qualifiers
REGION                  1..107
                        note = 5738-10-R3A-D11 LCVR
source                  1..107
                        mol_type = protein
                        organism = synthetic construct
SEQUENCE: 80
DIQLTQSPSS MSVSQGDTVT ITCRASQDVG IYVNWFQQKP GKSPRRMIYR ATNLADGVPS  60
RFSGSRSGSD YSLTIASLES EDVADYHCLQ YDEFPPTFGS GTNLEIK                107

SEQ ID NO: 81           moltype = AA  length = 107
FEATURE                 Location/Qualifiers
REGION                  1..107
                        note = 5738-10-R4A-E7 LCVR
source                  1..107
                        mol_type = protein
                        organism = synthetic construct
SEQUENCE: 81
DILMTQSPSS MSVSLGDTVT ITCRASQDVG IYVNWFQQIP GKSPRRLIYR ATNLADGVPS  60
RFSGSRSGSD YSLTIASLES EDVADYHCLQ YDEFPPTFGS GTKLEIK                107

SEQ ID NO: 82           moltype = AA  length = 107
FEATURE                 Location/Qualifiers
REGION                  1..107
                        note = 5738-10-R4A-E9 LCVR
source                  1..107
                        mol_type = protein
                        organism = synthetic construct
SEQUENCE: 82
DILMTQSPSS MSVSQGDTVT ITCRASQDVG IYVNWFQQKP GKSPRRMIHR ATNLADGVPS  60
RFSGSRSGSD YSLTITSLES EDVADYHCLQ YDEYPPTFGS GTNLEIK                107

SEQ ID NO: 83           moltype = AA  length = 107
FEATURE                 Location/Qualifiers
REGION                  1..107
                        note = 5738-10-R4A-F12 LCVR
source                  1..107
                        mol_type = protein
```

```
                          organism = synthetic construct
SEQUENCE: 83
DILMTQSPSS MSVSLGDTVT ITCRASQDVG IYVNWFQQKP GKSPRRMIHR ATNLADGVPS  60
RFSGSRSGSD YSLTISSLES EDVADYHCLQ YDEYPPTFGS GTKLEIK               107

SEQ ID NO: 84             moltype = AA  length = 107
FEATURE                   Location/Qualifiers
REGION                    1..107
                          note = 5738-10-R4A-G4 LCVR
source                    1..107
                          mol_type = protein
                          organism = synthetic construct
SEQUENCE: 84
DIVMTQSPSS MSVSLGDTVT ITCRASQDVG IYVNWFQQKP GKSPRRMIYR ATNLADGVPS  60
RFSGSRSGSD YSLTIASLES EDVADYHCLQ YDEFPPTFGS GTKLEIK               107

SEQ ID NO: 85             moltype = AA  length = 107
FEATURE                   Location/Qualifiers
REGION                    1..107
                          note = 5738-10-R4A-G11 LCVR
source                    1..107
                          mol_type = protein
                          organism = synthetic construct
SEQUENCE: 85
DILMTQSPSS MSVSLGDTVT ITCRASQDVG IYVNWFQQKP GKSPRRMIYR ATTLADGVPS  60
RFSGSRSGSD YSLTISSLES EDVADYHCLQ YDEYPPTFGS GTKLEIK               107

SEQ ID NO: 86             moltype = AA  length = 107
FEATURE                   Location/Qualifiers
REGION                    1..107
                          note = 5738-10-R4A-G12 LCVR
source                    1..107
                          mol_type = protein
                          organism = synthetic construct
SEQUENCE: 86
DILMTQSPSS MSVSLGDTVT ITCRASQDVG IYVNWFQQKP GKSPRRMIYR ATNLADGVPS  60
RFSGSRSGSD YSLTISSLES EDVADYHCLQ YDEYPPTFGG GTKLELK               107

SEQ ID NO: 87             moltype = AA  length = 106
FEATURE                   Location/Qualifiers
REGION                    1..106
                          note = 5738-13-R2A-C1 LCVR
source                    1..106
                          mol_type = protein
                          organism = synthetic construct
SEQUENCE: 87
DIQLTQSPAS LSASLEEIVT ITCQASQDIG NWLAWYQQKP GKSPHLLIYG ATTLADGVPS  60
RSGSRSGTQY SLKISRLQVE DVGMYYCQQT SSTPWTFGGG TKLELK                106

SEQ ID NO: 88             moltype = AA  length = 107
FEATURE                   Location/Qualifiers
REGION                    1..107
                          note = 5738-13-R2A-D3 LCVR
source                    1..107
                          mol_type = protein
                          organism = synthetic construct
SEQUENCE: 88
DIQMTQTPHS LSASLGETVS IECLASEGIS NYLAWYQQKP GKSPQLLISH ANPLHDGVPS  60
RFSGDGSGTQ YSLKIRNMQP EDEGVYYCQQ GYKFPYTFGA GTKLELK               107

SEQ ID NO: 89             moltype = AA  length = 107
FEATURE                   Location/Qualifiers
REGION                    1..107
                          note = 5738-13-R4A-D11 LCVR
source                    1..107
                          mol_type = protein
                          organism = synthetic construct
SEQUENCE: 89
DIQMTQTPAS LSASLEEIVT ITCQASQDIG NWLAWYQQKP GKSPHLLIYG ATTLADGVPS  60
RFSGSRSGTQ YSLKISRLQA EDIGIYYCQQ ASSAPWTFGG GTKLELK               107

SEQ ID NO: 90             moltype = AA  length = 107
FEATURE                   Location/Qualifiers
REGION                    1..107
                          note = 5738-13-R3A-F5 LCVR
source                    1..107
                          mol_type = protein
                          organism = synthetic construct
SEQUENCE: 90
```

```
DIQMTQTPHS LSASLGETVS IECLASEGIS NYLAWYQQKP GKSPQLLISH ANPLHDGVPS  60
RFSGSGSGTQ YSLKIRNMQP EDEGVYYCQQ GYKFPYSFGA GTKLELK               107

SEQ ID NO: 91          moltype = AA  length = 107
FEATURE                Location/Qualifiers
REGION                 1..107
                       note = 5738-13-R4A-F11 LCVR
source                 1..107
                       mol_type = protein
                       organism = synthetic construct
SEQUENCE: 91
DIQLTQSPAS LSASLGETVS IECLASEDIY SYLAWYQQKP GKSPQLLISH ANPLHDGVPS  60
RFSGSGSGTQ YSLKIRNMQP EDEGVYYCQQ GYKFPYTFGA GTKLELK               107

SEQ ID NO: 92          moltype = AA  length = 107
FEATURE                Location/Qualifiers
REGION                 1..107
                       note = 5738-13-R2A-H3 LCVR
source                 1..107
                       mol_type = protein
                       organism = synthetic construct
SEQUENCE: 92
DIQMTQTPHS LSASLGETVS IECLASEGIS NYLAWYQQKP GKSPQLLISH ANPLHDGVPS  60
RFSGSGSGTQ YSLKIRNMQP EDEGVYYCQQ GYKFPYTFGA GTKLELK               107

SEQ ID NO: 93          moltype = AA  length = 107
FEATURE                Location/Qualifiers
REGION                 1..107
                       note = 5738-13-R2A-H4 LCVR
source                 1..107
                       mol_type = protein
                       organism = synthetic construct
SEQUENCE: 93
DIQMTQTPHS LSASLGETVS IECLASEGIS NYLAWYQQKP GKSPQLLISY ANPLHDGVPS  60
RFSGSGSGTQ FSLKIRNMQP EDEGVYYCQQ GYKFPYTFGA GTKLELT               107

SEQ ID NO: 94          moltype = AA  length = 107
FEATURE                Location/Qualifiers
REGION                 1..107
                       note = 5738-13-R4A-H9 LCVR & 5738-13-R4A-H11 LCVR
source                 1..107
                       mol_type = protein
                       organism = synthetic construct
SEQUENCE: 94
DIQMTQTPHS LSASLGETVS IECLASEGIS NYLAWYQQKP GKSPQLLISH ANPLHDGVPS  60
RFSGSGSGTQ FSLKIRNMQP EDEGVYYCQQ GYKFPYTFGA GTKLELK               107

SEQ ID NO: 95          moltype =   length =
SEQUENCE: 95
000

SEQ ID NO: 96          moltype =   length =
SEQUENCE: 96
000

SEQ ID NO: 97          moltype =   length =
SEQUENCE: 97
000

SEQ ID NO: 98          moltype =   length =
SEQUENCE: 98
000

SEQ ID NO: 99          moltype =   length =
SEQUENCE: 99
000

SEQ ID NO: 100         moltype =   length =
SEQUENCE: 100
000

SEQ ID NO: 101         moltype = AA  length = 766
FEATURE                Location/Qualifiers
DOMAIN                 1..6
                       note = Cytoplasmic domain
REGION                 1..766
                       note = hDPP4
DOMAIN                 7..28
                       note = Transmembrane domain
```

```
DOMAIN                 29..766
                       note = Extracellular domain
SITE                   170..191
                       note = hDPP4 Peptide P2
SITE                   235..254
                       note = hDPP4 Peptide P3
SITE                   492..517
                       note = hDPP4 Peptide P5
SITE                   533..551
                       note = hDPP4 Peptide P6
source                 1..766
                       mol_type = protein
                       organism = Homo sapiens
SEQUENCE: 101
MKTPWKVLLG LLGAAALVTI ITVPVVLLNK GTDDATADSR KTYTLTDYLK NTYRLKLYSL  60
RWISDHEYLY KQENNILVFN AEYGNSSVFL ENSTFDEFGH SINDYSISPD GQFILLEYNY  120
VKQWRHSYTA SYDIYDLNKR QLITEERIPN NTQWVTWSPV GHKLAYVWNN DIYVKIEPNL  180
PSYRITWTGK EDIIYNGITD WVYEEEVFSA YSALWWSPNG TFLAYAQFND TEVPLIEYSF  240
YSDESLQYPK TVRVPYPKAG AVNPTVKFFV VNTDSLSSVT NATSIQITAP ASMLIGDHYL  300
CDVTWATQER ISLQWLRRIQ NYSVMDICDY DESSGRWNCL VARQHIEMST TGWVGRFRPS  360
EPHFTLDGNS FYKIISNEEG YRHICYFQID KKDCTFITKG TWEVIGIEAL TSDYLYYISN  420
EYKGMPGGRN LYKIQLSDYT KVTCLSCELN PERCQYYSVS FSKEAKYYQL RCSGPGLPLY  480
TLHSSVNDKG LRVLEDNSAL DKMLQNVQMP SKKLDFIILN ETKFWYQMIL PPHFDKSKKY  540
PLLLDVYAGP CSQKADTVFR LNWATYLAST ENIIVASFDG RGSGYQGDKI MHAINRRLGT  600
FEVEDQIEAA RQFSKMGFVD NKRIAIWGWS YGGYVTSMVL GSGSGVFKCG IAVAPVSRWE  660
YYDSVYTERY MGLPTPEDNL DHYRNSTVMS RAENFKQVEY LLIHGTADDN VHFQQSAQIS  720
KALVDVGVDF QAMWYTDEDH GIASSTAHQH IYTHMSHFIK QCFSLP                766

SEQ ID NO: 102         moltype = AA  length = 736
FEATURE                Location/Qualifiers
REGION                 1..736
                       note = hDPP4-ECD_6xHis
source                 1..736
                       mol_type = protein
                       organism = synthetic construct
SEQUENCE: 102
HHHHHHADSR KTYTLTDYLK NTYRLKLYSL RWISDHEYLY KQENNILVFN AEYGNSSVFL  60
ENSTFDEFGH SINDYSISPD GQFILLEYNY VKQWRHSYTA SYDIYDLNKR QLITEERIPN  120
NTQWVTWSPV GHKLAYVWNN DIYVKIEPNL PSYRITWTGK EDIIYNGITD WVYEEEVFSA  180
YSALWWSPNG TFLAYAQFND TEVPLIEYSF YSDESLQYPK TVRVPYPKAG AVNPTVKFFV  240
VNTDSLSSVT NATSIQITAP ASMLIGDHYL CDVTWATQER ISLQWLRRIQ NYSVMDICDY  300
DESSGRWNCL VARQHIEMST TGWVGRFRPS EPHFTLDGNS FYKIISNEEG YRHICYFQID  360
KKDCTFITKG TWEVIGIEAL TSDYLYYISN EYKGMPGGRN LYKIQLSDYT KVTCLSCELN  420
PERCQYYSVS FSKEAKYYQL RCSGPGLPLY TLHSSVNDKG LRVLEDNSAL DKMLQNVQMP  480
SKKLDFIILN ETKFWYQMIL PPHFDKSKKY PLLLDVYAGP CSQKADTVFR LNWATYLAST  540
ENIIVASFDG RGSGYQGDKI MHAINRRLGT FEVEDQIEAA RQFSKMGFVD NKRIAIWGWS  600
YGGYVTSMVL GSGSGVFKCG IAVAPVSRWE YYDSVYTERY MGLPTPEDNL DHYRNSTVMS  660
RAENFKQVEY LLIHGTADDN VHFQQSAQIS KALVDVGVDF QAMWYTDEDH GIASSTAHQH  720
IYTHMSHFIK QCFSLP                                                 736

SEQ ID NO: 103         moltype = AA  length = 760
FEATURE                Location/Qualifiers
REGION                 1..760
                       note = mDPP4
source                 1..760
                       mol_type = protein
                       organism = Mus musculus
SEQUENCE: 103
MKTPWKVLLG LLGVAALVTI ITVPIVLLSK DEAAADSRRT YSLADYLKST FRVKSYSLWW  60
VSDFEYLYKQ ENNILLLNAE HGNSSIFLEN STFESFGYHS VSPDRLFVLL EYNYVKQWRH  120
SYTASYNIYD VNKRQLITEE KIPNNTQWIT WSPEGHKLAY VWKNDIYVKV EPHLPSHRIT  180
STGEENVIYN GITDWVYEEE VFGAYSALWW SPNNTFLAYA QFNDTGVPLI EYSFYSDESL  240
QYPKTVWIPY PKAGAVNPTV KFFIVNIDSL SSSSSAAPIQ IPAPASVARG DHYLCDVVWA  300
TEERISLQWL RRIQNYSVMA ICDYDKINLT WNCPSEQQHV EMSTTGWVGR FRPAEPHFTS  360
DGSSFYKIIS DKDGYKHICH FPKDKKDCTF ITKGAWEVIS IEALTSDYLY YISNQYKEMP  420
GGRNLYKIQL TDHTNVKCLS CDLNPERCQY YAVSFSKEAK YYQLGCWGPG LPLYTLHRST  480
DHKELRVLED NSALDRMLQD VQMPSKKLDF IVLNETRFWY QMILPPHFDK SKKYPLLLDV  540
YAGPCSQKAD ASFRLNWATY LASTENIIVA SFDGRGSGYQ GDKIMHAINR RLGTLEVEDQ  600
IEAARQFVKM GFVDSKRVAI WGWSYGGYVT SMVLGSGSGV FKCGIAVAPV SRWEYYDSVY  660
TERYMGLPIP EDNLDHYRNS TVMSRAEHFK QVEYLLIHGT ADDNVHFQQS AQISKALVDA  720
GVDFQAMWYT DEDHGIASST AHQHIYSHMS HFLQQCFSLH                       760

SEQ ID NO: 104         moltype = AA  length = 5
FEATURE                Location/Qualifiers
REGION                 1..5
                       note = HCDR1
source                 1..5
                       mol_type = protein
                       organism = synthetic construct
```

```
SEQUENCE: 104
NYGMA                                                                  5

SEQ ID NO: 105          moltype = AA  length = 7
FEATURE                 Location/Qualifiers
REGION                  1..7
                        note = HCDR1
source                  1..7
                        mol_type = protein
                        organism = synthetic construct
SEQUENCE: 105
TSDRCVS                                                                7

SEQ ID NO: 106          moltype = AA  length = 5
FEATURE                 Location/Qualifiers
REGION                  1..5
                        note = HCDR1
source                  1..5
                        mol_type = protein
                        organism = synthetic construct
SEQUENCE: 106
NFGMA                                                                  5

SEQ ID NO: 107          moltype = AA  length = 5
FEATURE                 Location/Qualifiers
REGION                  1..5
                        note = HCDR1
source                  1..5
                        mol_type = protein
                        organism = synthetic construct
SEQUENCE: 107
DNYWG                                                                  5

SEQ ID NO: 108          moltype = AA  length = 5
FEATURE                 Location/Qualifiers
REGION                  1..5
                        note = HCDR1
source                  1..5
                        mol_type = protein
                        organism = synthetic construct
SEQUENCE: 108
TYDIG                                                                  5

SEQ ID NO: 109          moltype = AA  length = 5
FEATURE                 Location/Qualifiers
REGION                  1..5
                        note = HCDR1
source                  1..5
                        mol_type = protein
                        organism = synthetic construct
SEQUENCE: 109
GNYLA                                                                  5

SEQ ID NO: 110          moltype = AA  length = 5
FEATURE                 Location/Qualifiers
REGION                  1..5
                        note = HCDR1
source                  1..5
                        mol_type = protein
                        organism = synthetic construct
SEQUENCE: 110
SNYWG                                                                  5

SEQ ID NO: 111          moltype = AA  length = 5
FEATURE                 Location/Qualifiers
REGION                  1..5
                        note = HCDR1
source                  1..5
                        mol_type = protein
                        organism = synthetic construct
SEQUENCE: 111
TYDRG                                                                  5

SEQ ID NO: 112          moltype = AA  length = 5
FEATURE                 Location/Qualifiers
REGION                  1..5
                        note = HCDR1
source                  1..5
                        mol_type = protein
```

```
                        organism = synthetic construct
SEQUENCE: 112
GNYWG                                                                   5

SEQ ID NO: 113          moltype = AA  length = 17
FEATURE                 Location/Qualifiers
REGION                  1..17
                        note = HCDR2
source                  1..17
                        mol_type = protein
                        organism = synthetic construct
SEQUENCE: 113
TISYDGNDTY YRDSVKG                                                      17

SEQ ID NO: 114          moltype = AA  length = 17
FEATURE                 Location/Qualifiers
REGION                  1..17
                        note = HCDR2
source                  1..17
                        mol_type = protein
                        organism = synthetic construct
SEQUENCE: 114
TTSYDGNDTY YRDSVKG                                                      17

SEQ ID NO: 115          moltype = AA  length = 16
FEATURE                 Location/Qualifiers
REGION                  1..16
                        note = HCDR2
source                  1..16
                        mol_type = protein
                        organism = synthetic construct
SEQUENCE: 115
TICWDDSKGY NPSLKN                                                       16

SEQ ID NO: 116          moltype = AA  length = 17
FEATURE                 Location/Qualifiers
REGION                  1..17
                        note = HCDR2
source                  1..17
                        mol_type = protein
                        organism = synthetic construct
SEQUENCE: 116
TINYDGRNTY YRDSVKG                                                      17

SEQ ID NO: 117          moltype = AA  length = 17
FEATURE                 Location/Qualifiers
REGION                  1..17
                        note = HCDR2
source                  1..17
                        mol_type = protein
                        organism = synthetic construct
SEQUENCE: 117
TINYDGSNTY YRDSVKG                                                      17

SEQ ID NO: 118          moltype = AA  length = 17
FEATURE                 Location/Qualifiers
REGION                  1..17
                        note = HCDR2
source                  1..17
                        mol_type = protein
                        organism = synthetic construct
SEQUENCE: 118
TINYDGRDTY YRDSVKG                                                      17

SEQ ID NO: 119          moltype = AA  length = 16
FEATURE                 Location/Qualifiers
REGION                  1..16
                        note = HCDR2
source                  1..16
                        mol_type = protein
                        organism = synthetic construct
SEQUENCE: 119
HISHSGSSTY NPSLKS                                                       16

SEQ ID NO: 120          moltype = AA  length = 17
FEATURE                 Location/Qualifiers
REGION                  1..17
                        note = HCDR2
source                  1..17
```

```
                      mol_type = protein
                      organism = synthetic construct
SEQUENCE: 120
YINPGSGGIG YNEKFKG                                             17

SEQ ID NO: 121        moltype = AA  length = 17
FEATURE               Location/Qualifiers
REGION                1..17
                      note = HCDR2
source                1..17
                      mol_type = protein
                      organism = synthetic construct
SEQUENCE: 121
SINPGSGGIA YSEKFKG                                             17

SEQ ID NO: 122        moltype = AA  length = 16
FEATURE               Location/Qualifiers
REGION                1..16
                      note = HCDR2
source                1..16
                      mol_type = protein
                      organism = synthetic construct
SEQUENCE: 122
HIKSSGTTTY NPSLKS                                              16

SEQ ID NO: 123        moltype = AA  length = 17
FEATURE               Location/Qualifiers
REGION                1..17
                      note = HCDR2
source                1..17
                      mol_type = protein
                      organism = synthetic construct
SEQUENCE: 123
SINPGSGGIG YNERFKG                                             17

SEQ ID NO: 124        moltype = AA  length = 17
FEATURE               Location/Qualifiers
REGION                1..17
                      note = HCDR2
source                1..17
                      mol_type = protein
                      organism = synthetic construct
SEQUENCE: 124
YINPGGGGIG YNEKFKG                                             17

SEQ ID NO: 125        moltype = AA  length = 16
FEATURE               Location/Qualifiers
REGION                1..16
                      note = HCDR2
source                1..16
                      mol_type = protein
                      organism = synthetic construct
SEQUENCE: 125
QISHSGSTSY NPSLKS                                              16

SEQ ID NO: 126        moltype = AA  length = 17
FEATURE               Location/Qualifiers
REGION                1..17
                      note = HCDR2
source                1..17
                      mol_type = protein
                      organism = synthetic construct
SEQUENCE: 126
SINPGSGGIG YNEKFKG                                             17

SEQ ID NO: 127        moltype = AA  length = 17
FEATURE               Location/Qualifiers
REGION                1..17
                      note = HCDR2
source                1..17
                      mol_type = protein
                      organism = synthetic construct
SEQUENCE: 127
SINPGGGGTG YNEKFKG                                             17

SEQ ID NO: 128        moltype = AA  length = 16
FEATURE               Location/Qualifiers
REGION                1..16
                      note = HCDR2
```

```
source                  1..16
                        mol_type = protein
                        organism = synthetic construct
SEQUENCE: 128
QISHSGSTSY NPSLIS                                                           16

SEQ ID NO: 129          moltype = AA  length = 16
FEATURE                 Location/Qualifiers
REGION                  1..16
                        note = HCDR2
source                  1..16
                        mol_type = protein
                        organism = synthetic construct
SEQUENCE: 129
QISHTGSSTY NPSLKS                                                           16

SEQ ID NO: 130          moltype = AA  length = 16
FEATURE                 Location/Qualifiers
REGION                  1..16
                        note = HCDR3
source                  1..16
                        mol_type = protein
                        organism = synthetic construct
SEQUENCE: 130
HRLIYTTDYY YEVMDV                                                           16

SEQ ID NO: 131          moltype = AA  length = 16
FEATURE                 Location/Qualifiers
REGION                  1..16
                        note = HCDR3
source                  1..16
                        mol_type = protein
                        organism = synthetic construct
SEQUENCE: 131
HRLIYTTDYY YEVMDA                                                           16

SEQ ID NO: 132          moltype = AA  length = 9
FEATURE                 Location/Qualifiers
REGION                  1..9
                        note = HCDR3
source                  1..9
                        mol_type = protein
                        organism = synthetic construct
SEQUENCE: 132
NSGDGRFAY                                                                   9

SEQ ID NO: 133          moltype = AA  length = 16
FEATURE                 Location/Qualifiers
REGION                  1..16
                        note = HCDR3
source                  1..16
                        mol_type = protein
                        organism = synthetic construct
SEQUENCE: 133
HKLIYTTDYY YEVMDA                                                           16

SEQ ID NO: 134          moltype = AA  length = 16
FEATURE                 Location/Qualifiers
REGION                  1..16
                        note = HCDR3
source                  1..16
                        mol_type = protein
                        organism = synthetic construct
SEQUENCE: 134
HRLMYTTDYY YEVMDD                                                           16

SEQ ID NO: 135          moltype = AA  length = 16
FEATURE                 Location/Qualifiers
REGION                  1..16
                        note = HCDR3
source                  1..16
                        mol_type = protein
                        organism = synthetic construct
SEQUENCE: 135
HRLIYTTDYY YEVLDA                                                           16

SEQ ID NO: 136          moltype = AA  length = 16
FEATURE                 Location/Qualifiers
REGION                  1..16
```

```
                        note = HCDR3
source                  1..16
                        mol_type = protein
                        organism = synthetic construct
SEQUENCE: 136
HKLIYTTDYY YEVMDV                                                     16

SEQ ID NO: 137          moltype = AA  length = 9
FEATURE                 Location/Qualifiers
REGION                  1..9
                        note = HCDR3
source                  1..9
                        mol_type = protein
                        organism = synthetic construct
SEQUENCE: 137
YGAGASFDY                                                             9

SEQ ID NO: 138          moltype = AA  length = 8
FEATURE                 Location/Qualifiers
REGION                  1..8
                        note = HCDR3
source                  1..8
                        mol_type = protein
                        organism = synthetic construct
SEQUENCE: 138
PLRRVLDY                                                              8

SEQ ID NO: 139          moltype = AA  length = 8
FEATURE                 Location/Qualifiers
REGION                  1..8
                        note = HCDR3
source                  1..8
                        mol_type = protein
                        organism = synthetic construct
SEQUENCE: 139
HGHYVMDV                                                              8

SEQ ID NO: 140          moltype = AA  length = 9
FEATURE                 Location/Qualifiers
REGION                  1..9
                        note = HCDR3
source                  1..9
                        mol_type = protein
                        organism = synthetic construct
SEQUENCE: 140
YGAGSSFDY                                                             9

SEQ ID NO: 141          moltype = AA  length = 8
FEATURE                 Location/Qualifiers
REGION                  1..8
                        note = HCDR3
source                  1..8
                        mol_type = protein
                        organism = synthetic construct
SEQUENCE: 141
PLRRVLDN                                                              8

SEQ ID NO: 142          moltype = AA  length = 7
FEATURE                 Location/Qualifiers
REGION                  1..7
                        note = HCDR3
source                  1..7
                        mol_type = protein
                        organism = synthetic construct
SEQUENCE: 142
PLRVLDY                                                               7

SEQ ID NO: 143          moltype = AA  length = 17
FEATURE                 Location/Qualifiers
REGION                  1..17
                        note = LCDR1
source                  1..17
                        mol_type = protein
                        organism = synthetic construct
SEQUENCE: 143
KSSQSLLYNE NKKNYLA                                                    17

SEQ ID NO: 144          moltype = AA  length = 16
FEATURE                 Location/Qualifiers
```

```
REGION                  1..16
                        note = LCDR1
source                  1..16
                        mol_type = protein
                        organism = synthetic construct
SEQUENCE: 144
KSSQSLLHSN GNTYLN                                                  16

SEQ ID NO: 145          moltype = AA  length = 16
FEATURE                 Location/Qualifiers
REGION                  1..16
                        note = LCDR1
source                  1..16
                        mol_type = protein
                        organism = synthetic construct
SEQUENCE: 145
RSSQSLLHSN GNTYLN                                                  16

SEQ ID NO: 146          moltype = AA  length = 11
FEATURE                 Location/Qualifiers
REGION                  1..11
                        note = LCDR1
source                  1..11
                        mol_type = protein
                        organism = synthetic construct
SEQUENCE: 146
LASEGISNYL A                                                       11

SEQ ID NO: 147          moltype = AA  length = 11
FEATURE                 Location/Qualifiers
REGION                  1..11
                        note = LCDR1
source                  1..11
                        mol_type = protein
                        organism = synthetic construct
SEQUENCE: 147
RASQGISNKL N                                                       11

SEQ ID NO: 148          moltype = AA  length = 15
FEATURE                 Location/Qualifiers
REGION                  1..15
                        note = LCDR1
source                  1..15
                        mol_type = protein
                        organism = synthetic construct
SEQUENCE: 148
RASQSVSTST YNFMH                                                   15

SEQ ID NO: 149          moltype = AA  length = 11
FEATURE                 Location/Qualifiers
REGION                  1..11
                        note = LCDR1
source                  1..11
                        mol_type = protein
                        organism = synthetic construct
SEQUENCE: 149
RASQGIGNKL N                                                       11

SEQ ID NO: 150          moltype = AA  length = 11
FEATURE                 Location/Qualifiers
REGION                  1..11
                        note = LCDR1
source                  1..11
                        mol_type = protein
                        organism = synthetic construct
SEQUENCE: 150
RASQGISKKL N                                                       11

SEQ ID NO: 151          moltype = AA  length = 11
FEATURE                 Location/Qualifiers
REGION                  1..11
                        note = LCDR1
source                  1..11
                        mol_type = protein
                        organism = synthetic construct
SEQUENCE: 151
GASQGIGNKV N                                                       11

SEQ ID NO: 152          moltype = AA  length = 7
```

```
FEATURE                Location/Qualifiers
REGION                 1..7
                       note = LCDR2
source                 1..7
                       mol_type = protein
                       organism = synthetic construct
SEQUENCE: 152
WASTRES                                                                   7

SEQ ID NO: 153         moltype = AA  length = 7
FEATURE                Location/Qualifiers
REGION                 1..7
                       note = LCDR2
source                 1..7
                       mol_type = protein
                       organism = synthetic construct
SEQUENCE: 153
SVSKLES                                                                   7

SEQ ID NO: 154         moltype = AA  length = 7
FEATURE                Location/Qualifiers
REGION                 1..7
                       note = LCDR2
source                 1..7
                       mol_type = protein
                       organism = synthetic construct
SEQUENCE: 154
WASTREA                                                                   7

SEQ ID NO: 155         moltype = AA  length = 7
FEATURE                Location/Qualifiers
REGION                 1..7
                       note = LCDR2
source                 1..7
                       mol_type = protein
                       organism = synthetic construct
SEQUENCE: 155
WASTRKS                                                                   7

SEQ ID NO: 156         moltype = AA  length = 7
FEATURE                Location/Qualifiers
REGION                 1..7
                       note = LCDR2
source                 1..7
                       mol_type = protein
                       organism = synthetic construct
SEQUENCE: 156
SVSNLES                                                                   7

SEQ ID NO: 157         moltype = AA  length = 7
FEATURE                Location/Qualifiers
REGION                 1..7
                       note = LCDR2
source                 1..7
                       mol_type = protein
                       organism = synthetic construct
SEQUENCE: 157
YTSSLQD                                                                   7

SEQ ID NO: 158         moltype = AA  length = 7
FEATURE                Location/Qualifiers
REGION                 1..7
                       note = LCDR2
source                 1..7
                       mol_type = protein
                       organism = synthetic construct
SEQUENCE: 158
YTSRLQS                                                                   7

SEQ ID NO: 159         moltype = AA  length = 7
FEATURE                Location/Qualifiers
REGION                 1..7
                       note = LCDR2
source                 1..7
                       mol_type = protein
                       organism = synthetic construct
SEQUENCE: 159
YTSNLQS                                                                   7
```

```
SEQ ID NO: 160          moltype = AA  length = 7
FEATURE                 Location/Qualifiers
REGION                  1..7
                        note = LCDR2
source                  1..7
                        mol_type = protein
                        organism = synthetic construct
SEQUENCE: 160
DASHLAS                                                                  7

SEQ ID NO: 161          moltype = AA  length = 7
FEATURE                 Location/Qualifiers
REGION                  1..7
                        note = LCDR2
source                  1..7
                        mol_type = protein
                        organism = synthetic construct
SEQUENCE: 161
YTSSFQD                                                                  7

SEQ ID NO: 162          moltype = AA  length = 7
FEATURE                 Location/Qualifiers
REGION                  1..7
                        note = LCDR2
source                  1..7
                        mol_type = protein
                        organism = synthetic construct
SEQUENCE: 162
YTISLQD                                                                  7

SEQ ID NO: 163          moltype = AA  length = 7
FEATURE                 Location/Qualifiers
REGION                  1..7
                        note = LCDR2
source                  1..7
                        mol_type = protein
                        organism = synthetic construct
SEQUENCE: 163
YASSLQD                                                                  7

SEQ ID NO: 164          moltype = AA  length = 9
FEATURE                 Location/Qualifiers
REGION                  1..9
                        note = LCDR3
source                  1..9
                        mol_type = protein
                        organism = synthetic construct
SEQUENCE: 164
QEYYKFPWT                                                                9

SEQ ID NO: 165          moltype = AA  length = 9
FEATURE                 Location/Qualifiers
REGION                  1..9
                        note = LCDR3
source                  1..9
                        mol_type = protein
                        organism = synthetic construct
SEQUENCE: 165
QDYYHFPWT                                                                9

SEQ ID NO: 166          moltype = AA  length = 9
FEATURE                 Location/Qualifiers
REGION                  1..9
                        note = LCDR3
source                  1..9
                        mol_type = protein
                        organism = synthetic construct
SEQUENCE: 166
MQATHAPFT                                                                9

SEQ ID NO: 167          moltype = AA  length = 9
FEATURE                 Location/Qualifiers
REGION                  1..9
                        note = LCDR3
source                  1..9
                        mol_type = protein
                        organism = synthetic construct
SEQUENCE: 167
QQYYKFPWP                                                                9
```

```
SEQ ID NO: 168          moltype = AA  length = 9
FEATURE                 Location/Qualifiers
REGION                  1..9
                        note = LCDR3
source                  1..9
                        mol_type = protein
                        organism = synthetic construct
SEQUENCE: 168
QQYYKFPWT                                                          9

SEQ ID NO: 169          moltype = AA  length = 9
FEATURE                 Location/Qualifiers
REGION                  1..9
                        note = LCDR3
source                  1..9
                        mol_type = protein
                        organism = synthetic construct
SEQUENCE: 169
QQYYKFPYT                                                          9

SEQ ID NO: 170          moltype = AA  length = 9
FEATURE                 Location/Qualifiers
REGION                  1..9
                        note = LCDR3
source                  1..9
                        mol_type = protein
                        organism = synthetic construct
SEQUENCE: 170
QQGYKYPWT                                                          9

SEQ ID NO: 171          moltype = AA  length = 9
FEATURE                 Location/Qualifiers
REGION                  1..9
                        note = LCDR3
source                  1..9
                        mol_type = protein
                        organism = synthetic construct
SEQUENCE: 171
QQDASFPPT                                                          9

SEQ ID NO: 172          moltype = AA  length = 9
FEATURE                 Location/Qualifiers
REGION                  1..9
                        note = LCDR3
source                  1..9
                        mol_type = protein
                        organism = synthetic construct
SEQUENCE: 172
QQSRELPLT                                                          9

SEQ ID NO: 173          moltype = AA  length = 9
FEATURE                 Location/Qualifiers
REGION                  1..9
                        note = LCDR3
source                  1..9
                        mol_type = protein
                        organism = synthetic construct
SEQUENCE: 173
QQDTSFPPT                                                          9

SEQ ID NO: 174          moltype = AA  length = 125
FEATURE                 Location/Qualifiers
REGION                  1..125
                        note = 5826-8-R6A-A10 HCVR
source                  1..125
                        mol_type = protein
                        organism = synthetic construct
SEQUENCE: 174
EVQLEESGGG LVQPGRSLKL SCAASGFTFN NYGMAWVRQA PTKGLEWVAT ISYDGNDTYY  60
RDSVKGRFTV SRDNAKSTLY LQMDSLRSED TATYYCVRHR LIYTTDYYYE VMDVWGQGAS  120
VTVSS                                                              125

SEQ ID NO: 175          moltype = AA  length = 125
FEATURE                 Location/Qualifiers
REGION                  1..125
                        note = 5826-8-R6A-B11 HCVR
source                  1..125
                        mol_type = protein
```

```
                         organism = synthetic construct
SEQUENCE: 175
QVQLKESGGG LVQPGRSLKL SCAASGFTFS NYGMAWVRQA PTKGLEWVAT TSYDGNDTYY  60
RDSVKGRFTV SRDNAKNTLY LQMDSLRSED TATYYCVRHR LIYTTDYYYE VMDAWGQGAS  120
VTVSS                                                             125

SEQ ID NO: 176           moltype = AA  length = 119
FEATURE                  Location/Qualifiers
REGION                   1..119
                         note = 5826-8-R6A-D12 HCVR & 5826-8-R6A-H11 HCVR
source                   1..119
                         mol_type = protein
                         organism = synthetic construct
SEQUENCE: 176
QVTLKESGPG ILQPSQTLSL TCSFSGFSLS TSDRCVSWIR QPSGKGLEWL ATICWDDSKG  60
YNPSLKNRLT ISKDTSNNQA FLKITSVGTA DIAKYYCARN SGDGRFAYWG QGTLVTVSS   119

SEQ ID NO: 177           moltype = AA  length = 125
FEATURE                  Location/Qualifiers
REGION                   1..125
                         note = 5826-8-R6A-E10 HCVR
source                   1..125
                         mol_type = protein
                         organism = synthetic construct
SEQUENCE: 177
EVQLEESGGG LVQPGRSLKL SCAASGFTFS NYGMAWVRQA PTKGLEWVAT INYDGRNTYY  60
RDSVKGRFTI SRDNAKSTLY LQVDSLQSED TATYYCTRHK LIYTTDYYYE VMDAWGQGAS  120
VTVSS                                                             125

SEQ ID NO: 178           moltype = AA  length = 125
FEATURE                  Location/Qualifiers
REGION                   1..125
                         note = 5826-8-R5A-G6 HCVR
source                   1..125
                         mol_type = protein
                         organism = synthetic construct
SEQUENCE: 178
EVKLVESGGG LVQPGRSLKL SCAASGFSFT NYGMAWVRQA PTKGLEWVAT INYDGSNTYY  60
RDSVKGRFTI SRDNAKRTLD LQMDSLRSED TATYYCARHR LMYTTDYYYE VMDDWGQGAS  120
VTVSS                                                             125

SEQ ID NO: 179           moltype = AA  length = 125
FEATURE                  Location/Qualifiers
REGION                   1..125
                         note = 5826-8-R5A-G8 HCVR
source                   1..125
                         mol_type = protein
                         organism = synthetic construct
SEQUENCE: 179
EVKLVESGGG LVQPGRSLKL SCAASGFSFR NYGMAWVRQA PTKGQEWVAT ISYDGNDTYY  60
RDSVKGRFTV SRDNAKSTLY LQMDSLRSED TATYYCTRHR LIYTTDYYYE VLDAWGQGAS  120
VTVSS                                                             125

SEQ ID NO: 180           moltype = AA  length = 125
FEATURE                  Location/Qualifiers
REGION                   1..125
                         note = 5826-8-R6A-H9 HCVR
source                   1..125
                         mol_type = protein
                         organism = synthetic construct
SEQUENCE: 180
EVKLVESGGG LVQPGRSLKL SCTASGFTFS NYGMAWVRQA PTKGLEWVAT INYDGRNTYY  60
RDSVKGRFTI SRDNAKSTLY LQVDSLQSED TATYYCTRHK LIYTTDYYYE VMDVWGQGAS  120
VAVSS                                                             125

SEQ ID NO: 181           moltype = AA  length = 125
FEATURE                  Location/Qualifiers
REGION                   1..125
                         note = 5826-8-R6A-H12 HCVR
source                   1..125
                         mol_type = protein
                         organism = synthetic construct
SEQUENCE: 181
EVKLVESGGA LVQPGRSLKL SCAASGFTFS NFGMAWVRQA PTKGLEWVAT INYDGRDTYY  60
RDSVKGRFTV SRDNAKSTLY LQMDSLRSED TATYYCTRHR LIYTTDYYYE VMDAWGRGAS  120
VTVSS                                                             125

SEQ ID NO: 182           moltype = AA  length = 117
FEATURE                  Location/Qualifiers
```

```
REGION                  1..117
                        note = 5826-13-R3A-A10 HCVR
source                  1..117
                        mol_type = protein
                        organism = synthetic construct
SEQUENCE: 182
EVKLVESGPG LVKPSQSLSL ACSITDYSIT DNYWGWIRKF PGNKMEWIGH ISHSGSSTYN  60
PSLKSRISFT RDTSKNQFFL QLNSVTPEDT ATYFCARYGA GASFDYWGQG VMVTVSS     117

SEQ ID NO: 183          moltype = AA  length = 117
FEATURE                 Location/Qualifiers
REGION                  1..117
                        note = 5826-13-R3A-B1 HCVR
source                  1..117
                        mol_type = protein
                        organism = synthetic construct
SEQUENCE: 183
EVQLQQSGAE LTKPGSSVKI SCKASGFTFT TYDIGWLKQR PGQALEWIGY INPGSGGIGY  60
NEKFKGKATL TVDKSSSTAF MQLSSLTPED TAVYYCARPL RRVLDYWGQG VMVTVSS     117

SEQ ID NO: 184          moltype = AA  length = 117
FEATURE                 Location/Qualifiers
REGION                  1..117
                        note = 5826-13-R3A-B3 HCVR
source                  1..117
                        mol_type = protein
                        organism = synthetic construct
SEQUENCE: 184
EVQLQQSGAG LTKPGASVKI SCKASGYTFT TYDIGWIKQR PGQALEWIGS INPGSGGIAY  60
SEKFKGKATL TVDKSSSTAF MQLSSLTPED TAVYYCARPL RRVLDYWGQG VLVTVSS     117

SEQ ID NO: 185          moltype = AA  length = 116
FEATURE                 Location/Qualifiers
REGION                  1..116
                        note = 5826-13-R3A-D5 HCVR
source                  1..116
                        mol_type = protein
                        organism = synthetic construct
SEQUENCE: 185
EVKLVESGPG LVKPSQSLSL TCSVTGYFIT GNYLAWIRKF PGNKMEWIGH IKSSGTTTYN  60
PSLKSRVSIT RDTSKNQFFL QLNSVTSEDT ATYYCARHGH YVMDVWGQGA SVTVSS      116

SEQ ID NO: 186          moltype = AA  length = 117
FEATURE                 Location/Qualifiers
REGION                  1..117
                        note = 5826-13-R3A-D6 HCVR
source                  1..117
                        mol_type = protein
                        organism = synthetic construct
SEQUENCE: 186
EVQLQQSGAE LTKPGSSVKI SCKASGYTFT TYDIGWIKQR PGQALEWIGS INPGSGGIGY  60
NERFKGKATL TVDKSSSTAF MQLSSLTPED TAVYYCARPL RRVLDYWGQG VMVTVSS     117

SEQ ID NO: 187          moltype = AA  length = 117
FEATURE                 Location/Qualifiers
REGION                  1..117
                        note = 5826-13-R4A-E2 HCVR
source                  1..117
                        mol_type = protein
                        organism = synthetic construct
SEQUENCE: 187
QVQLKQSGAE LTKPGSSVKI SCKASGYTFT TYDIGWLKQR PGQALEWIGY INPGGGGIGY  60
NEKFKGKATL TVDKSSSTAF MQLSSLTPED TAVYYCARPL RRVLDYWGQG VMVTVSS     117

SEQ ID NO: 188          moltype = AA  length = 117
FEATURE                 Location/Qualifiers
REGION                  1..117
                        note = 5826-13-R4A-E6 HCVR
source                  1..117
                        mol_type = protein
                        organism = synthetic construct
SEQUENCE: 188
DVKLQESGPG LVKPSQSLSL TCSVTGHSIT SNYWGWIRKF PGNKMEWIGQ ISHSGSTSYN  60
PSLKSRISIT RDTSKNQFFL QLNSVTTEDT ATYYCGRYGA GSSFDYWGQG VMVTVSS     117

SEQ ID NO: 189          moltype = AA  length = 117
FEATURE                 Location/Qualifiers
REGION                  1..117
                        note = 5826-13-R4A-E9 HCVR
```

```
source                  1..117
                        mol_type = protein
                        organism = synthetic construct
SEQUENCE: 189
EVQLQQSGAE LTKPGSSVKI SCKASGYTFT TYDIGWIKQR PGQALEWIGS INPGSGGIGY  60
NEKFKGKATL TVDKSSSTVF MQLSSLTPED TAVYYCARPL RRVLDNWGQG VLVTVSS     117

SEQ ID NO: 190          moltype = AA  length = 117
FEATURE                 Location/Qualifiers
REGION                  1..117
                        note = 5826-13-R4A-F10 HCVR
source                  1..117
                        mol_type = protein
                        organism = synthetic construct
SEQUENCE: 190
EVQLQQSGAE LAKPGSSVKI SCKASGYTFT TYDIGWIKQR PGQALEWIGS INPGSGGIGY  60
NEKFKGKATL TVDKSSRTVF MQLSSLTPED TAVYYCARPL RRVLDYWGQG VMVTVSS     117

SEQ ID NO: 191          moltype = AA  length = 117
FEATURE                 Location/Qualifiers
REGION                  1..117
                        note = 5826-13-R4A-G11 HCVR
source                  1..117
                        mol_type = protein
                        organism = synthetic construct
SEQUENCE: 191
EVQLQQSGPE LAKPGSSVKI SCKASGYTFT TYDIGWIKQR PGQALEWIGS INPGSGGIGY  60
NEKFKGKATL TVDKSSSTAF MQLSSLTPED TAVYYCARPL RRVLDYWGQG VMVTVSS     117

SEQ ID NO: 192          moltype = AA  length = 117
FEATURE                 Location/Qualifiers
REGION                  1..117
                        note = 5826-13-R4A-G12 HCVR
source                  1..117
                        mol_type = protein
                        organism = synthetic construct
SEQUENCE: 192
EVQLQQSGAG LTKPGASVKI SCTASGYTFT TYDRGWLRQR PGQALEWIGS INPGGGGTGY  60
NEKFKGNATL TVDKSSSTAF MQLSSLTPED TADYYCARPL RRVLDYWGQG VLVTVSS     117

SEQ ID NO: 193          moltype = AA  length = 116
FEATURE                 Location/Qualifiers
REGION                  1..116
                        note = 5826-13-R4A-H1 HCVR
source                  1..116
                        mol_type = protein
                        organism = synthetic construct
SEQUENCE: 193
DVKLQESGPG LVKPSQSLSL TCSVTGHSIT SNYWGWIRKL PGNKMEWIGQ ISHSGSTSYN  60
PSLISRISIT RDTSNQFFLQ LNSVTTEDTA TYYCGRYGAG SSFDYWGQGV MVTVSS      116

SEQ ID NO: 194          moltype = AA  length = 117
FEATURE                 Location/Qualifiers
REGION                  1..117
                        note = 5826-13-R4A-H2 HCVR
source                  1..117
                        mol_type = protein
                        organism = synthetic construct
SEQUENCE: 194
EVQLQQSGAE LTKPGSSVKI SCKASGYTFT TYDIGWIKQR PGQALEWIGS INPGSGGIGY  60
NEKFKGKATL TVDRSSSTAF MQLSSLTPED TAVYYCARPL RRVLDNWGQG VLVTVSS     117

SEQ ID NO: 195          moltype = AA  length = 117
FEATURE                 Location/Qualifiers
REGION                  1..117
                        note = 5826-13-R4A-H3 HCVR
source                  1..117
                        mol_type = protein
                        organism = synthetic construct
SEQUENCE: 195
EVQLQQSGGE LTKPGSSVKI SCKASGYTFS TYDIGWIKQR PGQALEWIGS INPGSGGIGY  60
NEKFKGKATL TVDKSSSTAF MQLSSLTPED TAVYYCARPL RRVLDYWGQG VMVTVSS     117

SEQ ID NO: 196          moltype = AA  length = 117
FEATURE                 Location/Qualifiers
REGION                  1..117
                        note = 5826-13-R4A-H4 HCVR
source                  1..117
                        mol_type = protein
```

```
                          organism = synthetic construct
SEQUENCE: 196
DVKLQESGPG LVKPSQSLSL TCSVTGHSIT GNYWGWIRKF PGNKMEWIGQ ISHSGSTSYN  60
PSLKSRISIT RDTSKNQFFL QLNSVTTEDT ATYYCGRYGA GSSFDYWGQG VMVTVSS     117

SEQ ID NO: 197            moltype = AA  length = 117
FEATURE                   Location/Qualifiers
REGION                    1..117
                          note = 5826-13-R4A-H5 HCVR
source                    1..117
                          mol_type = protein
                          organism = synthetic construct
SEQUENCE: 197
EVQLQQSGAG LTKPGGSVKI SCKVSGYTFT TYDIGWLKQR PGQALEWIGS INPGGGGTGY  60
NEKFKGKATL TVDKSSSTAF MQLSSLTPED TAVYYCARPL RRVLDYWGQG VLVTVSS     117

SEQ ID NO: 198            moltype = AA  length = 116
FEATURE                   Location/Qualifiers
REGION                    1..116
                          note = 5826-13-R4A-H6 HCVR
source                    1..116
                          mol_type = protein
                          organism = synthetic construct
SEQUENCE: 198
EVQLQQSGAG LTKPGASVKI SCKASGYTFT TYDIGWLKQR PGQALEWIGS INPGGGGTGY  60
NEKFKGKATL TVDKSSSTAF MQLSSLTPED TAVYYCARPL RVLDYWGQGV LVTVSS      116

SEQ ID NO: 199            moltype = AA  length = 117
FEATURE                   Location/Qualifiers
REGION                    1..117
                          note = 5826-13-R4A-H9 HCVR
source                    1..117
                          mol_type = protein
                          organism = synthetic construct
SEQUENCE: 199
EVQLQQSGAE LTKPGSSVKI SCKASGYTFT TYDIGWIKQR PGQALEWIGS INPGSGGIGY  60
NERFKGKATL TVDKSSSTAF MQLSSLTPED TAVYYCARPL RRVLDYWGRG VMVTVSS     117

SEQ ID NO: 200            moltype = AA  length = 117
FEATURE                   Location/Qualifiers
REGION                    1..117
                          note = 5826-13-R4A-H10 HCVR & 5826-13-R4A-H12 HCVR
source                    1..117
                          mol_type = protein
                          organism = synthetic construct
SEQUENCE: 200
EVQLEESGPG LVKPSQSLSL TCSVTGHSIT SNYWGWIRKF PGNKMEWIGQ ISHSGSTSYN  60
PSLKSRISIT RDTSKNQFFL QLNSVTTEDT ATYYCGRYGA GSSFDYWGQG VMVTVSS     117

SEQ ID NO: 201            moltype = AA  length = 117
FEATURE                   Location/Qualifiers
REGION                    1..117
                          note = 5826-13-R4A-H11 HCVR
source                    1..117
                          mol_type = protein
                          organism = synthetic construct
SEQUENCE: 201
QVQLKESGPG LVKPSHSLSL TCSVTGHSIT SNYWGWIRKF PGNKMEWIGQ ISHTGSSTYN  60
PSLKSRISFT RDTSKNQFFL QLNSVTTEDS ATYYCGRYGA GSSFDYWGQG VMVTVSS     117

SEQ ID NO: 202            moltype = AA  length = 113
FEATURE                   Location/Qualifiers
REGION                    1..113
                          note = 5826-8-R6A-A10 LCVR
source                    1..113
                          mol_type = protein
                          organism = synthetic construct
SEQUENCE: 202
DVLMTQTPSS QAASAGEKVT MSCKSSQSLL YNENKKNYLA WFQQKPGQSP KLLIYWASTR  60
ESGVPDRFIG GGSGTDFTLT ISSVQAEDLA VYYCQEYYKF PWTFGGGTKL ELK         113

SEQ ID NO: 203            moltype = AA  length = 113
FEATURE                   Location/Qualifiers
REGION                    1..113
                          note = 5826-8-R6A-B11 LCVR & 5826-8-R5A-G6 LCVR
source                    1..113
                          mol_type = protein
                          organism = synthetic construct
SEQUENCE: 203
```

```
DIVMTQSPSS QAVSAGEKVT MSCKSSQSLL YNENKKNYLA WFQQKPGQSP KLLIYWASTR  60
ESGVPDRFIG SGSGTDFTLT ISSVQAEDLA VYYCQDYYHF PWTFGGGTKL ELK         113

SEQ ID NO: 204          moltype = AA  length = 112
FEATURE                 Location/Qualifiers
REGION                  1..112
                        note = 5826-8-R6A-D12 LCVR
source                  1..112
                        mol_type = protein
                        organism = synthetic construct
SEQUENCE: 204
DVLMTQTPPT LSATIGQSVS ISCKSSQSLL HSNGNTYLNW LLQRPGQSPQ LLIYSVSKLE  60
SGVPNRFSGS GSQTDFTLKI SEVEAEDMGV YYCMQATHAP FTFGSWTKLE IK          112

SEQ ID NO: 205          moltype = AA  length = 113
FEATURE                 Location/Qualifiers
REGION                  1..113
                        note = 5826-8-R6A-E10 LCVR
source                  1..113
                        mol_type = protein
                        organism = synthetic construct
SEQUENCE: 205
DIVMTQAPSS QAVSPGEKVT MSCKSSQSLL YNENKKNYLA WYQQKPGQSP KLLIYWASTR  60
EAGVPDRFIG SGSGTDFTLT ISSVQAEDLA VYYCQQYYKF PWPFGGGTKL ELK         113

SEQ ID NO: 206          moltype = AA  length = 113
FEATURE                 Location/Qualifiers
REGION                  1..113
                        note = 5826-8-R5A-G8 LCVR
source                  1..113
                        mol_type = protein
                        organism = synthetic construct
SEQUENCE: 206
DIVMTQAPSS QAVSAGEKVT MSCKSSQSLL YNENKKNYLA WFQQKPGQSP KLLIYWASTR  60
KSGVPDRFIG SGSGTDFTLT ISSVQAEDLA VYYCQQYYKF PWTFGGGTKL ELR         113

SEQ ID NO: 207          moltype = AA  length = 113
FEATURE                 Location/Qualifiers
REGION                  1..113
                        note = 5826-8-R6A-H9 LCVR
source                  1..113
                        mol_type = protein
                        organism = synthetic construct
SEQUENCE: 207
DIVMTQSPSS QAVSPGEKVT MNCKSSQSLL YNENKKNYLA WYQQKPGQSP KLLIYWASTR  60
EAGVPDRFIG SGSGTDFTLT ISSVQAEDLA VYYCQQYYKF PWPFGGGTKL ELK         113

SEQ ID NO: 208          moltype = AA  length = 112
FEATURE                 Location/Qualifiers
REGION                  1..112
                        note = 5826-8-R6A-H11 LCVR
source                  1..112
                        mol_type = protein
                        organism = synthetic construct
SEQUENCE: 208
DVLMTQTPPT LSATIGQSVS ISCRSSQSLL HSNGNTYLNW LLQRPGQSPQ LLIYSVSNLE  60
SGVPNRFSGS GSETDFTLKI SGVEAEDLGV YYCMQATHAP FTFGSGTKLE IK          112

SEQ ID NO: 209          moltype = AA  length = 113
FEATURE                 Location/Qualifiers
REGION                  1..113
                        note = 5826-8-R6A-H12 LCVR
source                  1..113
                        mol_type = protein
                        organism = synthetic construct
SEQUENCE: 209
DIVMTQSPSS QAVSPGEKVT MNCKSSQSLL YNENKKNYLA WYQQKPGQSP KLLIYWASTR  60
EAGVPDRFIG SGSGTDFTLT ISSVQAEDLA VYYCQQYYKF PYTFGAGTKL ELK         113

SEQ ID NO: 210          moltype = AA  length = 107
FEATURE                 Location/Qualifiers
REGION                  1..107
                        note = 5826-13-R3A-A10 LCVR
source                  1..107
                        mol_type = protein
                        organism = synthetic construct
SEQUENCE: 210
DIQLTQSPHS LSASLGETVS IECLASEGIS NYLAWYQQKP GKSPQLLIYY TSSLQDGVPS  60
RFSGSGSGTQ YSLKISNMQP EDEGVYYCQQ GYKYPWTFGG GTKLELK                107
```

```
SEQ ID NO: 211          moltype = AA  length = 107
FEATURE                 Location/Qualifiers
REGION                  1..107
                        note = 5826-13-R3A-B1 LCVR
source                  1..107
                        mol_type = protein
                        organism = synthetic construct
SEQUENCE: 211
DIVMTQSPSS LPASLGERVT ISCRASQGIS NKLNWYQQKP DGTIKPLIYY TSRLQSGVPS  60
RFSGSGSGTD YSLTISSLEP EDFAMYYCQQ DASFPPTFGA GTKVELK               107

SEQ ID NO: 212          moltype = AA  length = 107
FEATURE                 Location/Qualifiers
REGION                  1..107
                        note = 5826-13-R3A-B3 LCVR & 5826-13-R4A-H5 LCVR
source                  1..107
                        mol_type = protein
                        organism = synthetic construct
SEQUENCE: 212
DIQLTQSPSS LPASLGERVT ISCRASQGIS NKLNWYQQKP DGTIKPLIYY TSNLQSGVPS  60
RFSGSGSGTD YSLTISSLEP EDFAMYYCQQ DASFPPTFGG GTKLELK               107

SEQ ID NO: 213          moltype = AA  length = 110
FEATURE                 Location/Qualifiers
REGION                  1..110
                        note = 5826-13-R3A-D5 LCVR
source                  1..110
                        mol_type = protein
                        organism = synthetic construct
SEQUENCE: 213
DIVLTQSPVL AVSLGQRATI SCRASQSVST STYNFMHWYQ QKPGQQPRLL IYDASHLASS  60
VPARFSGSGS GTDFTLTINP VQADDIATYY CQQSRELPLT FGSGTKLEIK            110

SEQ ID NO: 214          moltype = AA  length = 107
FEATURE                 Location/Qualifiers
REGION                  1..107
                        note = 5826-13-R3A-D6 LCVR
source                  1..107
                        mol_type = protein
                        organism = synthetic construct
SEQUENCE: 214
DILMTQSPSS LSASLGERVT ISCRASQGIG NKLNWYQQKP DGTIKPLIYY TSNLQSGVPS  60
RFSGSGSGTD YSLTISSLEP EDFAMYYCQQ DASFPPTFGG GTKLELK               107

SEQ ID NO: 215          moltype = AA  length = 107
FEATURE                 Location/Qualifiers
REGION                  1..107
                        note = 5826-13-R4A-E2 LCVR
source                  1..107
                        mol_type = protein
                        organism = synthetic construct
SEQUENCE: 215
DIQLTQSPSS LPASLGERVT ISCRASQGIS NKLNWYQQKP DGTIKPLIYY TSNLQSGVPS  60
RFSGSGSGTD YSLTISSLEP EDFAMYFCQQ DASFPPTFGG GTKLELK               107

SEQ ID NO: 216          moltype = AA  length = 107
FEATURE                 Location/Qualifiers
REGION                  1..107
                        note = 5826-13-R4A-E6 LCVR
source                  1..107
                        mol_type = protein
                        organism = synthetic construct
SEQUENCE: 216
DIQMTQTPHS LSASLGETVS IECLASEGIS NYLAWYQQKP GKSPQLLIYY TSSFQDGVPS  60
RFSGSGSGTQ YSLKISNMQP EDEGVYYCQQ GYKYPWTFGG GTKLELK               107

SEQ ID NO: 217          moltype = AA  length = 107
FEATURE                 Location/Qualifiers
REGION                  1..107
                        note = 5826-13-R4A-E9 LCVR
source                  1..107
                        mol_type = protein
                        organism = synthetic construct
SEQUENCE: 217
DILMTQSPSS RPASLGERVT ISCRASQGIG NKLNWYQQKP DGTIKPLIYY TSNLQSGVPS  60
RFSGSGSGTD YSLTISSLEP EDFAMYYCQQ DASFPPTFGG GTKLELK               107

SEQ ID NO: 218          moltype = AA  length = 107
```

```
FEATURE                Location/Qualifiers
REGION                 1..107
                       note = 5826-13-R4A-F10 LCVR
source                 1..107
                       mol_type = protein
                       organism = synthetic construct
SEQUENCE: 218
DIQMTQTPSS LPASLGERVT ISCRASQGIS KKLNWYQQKP DGTIKPLIYY TSNLQSGVPS  60
RFSGSGSGTD YSLTISSLEP EDFAIYYCQQ DASFPPTFGG GTKLELK               107

SEQ ID NO: 219         moltype = AA  length = 106
FEATURE                Location/Qualifiers
REGION                 1..106
                       note = 5826-13-R4A-G11 LCVR
source                 1..106
                       mol_type = protein
                       organism = synthetic construct
SEQUENCE: 219
DIQLTQSPSS LPASLGERVT ISCRASQGIS KKLNWYQQKP DGTIKPLIYY TSNLQSGVPS  60
RFSGSSGTDY SLTISSLEPE DFAMYYCQQD ASFPPTFGGG TKLELK                106

SEQ ID NO: 220         moltype = AA  length = 107
FEATURE                Location/Qualifiers
REGION                 1..107
                       note = 5826-13-R4A-G12 LCVR
source                 1..107
                       mol_type = protein
                       organism = synthetic construct
SEQUENCE: 220
DILMTQSPSS LPASLGERVT ISCGASQGIG NKVNWYQQKP DGTIKPLIYY TSNLQSGVPS  60
RFSGSGTGTD YSLTISSLEP EDFAMYYCQQ DASFPPTFGG GTKLELK               107

SEQ ID NO: 221         moltype = AA  length = 107
FEATURE                Location/Qualifiers
REGION                 1..107
                       note = 5826-13-R4A-H1 LCVR
source                 1..107
                       mol_type = protein
                       organism = synthetic construct
SEQUENCE: 221
DIQMTQTPHS LSASLGETVS IECLASEGIS NYLAWYQRKP GKSPQLLIYY TISLQDGVPS  60
RFSGSGSGTQ YSLKISNMQP EDEGVFYCQQ GYKYPWTFGG GTKLELK               107

SEQ ID NO: 222         moltype = AA  length = 107
FEATURE                Location/Qualifiers
REGION                 1..107
                       note = 5826-13-R4A-H2 LCVR
source                 1..107
                       mol_type = protein
                       organism = synthetic construct
SEQUENCE: 222
DIQLTQSPSS LPASLGERVT ISCRASQGIG NKLNWYQQKP DGTIKPLIYY TSNLQSGVPS  60
RFSGSGSGTD YSLTISSLEP EDFAMYYCQQ DASFPPTFGG GTKLELK               107

SEQ ID NO: 223         moltype = AA  length = 107
FEATURE                Location/Qualifiers
REGION                 1..107
                       note = 5826-13-R4A-H3 LCVR
source                 1..107
                       mol_type = protein
                       organism = synthetic construct
SEQUENCE: 223
DILMTQSPSS LSASLGERVT ISCRASQGIG NKLNWYQQKP DGTIKPLIYY TSNLQSGVPS  60
RFSGSGSGTD YSLTISSLEP EDFAMYYCQQ DTSFPPTFGA GTKLELK               107

SEQ ID NO: 224         moltype = AA  length = 107
FEATURE                Location/Qualifiers
REGION                 1..107
                       note = 5826-13-R4A-H4 LCVR & 5826-13-R4A-H10 LCVR &
                        5826-13-R4A-H11 LCVR
source                 1..107
                       mol_type = protein
                       organism = synthetic construct
SEQUENCE: 224
DIQMTQTPHS LSASLGETVS IECLASEGIS NYLAWYQQKP GKSPQLLIYY TISLQDGVPS  60
RFSGSGSGTQ YSLKISNMQP EDEGVFYCQQ GYKYPWTFGG GTKLELK               107

SEQ ID NO: 225         moltype = AA  length = 106
FEATURE                Location/Qualifiers
```

-continued

```
REGION              1..106
                    note = 5826-13-R4A-H6 LCVR
source              1..106
                    mol_type = protein
                    organism = synthetic construct
SEQUENCE: 225
DIQMTQTPSS LPASLERVTI SCRASQGISN KLNWYQKKPD GTIKPLIYYT SNLQSGVPSR  60
FSGSGSGTDY SLTISSLEPE DFAMYFCQQD ASFPPTFGGG TQLELK                106

SEQ ID NO: 226      moltype = AA  length = 107
FEATURE             Location/Qualifiers
REGION              1..107
                    note = 5826-13-R4A-H9 LCVR
source              1..107
                    mol_type = protein
                    organism = synthetic construct
SEQUENCE: 226
DIQLTQSPSS RPASLGERVT ISCRASQGIG NKLNWYQQKP DGTIKPLIYY TSNLQSGVPS  60
RFSGSGSGTD YSLTISSLEP EDFAMYYCQQ DASFPPTFGG GTKLELK               107

SEQ ID NO: 227      moltype = AA  length = 107
FEATURE             Location/Qualifiers
REGION              1..107
                    note = 5826-13-R4A-H12 LCVR
source              1..107
                    mol_type = protein
                    organism = synthetic construct
SEQUENCE: 227
DIQMTQTPHS LSASLGETVS IECLASEGIS NYLAWYQQKP GKSPQLLIYY ASSLQDGVPS  60
RFSGSGSGTQ YSLKISNMQP EDEGVYYCQQ GYKYPWTFGG GTKLELK               107
```